(12) United States Patent
Singh et al.

(10) Patent No.: US 7,598,397 B2
(45) Date of Patent: Oct. 6, 2009

(54) SULFONAMIDE PERI-SUBSTITUTED BICYCLICS FOR OCCLUSIVE ARTERY DISEASE

(75) Inventors: Jasbir Singh, Naperville, IL (US); Mark E. Gurney, Grand Rapids, MI (US); Georgeta Hategan, Naperville, IL (US); Peng Yu, Lisle, IL (US); David Zembower, La Grange, IL (US); Nian Zhou, Naperville, IL (US)

(73) Assignee: deCODE genetics ehf, Reykjavik (IS)

( * ) Notice: Subject to any disclaimer, the term of this patent is extended or adjusted under 35 U.S.C. 154(b) by 135 days.

(21) Appl. No.: 11/169,161

(22) Filed: Jun. 27, 2005

(65) Prior Publication Data
US 2006/0079520 A1 Apr. 13, 2006

Related U.S. Application Data

(60) Provisional application No. 60/618,172, filed on Oct. 12, 2004.

(51) Int. Cl.
C07D 411/00 (2006.01)
(52) U.S. Cl. .................................... 548/467
(58) Field of Classification Search ................ 514/415; 548/469
See application file for complete search history.

(56) References Cited

U.S. PATENT DOCUMENTS

| 4,273,782 A | | 6/1981 | Cross et al. |
| 5,239,083 A | * | 8/1993 | Kumazawa et al. ......... 548/465 |
| 5,663,346 A | | 9/1997 | Buzzetti et al. |
| 5,994,378 A | | 11/1999 | Matsuo et al. |
| 6,166,219 A | | 12/2000 | Yamasaki et al. |
| 6,235,777 B1 | | 5/2001 | Ohuchida et al. |
| 6,242,493 B1 | | 6/2001 | Gareau et al. |
| 6,310,079 B1 | * | 10/2001 | Okumura et al. ............ 514/338 |
| 6,348,032 B1 | | 2/2002 | Sperl et al. |
| 6,348,474 B1 | | 2/2002 | Kayakiri et al. |
| 2008/0125477 A1 | | 5/2008 | Singh et al. |

FOREIGN PATENT DOCUMENTS

| EP | 0539117 A | 4/1993 |
| EP | 0620122 A | 10/1994 |
| EP | 0882718 A | 12/1998 |
| EP | 1378246 | 1/2004 |
| EP | 1431267 A | 6/2004 |

OTHER PUBLICATIONS

Bao et al., caplus an 2000:627993.*
O'Connell et al., Bioorg. & Med. Chem. Lett, 19(2009), 778-782.*
Juteau et al., "Structure-Activity Relationship of Cinnamic Acylsulfonamide Analogues on the Human $EP_3$ Prostanoid Receptor," Biorganic & Medicinal Chemistry 9, pp. 1977-1984 (2001).
Gallant et al., "Structure-Activity Relationship of Biaryl Acylsulfonamide Analogues on the Human $EP_3$ Prostanoid Receptor," Biooorganic & Medicinal Chemistry Letters 12, pp. 2583-2586 (2002).
International Search Report and Written Opinion for PCT/US2005/023009, dated Feb. 6, 2006 and mailed Feb. 21, 2006, 9 pages.

* cited by examiner

Primary Examiner—Golam M. M. Shameem
Assistant Examiner—Sun Jae Y. Loewe
(74) Attorney, Agent, or Firm—Heslin Rothenberg Farley & Mesiti P.C.

(57) ABSTRACT

Acyl sulfonamide, peri-substituted, fused bicyclic ring compounds useful for the treatment or prophylaxis of a prostaglandin-mediated disease or condition are disclosed. The compounds are of the general formula

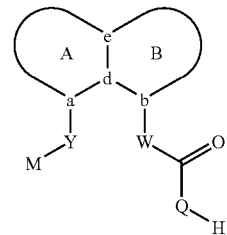

A representative example is:

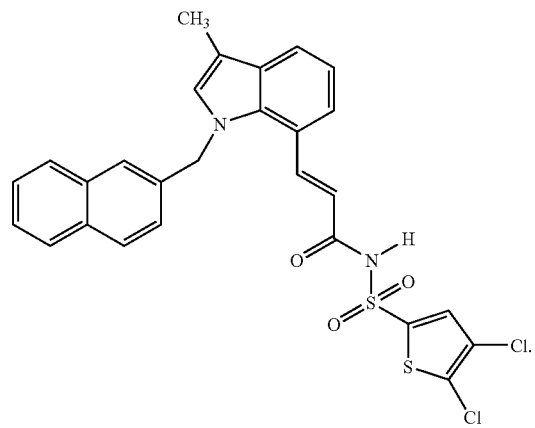

10 Claims, No Drawings

SULFONAMIDE PERI-SUBSTITUTED BICYCLICS FOR OCCLUSIVE ARTERY DISEASE

CROSS REFERENCE TO RELATED APPLICATIONS

This application claims benefit from U.S. Provisional Application 60/618,172 filed on Oct. 12, 2004.

FIELD OF THE INVENTION

The invention relates to a chemical genus of peri-substituted, bicyclic acyl sulfonamides useful for the treatment and prophylaxis of occlusive artery disease and related prostaglandin-mediated disorders.

BACKGROUND OF THE INVENTION

Atherosclerosis is the pathology underlying several of mankind's most lethal diseases, such as myocardial infarction and peripheral arterial occlusive disease (PAOD). PAOD represents atherosclerosis of the large and medium arteries of the limbs, particularly to the lower extremities, and includes the aorta and iliac arteries. It often coexists with coronary artery disease and cerebrovascular disease. Persons with PAOD are at increased risk of other vascular events such as myocardial infarction or stroke [Waters, R E, Terjung R L, Peters K G & Annex B H. J. Appl. Physiol. 2004; Ouriel K. Lancet, 2001, 258:1257-64; Kroger, K. Angiology, 2004, 55:135-138]. Clinically significant lesions may gradually narrow the peripheral arteries leading to pain on walking usually relieved by rest (claudication), ischemic ulcers, gangrene, and sometimes limb amputation. Medical therapy is generally ineffective but operations bypassing or replacing the lesion with artificial or venous grafts improve blood flow distally, at least until they become restenosed [Haustein, K. O., *Int. J. Clin. Pharmacol. Ther.*, 35:266 (1997)]. Recently, it has been discovered through human genetic linkage studies that DNA variants of the PTGER3 gene that encodes the prostaglandin $E_2$ receptor subtype 3 (known as EP3) increase the risk of an individual developing PAOD (see US published application 2003/0157599). Thus, antagonists of prostaglandin $E_2$ ($PGE_2$) binding to the EP3 receptor may provide effective treatment or prophylaxis for PAOD.

In response to various extracellular stimuli, prostaglandins are rapidly generated from free arachidonic acid through the consecutive action of the cyclo-oxygenases and synthases. The prostaglandins exert their action in close proximity to the site of their synthesis. To date, eight prostanoid receptors have been cloned and characterized. These receptors are members of the growing class of G-protein-coupled receptors. $PGE_2$ binds preferentially to the EP1, EP2, EP3, and EP4 receptors; $PGD_2$ to the DP and FP receptors; $PGF_{2\alpha}$ to the FP and EP3 receptors; $PGI_2$ to the IP receptor and $TXA_2$ to the TP receptor. $PGE_2$ binding to the EP3 receptor has been found to play a key role in the regulation of ion transport, smooth muscle contraction of the GI tract, acid secretion, uterine contraction during fertilization and implantation, fever generation and hyperalgesia. The EP3 receptor has been detected in many organs such as the kidney, the gastrointestinal tract, the uterus and the brain. In the cardiovascular system, EP3 is expressed by vascular endothelium and smooth muscle, and at least four isoforms of EP3 are expressed on human platelets [Paul, B. Z., B. Ashby, and S. B. Sheth, Distribution of prostaglandin IP and EP receptor subtypes and isoforms in platelets and human umbilical artery smooth muscle cells. British Journal of Haematology, 1998. 102(5): p. 1204-11.]

Prostanoids, acting through specific membrane receptors belonging to the superfamily of G protein-coupled receptors (GPCRs) have an essential role in vascular homeostasis, including platelet function regulation. Among the prostanoids, thomboxane A2 ($TxA_2$) is a potent stimulator of platelet aggregation, whereas prostaglandin (PG) $I_2$ inhibits their activation. On the other hand, prostaglandin $E_2$ ($PGE_2$) has been reported to have a biphasic effect on platelet response, potentiating their aggregation at low concentrations and inhibiting it at higher concentrations. It has been shown that the stimulatory effects of $PGE_2$ on platelet aggregation are exerted mainly through EP3 receptor, one of the four subtypes of receptors activated by $PGE_2$.

Local synthesis of prostaglandins in the arterial vessel wall may play a profound role in atherosclerosis. While only COX-1 is present in the healthy vessel wall, both COX-1 and COX-2 are present in arteriosclerotic plaque [Schonbeck, U., et al., Augmented expression of cyclooxygenase-2 in human atherosclerotic lesions. Am J Pathol, 1999. 155(4): p. 1281-91; Cipollone, F., et al., Overexpression of functionally coupled cyclooxygenase-2 and prostaglandin E synthase in symptomatic atherosclerotic plaques as a basis of $PGE_2$-dependent plaque instability. Circulation, 2001. 104(8): p. 921-7]. Their increased expression, together with increased expression of prostaglandin E synthase, may account for the increased production of $PGE_2$ noted above. In genetically modified mice lacking the low density lipoprotein receptor (LDL-R), formation of atherosclerotic plaque can be reduced by treatment with rofecoxib, a selective inhibitor of COX-2, through reducing production of $PGE_2$ and other prostaglandins [Burleigh M E, Babaev V R, Oates J A, Harris R C, Gautam S, Riendeau D, Marnett L J, Morrow J D, Fazio S, Linton M F. Cyclooxygenase-2 promotes early atherosclerotic lesion formation in LDL receptor-deficient mice. Circulation. 2002 Apr. 16; 105(15):1816-23].

Within the atherosclerotic plaque, vascular smooth muscle cells have been shown to express EP3 receptors and $PGE_2$ stimulates their proliferation and migration, a hallmark of atherosclerotic plaque formation [Blindt R, Bosserhoff A K, vom Dahl J, Hanrath P, Schror K, Hohlfeld T, Meyer-Kirchrath J. Activation of IP and EP(3) receptors alters cAMP-dependent cell migration. Eur J. Pharmacol. 2002 May 24; 444(1-2):31-7]. It is, therefore, plausible that chronically inflamed vessels produce sufficient quantities of $PGE_2$ to activate $EP_3$ receptors on vascular smooth muscles cells (contributing to atherosclerotic lesion formation) and on platelets (contributing to thrombosis). Locally produced $PGE_2$ (from platelets themselves, vessel wall components, and inflammatory cells) potentiates platelet aggregation by suboptimal amounts of prothrombotic tissue factors, which might not cause aggregation by themselves, through priming of protein kinase C. The intracellular events triggered by activation of the $EP_3$ receptor may enhance platelet aggregation by opposing the effect of $PGI_2$ and enhancing the effects of primary aggregating agents such as collagen. $EP_3$ receptor activation may therefore contribute to atherosclerosis and the risk of thrombosis observed in pathological states such as vasculitis and PAOD.

Current treatments for PAOD either address increased risk for cardiovascular events such as myocardial infarction and stroke, or provide symptomatic relief for claudication. All of these treatments affect platelet function. Treatments reducing risk for cardiovascular events include low dose asprin (sufficient to reduce platelet aggregation while still permitting the production of PGI2 by the vessel wall) and inhibitors of the platelet adenosine diphosphate receptor inhibitor (clopidogrel). Binding of adenosine diphosphate to the platelet adenosine diphosphate receptor causes a drop in platelet cAMP with consequent platelet activation and aggregation. Treatments providing symptomatic relief from claudication include platelet phosphodiesterase type 3 inhibitors such as cilostazol which act to increase intracellular levels of cAMP. Inhibitors of the platelet adenosine diphosphate receptor or the platelet phosphodiesterase type 3 act directly or indirectly to increase the content of cAMP in platelets, thereby inhibiting platelet activation and consequent aggregation with thrombus formation. $PGE_2$ binding to EP3 acts to decrease cAMP, therefore an antagonist of $PGE_2$ binding to the EP3 receptor, by opposing the $PGE_2$-dependent decrease in cAMP needed to induce platelet activation and consequent aggregation, or by opposing the $PGE_2$-dependent decrease in vascular smooth muscle cell cAMP needed to stimulate migration, might be expected to provide therapeutic benefit in PAOD. Such an antagonist may also be disease-modifying by inhibiting or reducing atherosclerotic plaque formation.

Prostaglandins furthermore have been implicated in a range of disease states including pain, fever or inflammation associated with rheumatic fever, influenza or other viral infections, common cold, low back and neck pain, skeletal pain, post-partum pain, dysmenorrhea, headache, migraine, toothache, sprains and strains, myositis, neuralgia, synovitis, arthritis, including rheumatoid arthritis, degenerative joint diseases (osteoarthritis), gout and ankylosing spondylitis, bursitis, burns including radiation and corrosive chemical injuries, sunburns, pain following surgical and dental procedures, immune and autoimmune diseases; cellular neoplastic transformations or metastatic tumor growth; diabetic retinopathy, tumor angiogenesis; prostanoid-induced smooth muscle contraction associated with dysmenorrhea, premature labor, asthma or eosinophil related disorders; Alzheimer's disease; glaucoma; bone loss; osteoporosis; Paget's disease; peptic ulcers, gastritis, regional enteritis, ulcerative colitis, diverticulitis or other gastrointestinal lesions; GI bleeding; coagulation disorders selected from hypoprothrombinemia, hemophilia and other bleeding problems; and kidney disease.

While circulating levels of prostanoids are extremely low in healthy individuals [FitzGerald G A, Brash A R, Falardeau P & Oates J A. JCI 1981 68:12472-1275], the local concentration of $PGE_2$ can dramatically increase in inflammatory states. For example, the local production of $PGE_2$ was shown in vitro to increase more than 30-fold in aortoiliac occlusive disease [Reilly J, Miralles M, Wester W & Sicard G. Surgery, 1999, 126:624-628]. It is, therefore, plausible that chronically inflamed vessels produce sufficient quantities of $PGE_2$ to activate $EP_3$ receptors on platelets. In this environment, the intracellular events triggered by activation of the $EP_3$ receptor may enhance platelet aggregation by opposing the effect of $PGI_2$ and enhancing the effects of primary aggregating agents such as ADP. $EP_3$ receptor activation may therefore contribute to the thrombosis observed in pathological states such as vasculitis and atherosclerosis. Peripheral Arterial Occlusive Disease (PAOD) is an atherosclerotic illness that affects primarily the elderly as a consequence of occlusion of the lumen of peripheral arteries, mainly the femoral artery and it is associated with an increased risk of vascular events as myocardial infraction or stroke [Waters, R E, Terjung R L, Peters K G & Annex B H. J. Appl. Physiol. 2004; Ouriel K. Lancet, 2001, 258:1257-64; Kroger, K. Angiology, 2004, 55:135-138]. Several clinical studies have shown that treatment with prostaglandins improves PAOD symptoms [Reiter M, Bucek R, Stumpflen A & Minar E. Cochrane Database Syst. Rev. 2004, 1:CD000986; Bandiera G, Forletta M, Di Paola F M, Cirielli C. Int. Angiol. 2003, 22:58-63; Matsui K, Ikeda U, Murakami Y, Yoshioka T, Shimada K. Am. Heart J. 2003, 145:330-333] supporting the linkage between PAOD and prostanoid receptor function.

Ortho-substituted phenyl acylsulfonamides and their utility for treating prostaglandin-mediated disorders are described in U.S. Pat. No. 6,242,493 and in two articles by Juteau et al. [BioOrg. Med. Chem. 9, 1977-1984 (2001)] and Gallant et al. [BioOrg. Med. Chem. Let. 12, 2583-2586 (2002)], the disclosures of which are incorporated herein by reference.

SUMMARY OF THE INVENTION

In one aspect the invention relates to compounds of formula I

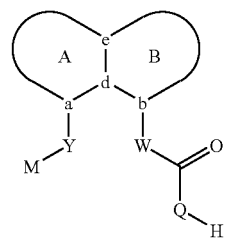

wherein A and B represent a pair of fused 5-, 6- or 7-membered rings. The fused A/B ring system may contain from zero to four heteroatoms chosen from nitrogen, oxygen and sulfur and may be additionally substituted with from zero to four substituents chosen independently from halogen, —OH, loweralkyl, —O-loweralkyl, fluoroloweralkyl, —O-lowerfluoroalkyl, methylenedioxy, ethylenedioxy, alkoxy-loweralkyl, hydroxyloweralkyl, oxo, oxide, —CN, nitro, —S-loweralkyl, amino, loweralkylamino, diloweralkylamino, diloweralkylaminoalkyl, carboxy, carboalkoxy, acyl, acylalkyl, carboxamido, loweralkylsulfoxide, acylamino, phenyl, benzyl, spirothiazolidinyl, phenoxy and benzyloxy. The nodes represented by a and b are the points of attachment of residues Y and W respectively, and a and b are in a peri relationship to one another on the fused A/B ring system. The nodes represented by d and e are points of fusion between ring A and ring B in the fused A/B ring system. Each of the nodes a, b, d and e may be either carbon or nitrogen.

W and Y are linkers comprising from zero to 8 atoms in a chain.

M is chosen from aryl, substituted aryl, heterocyclyl, substituted heterocyclyl, $C_6$ to $C_{20}$ alkyl and substituted $C_6$ to $C_{20}$ alkyl.

In one subgenus (Ia), Q is chosen from —N($SO_2R^1$)—, —N($COR^1$)—, —N[PO(O-alkyl)$_2$]-, —NHN$R^{10}$($SO_2R^1$), and, when W is —$CF_2$— or —$CH_2CF_2$—, Q may additionally be —NH—; $R^1$ is chosen from aryl, substituted aryl, heteroaryl, substituted heteroaryl, $C_3$-$C_{20}$ alkyl and fluoroalkyl; and $R^{10}$ is chosen from alkyl, aryl and heteroaryl. In another subgenus (Ib), Q is —O—, and the compounds are carboxylic acids. The claims below relate to subgenus (Ia). The claims in a related application, having the title "Carboxylic Acid Peri-substituted Bicyclics for Occlusive Artery Disease", to be filed subsequent to the filing of the instant application, relate to subgenus Ib.

Other related compounds having utility in treating occlusive artery disease and related prostaglandin-mediated disorders include compounds of formula Ic:

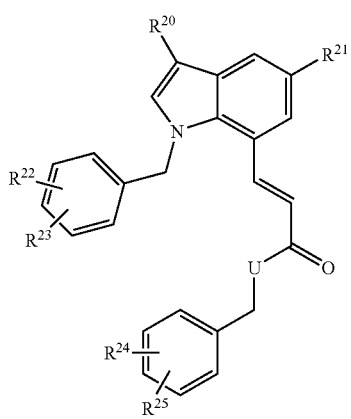

Ic wherein

U is chosen from —O— and —NH—; and $R^{20}$-$R^{25}$ are chosen independently from hydrogen, halogen and methyl.

In a second aspect the invention relates to pharmaceutical formulations comprising a pharmaceutically acceptable carrier and a compound as above, or an ester, a pharmaceutically acceptable salt or a hydrate of the compound.

In a third aspect, the invention relates to methods for the treatment or prophylaxis of a prostaglandin-mediated disease or condition. The methods comprise administering to a mammal a therapeutically effective amount of a compound described herein.

The disease or condition may be, for example, pain, fever or inflammation associated with rheumatic fever, influenza or other viral infections, common cold, low back and neck pain, skeletal pain, post-partum pain, dysmenorrhea, headache, migraine, toothache, sprains and strains, myositis, neuralgia, synovitis, arthritis, including rheumatoid arthritis, degenerative joint diseases (osteoarthritis), gout and ankylosing spondylitis, bursitis, burns including radiation and corrosive chemical injuries, sunburns, pain following surgical and dental procedures, immune and autoimmune diseases. EP3 antagonist compounds of the invention that penetrate the CNS are especially suited for pain management.

Compounds of the invention, which inhibit platelet aggregation and increase regional blood flow, are useful for treating primary thromboembolism, thrombosis and occlusive vascular diseases. The compounds can be used advantageously in combination with other platelet aggregation inhibitors and with inhibitors of cholesterol biosynthesis or uptake. The compounds can also be used advantageously in combination with a cyclooxygenase-2 inhibitor to treat inflammatory conditions.

Other diseases or conditions may also be treated, for example, cellular neoplastic transformations or metastatic tumor growth; diabetic retinopathy, tumor angiogenesis; prostanoid-induced smooth muscle contraction associated with dysmenorrhea, premature labor, asthma or eosinophil related disorders; Alzheimer's disease; glaucoma; bone loss, osteoporosis or Paget's disease; peptic ulcers, gastritis, regional enteritis, ulcerative colitis, diverticulitis or other gastrointestinal lesions; GI bleeding; coagulation disorders selected from hypoprothrombinemia, hemophilia and other bleeding problems and kidney disease. The method aspect of the invention also includes methods for the promotion of bone formation, for cytoprotection and for reducing plaque in the treatment of atherosclerosis.

In a fourth aspect, the invention relates to methods for screening for selective prostanoid receptors, particularly EP3 ligands. The screening method may be in vitro screening.

DETAILED DESCRIPTION OF THE INVENTION

Compounds of the genera represented by formulae Ia and Ic above are antagonists at the EP3 receptor. As such they have utility in treating and preventing prostaglandin-mediated conditions, as described above, particularly for such conditions as occlusive vascular disease.

Compositions of the invention comprise an effective dose or a pharmaceutically effective amount or a therapeutically effective amount of a compound described above and may additionally comprise other therapeutic agents, such as platelet aggregation inhibitors (tirofiban, dipyridamole, clopidogrel, ticlopidine and the like); HMG-CoA reductase inhibitors (lovastatin, simvastatin, pravastatin, rosuvastatin, mevastatin, atorvastatin, cerivastatin, pitavastatin, fluvastatin and the like); and cyclooxygenase inhibitors. A further listing of non-limiting examples of antihyperlipidemic agents that may be used in combination with the compounds of the present invention may be found in columns 5-6 of U.S. Pat. No. 6,498,156, the disclosure of which is incorporated herein by reference. Preferred cyclooxygenase-2 inhibitors are those that are selective for cyclooxygenase-2 over cyclooxygenase-1. Preferred cyclooxygenase-2 inhibitors include rofecoxib, meloxicam, celecoxib, etoricoxib, lumiracoxib, valdecoxib, parecoxib, cimicoxib, diclofenac, sulindac, etodolac, ketoralac, ketoprofen, piroxicam and LAS-34475, although the invention is not restricted to these or other known cyclooxygenase-2 inhibitors.

Methods of the invention parallel the compositions and formulations. The methods comprise administering to a patient in need of treatment a therapeutically effective amount of a peri-substituted, fused A/B ring compound according to the invention. The present invention is also directed to methods for in vitro screening for selective prostanoid receptor agonists and antagonists. Prostanoid receptors include EP1, EP2, EP3, EP4, IP and FP receptors. Selective EP3 ligands are of great interest, for which the method comprises bringing a labeled compound according to the invention into contact with a cloned human EP3 receptor and measuring its displacement by a test compound.

A genus according to the invention includes compounds of formula Ia:

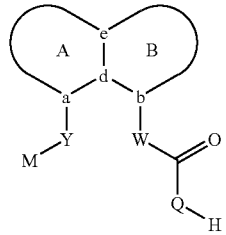

Ia wherein

Q is chosen from —N(SO$_2$R$^1$)—, —N(COR$^1$)— and —N[PO(O-alkyl)$_2$]-, and, when W is —CF$_2$—, Q may additionally be —NH—. The substituents on Q are chosen to render the hydrogen to which Q is attached acidic. In one subgenus, Q is —N[PO(O-alkyl)$_2$]. In another subgenus, Q is —N(COR$^1$)—. In a third subgenus, Q is —N(SO2R1). R$^1$ is chosen from aryl, substituted aryl, heteroaryl, substituted heteroaryl and CF3. In one embodiment, R$^1$ is chosen from phenyl, substituted phenyl, 5-membered ring heteroaryl, substituted 5-membered ring heteroaryl and CF$_3$.

Each of A and B represents independently a 5-, 6- or 7-membered ring. The fused A/B ring system contains from zero to four heteroatoms chosen from nitrogen, oxygen and sulfur, and the rings are additionally substituted with from zero to four substituents. Suitable substituents include halogen, —OH, loweralkyl, —O-loweralkyl, fluoroloweralkyl, —O-lowerfluoroalkyl, methylenedioxy, ethylenedioxy, alkoxy-loweralkyl, hydroxyloweralkyl, oxo, oxide, —CN, nitro, —S-loweralkyl, amino, loweralkylamino, diloweralkylamino, diloweralkylaminoalkyl, carboxy, carboalkoxy, orthoesters, acyl, carboxamido, loweralkylsulfoxide, acylamino, phenyl, benzyl, spirothiazolidinyl, phenoxy and benzyloxy. Since the fused A/B ring system may include nitrogen or sulfur, the substituents may include oxides, e.g. N→O and S→O.

In one subgenus, the A/B ring system is a pair of fused 5-membered rings:

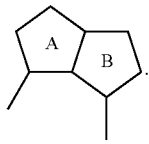

Examples of such 5/5 ring systems are:

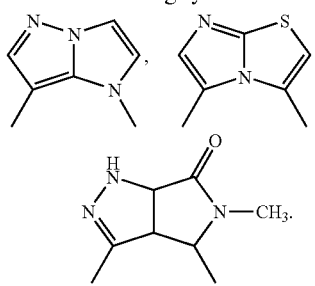

and

In another subgenus the A/B ring system is a pair of fused 6-membered rings:

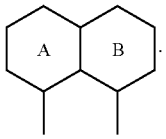

Examples of such 6/6 ring systems are:

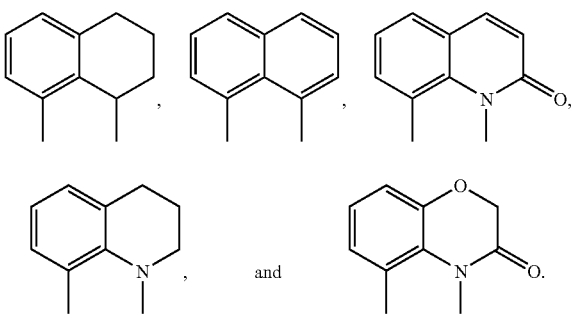

In another subgenus, the A/B ring system is a fused 5-and 6-membered ring pair:

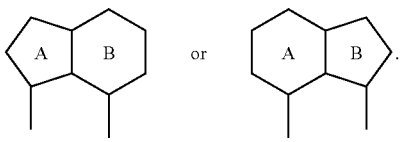

Examples of such 5/6 ring systems are indoles, indolines, indolones, isatins, benzimidazoles, benzoxazolinones, benzofurans and indazoles:

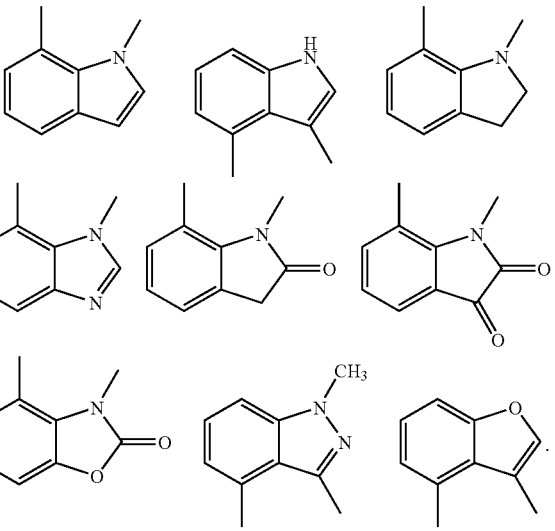

As indicated earlier, the ring systems may be substituted, for example:

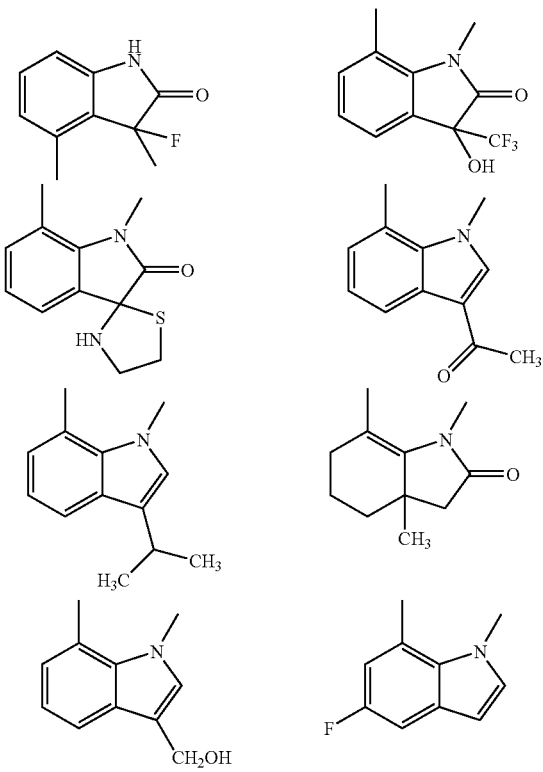

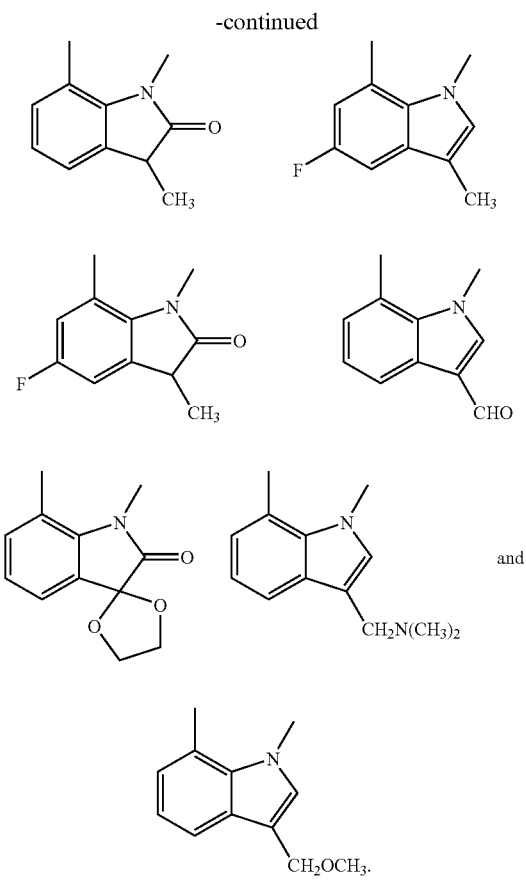

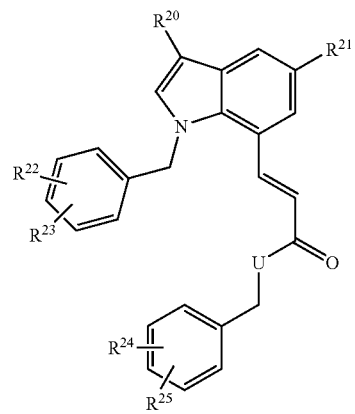

A preferred compound in this subgenus is that in which M is 2,4-dichlorophenyl and $R^1$ is 4,5-dichlorothien-2-yl (example P067).

W and Y are linkers comprising from zero to 8 atoms in a chain. Preferably they are from $C_1$ to $C_8$ alkyl in which one or two —$CH_2$— may be replaced by —O—, —C(=O)—, —CH=CH—, —$CF_2$—, —S—, —SO—, —$SO_2$—, —NH— or —N(alkyl)-. More preferably, W and Y are two-atom chains, i.e. $C_1$ or $C_2$ alkyl in which one or both —$CH_2$— may be replaced by the groups named above. In one embodiment, W is chosen from —$CH_2CH_2$—, —$OCH_2$—, —C(=O)—, —$CH_2O$—, —$OCF_2$—, —$OC(CH_3)_2$—, —$OCH(CH_3)$—, —CH=CH—, —NHC(=O)— and —$NHCH_2$—; and Y is chosen from —$CH_2$—, —O—, —$OCH_2$—, =N—, —S—, —SO—, and —$SO_2$—. The left-hand bond indicates the point of attachment to ring A or B.

M is chosen from aryl, substituted aryl, heterocyclyl, substituted heterocyclyl, $C_6$ to $C_{20}$ alkyl and substituted $C_6$ to $C_{20}$ alkyl. In one preferred embodiment, M is chosen from aryl, substituted aryl, heterocyclyl and substituted heteroaryl, more preferably from phenyl, substituted phenyl, naphthyl, substituted naphthyl, heteroaryl and substituted heteroaryl.

In one embodiment the A/B ring system is an indole. In a further embodiment Q is —$N(SO_2R^1)$— and $R^1$ is chosen from phenyl, substituted phenyl, 5-membered ring heteroaryl, substituted 5-membered ring heteroaryl and $CF_3$. In a further embodiment, M is chosen from substituted phenyl, naphthyl and bicyclic nitrogen heteroaryl. In a further embodiment, Y is —$CH_2$— and W is —CH=CH—.

A subgenus that incorporates all of the foregoing elements is the subgenus of disubstituted indoles of formula:

wherein

U is chosen from —O— and —NH—; and $R^{20}$-$R^{25}$ are chosen independently from hydrogen, halogen and methyl.

In some embodiments U is O. In other embodiments U is O and $R^{22}$, $R^{23}$, $R^{24}$ and $R^{25}$ are halogen. In specific embodiments $R^{22}$, $R^{23}$, $R^{24}$ and $R^{25}$ are all chlorine.

In other embodiments U is —NH—. In some embodiments U is —NH— and $R^{22}$ and $R^{23}$ are halogen.

The compounds of the invention are acidic, allowing them to be presented as salts. The term "pharmaceutically acceptable salt" refers to salts whose counter ion derives from pharmaceutically acceptable non-toxic acids and bases. Suitable pharmaceutically acceptable base addition salts for the compounds of the present invention include, but are not limited to, metallic salts made from aluminum, calcium, lithium, magnesium, potassium, sodium and zinc or organic salts made from lysine, N,N-dialkyl amino acid derivatives (e.g. N,N-dimethylglycine, piperidine-1-acetic acid and morpholine-4-acetic acid), N,N'-dibenzylethylenediamine, chloroprocaine, choline, diethanolamine, ethylenediamine, meglumine (N-methylglucamine) and procaine. When the compounds contain a basic residue, suitable pharmaceutically acceptable base addition salts for the compounds of the present invention include inorganic acids and organic acids. Examples include acetate, benzenesulfonate (besylate), benzoate, bicarbonate, bisulfate, carbonate, camphorsulfonate, citrate, ethane-sulfonate, fumarate, gluconate, glutamate, bromide, chloride, isethionate, lactate, maleate, malate, mandelate, methanesulfonate, mucate, nitrate, pamoate, pantothenate, phosphate, succinate, sulfate, tartrate, p-toluenesulfonate, and the like.

Definitions

Throughout this specification the terms and substituents retain their definitions.

Alkyl is intended to include linear, branched, or cyclic hydrocarbon structures and combinations thereof. Lower alkyl refers to alkyl groups of from 1 to 6 carbon atoms. Examples of lower alkyl groups include methyl, ethyl, propyl, isopropyl, butyl, s- and t-butyl and the like. Preferred alkyl and alkylene groups are those of $C_{20}$ or below. Cycloalkyl is a subset of alkyl and includes cyclic hydrocarbon groups of from 3 to 8 carbon atoms. Examples of cycloalkyl groups include c-propyl, c-butyl, c-pentyl, norbornyl, adamantyl and the like.

$C_1$ to $C_{20}$ Hydrocarbon includes alkyl, cycloalkyl, alkenyl, alkynyl, aryl and combinations thereof. Examples include benzyl, phenethyl, cyclohexylmethyl, camphoryl and naphthylethyl.

Alkoxy or alkoxyl refers to groups of from 1 to 8 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. Loweralkoxy refers to groups containing one to four carbons.

Oxaalkyl refers to alkyl residues in which one or more carbons (and their associated hydrogens) have been replaced by oxygen. Examples include methoxypropoxy, 3,6,9-trioxadecyl and the like. The term oxaalkyl is intended as it is understood in the art [see *Naming and Indexing of Chemical Substances for Chemical Abstracts*, published by the American Chemical Society, ¶196, but without the restriction of ¶127(a)], i.e. it refers to compounds in which the oxygen is bonded via a single bond to its adjacent atoms (forming ether bonds). Similarly, thiaalkyl and azaalkyl refer to alkyl residues in which one or more carbons have been replaced by sulfur or nitrogen, respectively. Examples include ethylaminoethyl and methylthiopropyl. The term "oxo" referring to a substituent intends double-bonded oxygen (carbonyl). Thus, for example, a 2-oxoquinoline of the invention would be:

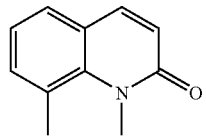

Acyl refers to groups of from 1 to 8 carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include formyl, acetyl, propionyl, isobutyryl, t-butoxycarbonyl, benzoyl, benzyloxycarbonyl and the like. Lower-acyl refers to groups containing one to four carbons. Acylalkyl refers to a residue in which an acyl group is attached to an alkyl group which is attached to the parent. An example would be $CH_3C(=O)CH_2—$. Such residues could also be characterized as "oxoalkyl" residues.

Aryl and heteroaryl mean a 5- or 6-membered aromatic or heteroaromatic ring containing 0-3 heteroatoms selected from O, N, or S; a bicyclic 9- or 10-membered aromatic or heteroaromatic ring system containing 0-3 heteroatoms selected from O, N, or S; or a tricyclic 13- or 14-membered aromatic or heteroaromatic ring system containing 0-3 heteroatoms selected from O, N, or S. Aromatic 6- to 14-membered carbocyclic rings include, e.g., benzene, naphthalene, indane, tetralin, and fluorene and the 5- to 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole.

Arylalkyl means an alkyl residue attached to an aryl ring. Examples are benzyl, phenethyl and the like.

Substituted alkyl, aryl, cycloalkyl, heterocyclyl etc. refer to alkyl, aryl, cycloalkyl, or heterocyclyl wherein up to three H atoms in each residue are replaced with halogen, loweralkyl, haloalkyl, hydroxy, loweralkoxy, carboxy, carboalkoxy (also referred to as alkoxycarbonyl), carboxamido (also referred to as alkylaminocarbonyl), cyano, carbonyl, nitro, amino, alkylamino, dialkylamino, mercapto, alkylthio, sulfoxide, sulfone, acylamino, amidino, phenyl, benzyl, heteroaryl, phenoxy, benzyloxy, or heteroaryloxy. In the claims below, methylenedioxy and ethylenedioxy are mentioned as substituents. While methylenedioxy is attached at adjacent carbons on the ring, ethylenedioxy can be attached either at adjacent carbons on the ring or at the same carbon, forming a spirodioxole (ketal), analogous to the spirothiazolidinyl. The various options are illustrated in compounds 114, 144 and 160.

The term "halogen" means fluorine, chlorine, bromine or iodine.

The term "prodrug" refers to a compound that is made more active in vivo. Activation in vivo may come about by chemical action or through the intermediacy of enzymes. Microflora in the GI tract may also contribute to activation in vivo.

In the characterization of the variables, it is recited that A and B represent a pair of fused 5-, 6- or 7-membered rings and that the fused A/B ring system may contain from zero to four heteroatoms chosen from nitrogen, oxygen and sulfur. It is intended that these rings may exhibit various degrees of unsaturation from fully saturated to aromatic. Aromatic and partially unsaturated rings are preferred.

In the characterization of the variables, it is recited that the fused rings may be additionally substituted with from zero to four substituents chosen independently from a list of variable definitions. The structure below illustrates the intent of that language. In this example, the fused rings are substituted with three substituents: $—CH_3$, $—OH$ and oxo:

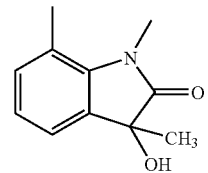

It will be recognized that the compounds of this invention can exist in radiolabeled form, i.e., the compounds may contain one or more atoms containing an atomic mass or mass number different from the atomic mass or mass number usually found in nature. Radioisotopes of hydrogen, carbon, phosphorous, fluorine, and chlorine include $^2H$, $^3H$, $^{13}C$, $^{14}C$, $^{15}N$, $^{35}S$, $^{18}F$, and $^{36}Cl$, respectively. Compounds that contain those radioisotopes and/or other radioisotopes of other atoms are within the scope of this invention. Tritiated, i.e. $^3H$, and carbon-14, i.e., $^{14}C$, radioisotopes are particularly preferred for their ease in preparation and detectability. Radiolabeled compounds of formula Ia and formula Ic of this invention and prodrugs thereof can generally be prepared by methods well known to those skilled in the art. Conveniently, such radiolabeled compounds can be prepared by carrying out the procedures disclosed in the Examples and Schemes by substituting a readily available radiolabeled reagent for a non-radiolabeled reagent.

As used herein, and as would be understood by the person of skill in the art, the recitation of "a compound" is intended to include salts, solvates, co-crystals and inclusion complexes of that compound.

The term "solvate" refers to a compound of Formula I in the solid state, wherein molecules of a suitable solvent are incorporated in the crystal lattice. A suitable solvent for therapeutic administration is physiologically tolerable at the dosage administered. Examples of suitable solvents for therapeutic administration are ethanol and water. When water is the solvent, the solvate is referred to as a hydrate. In general, solvates are formed by dissolving the compound in the appropriate solvent and isolating the solvate by cooling or using an antisolvent. The solvate is typically dried or azeotroped under ambient conditions. Co-crystals are combinations of two or more distinct molecules arranged to create a unique crystal form whose physical properties are different from those of its pure constituents. Pharmaceutical co-crystals have recently become of considerable interest for improving the solubility, formulation and bioavailability of such drugs as itraconazole [see Remenar et al. *J. Am. Chem. Soc.* 125, 8456-8457 (2003)] and fluoxetine. Inclusion complexes are described in *Remington: The Science and Practice of Pharmacy* 19$^{th}$ Ed. (1995) volume 1, page 176-177. The most commonly employed inclusion complexes are those with cyclodextrins, and all cyclodextrin complexes, natural and synthetic, with or without added additives and polymer(s), as described in U.S. Pat. Nos. 5,324,718 and 5,472,954, are specifically encompassed within the claims. The disclosures of Remington and the '718 and 954 patents are incorporated herein by reference.

The terms "methods of treating or preventing" mean amelioration, prevention or relief from the symptoms and/or effects associated with lipid disorders. The term "preventing" as used herein refers to administering a medicament beforehand to forestall or obtund an acute episode. The person of ordinary skill in the medical art (to which the present method claims are directed) recognizes that the term "prevent" is not an absolute term. In the medical art it is understood to refer to the prophylactic administration of a drug to substantially diminish the likelihood or seriousness of a condition, and this is the sense intended in applicants' claims. As used herein, reference to "treatment" of a patient is intended to include prophylaxis. Throughout this application, various references are referred to. The disclosures of these publications in their entireties are hereby incorporated by reference as if written herein.

The term "mammal" is used in its dictionary sense. Humans are included in the group of mammals, and humans would be the preferred subjects of the methods of treatment.

Stereoisomers

The compounds described herein may contain asymmetric centers and may thus give rise to enantiomers, diastereomers, and other stereoisomeric forms. Each chiral center may be defined, in terms of absolute stereochemistry, as (R)- or (S)-. The present invention is meant to include all such possible isomers, as well as, their racemic and optically pure forms. Optically active (R)- and (S)-, or (D)- and (L)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included.

The graphic representations of racemic, ambiscalemic and scalemic or enantiomerically pure compounds used herein are taken from Maehr *J. Chem. Ed.* 62, 114-120 (1985), solid and broken wedges are used to denote the absolute configuration of a chiral element; wavy lines and single thin lines indicate disavowal of any stereochemical implication which the bond it represents could generate; solid and broken bold lines are geometric descriptors indicating the relative configuration shown but denoting racemic character; and wedge outlines and dotted or broken lines denote enantiomerically pure compounds of indeterminate absolute configuration. Thus, the formula II is intended to encompass pure enantiomers as well as racemic mixtures and any intermediate mixture of enantiomers:

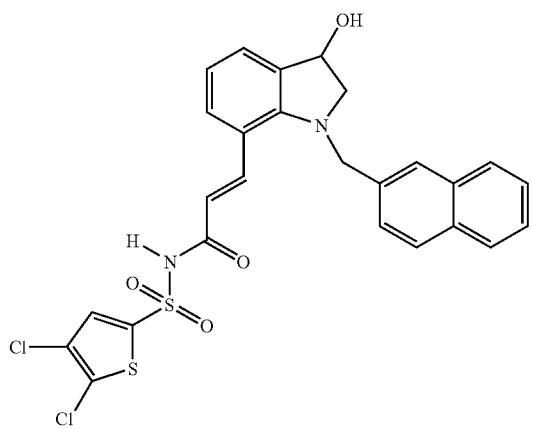

II whereas the formula III is intended to encompass either of the pure enantiomers of that structure:

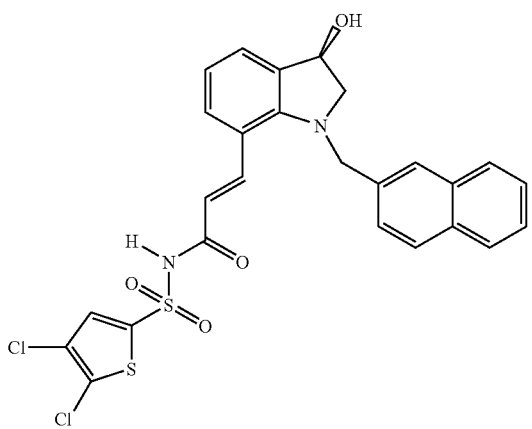

III and IV represents the pure, single, specified (S)-enantiomer:

IV

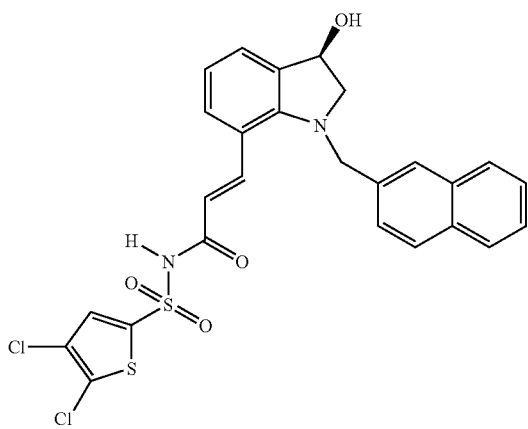

The configuration of any carbon-carbon double bond appearing herein is selected for convenience only and unless explicitly stated, is not intended to designate a particular configuration. Thus the carbon-carbon double bond depicted arbitrarily above as E may be Z, E, or a mixture of the two in any proportion.

Terminology related to "protecting", "deprotecting" and "protected" functionalities occurs throughout this application. Such terminology is well understood by persons of skill in the art and is used in the context of processes which involve sequential treatment with a series of reagents. In that context, a protecting group refers to a group which is used to mask a functionality during a process step in which it would otherwise react, but in which reaction is undesirable. The protecting group prevents reaction at that step, but may be subsequently removed to expose the original functionality. The removal or "deprotection" occurs after the completion of the reaction or reactions in which the functionality would interfere. Thus, when a sequence of reagents is specified, as it is in the processes of the invention, the person of ordinary skill can readily envision those groups that would be suitable as "protecting groups". Suitable groups for that purpose are discussed in standard textbooks in the field of chemistry, such as *Protective Groups in Organic Synthesis* by T. W. Greene [John Wiley & Sons, New York, 1991], which is incorporated herein by reference. Particular attention is drawn to the chapters entitled "Protection for the Hydroxyl Group, Including 1,2- and 1,3-Diols" (pages 10-86).

The abbreviations Me, Et, Ph, Tf, Ts and Ms represent methyl, ethyl, phenyl, trifluoromethanesulfonyl, toluenesulfonyl and methanesulfonyl respectively. A comprehensive list of abbreviations utilized by organic chemists (i.e. persons of ordinary skill in the art) appears in the first issue of each volume of the *Journal of Organic Chemistry*. The list, which is typically presented in a table entitled "Standard List of Abbreviations" is incorporated herein by reference.

Pharmaceutical Formulations

While it may be possible for the compounds of formula I or formula Ic to be administered as the raw chemical, it is preferable to present them as a pharmaceutical composition. According to a further aspect, the present invention provides a pharmaceutical composition comprising a compound of formula I, or a pharmaceutically acceptable salt or solvate thereof, together with one or more pharmaceutically carriers thereof and optionally one or more other therapeutic ingredients. According to a yet further aspect, the present invention provides a pharmaceutical composition comprising a compound of formula Ic, or a pharmaceutically acceptable salt or solvate thereof, together with one or more pharmaceutically carriers thereof and optionally one or more other therapeutic ingredients. The carrier(s) must be "acceptable" in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration. The most suitable route may depend upon the condition and disorder of the recipient. The formulations may conveniently be presented in unit dosage form and may be prepared by any of the methods well known in the art of pharmacy. All methods include the step of bringing into association a compound of formula I or formula Ic or a pharmaceutically acceptable salt or solvate thereof ("active ingredient") with the carrier, which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder (including micronized and nanoparticulate powders) or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide sustained, delayed or controlled release of the active ingredient therein.

The pharmaceutical compositions may include a "pharmaceutically acceptable inert carrier", and this expression is intended to include one or more inert excipients, which include starches, polyols, granulating agents, microcrystalline cellulose, diluents, lubricants, binders, disintegrating agents, and the like. If desired, tablet dosages of the disclosed compositions may be coated by standard aqueous or non-aqueous techniques, "Pharmaceutically acceptable carrier" also encompasses controlled release means.

Compositions of the present invention may also optionally include other therapeutic ingredients, anti-caking agents, preservatives, sweetening agents, colorants, flavors, desiccants, plasticizers, dyes, and the like. Any such optional ingredient must, of course, be compatible with the compound of the invention to insure the stability of the formulation.

The dose range for adult humans is generally from 0.1 μg to 10 g/day orally. Tablets or other forms of presentation provided in discrete units may conveniently contain an amount of compound of the invention which is effective at such dosage or as a multiple of the same, for instance, units containing 0.5 mg to 500 mg, usually around 5 mg to 200 mg. The precise amount of compound administered to a patient will be the responsibility of the attendant physician. However, the dose employed will depend on a number of factors, including the age and sex of the patient, the precise disorder being treated, and its severity. The frequency of administration will depend on the pharmacodynamics of the individual compound and the formulation of the dosage form, which may be optimized by methods well known in the art (e.g. controlled or extended release tablets, enteric coating etc.)

Combination therapy can be achieved by administering two or more agents, each of which is formulated and administered separately, or by administering two or more agents in a single formulation. Other combinations are also encompassed by combination therapy. For example, two agents can be formulated together and administered in conjunction with a separate formulation containing a third agent. While the two or more agents in the combination therapy can be administered simultaneously, they need not be.

Approximately three hundred compounds representative of the invention have been synthesized. Their structures are shown in Tables 1-2 below. In these tables, a dash means a direct bond. Thus, for example, compound P159, in which X2 and X6 are direct bonds, is an imidazolothiazole (i.e. a pair of fused five-membered rings). Saturation or unsaturation are indicated by the hydrogen count; thus compound P264 is a hexahydroindole-2-one:

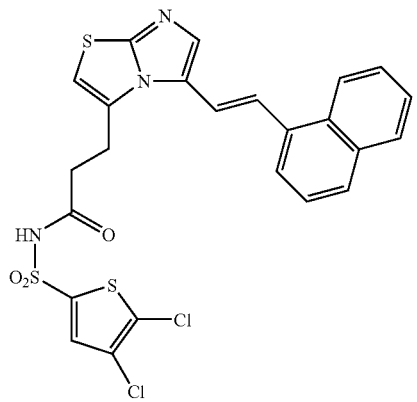
P159

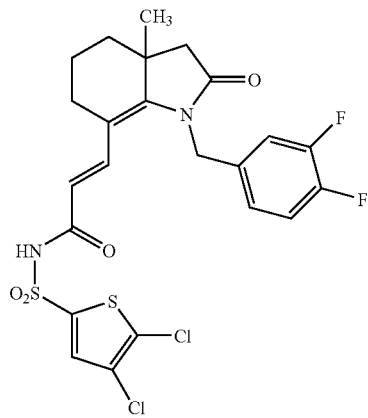
P264

TABLE 1

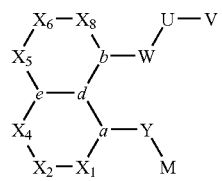

Compounds in Table 1, have 'd' = [C] and U = —NHSO2—; except for compound P159, for which 'd' = N while U = —HNSO2— and for compound P153 for which 'd' = [C] and U = NH2

| Cmpd.No | X1 | X2 | X4 | X5 | X6 | X8 | Y | —W(C=O)— |
|---|---|---|---|---|---|---|---|---|
| P001 | CH | — | CH | CH | CH | CH | CH2 | CH=CHC(=O) |
| P002 | CH | — | CH | CH | CH | CH | CH2 | CH=CHC(=O) |
| P003 | CH2 | — | CH2 | CH | CH | CH | CH2 | CH=CHC(=O) |
| P004 | C(=O) | CH | CH | CH | CH | CH | CH2 | OCH2C(=O) |
| P005 | CH | — | CH | CH | CH | CH | C(=O) | CH=CHC(=O) |
| P006 | CH | — | CH | CH | CH | CH | CH2 | CH=CHC(=O) |
| P007 | CH | — | CH | CH | CH | CH | CH2 | CH=CHC(=O) |
| P008 | CH | — | CH | CH | CH | CH | CH2 | CH=CHC(=O) |
| P009 | CH | — | CH | CH | CH | CH | CH2 | CH=CHC(=O) |
| P010 | CH | — | CH | CH | CH | CH | CH2 | CH=CHC(=O) |
| P011 | CH | — | CH | CH | CH | CH | CH2 | CH=CHC(=O) |
| P012 | CH | CH | CH | CH | CH | C(=O) | OCH2 | CH2O(=O) |
| P015 | CH | CH | CH | CH2 | CH2 | CH2 | OCH2 | CH2O(=O) |
| P016 | CH | — | CH | CH | CH | CH | CH2 | CH=CHC(=O) |
| P017 | CH | — | CH | CH | CH | CH | CH2 | CH=CHC(=O) |
| P018 | C(=O) | CH2 | O | CH | CH | CH | CH2 | OCH2C(=O) |
| P019 | C(=O) | CH2 | O | CH | CH | CH | CH2 | NC(=O)C(=O) |

TABLE 1-continued

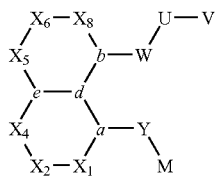

Compounds in Table 1, have 'd' = [C] and U = —NHSO2—; except for compound P159, for which
'd' = N while U = —HNSO2— and for compound P153 for which
'd' = [C] and U = NH2

| | | | | | | | | |
|---|---|---|---|---|---|---|---|---|
| P020 | C(=O) | CH2 | O | CH | CH | CH | CH2 | OCH2C(=O) |
| P021 | C(=O) | CH2 | O | CH | CH | CH | CH2 | OCH2C(=O) |
| P022 | C(=O) | CH2 | O | CH | CH | CH | CH2 | OCH2C(=O) |
| P023 | C(=O) | CH2 | O | CH | CH | CH | CH2 | OCH2C(=O) |
| P024 | C(=O) | CH2 | O | CH | CH | CH | CH2 | OCH2C(=O) |
| P025 | C(=O) | CH2 | O | CH | CH | CH | CH2 | OCH2C(=O) |
| P026 | C(=O) | CH2 | O | CH | CH | CH | CH2 | OCH2C(=O) |
| P027 | C(=O) | CH2 | O | CH | CH | CH | CH2 | OCH2C(=O) |
| P028 | C(=O) | CH2 | O | CH | CH | CH | CH2 | OCH2C(=O) |
| P029 | C(=O) | CH2 | O | CH | CH | CH | CH2 | OCH2C(=O) |
| P030 | C(=O) | CH2 | O | CH | CH | CH | CH2 | OCH2C(=O) |
| P031 | C(=O) | CH2 | O | CH | CH | CH | CH2 | OCH2C(=O) |
| P034 | CH | — | CH | N | — | CH | CH2 | CH=CHC(=O) |
| P035 | CH | — | CH | CH | CH | CH | CH2 | CH=CHC(=O) |
| P036 | CH | — | CH | CH | CH | CH | CH2 | CH=CHC(=O) |
| P037 | C(CH3) | — | N | CH | CH | CH | CH2 | OCH2C(=O) |
| P038 | CH | — | CH | CH | CH | CH | CH2 | CH2—OC(=O) |
| P039 | C(=O) | CH2 | O | CH | CH | CH | CH2 | OCH2C(=O) |
| P040 | C(=O) | CH2 | O | CH | CH | CH | CH2 | OCH2C(=O) |
| P041 | C(=O) | CH2 | O | CH | CH | CH | CH2 | OCH2C(=O) |
| P042 | C(=O) | CH2 | O | CH | CH | CH | CH2 | OCH2C(=O) |
| P043 | CH | — | CH | CH | CH | CH | CH2 | CH=CHC(=O) |
| P045 | CH2 | — | CH2 | CH | CH | CH | SO2 | CH=CHC(=O) |
| P046 | C(=O) | — | O | CH | CH | CH | CH2 | OCH2C(=O) |
| P047 | C(=O) | — | O | CH | CH | CH | CH2 | OCH2C(=O) |
| P048 | C(=O) | — | O | CH | CH | CH | CH2 | OCH2C(=O) |
| P049 | C(=O) | CH2 | O | CH | CH | CH | CH2 | NHCH2C(=O) |
| P050 | C(=O) | — | O | CH | CH | CH | CH2 | OCH2C(=O) |
| P051 | C(=O) | — | O | CH | CH | CH | CH2 | OCH2C(=O) |
| P052 | C(=O) | — | O | CH | CH | CH | CH2 | OCH2C(=O) |
| P053 | C(=O) | — | O | CH | CH | CH | CH2 | OCH2C(=O) |
| P054 | CH | — | CH | CH | CH | CH | CH2 | CH=CHC(=O) |
| P055 | CH | — | CH | CH | CH | CH | CH2 | CH=CHC(=O) |
| P056 | CH | — | C(CH3) | CH | CH | CH | CH2 | CH=CHO(=O) |
| P057 | CH | — | C(CH3) | CH | CH | CH | CH2 | CH=CHC(=O) |
| P058 | C(=O) | — | CH(CH3) | CH | CH | CH | CH2 | CH=CHC(=O) |
| P059 | C(=O) | — | CH(CH3) | CH | CH | CH | CH2 | CH=CHC(=O) |
| P060 | CH | — | CH | CH | OF | CH | CH2 | CH=CHC(=O) |
| P061 | CH | — | CH | CH | OF | CH | CH2 | CH=CHC(=O) |
| P062 | CH | — | C(CH2OH) | CH | CH | CH | CH2 | CH=CHC(=O) |
| P063 | CH | — | C(CH3) | CH | CF | CH | CH2 | CH=CHC(=O) |
| P064 | CH | — | C(CH3) | CH | CF | CH | CH2 | CH=CHC(=O) |
| P065 | C(=O) | — | CH(CH3) | CH | CF | CH | CH2 | CH=CHC(=O) |
| P066 | C(=O) | — | CH(CH3) | CH | OF | CH | CH2 | CH=CHC(=O) |
| P067 | CH | — | C(CH3) | CH | CF | CH | CH2 | CH=CHC(=O) |
| P068 | CH | — | C(CH3) | CH | CF | CH | CH2 | CH=CHC(=O) |
| P069 | CH | — | C(CH=O) | CH | CH | CH | CH2 | CH=CHC(=O) |
| P070 | CH | — | C(CH2OCH3) | CH | CH | CH | CH2 | CH=CHC(=O) |
| P071 | CH | | NH | CH | CH | CH | C(=O) | OCH2C(=O) |
| P072 | CH | — | C(CH3) | CH | CH | CH | CH2 | CH2CH2C(=O) |
| P073 | CH | — | C(CH3) | CH | CH | CH | CH2 | CH2CH2C(=O) |
| P074 | CH | — | CH | CH | CH | CH | CH2 | CH2CH2C(=O) |
| P075 | CH | — | NH | CH | CH | CH | CH2 | OCH2C(=O) |
| P077 | CH | — | C(CH3) | CH | CF | CH | CH2 | CH2CH2C(=O) |
| P079 | CH | — | C(CH3) | CH | CH | CH | CH2 | CH=CHC(=O) |
| P083 | C(=O) | — | C(OCH2CH2O) | CH | CH | CH | CH2 | CH=CHC(=O) |
| P084 | CH | — | C(CH3) | CH | CH | CH | CH2 | CH=CHC(=O) |
| P085 | CH | — | C[C(CH3)=O] | CH | CH | CH | CH2 | CH=CHC(=O) |
| P086 | CH | — | C(CH3) | CH | CH | CH | CH2 | CH=CHC(=O) |
| P087 | CH | — | C(CH3) | CH | CH | CH | CH2 | CH=CHC(=O) |
| P088 | CH | — | C(CH3) | CH | CH | CH | CH2 | CH=CHC(=O) |
| P089 | CH | — | C(CH3) | CH | CH | CH | CH2 | CH=CHC(=O) |
| P090 | CH | — | C(CH3) | CH | CH | CH | CH2 | CH=CHC(=O) |
| P091 | CH | — | C[CH(CH3)2] | CH | CH | CH | CH2 | CH2CH2C(=O) |

TABLE 1-continued

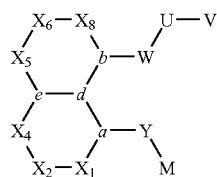

Compounds in Table 1, have 'd' = [C] and U = —NHSO2—; except for compound P159, for which
'd' = N while U = —HNSO2— and for compound P153 for which
'd' = [C] and U = NH2

| | | | | | | | | |
|---|---|---|---|---|---|---|---|---|
| P092 | CH | — | C[CH(CH3)2] | CH | CH | CH | CH2 | CH2CH2C(=O) |
| P093 | C(=O) | — | CH[CH(CH3)2] | CH | CH | CH | CH2 | CH2CH2C(=O) |
| P094 | CH | — | NH | CH | CH | CH | CH2 | CH=CHC(=O) |
| P095 | CH | — | NH | CH | CH | CH | CH2 | CH2CH2C(=O) |
| P096 | C(=O) | — | C(=O) | CH | CH | CH | CH2 | CH=CHC(=O) |
| P097 | C(=O) | — | C(OCH2CH2O) | CH | CH | CH | CH2 | CH2CH2C(=O) |
| P098 | CH | — | N(CH3) | CH | CH | CH | CH2 | CH2CH2C(=O) |
| P099 | CH | — | C(CH3) | CH | CH | CH | CH2 | CH=CHC(=O) |
| P100 | CH | — | C(CH3) | CH | CH | CH | CH2 | CH=CHC(=O) |
| P101 | CH | — | C(CH3) | CH | CH | CH | CH2 | CH=CHC(=O) |
| P102 | CH | — | C(CH3) | CH | CH | CH | CH2 | CH=CHC(=O) |
| P103 | CH | — | C(CH3) | CH | CH | CH | CH2 | CH=CHC(=O) |
| P104 | C(=O) | — | C(OH)CF3 | CH | CH | CH | CH2 | CH=CHC(=O) |
| P105 | C(=O) | — | NH | CH | CH | CH | CH2 | CH2CH2C(=O) |
| P106 | C(=O) | — | N(CH3) | CH | CH | CH | CH2 | CH2CH2C(=O) |
| P107 | C(=O) | — | CH(CH3) | CH | CH | CH | CH2 | CH=CHC(=O) |
| P108 | C(=O) | — | C(OCH2CH2O) | CH | CH | CH | CH2 | CH=CHC(=O) |
| P109 | CH | — | C(CH3) | CH | CH | CH | CH2 | CH=CHC(=O) |
| P110 | C(=O) | — | C(Br)CH3 | CH | CH | CH | CH2 | CH=CHC(=O) |
| P111 | C(=O) | — | C(OH)CH3 | CH | CH | CH | CH2 | CH=CHC(=O) |
| P112 | C(=O) | — | CHCH3 | CH | CH | CH | CH2 | CH=CHC(=O) |
| P113 | C(=O) | — | C(=O) | CH | CH | CH | CH2 | CH=CHC(=O) |
| P114 | C(=O) | — | C(OCH2CH2O) | CH | CH | CH | CH2 | CH=CHC(=O) |
| P115 | C(=O) | — | C(=O) | CH | CH | CH | CH2 | CH=CHC(=O) |
| P116 | N | — | NH | C(=O) | — | N(CH3) | CH2 | CH=CHC(=O) |
| P117 | N | — | NH | C(=O) | — | N(CH3) | CH2 | CH2CH2C(=O) |
| P118 | CH | — | C(CH3) | CH | CH | CH | CH2 | CH=CHC(=O) |
| P119 | CH | — | C(CH3) | CH | CH | CH | CH2 | CH=CHC(=O) |
| P120 | CH | — | C(CH3) | CH | CH | CH | CH2 | CH=CHC(=O) |
| P121 | CH | — | C(CH3) | CH | CH | CH | CH2 | CH=CHC(=O) |
| P122 | CH | — | C(CH3) | CH | CH | CH | CH2 | CH=CHC(=O) |
| P123 | CH | — | C(CH3) | CH | CH | CH | CH2 | CH=CHC(=O) |
| P124 | CH | — | C(CH3) | CH | CH | CH | CH2 | CH=CHC(=O) |
| P125 | CH | — | C(CH3) | CH | CH | CH | CH2 | CH=CHC(=O) |
| P126 | C(=O) | — | C(NHCH2CH2S) | CH | CH | CH | CH2 | CH=CHC(=O) |
| P127 | C(=O) | — | CH2 | CH | CH | CH | CH2 | CH=CHC(=O) |
| P128 | C(=O) | — | C(CH)CH2 C(=O)CH3 | CH | CH | CH | CH2 | CH=CHC(=O) |
| P129 | CH | — | CH | CH | CH | CH | CH2 | CH=CHC(=O) |
| P130 | C(=O) | — | CH(CH) | CH | CH | CH | CH2 | CH=CHC(=O) |
| P131 | C(=O) | — | C(CH3)2 | CH | CH | CH | CH2 | CH=CHC(=O) |
| P132 | C(=O) | — | CF2 | CH | CH | CH | CH2 | CH=CHC(=O) |
| P133 | C(=O) | — | C(OH)CH3 | CH | CH | CH | CH2 | CH=CHC(=O) |
| P134 | C(=O) | — | C(OH)CH2 NO2 | CH | CH | CH | CH2 | CH=CHC(=O) |
| P135 | CH | — | C(CH3) | CH | CH | CH | CH2 | CH=CHC(=O) |
| P136 | CH | — | C(CH3) | CH | CH | CH | CH2 | CH=CHC(=O) |
| P137 | CH | — | C(CH3) | CH | CH | CH | CH2 | CH=CHC(=O) |
| P138 | CH | — | C(CH3) | CH | CH | CH | CH2 | CH=CHC(=O) |
| P139 | CH | — | C(CH3) | CH | CH | CH | CH2 | CH=CHC(=O) |
| P140 | CH | — | C(CH3) | CH | CH | CH | CH2 | CH=CHC(=O) |
| P141 | CH | — | C(CH3) | CH | CH | CH | CH2 | CH=CHC(=O) |
| P142 | CH | — | C(CH3) | CH | CH | CH | CH2 | CH=CHC(=O) |
| P143 | CH | — | C(CH3) | CH | CH | CH | CH2 | CH=CHC(=O) |
| P144 | CH | — | C(CH3) | CH | CH | CH | CH2 | CH=CHC(=O) |
| P145 | CH | — | C(CH3) | CH | CH | CH | CH2 | CH=CHC(=O) |
| P146 | CH | — | C(CH3) | CH | CH | CH | CH2 | CH=CHC(=O) |
| P147 | CH | — | N(CH3) | CH | CH | CH | CH2 | CH=CHC(=O) |
| P148 | C(=O) | — | N(CH3) | CH | CH | CH | CH2 | CH=CHC(=O) |
| P149 | C(=O) | — | N | CH | CH | CH | CH2 | OCH2C(=O) |
| P150 | CH | — | NH | CH | CH | CH | SO2 | OCH2C(=O) |
| P151 | CH | — | NH | CH | CH | CH | S | OCH2C(=O) |
| P152 | CH | — | N | CH | CH | CH | CH2 | OCH2C(=O) |
| P154 | C(=O) | — | N(CH3) | CH | CH | CH | CH2 | CHCHC(=O) |
| P155 | C(=O) | — | NH | CH | CH | CH | CH2 | CH=CHC(=O) |

TABLE 1-continued

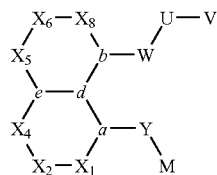

Compounds in Table 1, have 'd' = [C] and U = —NHSO2—; except for compound P159, for which
'd' = N while U = —HNSO2— and for compound P153 for which
'd' = [C] and U = NH2

| | | | | | | | | |
|---|---|---|---|---|---|---|---|---|
| P156 | C(=O) | — | N(CH3) | CH | CH | CH | CH2 | CH2CH2C(=O) |
| P157 | C(=O) | — | NH | CH | CH | CH | CH2 | OCH2C(=O) |
| P158 | C(=O) | — | NH | CH | CH | CH | CH2 | OCH2C(=O) |
| P159 | CH | — | N | S | — | CH | CH=CH | CH2CH2C(=O) |
| P160 | C(=O) | — | CF(CH3) | CH | CH | CH | CH2 | CH=CHC(=O) |
| P161 | C(=O) | — | CF(CH3) | CH | CH | CH | CH2 | CH=CHC(=O) |
| P162 | CH | — | NH | CH | CH | CH | CH2 | OCH(CH3)C(=O) |
| P163 | CH | — | NH | CH | CH | CH | SO2 | OCH2C(=O) |
| P164 | CH | — | NH | CH | CH | CH | S | OCH2C(=O) |
| P165 | CH | — | NH | CH | CH | CH | S | OCH2C(=O) |
| P166 | CH | — | NH | CH | CH | CH | S | OCH2C(=O) |
| P167 | CH | — | NH | CH | CH | CH | S | OCH2C(=O) |
| P168 | CH | — | NH | CH | CH | CH | S | OCH2C(=O) |
| P169 | CH | — | NH | CH | CH | CH | SO2 | OCH2C(=O) |
| P170 | CH | — | NH | CH | CH | CH | SO2 | OCH2C(=O) |
| P171 | CH | — | NH | CH | CH | CH | CH2 | OC(CH3)2C(=O) |
| P172 | CH | — | NH | CH | CH | CH | SO2 | OCH2C(=O) |
| P173 | CH | — | NH | CH | CH | CH | S | OCH2C(=O) |
| P174 | CH | — | NH | CH | CH | CH | S | OCH2C(=O) |
| P175 | CH | — | NH | CH | CH | CH | S | OCH2C(=O) |
| P176 | CH | — | NH | CH | CH | CH | S | OCH2C(=O) |
| P177 | CH | — | NH | CH | CH | CH | S | OCH2C(=O) |
| P178 | CH | — | NH | CH | CH | CH | S | OCH2C(=O) |
| P179 | C(=O) | — | CH2 | CH | CH | CH | CH2 | CH=CHC(=O) |
| P180 | C(=O) | — | CF2 | CH | CH | CH | CH2 | CH=CHC(=O) |
| P181 | CH | — | NH | CH | CH | CH | S | OCH2C(=O) |
| P182 | CH | — | NH | CH | CH | CH | S | OCH2C(=O) |
| P183 | CH | — | NH | CH | CH | CH | S | OCH2C(=O) |
| P184 | CH | — | NH | CH | CH | CH | S | OCH2C(=O) |
| P185 | CH | — | NH | CH | CH | CH | S | OCH2C(=O) |
| P186 | CH | — | NH | CH | CH | CH | SO2 | OCH2C(=O) |
| P187 | CH | — | NH | CH | CH | CH | SO2 | OCH2C(=O) |
| P188 | CH | — | NH | CH | CH | CH | SO2 | OCH2C(=O) |
| P190 | CH | — | NH | CH | CH | CH | SO2 | OCH2C(=O) |
| P191 | CH | — | NH | CH | CH | CH | SO2 | OCH2C(=O) |
| P192 | CH | — | NH | CH | CH | CH | SO2 | OCH2C(=O) |
| P193 | CH | — | NH | CH | CH | CH | SO2 | OCH2C(=O) |
| P194 | CH | — | NH | CH | CH | CH | S | OCH2C(=O) |
| P195 | CH | — | NH | CH | CH | CH | S | OCH2C(=O) |
| P196 | CH | — | NH | CH | CH | CH | SO2 | OCH2C(=O) |
| P197 | CH | — | NH | CH | CH | CH | S | OCH2C(=O) |
| P198 | CH | — | NH | CH | CH | CH | S | OCH2C(=O) |
| P199 | CH | — | NH | CH | CH | CH | S | OCH2C(=O) |
| P200 | CH | — | NH | CH | CH | CH | S | OCH2C(=O) |
| P201 | CH | — | NH | CH | CH | CH | S | OCH2C(=O) |
| P202 | CH | — | NH | CH | CH | CH | SO2 | OCH2C(=O) |
| P203 | CH | — | NH | CH | CH | CH | SO2 | OCH2C(=O) |
| P204 | CH | — | NH | CH | CH | CH | SO2 | OCH2C(=O) |
| P205 | CH | — | NH | CH | CH | CH | S | OCH2C(=O) |
| P206 | CH | — | NH | CH | CH | CH | SO2 | OCH2C(=O) |
| P207 | CH | — | NH | CH | CH | CH | SO2 | OCH2C(=O) |
| P208 | CH | — | NH | CH | CH | CH | SO2 | OCH2C(=O) |
| P209 | CH | — | NH | CH | CH | CH | S | OCH2C(=O) |
| P210 | CH | — | NH | CH | CH | CH | SO2 | OCH2C(=O) |
| P211 | CH | — | NH | CH | CH | CH | S | OCH2C(=O) |
| P212 | CH | — | NH | CH | CH | CH | S | OCH2C(=O) |
| P213 | CH | — | NH | CH | CH | CH | S | OCH2C(=O) |
| P214 | CH | — | NH | CH | CH | CH | S | OCH2C(=O) |
| P215 | CH | — | NH | CH | CH | CH | S | OCH2C(=O) |
| P216 | C(=O) | — | CF2 | CH | CH | CH | CH2 | CH=CHC(=O) |
| P217 | C(=O) | — | CH2 | CH | CH | CH | CH2 | CH=CHC(=O) |
| P218 | C(=O) | — | CF2 | CH | CH | CH | CH2 | CH=CHC(=O) |
| P219 | C(=O) | — | CH2 | CH | CH | CH | CH2 | CH=CHC(=O) |
| P220 | CH | — | NH | CH | CH | CH | S | OCH2C(=O) |
| P221 | CH | — | NH | CH | CH | CH | SO2 | OCH2C(=O) |

TABLE 1-continued

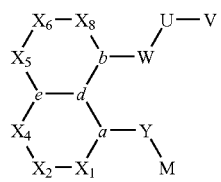

Compounds in Table 1, have 'd' = [C] and U = —NHSO2—; except for compound P159, for which
'd' = N while U = —HNSO2— and for compound P153 for which
'd' = [C] and U = NH2

| | | | | | | | | |
|---|---|---|---|---|---|---|---|---|
| P222 | CH | — | NH | CH | CH | CH | SO2 | OCH2C(=O) |
| P223 | CH | — | NH | CH | CH | CH | SO2 | OCH2C(=O) |
| P224 | CH | — | NH | CH | CH | CH | SO2 | OCH2C(=O) |
| P225 | CH | — | NH | CH | CH | CH | S | OCH2C(=O) |
| P226 | CH | — | NH | CH | CH | CH | S | OCH2C(=O) |
| P227 | CH | — | NH | CH | CH | CH | S | OCH2C(=O) |
| P228 | CH | — | NH | CH | CH | CH | S | OCH2C(=O) |
| P229 | C(=O) | — | N(CH3) | CH | CH | CH | S | OCH2C(=O) |
| P230 | CH | — | NH | CH | CH | CH | S | OCH2C(=O) |
| P231 | CH | — | NH | CH | CH | CH | SO2 | OCH2C(=O) |
| P232 | CH | — | NH | CH | CH | CH | SO2 | OCH2C(=O) |
| P233 | CH | — | NH | CH | CH | CH | S | OCH2C(=O) |
| P234 | CH | — | NH | CH | CH | CH | SO2 | OCH2C(=O) |
| P235 | CH | — | NH | CH | CH | CH | SO2 | OCH2C(=O) |
| P236 | CH | — | NH | CH | CH | CH | SO2 | OCH2C(=O) |
| P237 | CH | — | NH | CH | CH | CH | SO2 | OCH2C(=O) |
| P238 | CH | — | NH | CH | CH | CH | SO2 | OCH2C(=O) |
| P239 | CH | — | NH | CH | CH | CH | SO2 | OCH2C(=O) |
| P240 | CH | — | NH | CH | CH | CH | SO2 | OCH2C(=O) |
| P241 | C(=O) | — | NH | CH | CH | CH | NH | CH=CHC(=O) |
| P242 | C(=O) | — | N(CH3) | CH | CH | CH | NH | CH=CHC(=O) |
| P243 | CH | — | NH | CH | CH | CH | S | OCH2C(=O) |
| P244 | C(=O) | — | NH | CH | CH | CH | N | CH=CHC(=O) |
| P245 | C(=O) | — | N(CH3) | CH | CH | CH | N | CH=CHC(=O) |
| P246 | CH | — | O | CH | CH | CH | S | OCH2C(=O) |
| P247 | C(=O) | — | N(CH3) | CH | CH | CH | NHC(=O) | CH=CHC(=O) |
| P248 | C(=O) | — | N(CH3) | CH | CH | CH | SO2 | OCH2C(=O) |
| P249 | C(=O) | — | N(CH3) | CH | CH | CH | NSO2 | CH=CHC(=O) |
| P250 | C(=O) | — | N(CH3) | CH | CH | CH | N | CH=CHC(=O) |
| P251 | C(=O) | — | N(CH3) | CH | CH | CH | NHSO2 | CH=CHC(=O) |
| P252 | C(=O) | — | N(CH3) | CH | CH | CH | NH | CH=CHC(=O) |
| P253 | C(=O) | — | CH2 | CH2 | CH2 | CH2 | CH2 | CH=CHC(=O) |
| P254 | CH | — | O | CH | CH | CH | SO2 | OCH2C(=0) |
| P255 | C(=O) | — | N(CH3) | CH | CH | CH | NHC(=O) | OCH2C(=O) |
| P256 | CH | — | O | CH | CH | CH | SO | OCH2C(=O) |
| P257 | N | — | N(CH3) | CH | CH | CH | NHC(=O) | CH=CHC(=O) |
| P258 | C(=O) | — | N(CH3) | CH | CH | CH | NH | OCH2C(=O) |
| P259 | CH | — | O | CH | CH | CH | S | OCH2C(=O) |
| P260 | C(=O) | — | CH2 | CH2 | CH2 | CH2 | CH2 | CH=CHC(=O) |
| P262 | C(=O) | — | CH2 | CH2 | CH2 | CH2 | CH2 | CH=CHC(=O) |
| P263 | C(=O) | — | CH2 | CH2 | CH2 | CH2 | CH2 | CH=CHC(=O) |
| P264 | C(=O) | — | CH2 | CH2 | CH2 | CH2 | CH2 | CH=CHC(=O) |
| P265 | C(=O) | — | N(CH3) | CH | CH | CH | O | CH=CHC(=O) |
| P266 | C(=O) | — | CH2 | CH2 | CH2 | CH2 | CH2 | CH=CHC(=O) |
| P267 | C(=O) | — | CH2 | CH2 | CH2 | CH2 | CH2 | CH=CHC(=O) |
| P268 | C(=O) | — | NH | CH | CH | CH | NH | CH=CHC(=O) |
| P269 | C=O | — | CH2 | CH2 | CH2 | CH2 | CH2 | CH=CHC(=O) |
| P270 | C=O | — | N(CH3) | CH | CH | CH | NH | CH=CHC(=O) |
| P271 | C=O | — | N(CH3) | CH | CH | CH | NH | CH=CHC(=O) |
| P272 | C=O | — | N(CH3) | CH | CH | CH | NH | CH=CHC(=O) |
| P273 | CH2 | CH2 | CH2 | CH | CH | CH | C=O | OCH2C(=O) |
| P274 | C=O | — | CH2 | CH2 | CH2 | CH2 | CH2 | CH=CHC(=O) |
| P275 | C=O | — | CH2 | CH2 | CH2 | CH2 | CH2 | CH=CHC(=O) |
| P276 | C=O | — | CH2 | CH2 | CH2 | CH2 | CH2 | CH=CHC(=O) |
| P277 | CH | — | N(CH3) | CH | CH | CH | O | CH=CHC(=O) |
| P278 | C=O | — | CH2 | CH2 | CH2 | CH2 | CH2 | CH=CHC(=O) |
| P279 | C=O | — | CH2 | CH2 | CH2 | CH2 | CH2 | CH=CHC(=O) |
| P280 | C=O | — | CH2 | CH2 | CH2 | CH2 | CH2 | CH=CHC(=O) |
| P281 | C=O | — | CH2 | CH2 | CH2 | CH2 | CH2 | CH=CHC(=O) |
| P282 | C=O | — | CH2 | CH2 | CH2 | CH2 | CH2 | CH=CHC(=O) |
| P283 | C=O | — | CH2 | CH2 | CH2 | CH2 | CH2 | CH=CHC(=O) |
| P284 | CH | CH | CH | N(CH3) | N | O | | |
| P285 | C=O | — | CH2 | CH2 | CH2 | CH2 | CH2 | CH=CHC(=O) |
| P286 | C=O | — | NH | CH | CH | CH | NH | CH=CHC(=O) |
| P287 | C=O | — | NH | CH | CH | CH | NH | CH=CHC(=O) |

TABLE 1-continued

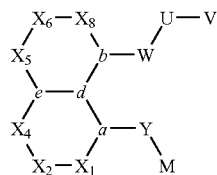

Compounds in Table 1, have 'd' = [C] and U = —NHSO2—; except for compound P159, for which
'd' = N while U = —HNSO2— and for compound P153 for which
'd' = [C] and U = NH2

| | | | | | | | | |
|---|---|---|---|---|---|---|---|---|
| P288 | C=O | — | NH | CH | CH | CH | NH | CH=CHC(=O) |
| P290 | CH | CH | CH | N(CH3) | — | CH | O | CH=CHC(=O) |
| P291 | CH | CH | CH | N(CH3) | — | CH | O | CH=CHC(=O) |
| P292 | CH | CH | CH | N(CH3) | — | CH | O | CH=CHC(=O) |
| P293 | CH | CH | CH | N(CH3) | — | CH | O | CH=CHC(=O) |
| P294 | C=O | — | CH2 | CH2 | CH2 | CH2 | CH2 | CH=CHC(=O) |
| P295 | C=O | — | CH2 | CH2 | CH2 | CH2 | CH2 | CH=CHC(=O) |
| P296 | C=O | — | CH2 | CH2 | CH2 | CH2 | CH2 | CH=CHC(=O) |
| P297 | C=O | — | CH2 | CH2 | CH2 | CH2 | CH2 | CH=CHC(=O) |
| P298 | C=O | — | CH2 | CH2 | CH2 | CH2 | CH2 | CH=CHC(=O) |
| P299 | C=O | — | CH2 | CH2 | CH2 | CH2 | CH2 | CH=CHC(=O) |
| P300 | C=O | — | CH2 | CH2 | CH2 | CH2 | CH2 | CH=CHC(=O) |
| P301 | CH | CH | CH | N(CH3) | — | CH | O | CH=CHC(=O) |
| P302 | CH | CH | CH | N(CH3) | — | CH | O | CH=CHC(=O) |
| P303 | CH | CH | CH | N(CH3) | — | CH | O | CH=CHC(=O) |
| P304 | C=O | — | CH2 | CH2 | CH2 | CH2 | CH2 | CH=CHC(=O) |
| P305 | C=O | — | CH2 | CH2 | CH2 | CH2 | CH2 | CH=CHC(=O) |
| P306 | C=O | — | CH2 | CH2 | CH2 | CH2 | CH2 | CH=CHC(=O) |
| P307 | C=O | — | CH2 | CH2 | CH2 | CH2 | CH2 | CH=CHC(=O) |
| P308 | C=O | — | CH2 | CH2 | CH2 | CH2 | CH2 | CH=CHC(=O) |
| P309 | CH | CH | CH | N(CH3) | — | CH | O | CH=CHC(=O) |
| P310 | CH | CH | CH | N(CH3) | — | CH | O | CH=CHC(=O) |
| P311 | CH | CH | CH | N(CH3) | — | CH | O | CH=CHC(=O) |
| P312 | CH | — | C(CH3) | CH | CF | CH | CH2 | CH=CHC(=O) |
| P313 | CH | — | C(CH3) | CH | CF | CH | CH2 | CH=CHC(=O) |
| P314 | CH | — | C(CH3) | CH | CF | CH | CH2 | CH=CHC(=O) |
| P315 | CH | — | C(CH3) | CH | CF | CH | CH2 | CH=CHC(=O) |
| P316 | CH | — | C(CH3) | CH | CF | CH | CH2 | CH=CHC(=O) |
| P317 | CH | — | C(CH3) | CH | CF | CH | CH2 | CH=CHC(=O) |
| P318 | CH | CH | CH | N(CH3) | — | CH | O | CH=CHC(=O) |
| P319 | CH | CH | CH | N(CH3) | — | CH | O | CH=CHC(=O) |
| P320 | CH | CH | CH | N(CH3) | — | CH | O | CH=CHC(=O) |
| P321 | CH | — | C(CH3) | CH | CF | CH | CH2 | CH=CHC(=O) |
| P322 | CH | — | C(CH3) | CH | CF | CH | CH2 | CH=CHC(=O) |
| P323 | CH | | C(CH3) | CH | CF | CH | CH2 | CH=CHC(=O) |
| P324 | CH | CH | CH | N(CH3) | — | CH | O | CH=CHC(=O) |
| P325 | CH | CH | CH | N(CH3) | — | CH | O | CH=CHC(=O) |
| P326 | CH | CH | CH | N(CH3) | — | CH | O | CH=CHC(=O) |
| P327 | CH | — | C(CH3) | CH | CF | CH | CD2 | CH=CHC(=O) |
| P328 | CH | CH | CH | N(CH3) | — | CH | O | CH=CHC(=O) |
| P329 | CH | CH | CH | N(CH3) | — | CH | O | CH=CHC(=O) |
| P330 | CH | CH | CH | N(CH3) | — | CH | O | CH=CHC(=O) |
| P331 | CH | CH | CH | N(CH3) | — | CH | O | CH=CHC(=O) |
| P332 | CH | CH | CH | N(CH3) | — | CH | O | CH=CHC(=O) |
| P333 | CH | CH | CH | N(CH3) | — | CH | O | CH=CHC(=O) |
| P334 | CH | CH | CH | N(CH3) | — | CH | O | CH=CHC(=O) |
| P335 | CH | — | C(CH3) | CH | CF | CH | CH2 | CH=CHC(=O) |
| P336 | CH | — | C(CH3) | CH | CF | CH | CH2 | CH=CHC(=O) |
| P337 | CH | CH | CH | N(CH3) | — | CH | O | CH=CHC(=O) |
| P338 | CH | CH | CH | N(CH3) | — | CH | O | CH=CHC(=O) |
| P339 | CH | CH | CH | N(CH3) | — | CH | O | CH=CHC(=O) |
| P340 | CH | CH | CH | N(CH3) | — | CH | O | CH=CHC(=O) |
| P341 | CH | CH | CH | N(CH3) | — | CH | O | CH=CHC(=O) |
| P342 | CH | CH | CH | N(CH3) | — | CH | O | CH=CHC(=O) |
| P343 | CH | CH | CH | N(CH3) | — | CH | O | CH=CHC(=O) |
| P344 | C=O | — | CH2 | CH2 | CH2 | CH2 | CH2 | CH=CHC(=O) |
| P345 | C=O | — | CH2 | CH2 | CH2 | CH2 | CH2 | CH=CHC(=O) |
| P346 | C=O | — | CH2 | CH2 | CH2 | CH2 | CH2 | CH=CHC(=O) |
| P347 | CH | CH | CH | N(CH3) | — | CH | O | CH=CHC(=O) |
| P348 | CH | — | C(CH3) | CH | N | CH | CH2 | CH=CHC(=O) |
| P349 | CH | — | C(CD3) | CH | CF | CH | CD2 | CH=CHC(=O) |
| P350 | CH | — | (CH3) | CH | CF | CH | CH2 | C(=O) |
| P351 | CH | CH | CH | N(CH3) | — | CH | O | CH=CHC(=O) |
| P352 | CH | CH | CH | N(CH3) | — | CH | O | CH=CHC(=O) |
| P353 | CH | CH | CH | N(CH3) | — | CH | O | CH=CHC(=O) |

TABLE 1-continued

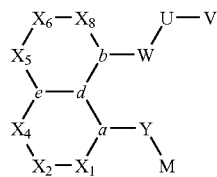

Compounds in Table 1, have 'd' = [C] and U = —NHSO2—; except for compound P159, for which
'd' = N while U = —HNSO2— and for compound P153 for which
'd' = [C] and U = NH2

| | | | | | | | | |
|---|---|---|---|---|---|---|---|---|
| P354 | CH | — | C(CH3) | CH | CF | CH | CH2 | C(=O)—C(=O) |
| P355 | CH | CH | CH | N(CH3) | — | CH | O | CH=CHC(=O) |
| P356 | CH | CH | CH | N(CH3) | — | CH | O | CH=CHC(=O) |
| P357 | CH | CH | CH | N(CH3) | — | CH | O | CH=CHC(=O) |
| P358 | CH | CH | CH | N(CH3) | — | CH | O | CH=CHC(=O) |
| P359 | CH | CH | CH | N(CH3) | — | CH | O | CH=CHC(=O) |
| P360 | CH | CH | CH | N(CH3) | — | CH | O | CH=CHC(=O) |
| P361 | CH | CH | CH | N(CH3) | — | CH | O | CH=CHC(=O) |
| P362 | CH | CH | CH | N(CH3) | — | CH | O | CH2CH2C(=O) |
| P363 | CH | CH | CH | N(CH3) | — | CH | O | CH=CHC(=O) |
| P364 | CH | CH | CH | N(CH3) | — | CH | O | CH=CHC(=O) |
| P365 | CH | CH | CH | N(CH3) | — | CH | O | CH=CHC(=O) |
| P366 | CH | CH | CH | N(CH3) | — | CH | O | CH=CHC(=O) |
| P367 | CH | — | C(CH3) | CH | CF | CH | CH2 | CH=CHC(=O) |
| P368 | CH | — | C(CH3) | CH | CF | CH | CH2 | CH=CHC(=O) |
| P369 | CH | — | C(CH3) | CH | CF | CH | CH2 | CH=CHC(=O) |
| P370 | CH | — | C(CH3) | CH | CF | CH | CH2 | CH=CHC(=O) |
| P371 | CH | CH | CH | N(CH3) | — | CH | O | CH=CHC(=O) |
| P372 | CH | CH | CH | N(CH3) | — | CH | O | CH=CHC(=O) |
| P373 | CH | CH | CH | N(CH3) | — | CH | O | CH=CHC(=O) |
| P374 | CH | — | C(CH3) | CH | CF | CH | CH2 | CH=CHC(=O) |
| P375 | CH | — | C(CH3) | CH | CF | CH | CH2 | CH=CHC(=O) |
| P376 | CH | CH | CH | N(CH3) | — | CH | O | CH=CHC(=O) |
| P377 | CH | CH | CH | N(CH3) | — | CH | O | CH=CHC(=O) |
| P378 | CH | CF | CH | C(CH3) | — | CH | O | CH2CH2C(=O) |
| P379 | CH | CF | CH | C(CH3) | — | CH | O | CH2CH2C(=O) |
| P380 | CH | CF | CH | C(CH3) | — | CH | O | CH2CH2C(=O) |
| P381 | CH | CF | CH | C(CH3) | — | CH | O | CH2CH2C(=O) |
| P382 | CH | CF | CH | C(CH3) | — | CH | O | CH2CH2C(=O) |
| P383 | CH | CF | CH | C(CH3) | — | CH | O | CH2CH2C(=O) |
| P384 | CH | CF | CH | C(CH3) | — | CH | O | CH2CH2C(=O) |
| P385 | CH | CF | CH | C(CH3) | — | CH | O | CH2CH2C(=O) |
| P386 | CH | CF | CH | C(CH3) | — | CH | O | CH2CH2C(=O) |
| P387 | CH | CF | CH | C(CH3) | — | CH | O | CH2CH2C(=O) |
| P388 | CH | CF | CH | C(CH3) | — | CH | O | CH2CH2C(=O) |
| P389 | CH | — | C(CH3) | CH | CF | CH | CH2 | CH=CHC(=O) |
| P390 | CH | — | C(CH3) | CH | CF | CH | CH2 | CH=CHC(=O) |
| P391 | CH | — | C(CH3) | CH | CF | CH | CH2 | CH=CHC(=O) |
| P393 | CH | CH | CH | N(CH3) | — | CH | O | CH=CHC(=O) |
| P394 | CH | CH | CH | N(CH3) | — | CH | O | CH=CHC(=O) |
| P395 | CH | — | C(CH3) | CH | CF | CH | CH2 | CH=CHC(=O) |
| P396 | CH | — | C(CHO) | CH | CF | CH | CH2 | CH=CHC(=O) |
| P397 | CH | — | C(CH2OH) | CH | CF | CH | CH2 | CH=CHC(=O) |
| P398 | CH | — | C(CO2H) | CH | CF | CH | CH2 | CH=CHC(=O) |
| P399 | CH | — | C(CH3) | CH | CF | CH | CH2 | CH=CHC(=O) |
| P400 | CH | — | C(CH3) | CH | CF | CH | CH2 | CH=CHC(=O) |
| P401 | CH | — | C(CH3) | CH | CF | CH | CH2 | CH=CHC(=O) |
| P402 | CH | — | C(CH3) | CH | CF | CH | CH2 | CH=CHC(=O) |
| P403 | CH | — | C(CH3) | CH | CF | CH | CH2 | CH=CHC(=O) |
| P404 | CH | — | C(CH3) | CH | CF | CH | CH2 | CH=CHC(=O) |
| P405 | CH | — | C(CH3) | CH | CF | CH | CH2 | CH=CHC(=O) |
| P406 | CH | — | C(CH3) | CH | CF | CH | CH2 | CH=CHC(=O) |
| P407 | CH | — | C(CH3) | CH | CF | CH | CH2 | CH=CHC(=O) |
| P408 | CH | — | C(CH3) | CH | CF | CH | CH2 | CH=CHC(=O) |
| P409 | CH | — | C(CH3) | CH | CF | CH | CH2 | CH=CHC(=O) |
| P410 | C=O | — | CH2 | CH2 | CH2 | CH2 | CH2 | CH2CH2C(=O) |
| P411 | C=O | — | CH2 | CH2 | CH2 | CH2 | CH2 | CH2CH2C(=O) |
| P412 | CH | CH | CH | N(CH3) | — | CH | O | CH2CH2C(=O) |
| P413 | CH | — | C(CH3) | CH | CF | CH | CH2 | CH=CHC(=O) |
| P414 | C=O | — | CH2 | CH2 | CH2 | CH2 | CH2 | CH2CH2C(=O) |
| P415 | C=O | — | CH2 | CH2 | CH2 | CH2 | CH2 | CH2CH2C(=O) |
| P416 | C=O | — | CH2 | CH | CH | CH | CH2 | CH=CHC(=O) |
| P417 | CH | — | C(CH3) | CH | CF | CH | CH2 | C(=O) |

TABLE 1-continued

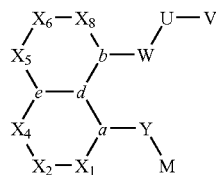

Compounds in Table 1, have 'd' = [C] and U = —NHSO2—; except for compound P159, for which
'd' = N while U = —HNSO2— and for compound P153 for which
'd' = [C] and U = NH2

| Cmpd.No | M | a | b | e | V |
|---|---|---|---|---|---|
| P001 | 2-Napth | N | C | C | 2-Thiophene |
| P002 | Ph | N | C | C | 2-Thiophene |
| P003 | 2-Napth | N | C | C | 2-Thiophene |
| P004 | 2-Napth | N | C | C | 2-Thiophene |
| P005 | 2-Napth | N | C | C | 2-Thiophene |
| P006 | (2-CF3)Ph | N | C | C | 2-Thiophene |
| P007 | (3-CF3)Ph | N | C | C | 2-Thiophene |
| P008 | [2,5(CH3)2]Ph | N | C | C | 2-Thiophene |
| P009 | [3,4-(CH3)2]Ph | N | C | C | 2-Thiophene |
| P010 | [2,6-Cl2]Ph | N | C | C | 2-Thiophene |
| P011 | [2,4-Cl2]Ph | N | C | C | 2-Thiophene |
| P012 | 2-Napth | C | N | C | 2-Thiophene |
| P015 | 2-Napth | C | N | C | 2-Thiophene |
| P016 | 2-Napth | N | C | C | CF3 |
| P017 | (4-OCH3)Ph | N | C | C | 2-Thiophene |
| P018 | 2-Napth | N | C | C | 2-Thiophene |
| P019 | 2-Napth | N | C | C | 2-Thiophene |
| P020 | [3,4-(CH3)2]Ph | N | C | C | 2-Thiophene |
| P021 | [2,5-(CH3)2]Ph | N | C | C | 2-Thiophene |
| P022 | Ph | N | C | C | 2-Thiophene |
| P023 | [4-CH3]Ph | N | C | C | 2-Thiophene |
| P024 | [4-F]Ph | N | C | C | 2-Thiophene |
| P025 | [4-Cl]Ph | N | C | C | 2-Thiophene |
| P026 | [4-OCF2]Ph | N | C | C | 2-Thiophene |
| P027 | [4-OCF3]Ph | N | C | C | 2-Thiophene |
| P028 | [3-OCF3]Ph | N | C | C | 2-Thiophene |
| P029 | [3-CF3]Ph | N | C | C | 2-Thiophene |
| P030 | [3-OCH3]Ph | N | C | C | 2-Thiophene |
| P031 | [2-CF3]Ph | N | C | C | 2-Thiophene |
| P034 | 2-Naphth | N | C | N | 2-Thiophene |
| P035 | [3,4-OCH2O]Ph | N | C | C | 2-Thiophene |
| P036 | [(3,5-OCH3)2]Ph | N | C | C | 2-Thiophene |
| P037 | 2-Naphth | N | C | C | 2-Thiophene |
| P038 | 2-Naphth | N | C | C | [4-Me]Ph |
| P039 | [3,4-Cl2]Ph | N | C | C | 2-Thiophene |
| P040 | [2,4-Cl2]Ph | N | C | C | 2-Thiophene |
| P041 | [3,5-(OCH3)2]Ph | N | C | C | 2-Thiophene |
| P042 | [3,4-(=N—O—N=)]Ph | N | C | C | 2-Thiophene |
| P043 | (2-Ph)Ph | N | C | C | 2-Thiophene |
| P045 | 2-Naphth | N | C | C | 2-Thiophene |
| P046 | 2-Naphth | N | C | C | 2-Thiophene |
| P047 | 2-Naphth | N | C | C | [2-MeO-5-Br]Ph |
| P048 | 2-Naphth | N | C | C | CF3 |
| P049 | 2-Naphth | N | C | C | 2-Thiophene |
| P050 | [3,4-OCH2O-]Ph | N | C | C | 2-Thiophene |
| P051 | [3,4-Cl2]Ph | N | C | C | 2-Thiophene |
| P052 | [2,4-Cl2]Ph | N | C | C | 2-Thiophene |
| P053 | [2,5-Me2]Ph | N | C | C | 2-Thiophene |
| P054 | 3-Pyridyl | N | C | C | 2-Thiophene |
| P055 | 2-[3,5-Me2-4-OMe]Pyridyl | N | C | C | 2-Thiophene |
| P056 | [2,4-Cl2]Ph | N | C | C | 2-Thiophene |
| P057 | 2-Naphth | N | C | C | 2-Thiophene |
| P058 | [2,4-Cl2]Ph | N | C | C | 2-Thiophene |
| P059 | 2-Naphth | N | C | C | 2-Thiophene |
| P060 | 2-Naphth | N | C | C | 2-Thiophene |
| P061 | [2,4-Cl2]Ph | N | C | C | 2-Thiophene |
| P062 | [2,4-Cl2]Ph | N | C | C | 2-Thiophene |
| P063 | [2,4-Cl2]Ph | N | C | C | 2-Thiophene |
| P064 | 2-Naphth | N | C | C | 2-Thiophene |
| P065 | [2,4-Cl2]Ph | N | C | C | 2-Thiophene |
| P066 | 2-Naphth | N | C | C | 2-Thiophene |

TABLE 1-continued

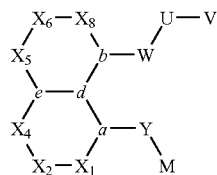

Compounds in Table 1, have 'd' = [C] and U = —NHSO2—; except for compound P159, for which
'd' = N while U = —HNSO2— and for compound P153 for which
'd' = [C] and U = NH2

| | | | | | |
|---|---|---|---|---|---|
| P067 | [2,4-Cl2]Ph | N | C | C | 4,5-Dichloro-2-thiophene |
| P068 | 2-Naphth | N | C | C | 4,5-Dichloro-2-thiophene |
| P069 | [2,4-Cl2]Ph | N | C | C | 2-Thiophene |
| P070 | [2,4-Cl2]Ph | N | C | C | 2-Thiophene |
| P071 | 2-Naphth | C | C | C | 2-Thiophene |
| P072 | [2,4-Cl2]Ph | N | C | C | 4,5-Dichloro-2-thiophene |
| P073 | 2-Naphth | N | C | C | 4,5-Dichloro-2-thiophene |
| P074 | 2-Naphth | N | C | C | 2-Thiophene |
| P075 | 2-Naphth | C | C | C | 4,5-Dichloro-2- |
| P077 | 2-Naphth | N | C | C | 2-Thiophene |
| P079 | [2,4-Cl2]Ph | N | C | C | 4,5-Dichloro-2-thiophene |
| P083 | 2-Naphth | N | C | C | 2-Thiophene |
| P084 | Phenyl | N | C | C | 2-Thiophene |
| P085 | [2,4-Cl2]Ph | N | C | C | 2-Thiophene |
| P086 | [2-Cl]Ph | N | C | C | 2-Thiophene |
| P087 | [3,4-Cl2]Ph | N | C | C | 2-Thiophene |
| P088 | [3,5-F2]Ph | N | C | C | 2-Thiophene |
| P089 | [2-Cl-4,5-OCH2O-]Ph | N | C | C | 2-Thiophene |
| P090 | [2,4-Cl2]Ph | N | C | C | Phenyl |
| P091 | [2,4-Cl2]Ph | N | C | C | 2-Thiophene |
| P092 | [2,4-Cl2]Ph | N | C | C | 4,5-Dichloro-2-thiophene |
| P093 | [2,4-Cl2]Ph | N | C | C | 2-Thiophene |
| P094 | 2-Naphth | C | C | C | 4,5-Dichloro-2-thiophene |
| P095 | 2-Naphth | C | C | C | 4,5-Dichloro-2-thiophene |
| P096 | 2-Naphth | N | C | C | 2-Thiophene |
| P097 | 2-Naphth | N | C | C | 2-Thiophene |
| P098 | 2-Naphth | C | C | C | 4,5-Dichloro-2-thiophene |
| P099 | 2-Quinolinyl | N | C | C | 2-Thiophene |
| P100 | 2-Pyridinyl | N | C | C | 2-Thiophene |
| P101 | [3,4-OCH2O-]Ph | N | C | C | 2-Thiophene |
| P102 | [(2,3-OCH2OCH2)-5 F]Ph | N | C | C | 2-Thiophene |
| P103 | [3,4-F2]Ph | N | C | C | 2-Thiophene |
| P104 | 2-Naphth | N | C | C | 2-Thiophene |
| P105 | 2-Naphth | CH | C | C | 4,5-Dichloro-2-thiophene |
| P106 | 2-Naphth | CH | C | C | 4,5-Dichloro-2-thiophene |
| P107 | [2,4-Cl2]Ph | N | C | C | 4,5-Dichloro-2-thiophene |
| P108 | [2,4-Cl2]Ph | N | C | C | 4,5-Dichloro-2-thiophene |
| P109 | 3-Pyridinyl | N | C | C | 2-Thiophene |
| P110 | 2-Naphth | N | C | C | 2-Thiophene |
| P111 | 2-Naphth | N | C | C | 2-Thiophene |
| P112 | 2-Naphth | N | C | C | 4,5-Dichloro-2-thiophene |
| P113 | [2,4-Cl2]Ph | N | C | C | 4,5-Dichloro-2-thiophene |
| P114 | 2-Naphth | N | C | C | 4,5-Dichloro-2-thiophene |
| P115 | 2-Naphth | N | C | C | 4,5-Dichloro-2-thiophene |
| P116 | [2,4-Cl2]Ph | C | C | C | 4,5-Dichloro-2-thiophene |

TABLE 1-continued

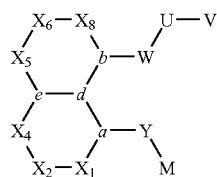

Compounds in Table 1, have 'd' = [C] and U = —NHSO2—; except for compound P159, for which 'd' = N while U = —HNSO2— and for compound P153 for which 'd' = [C] and U = NH2

| | | | | | |
|---|---|---|---|---|---|
| P117 | [2,4-Cl2]Ph | C | C | C | 4,5-Dichloro-2-thiophene |
| P118 | [3,4-Cl2]Ph | N | C | C | 4,5-Dichloro-2-thiophene |
| P119 | [3-CF3]Ph | N | C | C | 4,5-Dichloro-2-thiophene |
| P120 | [4-F]Ph | N | C | C | 4,5-Dichloro-2-thiophene |
| P121 | {2[5,6-(OCH3)2]-Pyridinyl} | N | C | C | 4,5-Dichloro-2-thiophene |
| P122 | Phenyl | N | C | C | 4,5-Dichloro-2-thiophene |
| P123 | [2-Cl]Ph | N | C | C | 4,5-Dichloro-2-thiophene |
| P124 | [2,6-Cl2]Ph | N | C | C | 4,5-Dichloro-2-thiophene |
| P125 | [2-Ph]Ph | N | C | C | 4,5-Dichloro-2-thiophene |
| P126 | [2,4-Cl2]Ph | N | C | C | 4,5-Dichloro-2-thiophene |
| P127 | [2,4-Cl2]Ph | N | C | C | 4,5-Dichloro-2-thiophene |
| P128 | [2,4-Cl2]Ph | N | C | C | 4,5-Dichloro-2-thiophene |
| P129 | [2,4-Cl2]Ph | N | C | C | 4,5-Dichloro-2-thiophene |
| P130 | [2,4-Cl2]Ph | N | C | C | 4,5-Dichloro-2-thiophene |
| P131 | [2,4-Cl2]Ph | N | C | C | 4,5-Dichloro-2-thiophene |
| P132 | [2,4-Cl2]Ph | N | C | C | 4,5-Dichloro-2-thiophene |
| P133 | [2,4-Cl2]Ph | N | C | C | 4,5-Dichloro-2-thiophene |
| P134 | [2,4-Cl2]Ph | N | C | C | 4,5-Dichloro-2-thiophene |
| P135 | [3,4-F2]Ph | N | C | C | 4,5-Dichloro-2-thiophene |
| P136 | [3,5-F2]Ph | N | C | C | 4,5-Dichloro-2-thiophene |
| P137 | [4-Cl]Ph | N | C | C | 4,5-Dichloro-2-thiophene |
| P138 | [2,5-Me2]Ph | N | C | C | 4,5-Dichloro-2-thiophene |
| P139 | [3,4-OCH2O-]Ph | N | C | C | 4,5-Dichloro-2-thiophene |
| P140 | [3-OCF3]Ph | N | C | C | 4,5-Dichloro-2-thiophene |
| P141 | [3,5-(OCH3)2]Ph | N | C | C | 4,5-Dichloro-2-thiophene |
| P142 | [3-OCH3]Ph | N | C | C | 4,5-Dichloro-2-thiophene |
| P143 | [4-OCF3]Ph | N | C | C | 4,5-Dichloro-2-thiophene |
| P144 | 4-Tetrahydropyranyl | N | C | C | 4,5-Dichloro-2-thiophene |
| P145 | [4-OCHF2]Ph | N | C | C | 4,5-Dichloro-2-thiophene |
| P146 | 2-Quinolinyl | N | C | C | 4,5-Dichloro-2-thiophene |
| P147 | 2-Naphth | C | C | C | 4,5-Dichloro-2-thiophene |
| P148 | 2-Naphth | C(CH3) | C | C | 4,5-Dichloro-2-thiophene |

TABLE 1-continued

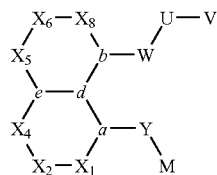

Compounds in Table 1, have 'd' = [C] and U = —NHSO2—; except for compound P159, for which
'd' = N while U = —HNSO2— and for compound P153 for which
'd' = [C] and U = NH2

| | | | | | |
|---|---|---|---|---|---|
| P149 | [2,4-Cl2]Ph | N | C | C | 4,5-Dichloro-2-thiophene |
| P150 | 2-Naphth | C | C | C | 4,5-Dichloro-2-thiophene |
| P151 | 2-Naphth | C | C | C | 4,5-Dichloro-2-thiophene |
| P152 | 2-Naphth | N | C | C | 4,5-Dichloro-2-thiophene |
| P154 | 2-Naphth | CH | C | C | 4,5-Dichloro-2-thiophene |
| P155 | 2-Naphth | CH | C | C | 4,5-Dichloro-2-thiophene |
| P156 | 2-Naphth | C(CH3) | C | C | 4,5-Dichloro-2-thiophene |
| P157 | 2-Naphth | CF | C | C | 4,5-Dichloro-2-thiophene |
| P158 | 2-Naphth | CH | C | C | 4,5-Dichloro-2-thiophene |
| P159 | 2-Naphth | C | C | C | 4,5-Dichloro-2-thiophene |
| P160 | 2-Naphth | N | C | C | 2-Thiophene |
| P161 | 2-Naphth | N | C | C | 4,5-Dichloro-2-thiophene |
| P162 | 2-Naphth | C | C | C | 4,5-Dichloro-2-thiophene |
| P163 | 2-Naphth | C | C | C | 2-Thiophene |
| P164 | 2-Quinolinyl | C | C | C | 4,5-Dichloro-2-thiophene |
| P165 | [2,4-(CH3)2]Ph | C | C | C | 4,5-Dichloro-2-thiophene |
| P166 | 2-Naphth | C | C | C | 2-Thiophene |
| P167 | [3,4-(OCH3)2]Ph | C | C | C | 4,5-Dichloro-2-thiophene |
| P168 | [2-Cl-4-F]Ph | C | C | C | 4,5-Dichloro-2-thiophene |
| P169 | 2-Quinolinyl | C | C | C | 4,5-Dichloro-2-thiophene |
| P170 | [3,4-(OCH3)2]Ph | C | C | C | 4,5-Dichloro-2-thiophene |
| P171 | 2-Naphth | C | C | C | 4,5-Dichloro-2-thiophene |
| P172 | [2,4-(CH3)2]Ph | C | C | C | 4,5-Dichloro-2-thiophene |
| P173 | [4-Cl]Ph | C | C | C | 4,5-Dichloro-2-thiophene |
| P174 | 2-Naphth | C | C | C | 5-Chloro-2-thiophene |
| P175 | 2-Naphth | C | C | C | Phenyl |
| P176 | 2-Naphth | C | C | C | [(2,5-OCH3)2]Ph |
| P177 | 2-Naphth | C | C | C | [3,5-Cl2]Ph |
| P178 | [3,4-Cl2]Ph | C | C | C | 4,5-Dichloro-2-thiophene |
| P179 | 2-Naphth | N | C | C | 4,5-Dichloro-2-thiophene |
| P180 | 2-Naphth | N | C | C | 4,5-Dichloro-2-thiophene |
| P181 | 2-Benzoxazole | C | C | C | 4,5-Dichloro-2-thiophene |
| P182 | 2-Benzothiazole | C | C | C | 4,5-Dichloro-2-thiophene |
| P183 | 2-Naphth | C | C | C | [2-Cl]Ph |
| P184 | 2-Naphth | C | C | C | [3-Cl]Ph |
| P185 | 2-Naphth | C | C | C | [4OCH3]Ph |
| P186 | 2-Naphth | C | C | C | [3,5-Cl2]Ph |
| P187 | 2-Naphth | C | C | C | 5-Chloro-2-thiophene |
| P188 | 2-Naphth | C | C | C | Phenyl |

TABLE 1-continued

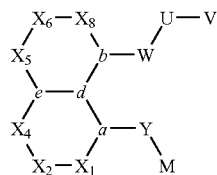

Compounds in Table 1, have 'd' = [C] and U = —NHSO2—; except for compound P159, for which
'd' = N while U = —HNSO2— and for compound P153 for which
'd' = [C] and U = NH2

| | | | | | |
|---|---|---|---|---|---|
| P190 | [4-Cl]Ph | C | C | C | 4,5-Dichloro-2-thiophene |
| P191 | 2-Naphth | C | C | C | [2-Cl]Ph |
| P192 | 2-Naphth | C | C | C | [3-Cl]Ph |
| P193 | 2-Naphth | C | C | C | [4-OCH3]Ph |
| P194 | [2,5-(OCH3)2]Ph | C | C | C | 4,5-Dichloro-2-thiophene |
| P195 | 2-(1-Methylbenzimidazole) | C | C | C | 4,5-Dichloro-2-thiophene |
| P196 | 2-Benzothiazole | C | C | C | 4,4-Dichloro-2-thiophene |
| P197 | [2,4-F2]Ph | C | C | C | 4,5-Dichloro-2-thiophene |
| P198 | Phenyl | C | C | C | 4,5-Dichloro-2-thiophene |
| P199 | 2-Naphth | C | C | C | 4-[3,5-(CH3)2]isoxazole |
| P200 | [4-OCH3]Ph | C | C | C | 4,5-Dichloro-2-thiophene |
| P201 | 2-Pyridinyl | C | C | C | 4,5-Dichloro-2-thiophene |
| P202 | [2,5-(OCH3)2]Ph | C | C | C | 4,5-Dichloro-2-thiophene |
| P203 | 2-Naphth | C | C | C | 4-[3,5-(CH3)2]isoxazole |
| P204 | [3,4-Cl2]Ph | C | C | C | 4,5-Dichloro-2-thiophene |
| P205 | [2,4-Cl2]Ph | C | C | C | 4,5-Dichloro-2-thiophene |
| P206 | [2,4-F2]Ph | C | C | C | 4,5-Dichloro-2-thiophene |
| P207 | Phenyl | C | C | C | 4,5-Dichloro-2-thiophene |
| P208 | [3-OMe]Ph | C | C | C | 4,5-Dichloro-2-thiophene |
| P209 | [3,4-F2]Ph | C | C | C | 4,5-Dichloro-2-thiophene |
| P210 | [4-OMe]Ph | C | C | C | 4,5-Dichloro-2-thiophene |
| P211 | 2-Pyrimidinyl | C | C | C | 4,5-Dichloro-2-thiophene |
| P212 | [2-OMe]Ph | C | C | C | 4,5-Dichloro-2-thiophene |
| P213 | [2-Cl]Ph | C | C | C | 4,5-Dichloro-2-thiophene |
| P214 | 2-Naphth | C | C | C | [3,5-F2}Ph |
| P215 | 2-Naphth | C | C | C | [3,4-F2}Ph |
| P216 | [2,4-Cl2]Ph | N | C | C | 2-Thiophene |
| P217 | 2-Naphth | N | C | C | 2-Thiophene |
| P218 | 2-Naphth | N | C | C | 2-Thiophene |
| P219 | [2,4-Cl2]Ph | N | C | C | 2-Thiophene |
| P220 | 2-Imidazolyl | C | C | C | 4,5-Dichloro-2-thiophene |
| P221 | 2-Pyridinyl | C | C | C | 4,5-Dichloro-2-thiophene |
| P222 | [2-OMe]Ph | C | C | C | 4,5-Dichloro-2-thiophene |
| P223 | 2-Naphth | C | C | C | [3,5-F2}Ph |
| P224 | 2-Naphth | C | C | C | [3,4-F2}Ph |
| P225 | 2-Naphth | C | C | C | [4-F}Ph |
| P226 | 2-Naphth | C | C | C | [2,4,5-F3}Ph |
| P227 | 5-[1-Methyltetrazolyl] | C | C | C | 4,5-Dichloro-2-thiophene |
| P228 | 3-[1,2,4-Triazolyl] | C | C | C | 4,5-Dichloro-2-thiophene |

TABLE 1-continued

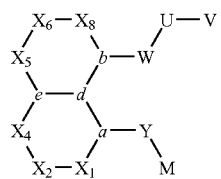

Compounds in Table 1, have 'd' = [C] and U = —NHSO2—; except for compound P159, for which 'd' = N while U = —HNSO2— and for compound P153 for which 'd' = [C] and U = NH2

| | | | | | |
|---|---|---|---|---|---|
| P229 | 2-Naphth | CH | C | C | 4,5-Dichloro-2-thiophene |
| P230 | 2-[5-Methyl-1,3,4-thiadiazolyl] | C | C | C | 4,5-Dichloro-2-thiophene |
| P231 | 2-[5-Methyl-1,3,4-thiadiazolyl] | C | C | C | 4,5-Dichloro-2-thiophene |
| P232 | [2-Cl]Ph | C | C | C | 4,5-Dichloro-2-thiophene |
| P233 | [4-NHC(=O)CH3]Ph | C | C | C | 4,5-Dichloro-2-thiophene |
| P234 | [2-Cl-4-F]Ph | C | C | C | 4,5-Dichloro-2-thiophene |
| P235 | [4-NHC(=O)CH3]Ph | C | C | C | 4,5-Dichloro-2-thiophene |
| P236 | 2-Naphth | C | C | C | [4-F]Ph |
| P237 | 2-Naphth | C | C | C | [2,4,5-F3]Ph |
| P238 | [2,4-Cl2]Ph | C | C | C | 4,5-Dichloro-2-thiophene |
| P239 | 5-[1-Methyltetrazolyl] | C | C | C | 4,5-Dichloro-2-thiophene |
| P240 | 3-[1,2,4-Triazolyl] | C | C | C | 4,5-Dichloro-2-thiophene |
| P241 | 2-Naphth | CH | C | C | 4,5-Dichloro-2-thiophene |
| P242 | 2-Naphth | CH | C | C | 4,5-Dichloro-2-thiophene |
| P243 | 2-Naphth | C | C | C | CF3 |
| P244 | 2-Naphth | C | C | C | 4,5-Dichloro-2-thiophene |
| P245 | 2-Naphth | C | C | C | 4,5-Dichloro-2-thiophene |
| P246 | 2-Naphth | C | C | C | 4,5-Dichloro-2-thiophene |
| P247 | 2-Naphth | CH | C | C | 4,5-Dichloro-2-thiophene |
| P248 | 2-Naphth | CH | C | C | 4,5-Dichloro-2-thiophene |
| P249 | 2-Naphth | C | C | C | 4,5-Dichloro-2-thiophene |
| P250 | [2,4-Cl2]Ph | C | C | C | 4,5-Dichloro-2-thiophene |
| P251 | 2-Naphth | CH | C | C | 4,5-Dichloro-2-thiophene |
| P252 | [2,4-Cl2]Ph | CH | C | C | 4,5-Dichloro-2-thiophene |
| P253 | 2-Naphth | N | C | C(CH3) | 4,5-Dichloro-2-thiophene |
| P254 | 2-Naphth | C | C | C | 4,5-Dichloro-2-thiophene |
| P255 | 2-Naphth | CH | C | C | 4,5-Dichloro-2-thiophene |
| P256 | 2-Naphth | C | C | C | 4,5-Dichloro-2-thiophene |
| P257 | 2-Naphth | C | C | C | 4,5-Dichloro-2-thiophene |
| P258 | [3,4-Cl2]Ph | CH | C | C | 4,5-Dichloro-2-thiophene |
| P259 | 2-[1-Ethylbenzimidazole] | C | C | C | 4,5-Dichloro-2-thiophene |
| P260 | [3-OMe]Ph | N | C | C(CH3) | 4,5-Dichloro-2-thiophene |
| P262 | [3-F]Ph | N | C | C(CH3) | 4,5-Dichloro-2-thiophene |

TABLE 1-continued

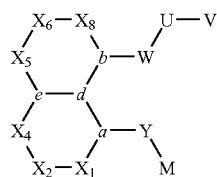

Compounds in Table 1, have 'd' = [C] and U = —NHSO2—; except for compound P159, for which 'd' = N while U = —HNSO2— and for compound P153 for which 'd' = [C] and U = NH2

| | | | | | |
|---|---|---|---|---|---|
| P263 | [4-F]Ph | N | C | C(CH3) | 4,5-Dichloro-2-thiophene |
| P264 | [3,4-F2]Ph | N | C | C(CH3) | 4,5-Dichloro-2-thiophene |
| P265 | 2-Naphth | CH | C | C | 4,5-Dichloro-2-thiophene |
| P266 | [3,4-F2]Ph | N | C | C(CH3) | [3,5-Cl2}Ph |
| P267 | [3,4-F2]Ph | N | C | C(CH3) | [2,4,5-F3}Ph |
| P268 | [3,4-Cl2]Ph | CH | C | C | 4,5-Dichloro-2-thiophene |
| P269 | 2-Naphthyl | N | C | C(CH3) | [4-OCF3]Ph |
| P270 | [2,4-F2]Ph | CH | C | C | 4,5-Dichloro-2-thiophene |
| P271 | [3,4-Cl2]Ph | CH | C | C | 4,5-Dichloro-2-thiophene |
| P272 | [3,4-F2]Ph | CH | C | C | 4,5-Dichloro-2-thiophene |
| P273 | OC(CH3)3 | N | C | C | 2-Thiophene |
| P274 | [2,4-Cl2]Ph | N | C | C(CH3) | [4-F]Ph |
| P275 | [2,4-Cl2]Ph | N | C | C(CH3) | [2,4,5-F3]Ph |
| P276 | [2,4-Cl2]Ph | N | C | C(CH3) | 2-Thiophene |
| P277 | 2-Naphthyl | C | C | C | 4,5-Dichloro-2-thiophene |
| P278 | [2,4-Cl2]Ph | N | C | C(CH3) | 4,5-Dichloro-2-thiophene |
| P279 | [2,4-Cl2]Ph | N | C | C(CH3) | 5-Chloro-2-thiophene |
| P280 | [2,4-Cl2]Ph | N | C | C(CH3) | [3,5-Cl2]Ph |
| P281 | [2,4-Cl2]Ph | N | C | C(CH3) | [3-Cl]Ph |
| P282 | [2,4-Cl2]Ph | N | C | C(CH3) | [3,5-F2]Ph |
| P283 | [2,4-Cl2]Ph | N | C | C(CH3) | [3,4-F2]Ph |
| P284 | 2-Naphthyl | C | C | C | 4,5-Dichloro-2-thiophene |
| P285 | [3-Cl]Ph | N | C | C(CH3) | 4,5-Dichloro-2-thiophene |
| P286 | [3,5-Cl2]Ph | CH | C | C | 4,5-Dichloro-2-thiophene |
| P287 | [2,4-Cl2]Ph | CH | C | C | 4,5-DiChloro-2-thiophene |
| P288 | [3,4-F2]Ph | CH | C | C | 4,5-Dichloro-2-thiophene |
| P290 | [3,4-Cl2]Ph | C | C | C | 4,5-Dichloro-2-thiophene |
| P291 | [2,3-Cl2]Ph | C | C | C | 4,5-Dichloro-2-thiophene |
| P292 | [3,4-Cl2]Ph | C | C | C | [2,4,5-F3]Ph |
| P293 | [3,4-Cl2]Ph | C | C | C | [3,4-F2]Ph |
| P294 | [4-F]Ph | N | C | C(CH3) | [3,4-F2]Ph |
| P295 | [4-F]Ph | N | C | C(CH3) | [3,5-F2]Ph |
| P296 | [2,3-Cl2]Ph | N | C | C(CH3) | [2,4,5-F3]Ph |
| P297 | [2,3-Cl2]Ph | N | C | C(CH3) | [3,4-F2]Ph |
| P298 | [2,3-Cl2]Ph | N | C | C(CH3) | [3,5..F2]Ph |
| P299 | [2,3-Cl2]Ph | N | C | C(CH3) | 4,5-Dichloro-2-thiophene |
| P300 | [4-F]Ph | N | C | C(CH3) | [2,4,5-F3]Ph |
| P301 | [2,4-Cl2]Ph | C | C | C(CH3) | [2,4,5-F3]Ph |
| P302 | [2,4-Cl2]Ph | C | C | C | [3,4-F2]Ph |
| P303 | [2,4-Cl2]Ph | C | C | C | 4,5-Dichloro-2-thiophene |
| P304 | [3,4-F2]Ph | N | C | C(CH3) | [3,4-F2]Ph |
| P305 | [3,4-F2]Ph | N | C | C(CH3) | [3,5-F2]Ph |
| P306 | [3-MeO]Ph | N | C | C(CH3) | [2,4,5-F3]Ph |
| P307 | [3-MeO]Ph | N | C | C(CH3) | [3,5-F2]Ph |
| P308 | [3-MeO]Ph | N | C | C(CH3) | [3,4-F2]Ph |
| P309 | [4-Cl]Ph | C | C | C | [2,4,5-F3]Ph |
| P310 | [4-Cl]Ph | C | C | C | [3,4-F2]Ph |

TABLE 1-continued

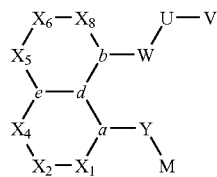

Compounds in Table 1, have 'd' = [C] and U = —NHSO2—; except for compound P159, for which
'd' = N while U = —HNSO2— and for compound P153 for which
'd' = [C] and U = NH2

| | | | | | |
|---|---|---|---|---|---|
| P311 | [4-Cl]Ph | C | C | C | 4,5-Dichloro-2-thiophene |
| P312 | [4-F]Ph | N | C | C | [2,4,5-F3]Ph |
| P313 | [3,4-F2]Ph | N | C | C | [2,4,5-F3]Ph |
| P314 | [4-F]Ph | N | C | C | [3,4-F2]Ph |
| P315 | [3,4-F2]Ph | N | C | C | [3,4-F2]Ph |
| P316 | [4-F]Ph | N | C | C | [3,5-F2]Ph |
| P317 | [3,4-F2]Ph | N | C | C | [3,5-F2]Ph |
| P318 | [3,4-F2]Ph | C | C | C | [2,4,5-F3]Ph |
| P319 | [3,4-F2]Ph | C | C | C | [3,4-F2]Ph |
| P320 | [3,4-F2]Ph | C | C | C | 4,5-Dichloro-2-thiophene |
| P321 | [3,4-F2]Ph | N | C | C | 4,5-Dichloro-2-thiophene |
| P322 | [4-F]Ph | N | C | C | 4,5-Dichloro-2-thiophene |
| P323 | [2,4-Cl2]Ph | N | C | C | [2,4,5-F3]Ph |
| P324 | [2,4-F2]Ph | C | C | C | [2,4,5-F3]Ph |
| P325 | [2,4-F2]Ph | C | C | C | [3,4-F2]Ph |
| P326 | [2,4-F2]Ph | C | C | C | 4,5-Dichloro-2-thiophene |
| P327 | [2,4-Cl2]Ph | N | C | C | 4,5-Dichloro-2-thiophene |
| P328 | [3-Cl-4-F]Ph | C | C | C | [2,4,5-F3]Ph |
| P329 | [3-Cl-4-F]Ph | C | C | C | [3,4-F2]Ph |
| P330 | [3-Cl-4-F]Ph | C | C | C | 4,5-Dichloro-2-thiophene |
| P331 | [4-Cl-3-F]Ph | C | C | C | [2,4,5-F3]Ph |
| P332 | [4-Cl-3-F]Ph | C | C | C | [3,4-F2]Ph |
| P333 | [4-Cl-3-F]Ph | C | C | C | 4,5-Dichloro-2-thiophene |
| P334 | 2-Naphthyl | C | C | C | [3,4-F2]Ph |
| P335 | [2,4-Cl2]Ph | N | C | C | [3,4-F2]Ph |
| P336 | [2,4-Cl2]Ph | N | C | C | [3,5-F2]Ph |
| P337 | [4-Cl-2-F]Ph | C | C | C | [2,4,5-F3]Ph |
| P338 | [4-Cl-2-F]Ph | C | C | C | [3,4-F2]Ph |
| P339 | [4-Cl-2-F]Ph | C | C | C | 4,5-Dichloro-2-thiophene |
| P340 | [2-Cl-4-F]Ph | C | C | C | [2,4,5-F3]Ph |
| P341 | [2-Cl-4-F]Ph | C | C | C | [3,4-F2]Ph |
| P342 | [2-Cl-4-F]Ph | C | C | C | 4,5-Dichloro-2-thiophene |
| P343 | 2-Naphthyl | C | C | C | [2,4,5-F3]Ph |
| P344 | [2,4-Cl2]Ph | N | C | C(CO2Et) | [2,415-F3]Ph |
| P345 | [2,4-Cl2]Ph | N | C | C(CO2Et) | 4,5-Dichloro-2-thiophene |
| P346 | [2,4-Cl2]Ph | N | C | C(CO2Et) | [3,4-F2]Ph |
| P347 | [3,4-Cl2]Ph | C | C | C | 4,5-Dichloro-2-thiophene |
| P348 | [2,4-Cl2]Ph | N | C | C | 4,5-Dichloro-2-thiophene |
| P349 | [2,4-Cl2]Ph | N | C | C | 4,5-Dichloro-2-thiophene |
| P350 | [2,4-Cl2]Ph | N | C | C | 4,5-Dichloro-2-thiophene |
| P351 | 2-Naphthyl | C | C | C | [4-F]Ph |
| P352 | 2-Naphthyl | C | C | C | [2-Cl]Ph |
| P353 | 2-Naphthyl | C | C | C | [3-Cl]Ph |
| P354 | [2,4-Cl2]Ph | N | C | C | [2,4,5-F3]Ph |
| P355 | 2-Naphthyl | C | C | C | [3,4-Cl2]Ph |
| P356 | 2-Naphthyl | C | C | C | [2,4-Cl2]Ph |
| P357 | 2-Naphthyl | C | C | C | [3,5-Cl2]Ph |
| P358 | 2-Naphthyl | C | C | C | [2,4-F2]Ph |

TABLE 1-continued

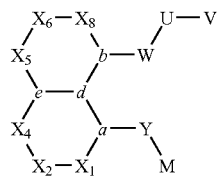

Compounds in Table 1, have 'd' = [C] and U = —NHSO2—; except for compound P159, for which
'd' = N while U = —HNSO2— and for compound P153 for which
'd' = [C] and U = NH2

| | | | | | |
|---|---|---|---|---|---|
| P359 | 2-Naphthyl | C | C | C | [2,5-F2]Ph |
| P360 | 2-Naphthyl | C | C | C | [2,6-F2]Ph |
| P361 | 2-Naphthyl | C | C | C | [3,5-F2]Ph |
| P362 | 2-Naphthyl | C | C | C | [3,4-F2]Ph |
| P363 | 2-Naphthyl | C | C | C | [3-F]Ph |
| P364 | 2-Naphthyl | C | C | C | [2-F]Ph |
| P365 | 2-Naphthyl | C | C | C | [4-Cl]Ph |
| P366 | 2-Naphthyl | C | C | C | [4-OCH3]Ph |
| P367 | [3-OCH3]Ph | N | C | C | [2,4,5-F3]Ph |
| P368 | [3-OCH3]Ph | N | C | C | [3,4-F2]Ph |
| P369 | 4-[3,5-(CH3)2]isoxazole | N | C | C | [3,4-F2]Ph |
| P370 | 4-[3,5-(CH3)2]isoxazole | N | C | C | [2,4,5-F3]Ph |
| P371 | [3-OCH3]Ph | C | C | C | [3,4-F2]Ph |
| P372 | [3-OCH3]Ph | C | C | C | [2,4,5-F3]Ph |
| P373 | 2-Naphthyl | C | C | C | [2,3,4,5,6-F5]Ph |
| P374 | [3,5-(OCH3)2]Ph | N | C | C | [3,4-F2]Ph |
| P375 | [3,5-(OCH3)2]Ph | N | C | C | [2,4,5-F3]Ph |
| P376 | 6-quinolinyl | C | C | C | [3,4-F2]Ph |
| P377 | 6-quinolinyl | C | C | C | [2,4,5-F3]Ph |
| P378 | 2-Naphthyl | C | N | C | [2,4,5-F3]Ph |
| P379 | 2-Naphthyl | C | N | C | [3,4-F2]Ph |
| P380 | 2-Naphthyl | C | N | C | 4,5-Dichloro-2-thiophene |
| P381 | 2-Naphthyl | C | N | C | [3-Cl]Ph |
| P382 | [2,4-Cl2]Ph | C | N | C | [2,4,5-F3]Ph |
| P383 | [2,4-Cl2]Ph | C | N | C | [3,4-F2]Ph |
| P384 | [2,4-Cl2]Ph | C | N | C | 4,5-Dichloro-2-thiophene |
| P385 | [2,4-Cl2]Ph | C | N | C | [3-Cl]Ph |
| P386 | [3,4-Cl2]Ph | C | N | C | [2,4,5-F3]Ph |
| P387 | [3,4-Cl2]Ph | C | N | C | [3,4-F2]Ph |
| P388 | [3,4-Cl2]Ph | C | N | C | 4,5-Dichloro-2-thiophene |
| P389 | [2-CN]Ph | N | C | C | 4,5-Dichloro-2-thiophene |
| P390 | [3-CN]Ph | N | C | C | 4,5-Dichloro-2-thiophene |
| P391 | [4-CN]Ph | N | C | C | 4,5-Dichloro-2-thiophene |
| P393 | 2-Quinoxalinyl | C | C | C | [3,4-F2]Ph |
| P394 | 2-Quinoxalinyl | C | C | C | [2,4,5-F3]Ph |
| P395 | 2-Imidazo[1,2a]pyridinyl | N | C | C | 4,5-Dichloro-2-thiophene |
| P396 | [2,4-Cl2]Ph | N | C | C | 4,5-Dichloro-2-thiophene |
| P397 | [2,4-Cl2]Ph | N | C | C | 4,5-Dichloro-2-thiophene |
| P398 | [2,4-Cl2]Ph | N | C | C | 4,5-Dichloro-2-thiophene |
| P399 | 2-Imidazo[1,2a]pyridinyl | N | C | C | [3,4-F2]Ph |
| P400 | 2-Imidazo[1,2a]pyridinyl | N | C | C | [3-Cl]Ph |
| P401 | 2-Imidazo[1,2a]pyridinyl | N | C | C | [3-F]Ph |
| P402 | 2-Imidazo[1,2a]pyridinyl | N | C | C | [2,4,5-F3]Ph |
| P403 | 2-Imidazo[1,2a]pyridinyl | N | C | C | [4-F]Ph |
| P404 | 2-Imidazo[1,2a]pyridinyl | N | C | C | [3,5-F2]Ph |
| P405 | 2-Imidazo[1,2a]pyridinyl | N | C | C | [4-Cl]Ph |

TABLE 1-continued

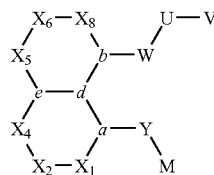

Compounds in Table 1, have 'd' = [C] and U = —NHSO2—; except for compound P159, for which 'd' = N while U = —HNSO2— and for compound P153 for which 'd' = [C] and U = NH2

| | | | | | |
|---|---|---|---|---|---|
| P406 | 2-Imidazo[1,2a]pyridinyl | N | C | C | [3,4-Cl2]Ph |
| P407 | 2-Imidazo[1,2a]pyridinyl | N | C | C | [2,5-F2]Ph |
| P408 | 2-Imidazo[1,2a]pyridinyl | N | C | C | [3,5-Cl2]Ph |
| P409 | 2-Imidazo[1,2a]pyridinyl | N | C | C | [2-F]Ph |
| P410 | [3,4-F2]Ph | N | CH | C(CH3) | [2,4,5-F3]Ph |
| P411 | [3,4-F2]Ph | N | C | C(CH3) | [2,4,5-F3]Ph |
| P412 | 2-Naphthyl | C | C | C | [2,4,5-F3]Ph |
| P413 | 2-Imidazo[1,2a]pyridinyl | N | C | C | [2,4-F2]Ph |
| P414 | [3-OCH3]Ph | N | C | C(CH3) | [2,4,5-F3]Ph |
| P415 | [3,4-F2]Ph | N | CH | C(CH3) | 4,5-Dichloro-2-thiophene |
| P416 | 2-Naphthyl | N | C | C | [2,4,5-F3]Ph |
| P417 | [2,4-Cl2]Ph | N | C | C | [3,4-F2]Ph |

TABLE 2

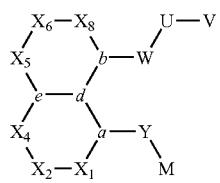

Where: 'a' = [N], and 'b' = 'e' = 'd' = [C]

| Cmpd.No. P(x) | X1 | X2 | X4 | X5 | X6 | X8 | Y | —W(C=O)— | M | U | V |
|---|---|---|---|---|---|---|---|---|---|---|---|
| P76 | CH | — | C(CH3) | CH | CF | CH | CH2 | CH=CHC(=O) | 2-Naphth | N(CH3)SO2 | 4,5-Dichloro-2-thiophene |
| P44 | CH | — | CH | CH | CH | CH | CH2 | CH2—OC(=O) | 2-Naphth | NH(P=O)(OEt)2 | — |

The compounds of the invention were assayed for their binding on prostanoid EP3 receptors according to the method of Abramovitz et al. [*Bioch. Biophys. Acta*, 1473, 285-293 (2000)]. Chart 1 shows the activity in column 2. Compounds with $IC_{50}$<1 μM are shown as ++++; compounds with $IC_{50}$ 1-10 μM are shown as +++; and compounds with $IC_{50}$>10 μM are shown as ++. All of the examples in table 1 and 2 have been synthesized, characterized and tested for EP3 receptor binding.

The compounds of the invention were assayed for their effects on platelet aggregation in vitro. In experiments with human platelets, whole blood was extracted from overnight-fasted human donors. Each experiment was performed with blood from single individual. In experiments with rodent platelets, whole blood was gathered from the heart of female mice or male rats under isofluran (Abbott) anaesthesia. Blood was pooled from two or ten individual rodents for each experiment in the case of rat and mouse experiments, respectively. In all cases, blood was collected into 3.8% sodium citrate tubes (Greiner Bio-one). Platelet-rich plasma (PRP) was obtained by centrifugation at 100×g for 15 min at 25° C. for humans, at 150×g for rats, or at 80×g for 10 min for mice. Platelet-poor plasma was obtained by centrifugation of the remaining blood at 2,400×g for 10 min at 25° C. After counting in an Autocounter (Model 920 EO, Swelab) platelets were diluted when necessary to the desired stock concentrations (200,000-300,000 platelets/μl) using 0.9% NaCl isotonic solution (Braun).

Platelet aggregation was determined by light absorbance using a platelet aggregometer with constant magnetic stirring (Model 490, Chronolog Cop., Havertown, Pa., USA), using a volume of 500 μl per cuvette. During the performance of the experiments, platelet solution was continually agitated by mild horizontal shaking. Collagen (Sigma) and $PGE_2$ or sulprostone (Cayman Chemicals) were used as accelerants of platelet aggregation. Compounds used for this assay were dissolved and stored in a 100% DMSO solution. After dilution, the final DMSO concentration in the assay was lower than 0.1% v/v. It was determined that this concentration of DMSO did not inhibit platelet aggregation in the assay. Acceleration agents and $EP_3$ test compounds were diluted in isotonic solution at the desired concentration. Sigmoidal non-lineal regression was used to calculate the concentration of test compound required to inhibit platelet aggregation by 50% (IC50). $IC_{50}$ values of test compounds were calculated using GraphPad Prism 3.02 for Windows (GraphPad Software, San Diego Calif. USA). The data are shown in Table 3.

TABLE 3

$EC_{50}$ values of test compounds in the platelets aggregation assay.

| Species | Agonist | Serum % | $IC_{50}$ (nM) for Test Compounds | | |
|---|---|---|---|---|---|
| | | | P67 | P75 | P253 |
| Human | Sulprostone | 50 | 9.21 | 14.1 | 15.88 |
| | $PGE_2$ | 50 | 5.15 | | |
| Rat | Sulprostone | 20 | 87.85 | 78.54 | |
| | $PGE_2$ | 20 | 304.35 | | |

Compounds were tested against $PGE_2$ (940 nM) or Sulprostone (100 nM) and collagen (0.125 ug.mL) for human which produced 90% aggregation.

Compounds were tested against $PGE_2$ (940 nM) or Sulprostone (100 nM) and collagen (2.0 ug.mL) for rat, which produced 60% aggregation.

The compounds of the invention also were assayed for their effects on platelet aggregation in vivo. An in vivo test of platelet activation is the induction of pulmonary thromboembolism by arachidonic acid, a precursor of prostaglandin formation. Inhibitors of prostaglandin synthesis, e.g., a COX-1 inhibitor such as asprin, are protective in the assay. For the pulmonary thromboembolism assay, concious female C57BL/6 mice were dosed orally with the test compounds and 30 min later thromboembolism was induced by injection of arachidonic acid into a tail vein at a dose of 30 mg per kg body weight. Survival was evaluated one hour after the challenge with arachidonic acid, as mice that survive for that length of time usually recovered fully. The arachidonic acid injection was given via a lateral tail vein in a mouse that had been warmed briefly under a heat lamp (dilation of the tail veins using heat facilitates placing the injection). An insulin syringe, 0.5 mL (from Becton Dickinson) was used for dosing. The dose volume given of both the test compound and the arachidonic acid was adjusted to the weight of the mouse (the dose volume p.o. for test compounds and i.v. for arachidonic acid solution was 10 μL and 5 μL per gram body weight, respectively). The survival rate for mice treated with arachidonic acid only was 1 per 10 mice evaluated or 10%. Survival rates for mice treated with test compounds (100 mg/kg, orally) and then arachidonic acid are shown below in Table 4.

TABLE 4

| Compound no. | No. mice surviving/ Total no. of mice evalauted | Survival rate |
|---|---|---|
| P67 | 15/22 | 68% |
| P68 | 4/14 | 28% |
| P75 | 20/43 | 46% |
| P150 | 4/8 | 50% |

In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants that are in themselves known, but are not mentioned here. The starting materials, in the case of suitably substituted fused A/B ring compounds, are either commercially available or may be obtained by the methods well known to persons of skill in the art.

CHART 1

| Cmpd.No. | Activity |
|---|---|
| P001 | ++++ |
| P002 | ++++ |
| P003 | ++++ |
| P004 | ++++ |
| P005 | ++++ |
| P006 | ++++ |
| P007 | ++++ |
| P008 | ++++ |
| P009 | ++++ |
| P010 | ++++ |
| P011 | ++++ |
| P012 | ++ |
| P015 | +++ |
| P016 | ++++ |
| P017 | ++++ |
| P018 | ++++ |
| P019 | +++ |
| P020 | +++ |
| P021 | +++ |
| P022 | +++ |
| P023 | +++ |
| P024 | ++ |
| P025 | ++ |
| P026 | +++ |
| P027 | +++ |
| P028 | +++ |
| P029 | +++ |
| P030 | +++ |
| P031 | +++ |
| P034 | ++++ |
| P035 | ++++ |
| P036 | ++++ |
| P037 | +++ |
| P038 | ++++ |
| P039 | ++++ |
| P040 | ++++ |
| P041 | +++ |
| P042 | +++ |
| P043 | ++++ |
| P044 | +++ |
| P045 | ++++ |
| P046 | ++++ |
| P047 | ++++ |
| P048 | +++ |
| P049 | +++ |
| P050 | +++ |
| P051 | ++++ |
| P052 | ++++ |
| P053 | +++ |
| P054 | +++ |
| P055 | +++ |
| P056 | ++++ |
| P057 | ++++ |
| P058 | ++++ |
| P059 | ++++ |
| P060 | ++++ |
| P061 | ++++ |
| P062 | ++++ |
| P063 | ++++ |
| P064 | ++++ |
| P065 | ++++ |
| P066 | ++++ |
| P067 | ++++ |
| P068 | ++++ |
| P069 | ++++ |

CHART 1-continued

| Cmpd.No. | Activity |
|---|---|
| P070 | ++++ |
| P071 | ++++ |
| P072 | ++++ |
| P073 | ++++ |
| P074 | ++++ |
| P075 | ++++ |
| P076 | ++++ |
| P077 | ++++ |
| P078 | +++ |
| P079 | ++++ |
| P080 | +++ |
| P083 | ++++ |
| P084 | ++++ |
| P085 | ++++ |
| P086 | ++++ |
| P087 | ++++ |
| P088 | ++++ |
| P089 | ++++ |
| P090 | ++++ |
| P091 | +++ |
| P092 | ++++ |
| P093 | +++ |
| P094 | ++++ |
| P095 | ++++ |
| P096 | ++++ |
| P097 | ++++ |
| P098 | ++++ |
| P099 | ++++ |
| P100 | ++ |
| P101 | ++++ |
| P102 | ++++ |
| P103 | ++++ |
| P104 | ++++ |
| P105 | ++++ |
| P106 | ++++ |
| P107 | ++++ |
| P108 | ++++ |
| P109 | +++ |
| P110 | ++++ |
| P111 | ++++ |
| P112 | ++++ |
| P113 | ++++ |
| P114 | ++++ |
| P115 | ++++ |
| P116 | +++ |
| P117 | +++ |
| P118 | ++++ |
| P119 | ++++ |
| P120 | ++++ |
| P121 | ++++ |
| P122 | ++++ |
| P123 | ++++ |
| P124 | ++++ |
| P125 | ++++ |
| P126 | ++++ |
| P127 | ++++ |
| P128 | ++++ |
| P129 | ++++ |
| P130 | ++++ |
| P131 | ++++ |
| P132 | ++++ |
| P133 | ++++ |
| P134 | ++++ |
| P135 | ++++ |
| P136 | ++++ |
| P137 | ++++ |
| P138 | ++++ |
| P139 | ++++ |
| P140 | ++++ |
| P141 | ++++ |
| P142 | ++++ |
| P143 | ++++ |
| P144 | ++++ |
| P145 | ++++ |
| P146 | ++++ |
| P147 | ++++ |
| P148 | ++++ |

CHART 1-continued

| Cmpd.No. | Activity |
|---|---|
| P149 | ++++ |
| P150 | ++++ |
| P151 | ++++ |
| P154 | ++++ |
| P155 | ++++ |
| P156 | ++++ |
| P157 | ++++ |
| P158 | ++++ |
| P159 | ++++ |
| P160 | ++++ |
| P161 | ++++ |
| P161 | ++++ |
| P162 | ++++ |
| P163 | ++++ |
| P164 | ++++ |
| P165 | ++++ |
| P166 | ++++ |
| P167 | ++++ |
| P168 | ++++ |
| P169 | ++++ |
| P170 | ++++ |
| P171 | ++++ |
| P172 | ++++ |
| P173 | ++++ |
| P174 | ++++ |
| P175 | ++++ |
| P176 | ++++ |
| P177 | ++++ |
| P178 | ++++ |
| P179 | ++++ |
| P180 | ++++ |
| P181 | ++++ |
| P182 | ++++ |
| P183 | ++++ |
| P184 | ++++ |
| P185 | ++++ |
| P186 | ++++ |
| P187 | ++++ |
| P188 | ++++ |
| P190 | ++++ |
| P191 | ++++ |
| P192 | ++++ |
| P193 | ++++ |
| P194 | ++++ |
| P195 | ++++ |
| P196 | ++++ |
| P197 | ++++ |
| P198 | ++++ |
| P199 | ++++ |
| P200 | ++++ |
| P201 | ++++ |
| P202 | ++++ |
| P203 | ++++ |
| P204 | ++++ |
| P205 | ++++ |
| P206 | ++++ |
| P207 | ++++ |
| P208 | ++++ |
| P209 | ++++ |
| P210 | ++++ |
| P211 | ++++ |
| P212 | ++++ |
| P213 | ++++ |
| P214 | ++++ |
| P215 | ++++ |
| P216 | ++++ |
| P217 | ++++ |
| P218 | ++++ |
| P219 | ++++ |
| P220 | ++++ |
| P221 | ++++ |
| P222 | ++++ |
| P223 | ++++ |
| P224 | ++++ |
| P225 | ++++ |
| P226 | ++++ |
| P227 | ++++ |

CHART 1-continued

| Cmpd.No. | Activity |
|---|---|
| P228 | ++++ |
| P229 | ++++ |
| P230 | ++++ |
| P231 | ++++ |
| P232 | ++++ |
| P233 | ++++ |
| P234 | ++++ |
| P235 | ++++ |
| P236 | ++++ |
| P237 | ++++ |
| P238 | ++++ |
| P239 | ++++ |
| P240 | ++++ |
| P241 | ++++ |
| P242 | ++++ |
| P243 | ++++ |
| P244 | ++++ |
| P245 | ++++ |
| P246 | ++++ |
| P247 | ++++ |
| P248 | ++++ |
| P249 | ++++ |
| P250 | ++++ |
| P251 | ++ |
| P252 | ++++ |
| P253 | ++++ |
| P254 | ++++ |
| P255 | ++++ |
| P256 | ++++ |
| P257 | ++++ |
| P258 | ++++ |
| P259 | ++++ |
| P260 | ++++ |
| P262 | ++++ |
| P263 | ++++ |
| P264 | ++++ |
| P265 | ++++ |
| P266 | ++++ |
| P267 | ++++ |
| P268 | ++++ |
| P269 | ++++ |
| P270 | ++++ |
| P271 | ++++ |
| P272 | ++++ |
| P273 | ++++ |
| P274 | ++++ |
| P275 | ++++ |
| P276 | ++++ |
| P277 | ++++ |
| P278 | ++++ |
| P279 | ++++ |
| P280 | ++++ |
| P281 | ++++ |
| P282 | ++++ |
| P283 | ++++ |
| P284 | +++ |
| P285 | ++++ |
| P286 | ++++ |
| P287 | ++++ |
| P288 | ++++ |
| P290 | ++++ |
| P291 | ++++ |
| P292 | ++++ |
| P293 | ++++ |
| P294 | ++++ |
| P295 | ++++ |
| P296 | ++++ |
| P297 | ++++ |
| P298 | ++++ |
| P299 | ++++ |
| P300 | ++++ |
| P301 | ++++ |
| P302 | ++++ |
| P303 | ++++ |
| P304 | ++++ |
| P305 | ++++ |
| P306 | ++++ |
| P307 | ++++ |
| P308 | ++++ |
| P309 | ++++ |
| P310 | ++++ |
| P311 | ++++ |
| P312 | ++++ |
| P313 | ++++ |
| P314 | ++++ |
| P315 | ++++ |
| P316 | ++++ |
| P317 | ++++ |
| P318 | ++++ |
| P319 | ++++ |
| P320 | ++++ |
| P321 | ++++ |
| P322 | ++++ |
| P323 | ++++ |
| P324 | ++++ |
| P325 | ++++ |
| P326 | ++++ |
| P327 | ++++ |
| P328 | ++++ |
| P330 | ++++ |
| P331 | ++++ |
| P332 | ++++ |
| P333 | ++++ |
| P334 | ++++ |
| P335 | ++++ |
| P336 | ++++ |
| P337 | ++++ |
| P338 | ++++ |
| P339 | ++++ |
| P340 | ++++ |
| P341 | ++++ |
| P342 | ++++ |
| P343 | ++++ |
| P344 | ++++ |
| P345 | ++++ |
| P346 | ++++ |
| P347 | ++++ |
| P348 | ++++ |
| P349 | ++++ |
| P350 | ++++ |
| P351 | ++++ |
| P352 | ++++ |
| P353 | ++++ |
| P354 | +++ |
| P355 | ++++ |
| P356 | ++++ |
| P357 | ++++ |
| P358 | ++++ |
| P359 | ++++ |
| P360 | ++++ |
| P361 | ++++ |
| P362 | ++++ |
| P363 | ++++ |
| P364 | ++++ |
| P365 | ++++ |
| P366 | ++++ |
| P367 | ++++ |
| P368 | ++++ |
| P369 | ++++ |
| P370 | ++++ |
| P371 | ++++ |
| P372 | ++++ |
| P373 | ++++ |
| P374 | ++++ |
| P375 | ++++ |
| P376 | ++++ |
| P377 | ++++ |
| P378 | ++++ |
| P379 | ++++ |
| P380 | ++++ |
| P381 | ++++ |
| P382 | ++++ |
| P383 | ++++ |
| P384 | ++++ |

CHART 1-continued

| Cmpd.No. | Activity |
|---|---|
| P385 | ++++ |
| P386 | ++++ |
| P387 | ++++ |
| P388 | ++++ |
| P389 | ++++ |
| P390 | ++++ |
| P391 | ++++ |
| P393 | ++++ |
| P394 | ++++ |
| P395 | ++++ |
| P396 | ++++ |
| P397 | ++++ |
| P398 | ++++ |
| P399 | ++++ |
| P400 | ++++ |
| P401 | ++++ |
| P402 | ++++ |
| P403 | ++++ |
| P404 | ++++ |
| P405 | ++++ |
| P406 | ++++ |
| P407 | ++++ |
| P408 | ++++ |
| P409 | ++++ |
| P410 | ++++ |
| P411 | ++++ |
| P412 | ++++ |

CHART 1-continued

| Cmpd.No. | Activity |
|---|---|
| P413 | ++++ |
| P414 | ++++ |
| P415 | ++++ |
| P416 | ++++ |
| P417 | ++++ |

Chemical Synthesis

Generally compounds of the Formula I, may be prepared from appropriately functionalized substituted bicyclo cores as shown in schemes 1 to 17. In particular when node "a" is a nitrogen atom, one may either first functionalize the carbon atom, node "b", of bicycle core G1 (which in Scheme 1 is a halogen atom) via palladium mediated Heck coupling to provide carbon linked ester (G2) or amide (G4). Otherwise the linkage at 'node b=C' may be thru a heteroatom (G6) as shown in Scheme 2. The intermediates G2 and G6 then may be functionalized at the node "a" (a nitrogen atom of a bicycle core) to provide peri-substituted esters G3 and G7, Schemes 1 and 2 respectively. The introduction of nitrogen substituents may be achieved either prior to (G3 or G7) or following functionalization of the carboxylic acid (G4 or G8) to provide the acylamide/acylsulphonamides G5 and G9, which are encompassed by the formula I.

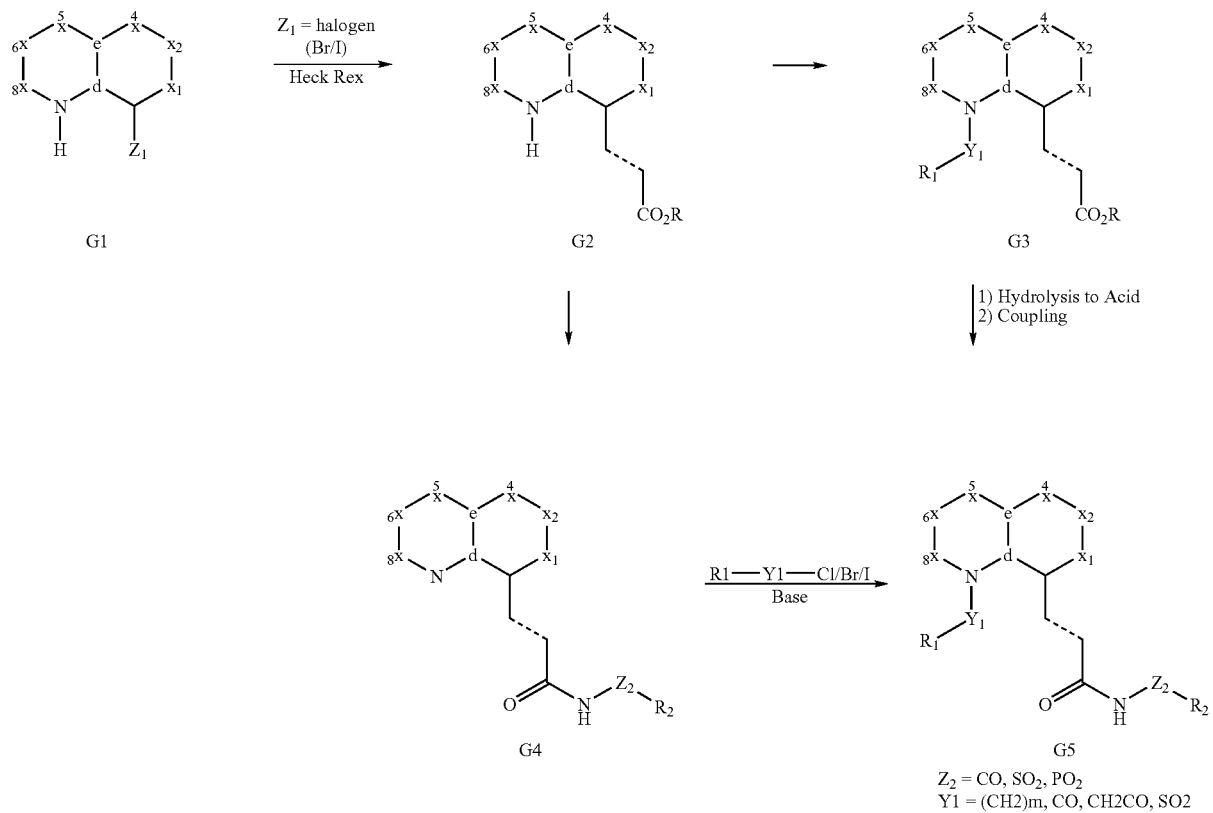

Scheme 1.

----- denotes single or double bond

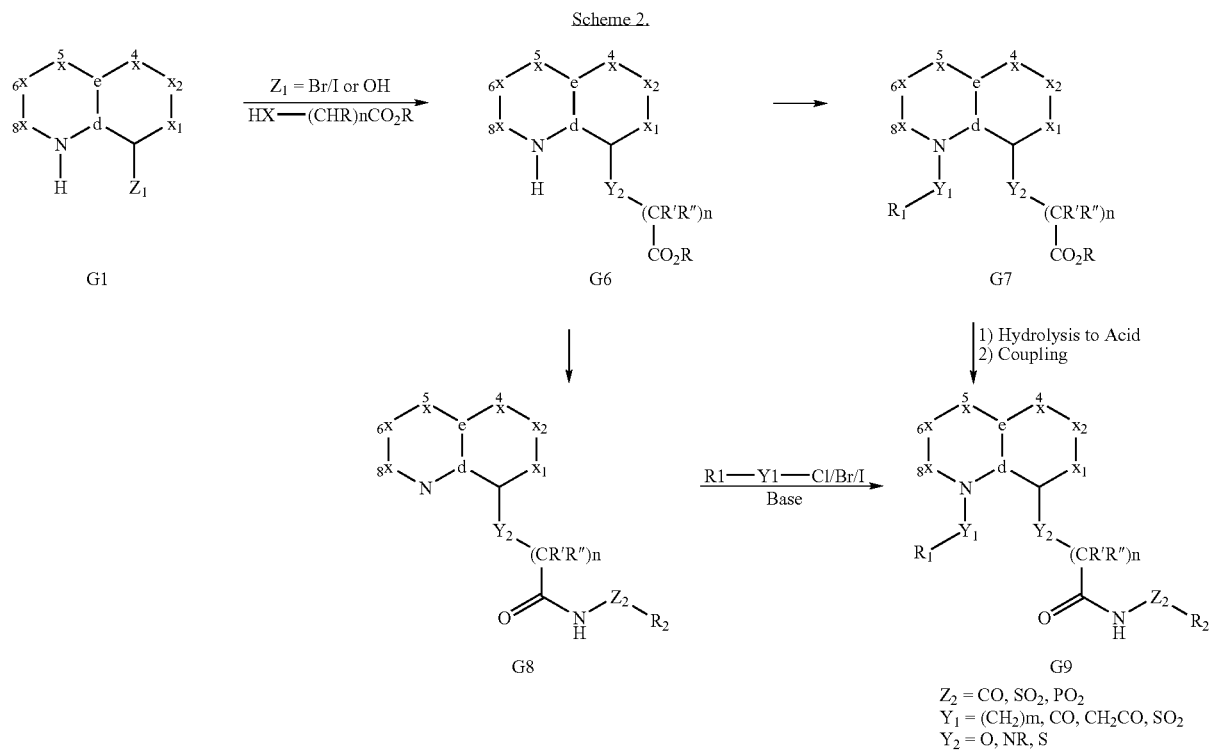

Scheme 2.

When the node "b" as carbon bears an ester or a nitrile functional group, reduction provides the corresponding alcohol or amine, G10, as in Scheme 3 and 4. The alcohol or amine may be subsequently alkylated, acylated or reacted with an isocyanate to provide peri-substituted bicyclic intermediate G11 which in turn can be converted to compounds of formula I where the acylsulphonamide etc. contain diverse tethers, as depicted in G12. Alternatively, amine G10 may be reacted with cyclic (saturated or aryl/heteroaryl) isocyanates bearing a carboxylate ester to provide a more rigid cyclic linker separating the bicyclic core and the acyl sulphonamide functionality as in G14 (Scheme 4). In similar fashion, the derivatives wherein the carbon of the bicylic core G1 directly bears a nitrogen (e.g. nitro/amine, G15/G16) provide corresponding amides or ureas as spacer for the acylsulphonamides G18, as shown in Scheme 5.

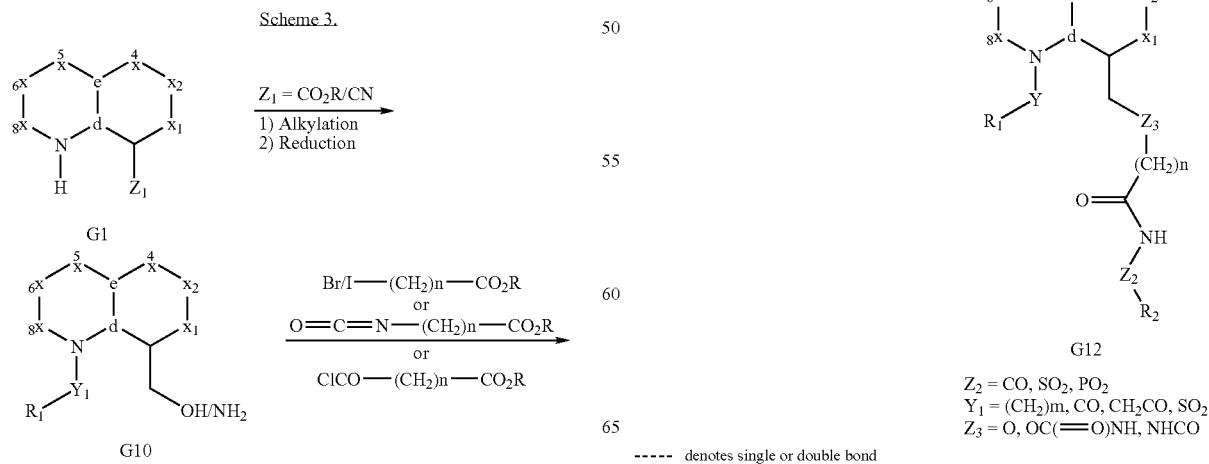

----- denotes single or double bond

Scheme 4.
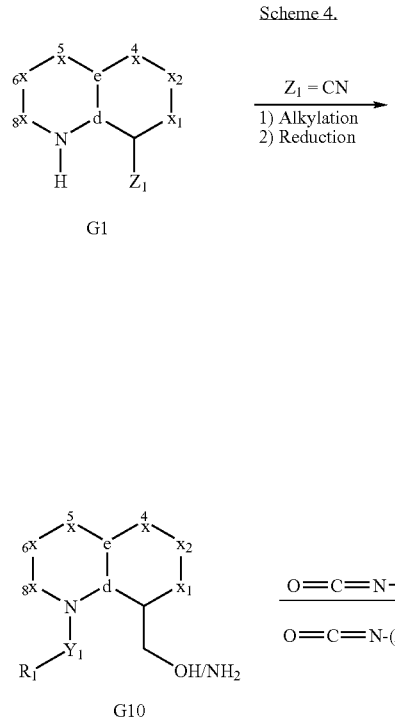
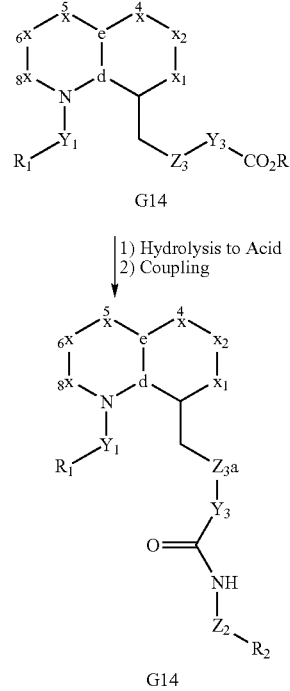
$Z_2 = CO, SO_2, PO_2$
$Y_1 = (CH_2)m, CO, CH_2CO, SO_2$
$Z_{3a} = O(CO)NH, NHCONH$
$Y_3 = $ cycloalkyl, aryl hetroaryl
Scheme 5.
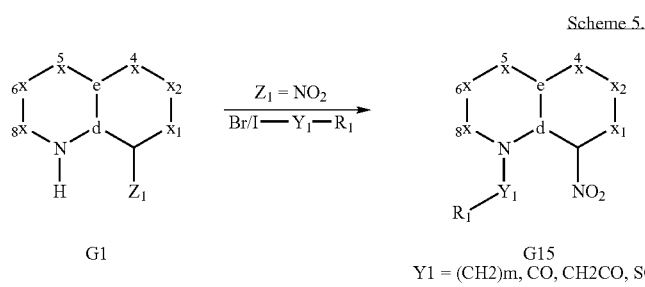
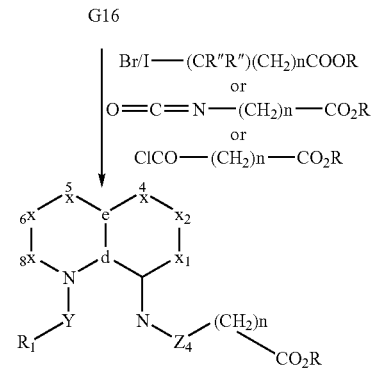
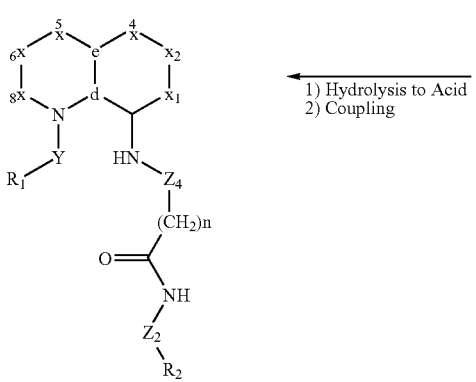
$Z_2 = CO, SO_2, PO_2$
$Z_4 = CR'R'', CO, CONH$ Bicyclic cores wherein both the nodes "a" and "b" are carbons, can be obtained from starting materials such as G19. The functionalization of the halogen bearing carbon through a palladium-mediated ether or amine formation via Buchwald chemistry is followed by introduction of an acyl or formyl group via electrophilic reaction to provide the key peri-functionalized intermediate G20. The latter reaction is particularly applicable where the ring (b) of the bicyclic core is electron rich. Reaction of the ketone or aldehyde by a Wittig reagent yields the desired olefin linked ester, which may be reduced to provide corresponding saturated linker, if desired. Alternatively, the ketones or aldehydes may be reacted with appropriate enolate (or even homo-enolate) to provide additional functional groups (Y4=OH, e.g.) in the linker portion, to provide G22. The functional group Y4 may be further derivatized or eliminated to provide the olefin linkage. In addition, the benzylic alcohol of G21 may be converted to a halide (e.g. Br) and the benzylic halide may thus be converted via Heck coupling or alternatively reacted with ICH2CH2COOR [Higuchi K. et. Al. Org. Letters 2003 3704-3704] to provide product G24. The aldehyde/ketone G20 upon. reaction with a homo-enolate provides the ester G22. Subsequent derivatization of G22 or G24 leads to the prodcuts G23 and G26, respectively.

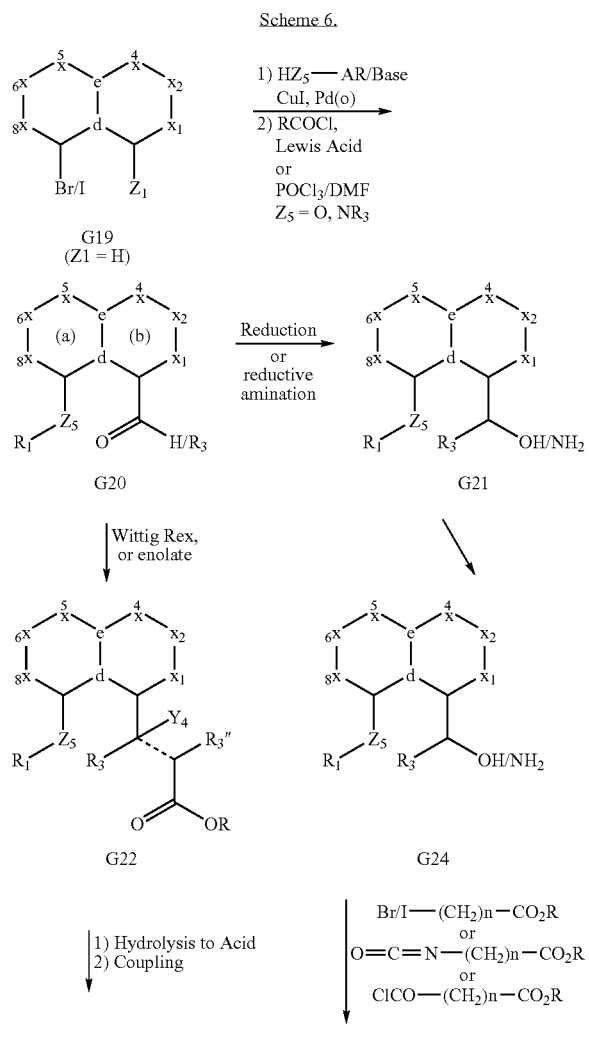

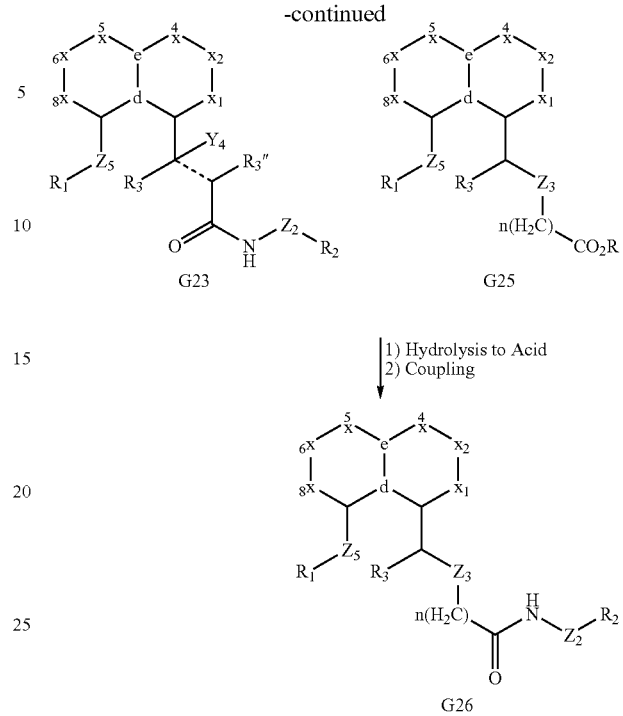

$Z_2$ = CO, $SO_2$, $PO_2$
$Z_3$ = O, OC(=O)NH, NHCO

----- denotes single or double bond

Additional examples of highly reactive/electrophilic bicyclic cores, in which introduction of heteroatom-linked functionalities provides access to both carbon-linked peri-functionalities, are shown in scheme 7 and 8. These synthetic routes provide means to introduce the acyl portion of the fragment containing diverse linkers. These chemistries provide for introduction of sulphur linked aryl and heteroaryl groups and allow for adjustment of sulphur oxidation state, as well, thus providing access to analogs represented by G31 and G36. Alternatively, by use of ketones G37, one may prepare compounds related to G31/G36, which provide access to cores such as benzofuran and benzothiophene, G40

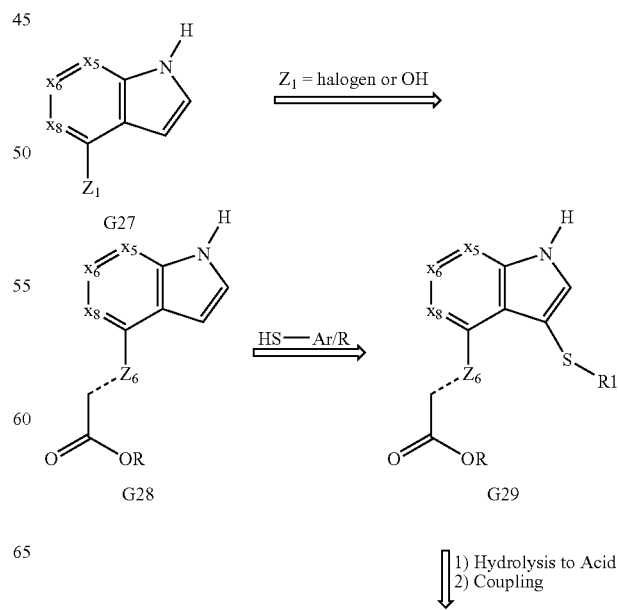

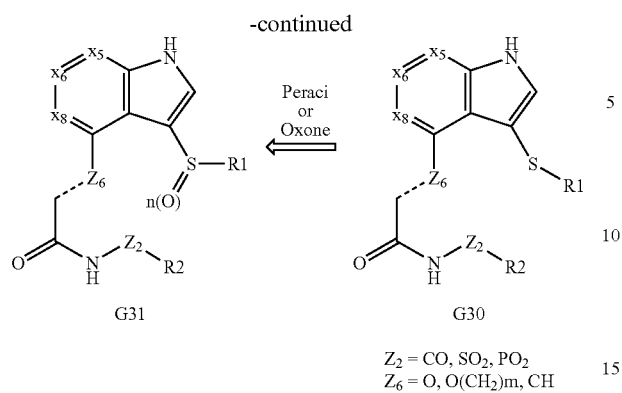
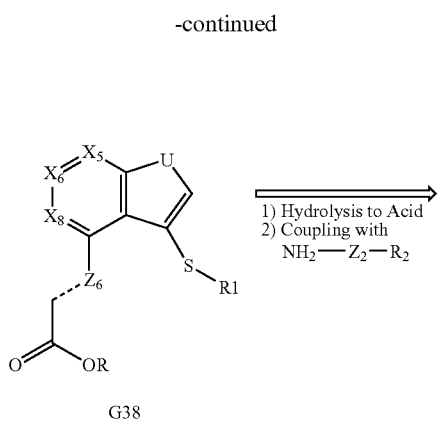
Z$_2$ = CO, SO$_2$, PO$_2$
Z$_6$ = O, O(CH$_2$)m, CH
---- denotes single or double bond
Scheme 8.
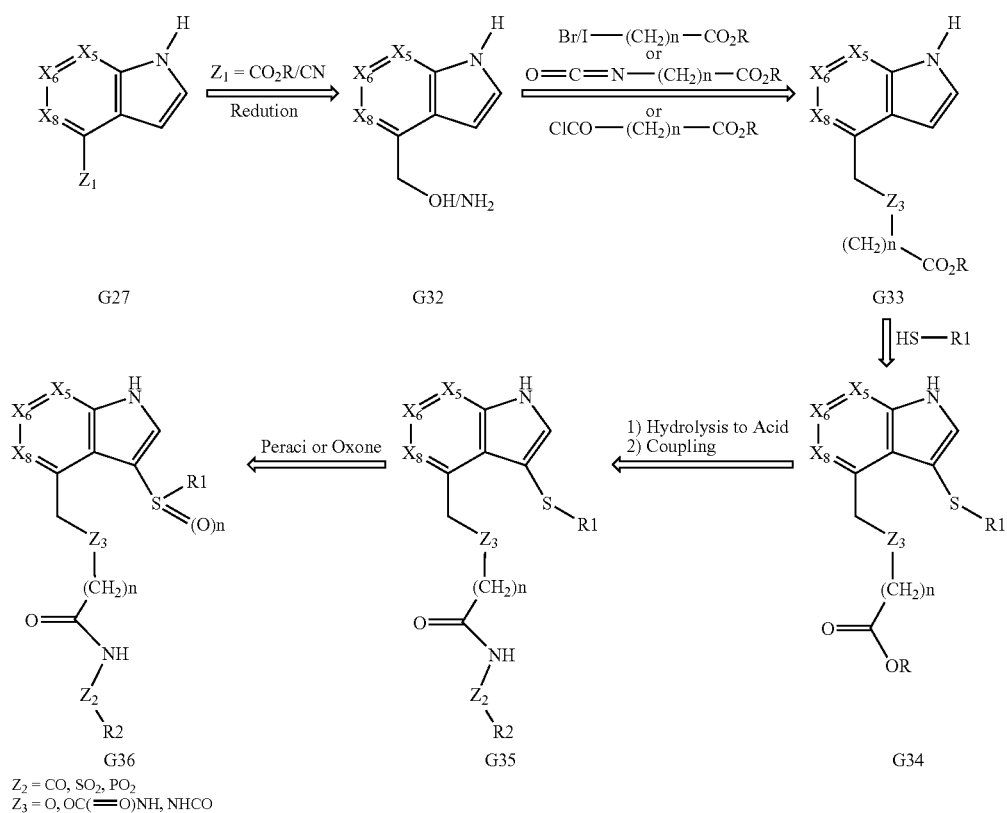
Z$_2$ = CO, SO$_2$, PO$_2$
Z$_3$ = O, OC(=O)NH, NHCO
Scheme 9.
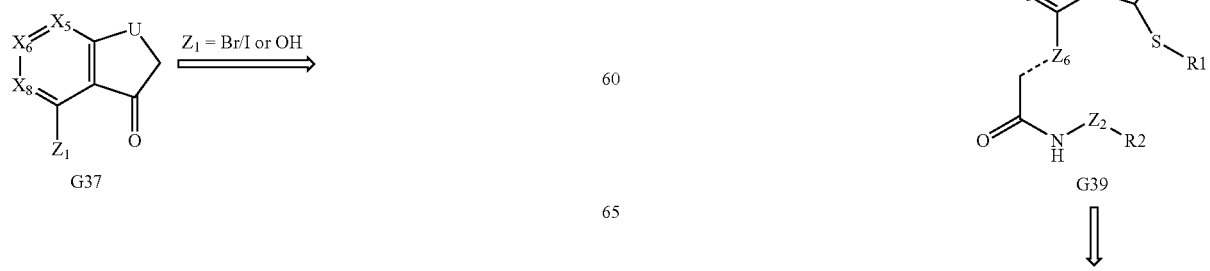

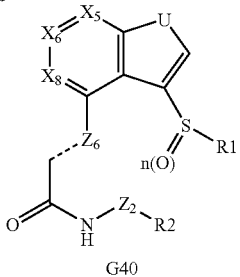

G40

$Z_2$ = CO, SO$_2$, PO$_2$
$Z_6$ = O, O(CH$_2$)m, CH
U = O, S, CH2, C(RaRb)

The high nucleophilicity of thiols permits the use of cores such as G27, as shown in the conversion of G33 to G34 in Scheme 8. In order to prepare corresponding aza (or oxa) linked aryl/heteroaryl/alkyl groups (R1), one may utilize reactive intermediates related to isatin, as shown by G43, which is derived from G41, Scheme 10. As shown in scheme 10, the intermediate G43 provides access to a variety of aza linked compounds, which are all derived by carbon linked attachment to the bicyclic core. Another, isatin based intermediate (shown in Scheme 11) provides peri-substituted bicyclic compounds; this route provides access to functionalities which are linked through carbon and nitrogen atoms of the core bicyclic system. In addition, access to the key intermediate G56, which contains a reactive carbonyl, distal to the peri-substituents ending in R1 and R2, allows for applying a range of chemistries as outlined in Scheme 11. These chemistries, e.g. ketal formation, addition to carbonyl and reaction with DAST provide access to analogs which bear diverse functionalities, as shown by G56-to-G60. Analogs in scheme 10 and 11 also provide access to bicyclic cores which contain one or both rings that are non-aromatic.

Scheme 10

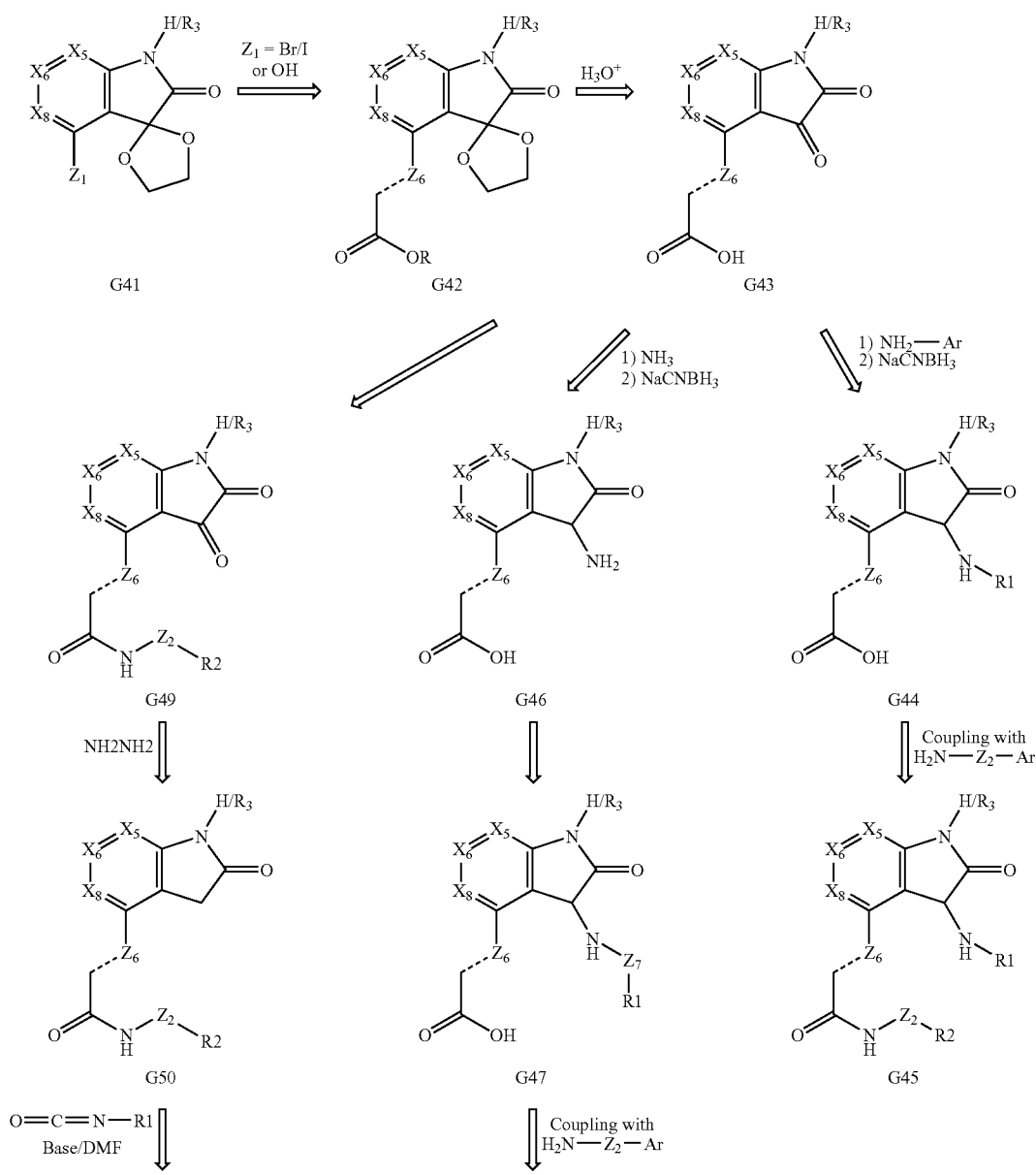

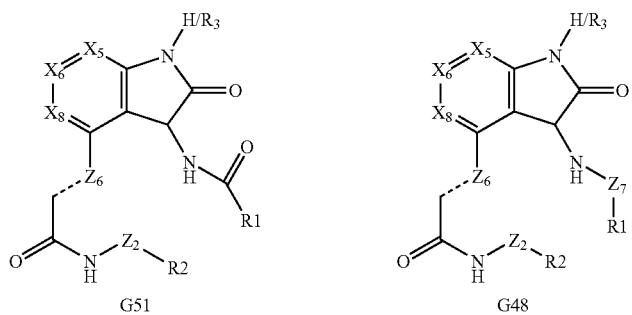
$Z_2$ = CO, SO$_2$, PO$_2$
$Z_6$ = O, O(CH$_2$)m, CH
$Z_7$ = CO, SO$_2$
Scheme 11.
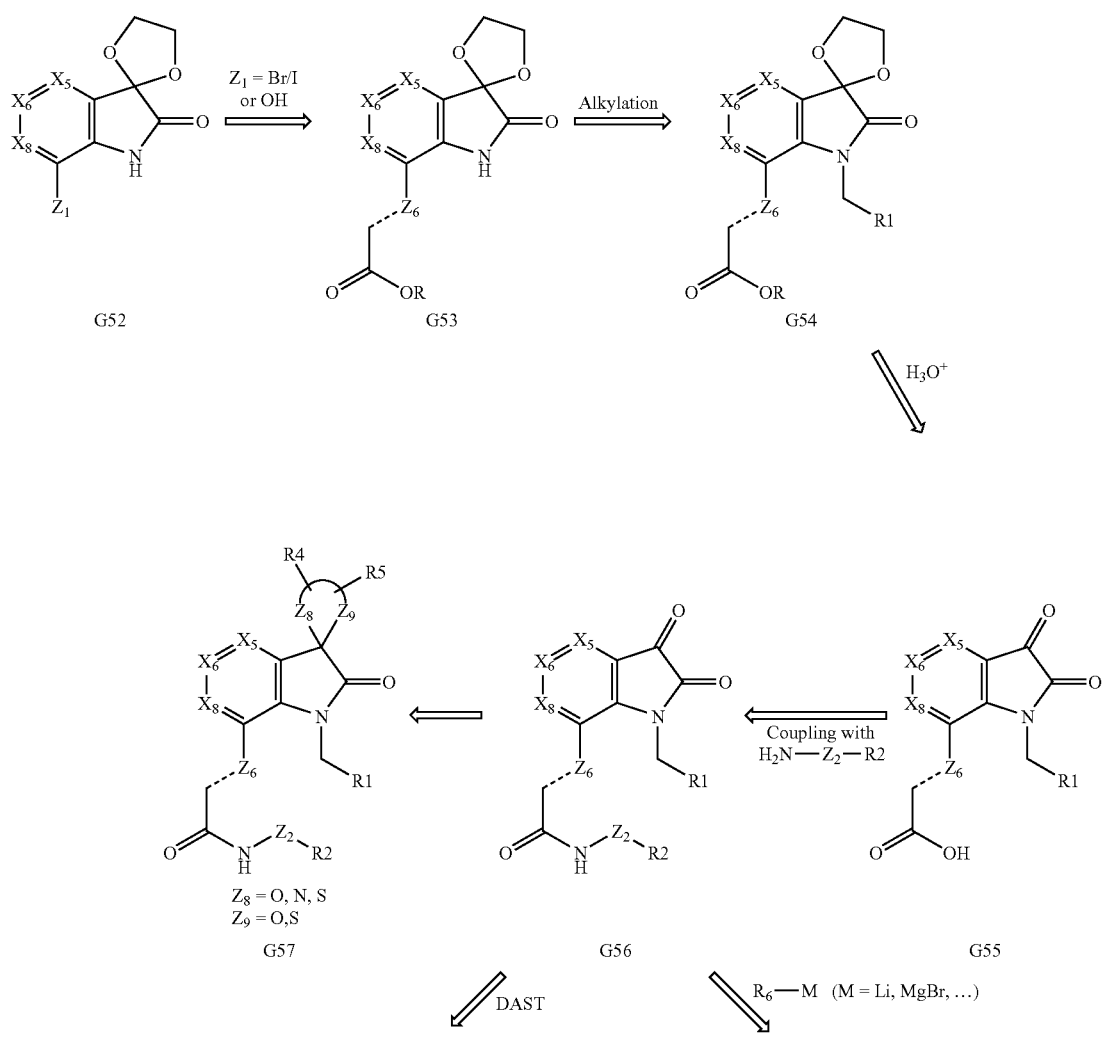
$Z_8$ = O, N, S
$Z_9$ = O, S -continued

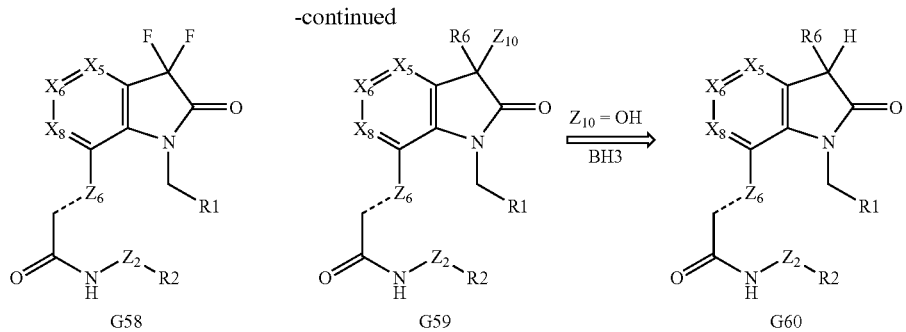

$Z_2$ = CO, SO$_2$, PO$_2$
$Z_6$ = O, O(CH)m, CH
$Z_{10}$ = OH, OR$_3$, F(w/ DAST)

The synthetic routes outlined above essentially all utilize a bicyclic core, which is appropriately derivatized to obtain compounds described by formula I. The following chemistries provide for introduction of at least the peri-fragments as part of the construction of bicyclic core. The chemistry in Scheme 12, involves a three component condensation reaction, whereby an α,γ-diketoester (G62), upon reaction with an aldehyde and a primary amine, provides a monocyclic product G63. The product G63 upon reaction with e.g. hydrazine (or mono substituted hydrazine) provides the peri-substituted bicyclic core (in this case a 5-5 ring system, as shown by G64), which then leads to the analog G65.

Other examples of chemistries that involve formation of bicyclic cores are outlined in Schemes 13 and 14, which present syntheses of benzimidazole-based cores. In order to prepare a peri-substituted system, the R1 group is introduced regiospecifically at step G67-G68, which, upon subsequent ring closure, provides the desired peri-substituted derivative G69. In Scheme 14, the desired regiospecific introduction of the R1 group is accomplished by O to N acyl migration followed by reduction of amide to secondary amine. In this case ring closure also provides the desired peri-substituents, as in G77.

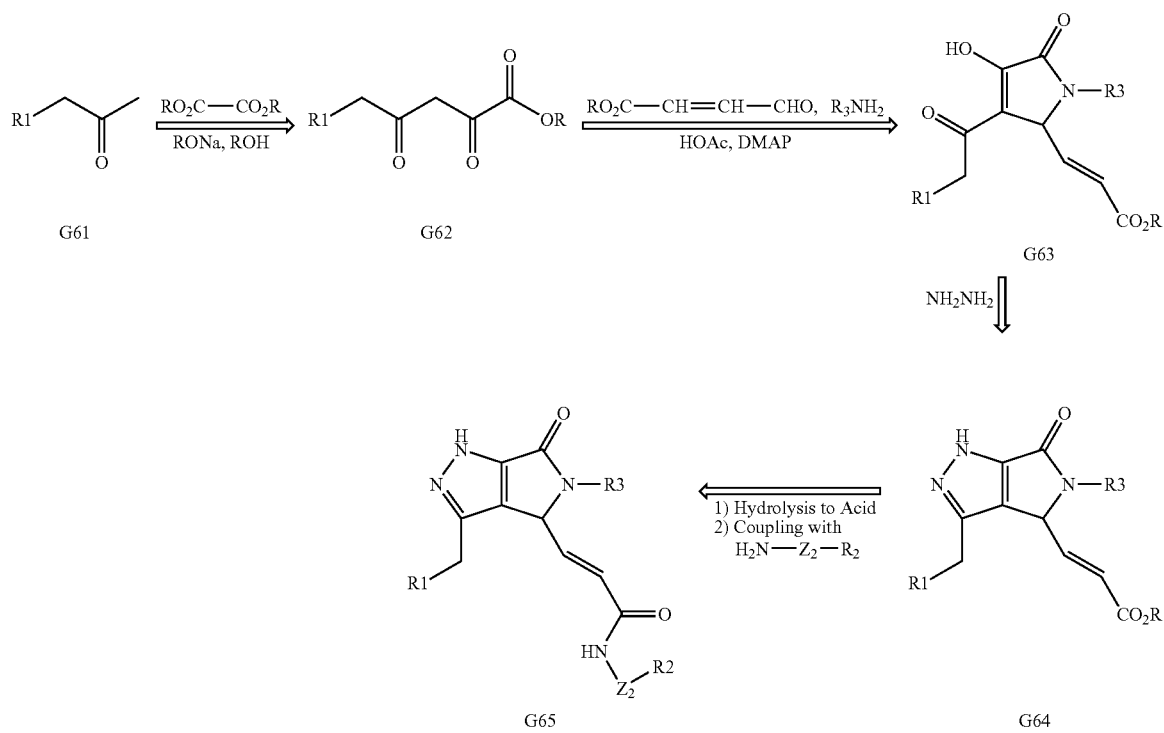

Scheme 13.

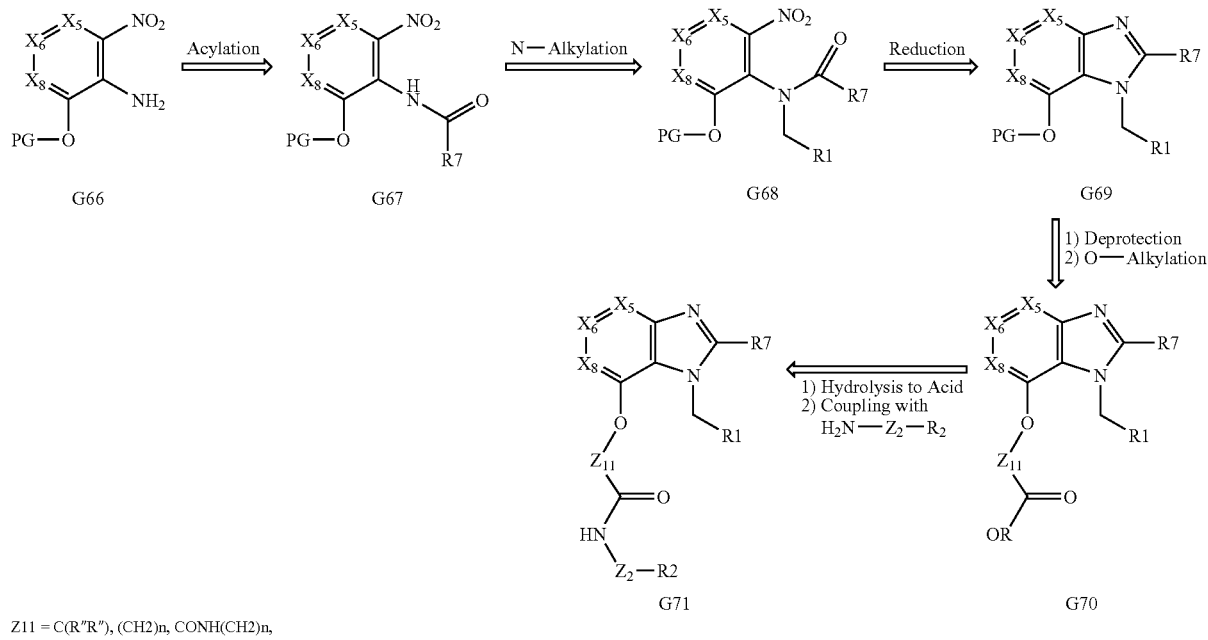

Z11 = C(R″R″), (CH2)n, CONH(CH2)n,

Scheme 14.

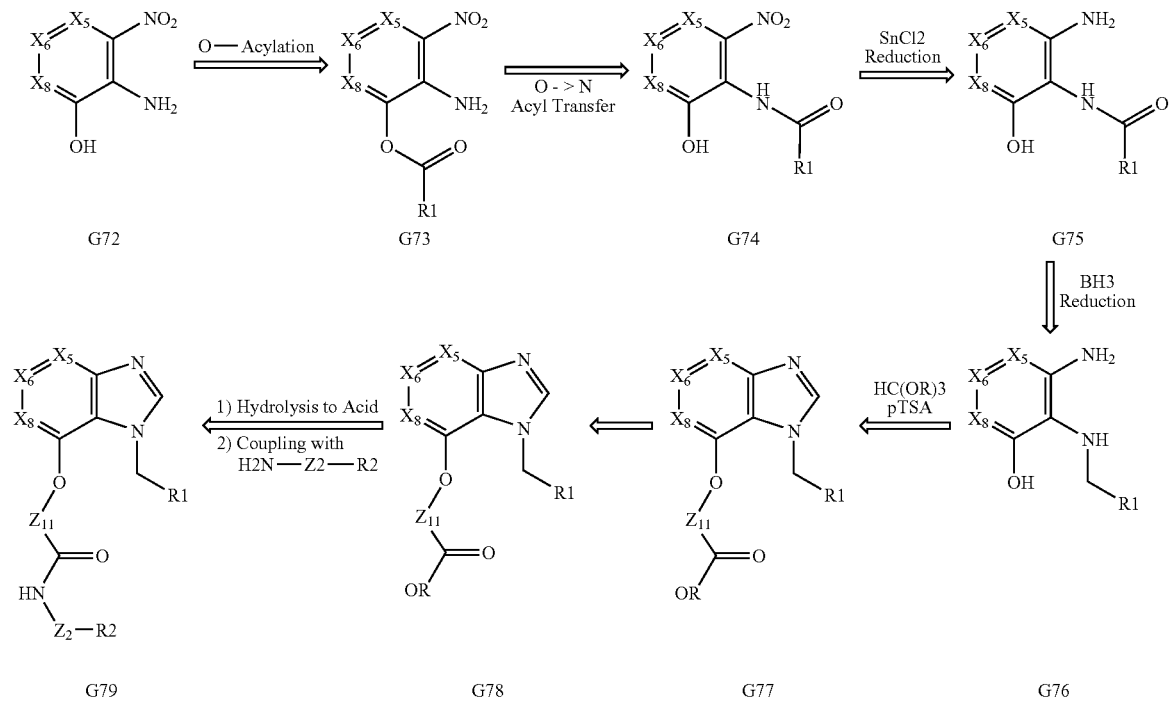

Z11 = C(R″R″), (CH2)n, CONH(CH2)n,

Another example of the chemistries involved in formation of bicyclic cores with desired peri-functionalization is depicted in Scheme 15. Here, a thermal cyclization of an amine with a cyclic disposed γ-keto acid G82 provides the required bicyclic intermediate G83. Bromination followed by e.g. Heck reaction provides the desired peri-bicyclic derivative G85 that upon further derivatization provides compound G87. This chemistry allows synthesis of essentially non aromatic ring systems and also provides for formation of bicyclic ring systems wherein the ring (a) is 5-membered. Ring (a) is produced during the cyclization reaction, whereas the size of the ring (b) is controlled by the use of the cyclic ketone at the initial step of the synthesis and thus allow for formation of "5-N" bicyclic system. In addition to the size, the substituent and presence of heteroatoms in the cyclic ketone also allows flexibility. The nature of the tertiary group may also be varied and this may be introduced at the cyclic ketone stage, which allows significant control over its regiochemistry. The positions X5/X6 may be heteroatoms and/or contain additional substituents as well.

Scheme 15.

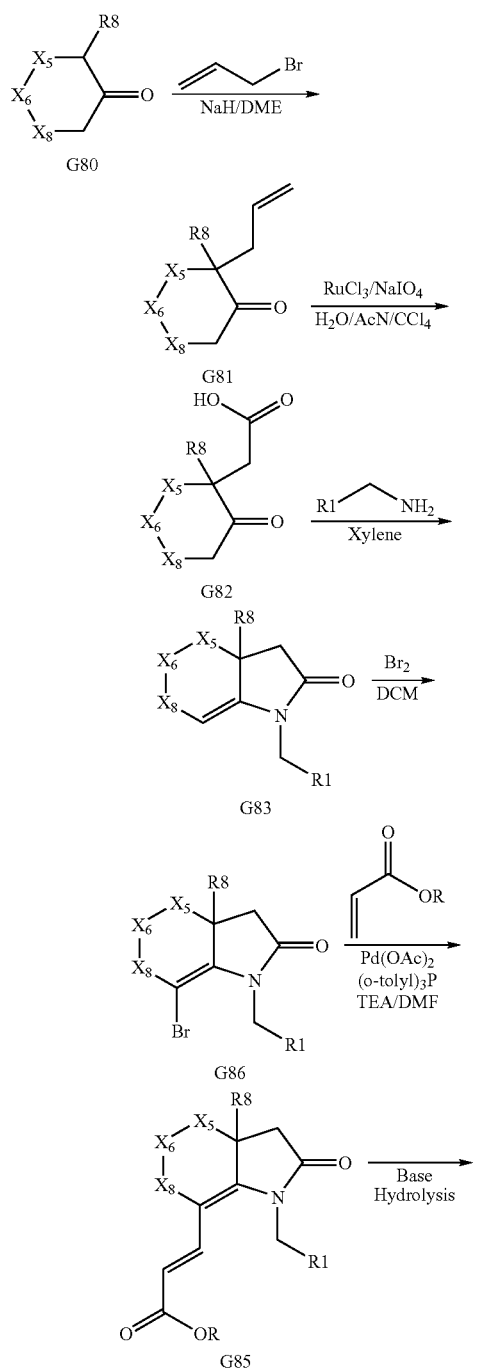

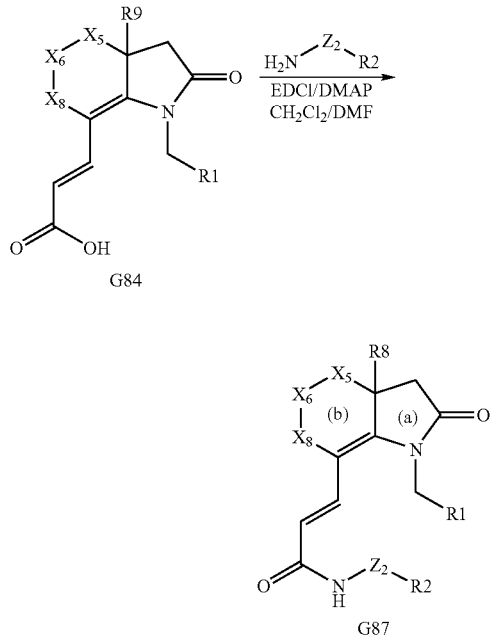

An example which allows the introduction of an acyl fragment (bearing $R^2$) via electrophilic reaction is shown in Scheme 16. This leads to preparation of analogs represented by G90 and G91. The benzylic carbonyl group present in G90 and G91 may be further derivatized, e.g. by reduction to alcohol or $CH_2$, formation of oxime, imines or hydrzides, ketals, etc.etc. The late stage reduction also allows one tom introduce radiolabled carbon ($^{14}C$) or tritium ($^3H$) to provide analogs for various in-vitro and or in-vivo studies.

Scheme 16.

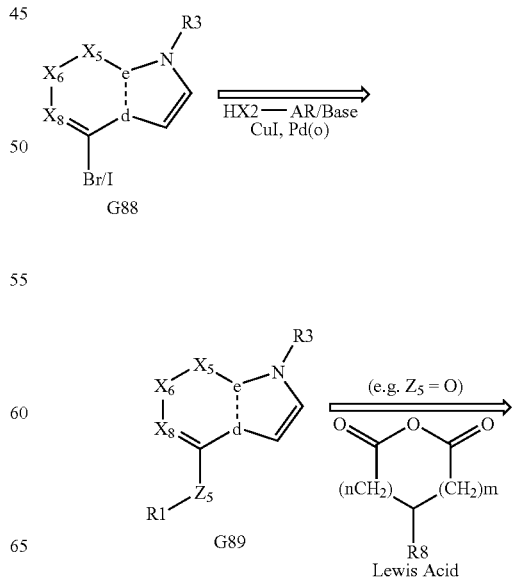

-continued

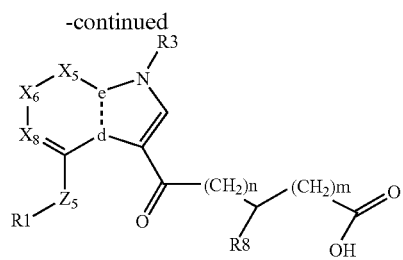

G90

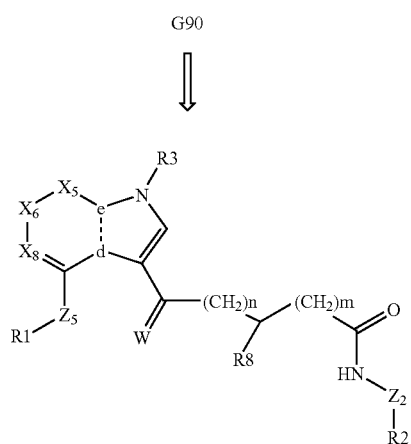

G91
W = O, H2, N(OH), N(OR), N(R)
—[QCH$_2$(CR″, R‴)n(CH$_2$)P]—
Q/P = O, N, S,

Compounds of general structure G92 (shown below) are either commercially available or easily accessible from commercially available materials by procedures described in the literature. Replacement of the Y (halogen/triflate) of G92 can be accomplished to provide aryl ethers, sulfides or anilines, respectively (G93). In G93, where W is NH, the N-derivatized product G94 could be obtained either via N-alkylation or Michael addition to an acrylate (or propiolate). Ester G94 is subsequently elaborated as described in schemes above to compounds G95. However, when G93 represents a bicyclic heterocycle, where W=CH, introduction of side chain bearing an ester functionality leads to G97. The derivatization from G93 could be via formylation (G96, X=CHO) followed by Wittig or derived chemistries to afford the corresponding esters G97. Alternatively, G93 could be halogenated to provide G96 (X=halogen). Displacement of this halogen with heteroatomic nucleophiles (hydroxyl, mercapto or animoesters) provides ether, thioether or anime derived product G97 (where $Z_7$=O, N, or S). These compounds are then elaborated to the desired acylsulfonamides or related products, G98, as described above. G98 may be derivatized further to give compounds G99. In addition, the carboxylic acid derived from G94 and/or G97 may be coupled with H2N-Z3, where Z3=NH2-Z2-R2 (when Z2=NHSO2, NHCO or NHPO) resulting in acyl hydrazide (RC(=O)NHNHC(=O)R), acylsulphydrazide (RC(=O)NHNHS(=O)2R), or acyl phosphorhydrazide (RC(=O)NHNHP(=O)R1R2), respectively. In fact, such transformations may also be carried out for the carboxylic acids that are derived from chemistries described in schemes 1-16, above.

Scheme 17

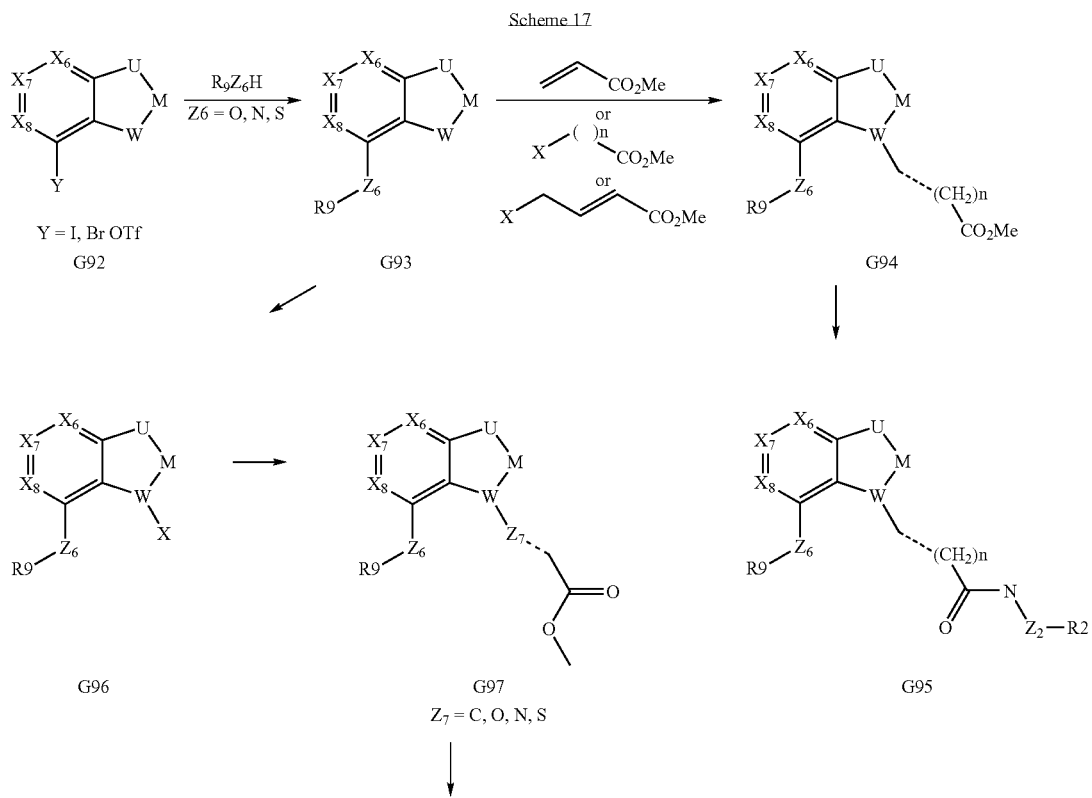

-continued

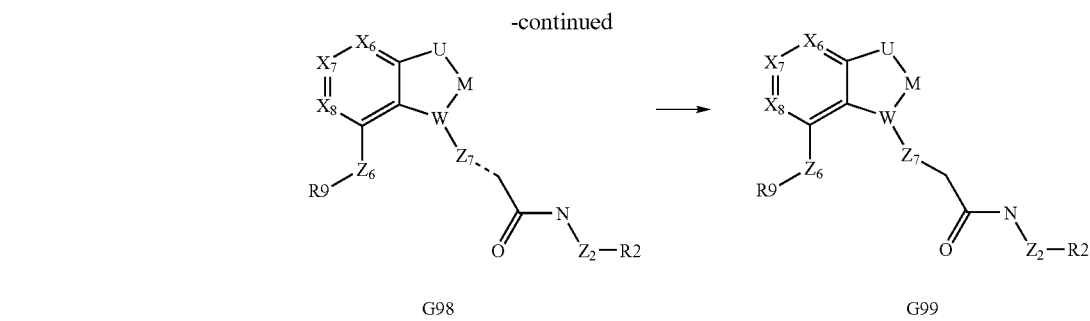

G98 G99

- - - - - represents a single or a double bond

Finally, several appropriately functionalized bicylic cores are either commercially available or their syntheses are described in the published literature or could be inferred by one skill in the art. Examples of several of these are described as part of the Specific Examples. Some of these are summarized below.

For bicyclic systems wherein one of the nodes is nitrogen, indole derivatives serve as a readily accessible and useful core. The 4-bromo and 4-hydroxy indoles are commercially available. The 7 substituted indoles, e.g. 7-$CO_2$R, 7-alkoxy, 7-benzyloxy, etc. can be prepared by Batcho-Leimgruber chemistry from appropriately substituted 2-nitrotoluene, (Org Synthesis Co, Vol. 7). This approach also provides access to 7-Me, 7-CHO, 7-CN, and 7-OH indoles by functional group manipulations. Alternatively, the 7-halo indoles are accessible from 2-halo anilines via Bartoli chemistry (Bartoli, G. et. al. Tett. Letters, 1989, 30, 2129-2132). Diverse 7-substituted indoles may also be prepared via selective functionaliztion of indole via directed ortho metalation according to the procedure of Snieckus, [Snieckus V. et.al. Org Letters 2003, 1899-1902]. These various approaches also provide access to other substituted indole derivatives. The 8-hydroxytetrahydroquinolines, a [6:6]-based core, can be obtained from commercially available 8-hydroxy quinoline by reduction. 8-OH-1H-Quinolin-2-one, 8-OH-3,4 dihydro-1H-Quinolin-2-one. 2,6-dihydroxy anilines or related heterocycles may be transformed to 5-hydroxy-4H-benzo[1,4]oxazin-3-one, 5-hydroxy-4H-benzo[1,4]oxazin-2,3-dione, 4-hydroxy-3H-benzooxazol-2-one, bicyclic derivatives. Oxidation of indole based 1,7-disubstituted or 3,4-disubstituted bicyclo analogs provides corresponding oxy-indole derivatives. Various anilines may be converted to isatin analogs using the literature procedures, and examples of these are described in the specific example section below. Synthesis of a series of [5:5] bicyclic cores (e.g. imidazothiazole and pyrrolopyarzolone) are described in the specific examples. A diverse group of [6:5] bicyclo cores can also be obtained analogous to literature syntheses of cores such as imidazopyridine and imidazopyrimidine [Katritzky A. R. et.al. JOC 2003, 68, 4935-37], pyrrolopyrimides [Norman M. et.al. JMC 2000, 43, 4288-4312]. These diverse bicyclo cores may then be derivatized to provide analogs of formula I.

Overall, the range of chemistries shown above allows for preparation of potent prostenoid antagonists/agonists. The chemistry allows manipulation of the core structure and introduction of optimal functional groups to provide a desired balance of hydrophobicity-hydrophilicity; it allows introduction of hydrogen bond donor and acceptors with desired topology; it allows adjustment of desired physical characteristics suitable for achieving desired pharmaceutical and ADME properties (e.g. membrane permeability, low plasma protein binding, desired metabolic profile etc.). The ability to adjust physiochemical characteristics permits suitable formulation for oral bioavailability, which in turn allows for control over the size and frequency of dose administered to mammals to achieve desired pharmacological response. The ability to adjust metabolic profile allows for minimizing potential for drug-drug interactions. Thus the scope of this invention not only provides for preparation of potent prostenoid antagonists with proper isozyme selectivity to be useful tools for research, it also provides compounds are of value in therapy.

EXAMPLES

The following specific non-limiting examples are illustrative of the invention.

Example 1

Preparation of P001

Indole-7 carboxyldehyde (I-1). Ethyl Indole-7 m carboxylate was prepared according to literature procedure {Batcho B. and Leimgruber, K., Org. Syn. Vol IIV, page 34-40). To a solution of methyl 7-indolecarboxylate (13 g, 74.2 mmol) in 250 ml of anhydrous THF was added LiAlH$_4$ (10.9 g, 0.288 mol) in portions, and reaction mixture was heated to reflux for 2 h. After cooling to room temperature, the excess hydride was quenched by addition of water (12 mL), 15% NaOH (12 mL) and water (26 mL). The solids were removed by filtration through a pad of Celite and filtrate was evaporated in vacuo to yield (1H-indol-7-yl)-methanol (10.7 g, 98%). $^1$HNMR (CDCl$_3$). To a solution of the alcohol, (1H-indol-7-yl)-methanol (8.0 g, 54.3 mmol) in 400 mL of methylene chloride was added activated manganese (IV) oxide (85%, 41.0 g, 0.40 mol), and stirred at ambient temperature for 72 h. After additional of 200 mL of methylene chloride and 400 mL of methanol to the reaction mixture, the whole mixture was filtered through a pad of silica gel to remove solid materials. The filtrate was concentrated to afford a crude product, which was purified by a column chromatography on silica gel to yield 1H-indole-7-carbaldehyde, I-1 (6.55 g, 83%). $^1$HNMR (CDCl$_3$).

3-(1H-Indol-7-yl)-acrylic acid ethyl ester (I-2). To a round bottom flask (100 mL) which contained a suspension of NaH (60% in mineral oil, 320 mg, 8 mmol) in THF (20 mL) was added triethylphosphonoacetate (1.5 g, 6.6 mmol) at 0° C. The mixture which resulted was allowed to warm to rt and stir for 2 h and then cooled to 0° C. To this solution, indole-7- carboxaldehyde I-1 (450 mg, 3 mmol) was added at 0° C. The reaction mixture that resulted was allowed to warm to rt and stir for 2 h, then heated to 78° C. and stirred at 78° C. for 14 h. The reaction mixture was cooled to 5° C. and was quenched with the addition of aq NH₄Cl (saturated, 15 mL) followed by extraction of EtOAc (3×30 mL). The combined organic layers were washed with brine (2×20 mL), dried (Na₂SO₄) and the solvent was removed under reduced pressure. The residue was purified by flash chromatography (silica gel, EtOAc/hexane=1:20-1:8) to afford desired 3-(1H-indol-7-yl)-acrylic acid ethyl ester I-2 (450 mg, 68%) as a white solid. MS(ESI⁻) m/z(216.3, 100%). 1H NMR (CDCl3), 13C NMR (CDCl3).

3-(1H-Indol-7-yl)-acrylic acid (I-3) To a round bottom flask (500 mL) which contained a solution of NaOH (1.2 g, 30 mmol) in EtOH (100 mL) and H₂O (30 mL) was added 3-(1H-Indol-7-yl)-acrylic acid ethyl ester 2 (3.2 g, 15 mmol) at 5° C. The resulted mixture was allowed to warm to rt and stir for 10 min, then heated to 78° C. and stirred for 4 h. The reaction mixture was cooled to 5° C. and was acidified with addition of aq HCl (10%) until pH=1, which was followed by extraction with CH₂Cl₂/MeOH (95/5, 3×150 mL). The combined organic layers were washed with brine (2×20 mL), dried (Na₂SO₄) and the solvent was removed under reduced pressure to provide the crude product, which was purified by recrystallization from acetone/EtOAc/hexane to yield desired 3-(1H-indol-7-yl)-acrylic acid I-3 (2.4 g, 86%) as a white solid. MS(APCI−)m/z(186.2, 100%). LCMS(APCI−)>95%.

Thiophene-2-sulfonic acid ((E)-3-1H-indol-7-yl-acryloyl)-amide (I-4) To a round bottom flask (500 mL) which contained a solution of thiophenesulfonamide (1.05 g, 6 mmol), 4-dimethyaminopyridine (DMAP, 1.56 g, 13 mmol) and 1-[3-(dimethyamino)propyl]-3-ethylcarbodiimide hydrochloride (EDCI, 2.4 g, 13 mmol) in CH2Cl2 (150 mL) was added 3-(1H-indol-7-yl)-acrylic acid I-3 (1.2 g, 6 mmol) at rt. The mixture which resulted was allowed to stir at rt for 72 h, then was cooled to 5° C. and was acidified with addition of aq HCl (10%) until pH=1, which was followed by extraction of CH2Cl2/MeOH (9/1, 3×100 mL). The combined organic layers were dried over anhyd. Na2SO4 and the solvent was removed under reduced pressure to provide the crude product which was purified by flash chromatography (silica gel, CH2Cl2; CH2Cl2/EtOAc/hexane=1:10:20-1:20:10) to afford desired thiophene-2-sulfonic acid (3-1H-indol-7-yl-acryloyl)-amide I-4 (1.2 g, 56%) as a white solid. MS(ESI⁻)m/z(331.1, 100%). LCMS(ESI−)>95%.

General procedure for N-alkylation of Thiophene-2-sulfonic acid (3-1H-indol-7-yl-acryloyl)-amide (A-1). To a suspension of NaH (60% in mineral oil, 5 mg, 0.11 mmol) in DMF (5 mL) was added thiophene-2-sulfonic acid (3-1H-indol-7-yl-acryloyl)-amide I-4 (20 mg, 0.066 mmol) at 0° C. [Except, when the Ar/R—CH2Br(Cl) used was in the form of a salt, e.g. HCl salt, an additional eq. of NaH was used]. The mixture which resulted was allowed to warm to rt and stir for 2 h and then cooled to 0° C. To this solution, ArCH₂Br(or Cl) (0.072 mmol, 1.1 eq) was added at 0° C. and the reaction mixture which resulted was allowed to warm to rt and stir for 16-48 h, The reaction mixture was cooled to 5° C. and was acidified with addition of aq HCl (10%) until pH=1, which was followed by extraction of CH2Cl2/MeOH (9/1, 3×10 mL). The combined organic layers were dried over anhydrous Na2SO4, and the solvent was removed under reduced pressure to provide the crude product which was purified by flash chromatography (silica gel, CH2Cl2; /EtOAc/hexane,=1:8-1:2); recrystallization or trituration from ether to afford desired N-alkylated thiophene-2-sulfonic acid (3[CH2R]-1H-indol-7-yl-acryloyl)-amides.

Example 2

Preparation of P002

General procedure (A-1) was used to alkylate thiophene-2-sulfonic acid (3-1H-indol-7-yl-acryloyl)-amide (I-4) with benzyl bromide to provide compound P002: MS(ESI⁻)m/z 421.2, (100%). LCMS(ESI⁻)>80%.

Example 3

Preparation of P006

General procedure (A-1) was used to alkylate thiophene-2-sulfonic acid (3-1H-indol-7-yl-acryloyl)-amide (I-4) with 2-trifluromethyl benzyl bromide to provide compound P006 MS(ESI⁻)m/z.=489.4, (100%), LCMS(ESI⁻)>85%.

Example 4

Preparation of P007

General procedure (A-1) was used to alkylate thiophene-2-sulfonic acid (3-1H-indol-7-yl-acryloyl)-amide (I-4) with 3-trifluromethyl benzyl bromide to provide compound P007. ¹H NMR (500 MHz, acetone-d6); 5.75 (2H, s), 6.47 (d, J=15 Hz, 1H), 6.65 (d, J=3.0 Hz, 1H), 7.08 (t, J=7.5 Hz, 1H), 7.24-7.34 (m, 4H), 7.45 (t, J=8.0 Hz, 1H), 7.52-7.57 (m, 2H), 7.70 (d, J=8.0 Hz, 1H), 7.92 (m, 1H), 8.00 (m, 1H), 8.23 (d, J=15 Hz, 1H). LC/MS (86%) ESI⁻ Calcd.: 0.490.5 m/z, found: 489.4 m/z (M−1).

Example 5

Preparation of P008

General procedure (A-1) was used to alkylate thiophene-2-sulfonic acid (3-1H-indol-7-yl-acryloyl)-amide (I-4) with 2,5-dimethyl benzyl bromide to provide compound P008 MS(ESI⁻)m/z. 449.3, (100%), LCMS(ESI⁻)>70%.

Example 6

Preparation of P009

General procedure (A-1) was used to alkylate thiophene-2-sulfonic acid (3-1H-indol-7-yl-acryloyl)-amide (I-4) with 3,4-dimethyl benzyl bromide to provide compound P009. MS(ESI⁻)m/z.=449.4, (100%), LCMS(ESI⁻)>91%.

Example 7

Preparation of P010

General procedure (A-1) was used to alkylate thiophene-2-sulfonic acid (3-1H-indol-7-yl-acryloyl)-amide (I-4) with 2,6-dichloro benzyl bromide to provide compound P010. MS(ESI⁻)m/z=489.3, (100%), LCMS(ESI⁻)>70%.

Example 8

Preparation of P011

General procedure (A-1) was used to alkylate thiophene-2-sulfonic acid (3-1H-indol-7-yl-acryloyl)-amide (I-4) (100 mg, 0.3 mmol) with 3,4-dichloro benzyl bromide (50 mg, 0.33 mmol) to provide a crude product (75 mg, 51%) which was further purified by recrystallization from ether to yield 53 mg (>90%) compound P011 as a light yellow solid. MS(ESI$^-$) m/z=489.4, (100%). LCMS(ESI$^-$)>90%. 1H NMR (CDCl3),

Example 9

Preparation of P017

General procedure (A-1) was used to alkylate thiophene-2-sulfonic acid (3-1H-indol-7-yl-acryloyl)-amide (I-4) with 4-methoxybenzyl bromide to provide compound P017.

$^1$H NMR (500 MHz, methanol-d4); 6.62 (d, J=16 Hz, 1H), 7.01 (d, J=3.5 Hz, 1H), 7.12 (t, J=7.5 Hz, 1H), 7.19 (t, J=7.5 Hz, 1H), 7.37 (dd, J=8.5, 2.0 Hz, 1H), 7.60 (t, J=7.5 Hz, 1H), 7.65-7.68 (m, 2H), 7.73 (m, 1H), 7.80 (1H, br), 7.86-7.89 (m, 2H), 7.93 (d, J=8.5 Hz, 1H), 8.06 (s, 1H), 8.19 (d, J=8.0 Hz, 1H). LC/MS (65%) ESI$^-$ Calcd.: 524.6 m/z, found: 523.5 m/z (M−1).

Example 10

Preparation of P035

General procedure (A-1) was used to alkylate thiophene-2-sulfonic acid (3-1H-indol-7-yl-acryloyl)-amide (I-4) with 5-bromomethyl-benzo[1,3]dioxole to provide compound P035. MS(ESI$^-$)m/z.=465.3, (100%), LCMS(ESI$^-$)>81%.

Example 11

Preparation of P36

General procedure (A-1) was used to alkylate thiophene-2-sulfonic acid (3-1H-indol-7-yl-acryloyl)-amide (I-4) with 3,5-dimethoxy-benzyl bromide to provide compound P36. MS(ESI$^-$)m/z=481.2, (100%), LCMS(ESI$^-$)>77%.

Example 12

Preparation of P043

General procedure (A-1) was used to alkylate thiophene-2-sulfonic acid (3-1H-indol-7-yl-acryloyl)-amide (I-4) with (2-phenyl)benzyl bromide to provide compound P043. MS(ESI$^-$)m/z=497.6 (100%), LCMS(ESI$^-$)>85%.

Example 13

Preparation of P054

General procedure (A-1) was used to alkylate thiophene-2-sulfonic acid (3-1H-indol-7-yl-acryloyl)-amide (I-4) with 3-pyridyl methyl bromide hydrobromide to provide compound P054. MS(ESI$^-$)m/z.=, 422.3, (100%), LCMS(ESI$^-$)>95%.

Example 14

Preparation of P055

General procedure (A-1) was used to alkylate thiophene-2-sulfonic acid (3-1H-indol-7-yl-acryloyl)-amide (I-4) with 2-(3,5-dimethyl-4-methoxy)pyridyl methyl bromide hydrobromide to provide compound P055. MS(ESI$^-$) m/z=480.3, (100%), LCMS(ESI$^-$)>80%.

Example 15

Preparation of P056

Preparation of 7-bromo-3-methyl-1H-indole (I-5). 2-Bromo nitrobenzene was reacted with allyl magnesium bromide according to the literature procedure (Dobbs A. J. Org Chem. 2001, 66, 638-641), to provide 7-bromo-3-methyl-1H-indole.

Preparation of (E)-3-(3-methyl-1H-indol-7-yl)-acrylic acid methyl ester (I-6). To a mixture of compound I-5 (300 mg, 1.42 mmol) and methyl acrylate (183 mg, 2.13 mmol) in triethylamine (1 ml), palladium(II) acetate (31 mg, 0.14 mmol) and tri-o-tolylphosphine (129 mg, 0.42 mmol) were added under argon at rt The reaction mixture was stirred at 100° C. for 4 hrs in a sealed pressure tube and then cooled to rt. The reaction mixture was diluted with methylene chloride (50 ml), washed with water (3×30 ml), brine, and dried over sodium sulfate. After removal of solvent, the residue was purified by column chromatography on silica gel with EtOAc/hexane as an eluent to give 250 mg of compound I-6 as a yellow solid. 1H-NMR (500 MHz, CDCl3) MS(ESI$^-$). 214.5 (M−1).

Preparation of (E)-3-(3-Methyl-1H-indol-7-yl)-acrylic acid. (I-7). To a solution of (E)-3-(3-methyl-1H-indol-7-yl)-acrylic acid methyl ester (2, 180 mg, 0.84 mmol) in THF (5 ml) and methanol (4 ml), NaOH aq. (4 ml) was added at rt. The reaction mixture was stirred at rt over night and then the pH was adjusted to acidic by adding aqueous 2N HCl. The reaction mixture was extracted with EtOAc (2×30 ml). The combined organic phases were washed with water, brine and dried over sodium sulfate. After removal of solvent, 170 mg of I-7 was obtained. $^1$H-NMR (500 MHz, DMSO-d$_6$).

Preparation of Thiophene-2-sulfonic acid [(E)-3-(3-methyl-1H-indol-7-yl)acryloyl]-amide (I-8). A mixture of the acid I-7 (170 mg, 0.84 mmol), 2-thiophenesulfonamide (163 mg, 1 mmol), 4-dimethylamino pyridine (207 mg, 1.7 mmol) and EDCI (325 mg, 1.7 mmol) in dichloromethane (20 ml) and DMSO (0.5 ml) was stirred at rt over night. The solution was diluted with dichloromethane, washed with diluted HCl aq., water, brine and dried over sodium sulfate. After removal of solvent, the residue was purified by column chromatography on silica gel with methanol/CH2Cl2 as an eluent to give 170 mg of compound I-8. $^1$H-NMR (500 MHz, DMSO-d$_6$)

General procedure (A-2) for N-alkylation of I-8. To a solution of acylsulfonamide (I-8) in DMF at room temperature was added 2.8 eq. of NaH (60% suspension in mineral oil); [except, when the Ar/R—CH2Br(Cl) used was in the form of a salt, e.g. HCl salt, an additional eq. of NaH was used]. The corresponding aryl halide was added and the mixture stirred at room temperature overnight. The reaction mixture was diluted with EtOAc, and acidified with 10% HCl. The organics were washed with water (3×), brine, and dried over anhydrous Na2SO4. The solution was filtered, concentrated in vacuo and the residue purified via SiO2 flash column chromatography using dichloromethane as the eluent or recrystallized to obtain the title compound.

Example 16

Preparation of P057

General procedure (A-2) was used to alkylate thiophene-2-sulfonic acid [(E)-3-(3-methyl-1H-indol-7-yl)-acryloyl]-amide (I-8) with 2-(bromomethyl)naphthalene to provide compound P057. $^1$H-NMR (500 MHz, DMSO-d$_6$). MS (ESI$^-$): 485.5 (M−1), LC-MS: 97% pure.

Example 17

Preparation of P084

General procedure (A-2) was used to alkylate thiophene-2-sulfonic acid [(E)-3-(3-methyl-1H-indol-7-yl)-acryloyl]-amide (I-8) with benzyl bromide to provide compound P084. ESI M.S. gave (M−1): 435.4 with 91% 1H-NMR (500 MHz, CDCl3)

Example 18

Preparation of P086

General procedure (A-2) was used to alkylate thiophene-2-sulfonic acid [(E)-3-(3-methyl-1H-indol-7-yl)-acryloyl]-amide (I-8) with 2-chlorophenyl chloride to provide compound P086

Example 19

Preparation of P087

General procedure (A-2) was used to alkylate thiophene-2-sulfonic acid [(E)-3-(3-methyl-1H-indol-7-yl)-acryloyl]-amide (I-8) with 3,4-dichlorobenzyl bromide to provide compound P087. ESI M.S. gave (M−1): 503.3, LCMS=84% 1H-NMR (500 MHz, CDCl3)

Example 20

Preparation of P088

General procedure (A-2) was used to alkylate thiophene-2-sulfonic acid [(E)-3-(3-methyl-1H-indol-7-yl)-acryloyl]-amide (I-8) with 3,5-difluoro benzyl bromide to provide compound P088. ESI M.S. gave (M−1): 471.4 LCMS 84% 1H-NMR (500 MHz, CDCl3)

Example 21

Preparation of P089

General procedure (A-2) was used to alkylate thiophene-2-sulfonic acid [(E)-3-(3-methyl-1H-indol-7-yl)-acryloyl]-amide (I-8) with 5-chloro-6-chloromethyl-benzo[1,3]dioxole to provide compound P089. ESI-M.S. gave (M−1): 513.6, LCMS=80%. 1H-NMR (500 MHz, CDCl3)

Example 22

Preparation of P099

General procedure (A-2) was used to alkylate thiophene-2-sulfonic acid [(E)-3-(3-methyl-1H-indol-7-yl)-acryloyl]-amide (I-8) with 2-chloromethylquinoline to provide compound P099. ESI M.S. gave (M−1): 486.5, LCMS=92%

Example 23

Preparation of P100

General procedure (A-2) was used to alkylate thiophene-2-sulfonic acid [(E)-3-(3-methyl-1H-indol-7-yl)-acryloyl]-amide (I-8) with 2-pyridinyl methyl bromide hydrobromide to provide compound P100. ESI M.S. gave (M−1)=436.4, LCMS=86%

Example 24

Preparation of P102

General procedure (A-2) was used to alkylate thiophene-2-sulfonic acid [(E)-3-(3-methyl-1H-indol-7-yl)-acryloyl]-amide (I-8) with 5-bromomethyl-benzo[1,3]dioxole to provide compound P101. ESI M.S. gave (M−1): 479.3, LCMS=87% 1H-NMR (500 MHz, CDCl3

Example 25

Preparation of P102

General procedure (A-2) was used to alkylate thiophene-2-sulfonic acid [(E)-3-(3-methyl-1H-indol-7-yl)-acryloyl]-amide (I-8) with 5-bromomethyl-7-fluoro-2,3-dihydro-benzo[1,4]dioxine to provide compound P102. 1H NMR (500 MHz, CDCl$_3$) 2.35 (s, 3H), 4.93 (s, 2H), 5.34 (s, 2H), 5.40 (s, 2H), 5.98 (dd, J=8.5, 2.5 Hz, 1H), 6.15 (d, J=15.0 Hz, 1H), 6.57 (dd, J=8.5, 2.5 Hz, 1H), 6.91 (s, 1H), 7.12 (m, 2H), 7.23 (d, J=7.5 Hz, 1H), 7.66 (d, J=7.5 Hz, 1H), 7.70 (dd, J=5.0, 1.5 Hz, 1H), 7.90 (dd, J=4.0, 1.5 Hz, 1H), 7.96 (d, J=15.0 Hz, 1H), 7.97 (br s, 1H). LC/MS=85% purity, MS (ESI−) Calcd. (M-H) 511.6; Found: 511.5.

Example 26

Preparation of P103

General procedure (A-2) was used to alkylate thiophene-2-sulfonic acid [(E)-3-(3-methyl-1H-indol-7-yl)-acryloyl]-amide (I-8) with 3,4-difluoro benzyl bromide to provide compound P103. ESI M.S (M−1)=471.4, LCMS=84%. 1H-NMR (500 MHz, CDCl3)

Example 27

Preparation of P109

General procedure (A-2) was used to alkylate thiophene-2-sulfonic acid [(E)-3-(3-methyl-1H-indol-7-yl)-acryloyl]-amide (I-8) with 3-pyridinyl methyl bromide to provide compound P109. ESI M.S (M−1)=436.4, LCMS=88% 1H-NMR (500 MHz, CDCl3)

Preparation of 4,5-dichloro-thiophene-2-sulfonic acid [(E)-3-(3-methyl-1H-indol-7-yl)-acryloyl]-amide (I-9). (E)-3-(3-Methyl-1H-indol-7-yl)-acrylic acid (I-7) (1 mmol), 4-dimethyaminopyridine (DMAP, 2 mmol) and 1-[3-(dimethyamino)propyl]-3-ethylcarbodiimide hydrochloride (EDCI, 2 mmol) in CH$_2$Cl$_2$ (30 mL) was added 4,5-dichloro-thiophene-2-sulfonic acid amide (1.1 mmol). The reaction mixture was stirred at room temperature for 24-40 hr. Reaction mixture was diluted with another 30 ml of dichloromethane and then acidified with 10% aqueous HCl solution until pH~1-2 (pH stripes). Organic layers was washed with saturated brine, dried over anhydrous Na$_2$SO$_4$ and concentrated under reduced pressure to provide the crude product which was purified by flash chromatography (silica gel, CH$_2$Cl$_2$; CH$_2$Cl$_2$/EtOAc/hexane=1:10:20-1:20:10) to afford desired product, I-9. $^1$H-NMR (500 MHz, CDCl$_3$) ESI M.S. gave (M−1): 436.4 with 88%.

Example 28

Preparation of P118

General procedure (A-2) was used to alkylate 4,5-dichloro-thiophene-2-sulfonic acid [(E)-3-(3-methyl-1H-indol-7-yl)- acryloyl]-amide (I-9) with 3,4-dichloro benzyl bromide to provide compound P118. ESI MS (M−1)=573.1, LCMS=97%. $^1$H NMR(DMSO-d$_6$) confirms structure.

Example 29

Preparation of P119

General procedure (A-2) was used to alkylate 4,5-dichloro-thiophene-2-sulfonic acid [(E)-3-(3-methyl-1H-indol-7-yl)-acryloyl]-amide (I-9) with 3-trifluoromethyl benzyl bromide to provide compound P119. ESI MS (M−1)=573.0 LCMS=96%. 1H-NMR (500 MHz, CDCl3

Example 30

Preparation of P120

General procedure (A-2) was used to alkylate 4,5-dichloro-thiophene-2-sulfonic acid [(E)-3-(1,3-dimethyl-1H-indol-7-yl)-acryloyl]-amide (I-9) with 4-fluoro benzyl bromide to provide compound P120. ESI MS (M−1)=523.1 LCMS=88%. 1H-NMR (500 MHz, CDCl3

Example 31

Preparation of P121

General procedure (A-2) was used to alkylate 4,5-dichloro-thiophene-2-sulfonic acid [(E)-3-(1,3-dimethyl-1H-indol-7-yl)-acryloyl]-amide (I-9) with 3,4-dimethoxy-2-pyridyl methyl bromide to provide compound P121. ESI MS (M−1)= 568.3 LCMS=96%. 1H-NMR (500 MHz, CDCl3

Example 32

Preparation of P122

General procedure (A-2) was used to alkylate 4,5-dichloro-thiophene-2-sulfonic acid [(E)-3-(1,3-dimethyl-1H-indol-7-yl)-acryloyl]-amide (I-9) with benzyl bromide to provide compound P122. ESI MS (M−1)=505.0, LCMS=91%. 1H NMR(DMSO-d6) confirms structure

Example 33

Preparation of P123

General procedure (A-2) was used to alkylate 4,5-dichloro-thiophene-2-sulfonic acid [(E)-3-(1,3-dimethyl-1H-indol-7-yl)-acryloyl]-amide (I-9) with 2-chloro benzyl bromide to provide compound P123. ESI MS (M−1)=539.3, LCMS=94%. 1H NMR(DMSO-d6) confirms structure.

Example 34

Preparation of P124

General procedure (A-2) was used to alkylate 4,5-dichloro-thiophene-2-sulfonic acid [(E)-3-(3-methyl-1H-indol-7-yl)-acryloyl]-amide (I-9) with 2,6-dichloro benzyl bromide to provide compound P124. ESI MS (M−1)=573.2, LCMS=99%. 1H NMR(DMSO-d6) confirms structure.

Example 35

Preparation of P125

General procedure (A-2) was used to alkylate 4,5-dichloro-thiophene-2-sulfonic acid [(E)-3-(3-methyl-1H-indol-7-yl)-acryloyl]-amide (I-9) with 2-bromomethyl-biphenyl to provide compound P125. ESI MS (M−1)=579.5, LCMS=88%. 1H NMR(DMSO-d6) confirms structure.

Example 36

Preparation of P135

General procedure (A-2) was used to alkylate 4,5-dichloro-thiophene-2-sulfonic acid [(E)-3-(3-methyl-1H-indol-7-yl)-acryloyl]-amide (I-9) with 3,4-difluoro benzyl bromide to provide compound P135. ESI MS (M−1)=541.2 LCMS=96%. 1H-NMR (500 MHz, CDCl3

Example 37

Preparation of P136

General procedure (A-2) was used to alkylate 4,5-dichloro-thiophene-2-sulfonic acid [(E)-3-(3-methyl-1H-indol-7-yl)-acryloyl]-amide (I-9) with 3,5-difluoro benzyl bromide to provide compound P136. ESI MS (M−1)=541.2 LCMS=96%. 1H-NMR (500 MHz, CDCl3

Example 38

Preparation of P137

General procedure (A-2) was used to alkylate 4,5-dichloro-thiophene-2-sulfonic acid [(E)-3-(3-methyl-1H-indol-7-yl)-acryloyl-amide (I-9) with 4-chloro benzyl bromide to provide compound P137. ESI M.S. gave (M−1): 539.2, with 99% $^1$H NMR(DMSO-d$_6$) confirms structure.

Example 39

Preparation of P138

General procedure (A-2) was used to alkylate 4,5-dichloro-thiophene-2-sulfonic acid [(E)-3-(3-methyl-1H-indol-7-yl)-acryloyl]-amide (I-9) with 2,5-dimethylbenzyl bromide to provide compound P138. ESI MS (M−1)=531.3, LCMS=99%. 1H NMR(DMSO-d6) confirms structure.

Example 40

Preparation of P139

General procedure (A-2) was used to alkylate 4,5-dichloro-thiophene-2-sulfonic acid [(E)-3-(3-methyl-1H-indol-7-yl)-acryloyl]-amide (I-9) with 5-bromomethyl-benzo[1,3]dioxole to provide compound P139. 1H NMR (500 MHz, DMSO-d6) 2.27 (s, 3H), 5.40 (s, 2H), 5.93 (s, 2H), 6.33 (d, J=15.0 Hz, 1H), 6.42 (d, J=7.5 Hz, 1H), 6.47 (s, 1H), 6.68 (d, J=8.0 Hz, 1H), 7.08 (dd, J=8.0, 7.5 Hz, 1H), 7.24 (d, J=7.5 Hz, 1H), 7.29 s, 1H), 7.61 (d, J=7.5 Hz, 1H), 7.90 (s 1H), 8.17 (d, J=15.0 Hz, 1H), 12.6 (br s, 1H). LC/MS=95% purity, MS (ESI−) Calcd. (M−H+2) 549; Found: 549.

Example 41

Preparation of P140

General procedure (A-2) was used to alkylate 4,5-dichloro-thiophene-2-sulfonic acid [(E)-3-(3-methyl-1H-indol-7-yl)-acryloyl]-amide (I-9) with 3-trifluoromethoxy benxyl bro-

Example 42

Preparation of P141

General procedure (A-2) was used to alkylate 4,5-dichloro-thiophene-2-sulfonic acid [(E)-3-(3-methyl-1H-indol-7-yl)-acryloyl]-amide (I-9) with 3,5-dimethoxy benxyl bromide to provide compound P141. ESI MS (M−1)=563.3, LCMS=93%. 1H NMR(DMSO-d6) confirms structure.

Example 43

Preparation of P142

General procedure (A-2) was used to alkylate 4,5-dichloro-thiophene-2-sulfonic acid [(E)-3-(3-methyl-1H-indol-7-yl)-acryloyl]-amide (I-9) with 3-methoxy benxyl bromide to provide compound P142. ESI MS (M−1)=535.2, LCMS=86%. 1H NMR(DMSO-d6) confirms structure

Example 44

Preparation of P143

General procedure (A-2) was used to alkylate 4,5-dichloro-thiophene-2-sulfonic acid [(E)-3-(3-methyl-1H-indol-7-yl)-acryloyl]-amide (I-9) with 4-trifluoromethoxy benxyl bromide to provide compound P143 ESI MS (M−1)=587.5, LCMS=99%. 1H NMR(DMSO-d6) confirms structure.

Example 45

Preparation of P144

General procedure (A-2) was used to alkylate 4,5-dichloro-thiophene-2-sulfonic acid [(E)-3-(3-methyl-1H-indol-7-yl)-acryloyl]-amide (I-9) with 4-bromomethyl-tetrahydro-pyran to provide compound P144. $^1$H NMR (DMSO-$d_6$) 1.02 (m, 2H), 1.39 (m, 2H), 1.89 (m, 1H), 2.21 (s, 3H), 3.10 (m, 2H), 3.77 (m, 2H), 4.10 (d, J=5.6 Hz, 2H), 6.39 (d, J=12.4 Hz, 1H), 7.05 (dd, J=6.4, 6.0 Hz, 1H), 7.10 (s, 1H), 7.28 (d, J=5.6 Hz, 1H), 7.55 (d, J=6.4 Hz, 1H), 7.76 (s, 1H), 8.27 (d, J=12 Hz, 1H). LC/MS (96%) ESI− Calcd. 513.5 m/z Found: 511.5 m/z

Example 46

Preparation of P145

General procedure (A-2) was used to alkylate 4,5-dichloro-thiophene-2-sulfonic acid [(E)-3-(3-methyl-1H-indol-7-yl)-acryloyl]-amide (I-9) with 4-difluoromethoxy benzyl bromide to provide compound P145. 1H NMR (500 MHz, DMSO-d6) 2.28 (s, 3H), 5.51 (s, 2H), 6.28 (d, J=15.0 Hz, 1H), 6.99 (m, 4H), 7.08 (t, J=7.5 Hz, 1H), 7.19 (t, J=74 Hz, 1H) 7.22 (d, J=7.5 Hz, 1H), 7.33 (s, 1H), 7.62 (d, J=7.5 Hz, 1H, 7.91 (s, 1H), 8.12 (d, J=15.0 Hz). LC/MS=95% purity, MS ESI−) Calcd. (M−H) 569; Found: 569.

Example 47

Preparation of P146

General procedure (A-2) was used to alkylate 4,5-dichloro-thiophene-2-sulfonic acid [(E)-3-(3-methyl-1H-indol-7-yl)-acryloyl]-amide (I-9) with 2-bromomethyl-quinoline to provide compound P146 ESI MS (M−1)=556.0, LCMS=96%. 1H NMR(DMSO-d6) confirms structure

Example 48

Preparation of P072

(3-(3-Methyl-1H-indol-7-yl)-propionic acid methyl ester), (I-10). A mixture of (E)-3-(3-methyl-1H-indol-7-yl)-acrylic acid methyl ester (I-6a) (190 mg, 0.88 mmol) and Pd/C (5%, 100 mg) in methanol (15 ml) and EtOAc (5 ml) was hydrogenated at 40 psi of hydrogen pressure at rt overnight. The reaction mixture was filtered through a celite pad and the pad was washed with EtOAc and methanol. Concentration of the filtrate gave 170 mg of product I-10 (3-(3-methyl-1H-indol-7-yl)-propionic acid methyl ester), was obtained. 1H-NMR (500 MHz, CDCl3).

3-Methyl-1H-indol-7-yl)-propionic acid, (I-11): To a solution of ester I-10 (170 mg, 0.78 mmol) in THF (8 ml) and methanol (8 ml), was added 2N aqueous NaOH (3 ml) at rt. The reaction mixture was stirred at rt over night and then the pH was made acidic by the addition of aqueous 2N HCl. The reaction mixture was extracted with EtOAc (2×40 ml). The combined organic phase was washed with water, brine and dried over sodium sulfate. After filtration and removal of the solvent, the residue was washed with ether/hexane to give 75 mg of 3-(3-Methyl-1H-indol-7-yl)-propionic acid (I-11). 1H-NMR (500 MHz, DMSO-d6).

4,5-Dichloro-thiophene-2-sulfonic acid [3-(3-methyl-1H-indol-7-yl)-propionyl]-amide, I-12: A mixture of the acid I-11 (75 mg, 0.37 mmol), 4,5-dichloro-2-thiophene sulfonamide (103 mg, 0.44 mmol), 4-dimethylamino pyridine (90 mg, 0.74 mmol) and EDCI (141 mg, 0.74 mmol) in dichloromethane (10 ml) was stirred at rt over night. The solution was diluted with dichloromethane, washed with dilute aqueous HCl, water and dried over sodium sulfate. After filtration and removal of solvent, the residue was washed with ether to give 60 mg of acyl-sulfonamide I-12. 1H-NMR (500 MHz, DMSO-d6).

Synthesis of compound P072. To a solution of sulfonamide I-12 (35 mg, 0.084 mmol) in DMF (3 ml) was added NaH (60% in oil, 15 mg, 0.37 mmol) at 0° C. After stirring at rt for 20 min., 2,4-dichloro-benzyl chloride (47 mg, 0.24 mmol) was added. The reaction mixture was stirred at rt over night and then diluted with methylene chloride (12 ml). The reaction mixture was washed with dilute aqueous HCl (2×8 ml), water (4×8 ml), brine and dried over sodium sulfate. After filtration and removal of solvent, the residue was washed with ether/hexane to give 33 mg of P072. MS (ESI−)=575.2 (M−1), LCMS: 86%. 1H-NMR (500 MHz, DMSO-d6).

Example 49

Preparation of P073

To a solution of sulfonamide I-12 (35 mg, 0.084 mmol) in DMF (3 ml) was added NaH (60% in oil, 15 mg, 0.37 mmol) at 0° C. After stirring at rt for 20 min., 2-(bromomethyl) naphthalene (53 mg, 0.24 mmol) was added. The reaction mixture was stirred at rt over night and then diluted with methylene chloride (12 ml). The reaction mixture was washed with dilute aqueous HCl (2×8 ml), water (4×8 ml), brine and dried over sodium sulfate. After filtration and removal of solvent, the residue was washed with ether/hexane to give 35 mg of compound P073. MS(ESI−)=557.0 (M−1), LCMS: 70%. 1H-NMR (500 MHz, DMSO-d6).

Example 50

Preparation of P078 and P079

Synthesis of (E)-3-[1-(2,4-Dichloro-benzyl)-3-methyl-1H-indol-7-yl]-acrylic acid methyl ester, (I-13). To a solution of the methyl ester (I-6a) (730 mg, 3.4 mmol) in DMF (15 ml), was added NaH (60% in oil, 272 mg, 6.8 mmol) at 0° C. After stirring at rt for 30 min, 2,4-dichlorobenzyl chloride (1326 mg, 6.8 mmol) was added. The reaction mixture was stirred at rt over night and then diluted with methylene chloride (150 ml). The reaction mixture was washed with dilute aqueous HCl (2×50 ml), water (4×100 ml), brine and dried over sodium sulfate. After filtration and removal of solvent, the residue was purified by column chromatography on silica gel with hexane and EtOAc/hexane as an eluent to give 60 mg of the methyl ester, I-13 and 470 mg of the ester I-14 (3-[1-(2, 4-Dichloro-benzyl)-3-methyl-1H-indol-7-yl]-acrylic acid 2,4-dichloro-benzyl ester). 1H-NMR (500 MHz, DMSO-d6).

Synthesis of (E)-3-[1-(2,4-Dichloro-benzyl)-3-methyl-1H-indol-7-yl]-acrylic acid, I-15. To a solution of ester I-13 (300 mg, 0.8 mmol) in THF (6 ml) and methanol (6 ml), was added aqueous 2N NaOH (3 ml) at rt. The reaction mixture was stirred at rt over night and then the pH was made acidic by adding aqueous 2N HCl. The reaction mixture was extracted with EtOAc (2×40 ml). The combined organic phase was washed with water, brine and dried over sodium sulfate. After filtration and removal of the solvent, the residue was washed with ether to give 280 mg of acid I-15. 1H-NMR (500 MHz, DMSO-d6).

Synthesis of P079. A mixture of the acid I-15 (54 mg, 0.15 mmol), 4,5-dichloro-2-thiophenesulfonamide (42 mg, 0.18 mmol), 4-dimethylamino pyridine (37 mg, 0.3 mmol) and EDCI (57 mg, 0.3 mmol) in dichloromethane (5 ml) was stirred at rt over night. The solution was diluted with dichloromethane, washed with dilute aqueous HCl (2×10 ml), water (4×10 ml), and brine and dried over sodium sulfate. After filtration and removal of the solvent, the residue was purified by column chromatography on silica gel with dichloromethane and methanol/dichloromethane as eluents to give 45 mg of compound P079. MS(ESI⁻)=573.1 (M−1), LCMS: 93%. 1H-NMR (500 MHz, DMSO-d6).

Example 51

Preparation of P090

A mixture of the acid I-15 (54 mg, 0.15 mmol), benzenesulfonamide (28 mg, 0.18 mmol), 4-dimethylamino pyridine (37 mg, 0.3 mmol) and EDCI (57 mg, 0.3 mmol) in dichloromethane (5 ml) was stirred at rt over night. The solution was diluted with dichloromethane, washed with dilute aqueous HCl (2×10 ml), water (4×10 ml), brine and dried over sodium sulfate. After filtration removal of the solvent, the residue was purified by column chromatography on silica gel with dichloromethane and methanol/dichloromethane as eluents to give 40 mg of compound P090. MS (ESI⁻)=499.3 (M−1), LCMS: 92%. 1H-NMR (500 MHz, DMSO-d6).

Example 52

Preparation of P074

To a round bottom flask (50 mL) which contained a solution of P001 (40 mg, 0.8 mmol) in EtOH (5 mL) was added Pd/C (60 mg) at rt. The flask was evacuate and charged with H2 (3×) and the resulting reaction mixture was stirred at rt under the atmosphere of H2 for 72 h. The catalyst was filtered out and washed with EtOH (3×10 mL). The solvent was removed under vacuum to afford a residue which was purified by recrystallization with acetone/EtOAc/hexanes to afford desired P074 (25 mg, 60% yield) as an off-white solid. MS (ESI⁻)=473.4 (M−1), LCMS (ESI⁻)>90%. 1H-NMR (500 MHz).

Example 53

Preparation of P005

To a suspension of NaH (60% in mineral oil, 5 mg, 0.122 mmol) in anhydrous DMF (1 ml), at 0° C. was added a solution of thiophene-2-sulfonic acid (3-1H-indol-7-yl-acryloyl)-amide I-8 (20 mg, 0.061 mmol) in DMF (1 ml). This mixture was stirred at rt for 0.5 hour, cooled to 0° C. and 2-naphthoyl chloride (13 mg, 0.067 mmol) was added. The reaction mixture was stirred at rt for 18 hours. Saturated aqueous NH4Cl (1 ml) was then added and the mixture was extracted with ether/EtOAc 8:2 (2×15 ml). The combined organic layers were dried over MgSO4, the mixture was filtered and the solvent was removed, and the crude product was purified by column chromatography using methylene chloride, 2% MeOH/methylene chloride to afford 4.5 mg compound P005.

Example 54

Preparation of P016

Synthesis of Trifluoro-N-(3-1H-indol-7-yl-propionyl)-methanesulfonamide, I-17. To a suspension of NaH (60% in mineral oil, 360 mg, 9.0 mmol) in DMF (30 mL) was added 3-(1H-Indol-7-yl)-acrylic acid, I-7 (560 mg, 3.0 mmol) at 0° C. The resulting mixture was allowed to warm to rt and stir for 2 h and then recooled to 0° C. To this solution, 2-bromomethylnaphthalene (680 mg, 3.1 mmol) was added at 0° C. and the resulting reaction mixture was allowed to warm to rt and stir for 16 h, The reaction mixture was cooled to 5° C. and was acidified through the addition of aqueous 10% HCl until a pH of 1 was reached. This mixture was extracted with CH2Cl2/MeOH (9/1, 3×50 mL). The combined organic extracts were dried (Na2SO4), filtered and the solvent was removed under reduced pressure to provide the crude product which was purified by flash chromatography (silica gel, CH2C2; /EtOAc/hexane,=1:8-1:2) to afford desired acrylic acid, I-17 (400 mg, 41%) as a white solid. MS(ESI⁻) m/z (326, 100%), LCMS(ESI⁻)>95%. 1H NMR (CDCl3), 13C NMR (CDCl3).

Synthesis of P016. To a stirring solution of trifluromethyl-sulfonamide (17 mg, 0.11 mmol), 4-dimethyaminopyridine (DMAP, 20 mg, 0.18 mmol) and 1-[3-(dimethyamino)propyl]-3-ethylcarbodiimide hydrochloride (EDCI, 32 mg, 0.18 mmol) in $CH_2Cl_2$ (5 mL) was added intermediate I-17 (33 mg, 0.1 mmol) at rt. The reaction mixture which resulted was allowed to stir at rt for 72 h, then was cooled to 5° C. and was acidified with the addition of aq HCl (10%) until PH=1, which was followed by extraction of $CH_2Cl_2$/MeOH (9/1, 3×10 mL). The combined organic layers were dried ($Na_2SO_4$) and the solvent was removed under reduced pressure to provide the crude product which was purified by flash chromatography (silica gel, $CH_2Cl_2$; EtOAc/hexane=1:4-2:1) to provide P016 (26 mg, 56%) a light yellow solid. ¹H NMR (500 MHz, CDCl3); 6.62 (d, J=16.0 Hz, 1H), 7.01 (d, J=3.5 Hz, 1H), 7.12 (t, J=7.5 Hz, 1H), 7.19 (t, J=8.0 Hz, 1H), 7.25-7.30 (m, 3H), 7.43-7.48 (m, 2H), 7.70 (m, 1H), 7.78-7.81 (m, 3H), 8.45 (d, J=15 Hz, 1H). LC/MS (99%) ESI⁻ Calcd.: 0.458.5 m/z, found: 457.4 m/z (M−1).

Example 55

Preparation of P003

To a suspension of thiophene-2-sulfonic acid ((E)-3-1H-indol-7-yl-acryloyl)-amide I-8 (20 mg, 0.062 mmol) in glacial acetic acid(1 ml), was added sodium cyanoborohydride (95%, 8 mg, 0.124 mmol) at 0° C. in small portions. The mixture was allowed to warm to rt and stir for 4 h. The reaction mixture was concentrated and then quenched with water (1 ml). The mixture was adjusted to pH=5 by adding aqueous 5% NaHCO3 and extracted with methylene chloride (2×5 ml). The combined organic layers were washed with water and dried (MgSO4). The solution was filtered and the solvent was removed under reduced pressure to provide the product, I-18. This was used without further purification. To a suspension of potassium carbonate (17 mg, 0.123 mmol) in anhydrous DMF (1 ml), were added the indoline I-18 (20 mg, 0.061 mmol), 2-bromomethyl naphthalene (13.5 mg, 0.061 mmol) and potassium iodide (10 mg, 0.061 mmol). The reaction mixture was stirred at rt for 2 days. Water (6 ml) was added and the mixture was extracted with ether (2×10 ml). Combined organic layers were washed with water (2 ml), brine (2 ml), dried over MgSO4 and concentrated in vacuum. Crude was purified by preparative chromatography to afford product P003.

Example 56

Preparation of P045

To a suspension of thiophene-2-sulfonic acid ((E)-3-1H-indol-7-yl-acryloyl)-amide I-4 (120 mg, 0.39 mmol) in acetic acid (glacial, 10 mL) was added sodium cyanoborohydride (95%, 150 mg, 2.5 mmol) portion wise at rt. The mixture which resulted was allowed to heat and stir at 70° C. for 4 h. The reaction mixture was cooled to 0° C. and the reaction was quenched with the addition of water (10 mL) at 0° C. The mixture was acidified with addition of aq HCl (10%) until PH=1, which was followed by extraction of CH2Cl2/MeOH (20:1, 3×30 mL). The combined organic layers were dried (Na2SO4) and the solvent was removed under reduced pressure to provide the crude product which was purified by flash chromatography (silica gel, EtOAc/hexane,=1:5-1:1) to afford desired indoline I-18 (80 mg, 65%) as a white solid. MS(ESI$^-$)m/z=335.2. To a stirring solution of the indoline I-18 (37 mg, 0.11 mmol) in CH2Cl2 (7 mL) was added triethylamine (21 mg, 0.22 mmol) and then 2-naphthalenesulfonyl chloride (25 mg, 0.1 mmol) at 0° C. The mixture which resulted was allowed to warm to rt and stir at rt for 24 h. The reaction mixture was cooled to 0° C. then acidified with addition of aq HCl (10%) until PH=1, which was followed by extraction of CH2Cl2/MeOH (10:1, 3×20 mL). The combined organic layers were dried (Na2SO4) and the solvent was removed under reduced pressure to provide the crude product which was purified by flash chromatography (silica gel, EtOAc/hexane,=1:5-1:1) to afford desired product P045 (12 mg, 21%) as a light yellow solid. MS(ESI$^-$)m/z=523.5, 100%), LCMS(ESI$^-$)>70%. 1H NMR (500 MHz, CD3OD) 2.11 (t, J=8.0 Hz, 2H), 4.08 (t, J=8.0 Hz, 2H), 6.62 (d, J=16.0 Hz, 1H), 7.01 (dd, J=7.5, 1.0 Hz, 1H) 7.11 (dd, J=5.0, 4.0 Hz, 1H), 7.19 (dd, J=7.5, 7.5 Hz, 1H), 7.36 (dd, J=8.5, 2.0 Hz, 1H), 7.60 (m, 1H), 7.67 (m, 2H), 7.73 (dd, J=5.5, 1.5 Hz, 1H), 7.79 (dd, J=3.5, 0.5 Hz, 1H), 7.87 (m, 2H), 7.93 (d, J=8.5 Hz, 1H), 8.06 (s, 1H), 8.19 (d, J=16.0 Hz, 1H).

Example 57

Preparation of P085

(E)-3-(3-Acetyl-1H-indol-7-yl)-acrylic acid methyl ester, I-19. To a predried round bottom flask (100 mL) which contained a solution of the methyl ester I-2a (645 mg, 3 mmol) in DMA (5 mL) was added POCl3 (330 uL) at 0-5° C. drop wise. The reaction mixture which resulted was allowed to warm to rt and stir at rt for 20 min and then heated to 40° C. and stirred at 40° C. for 1 h. The reaction mixture was cooled to 0° C. and was poured into ice-water suspension (50 mL) which was followed by the addition of aq NaOH (0.5 g in 10 mL water). The mixture was extracted with EtOAc (3×50 mL), the combined organic layers were washed with water (3×50 mL), dried (Na2SO4) and the solvent was removed under reduced pressure to provide the desired I-19 (450 mg, 58% yield) as an yellow solid. MS (ESI$^-$)=256.3 (M−1). 1H-NMR (500 MHz, CDCl3).

(E)-3-[3-Acetyl-1-(2,4-dichloro-benzyl)-1H-indol-7-yl]-acrylic acid methyl ester, I-20. To a RBF (250 mL) which contained a stirring suspension of I-19 (400 mg, 1.6 mmol), KI (300 mg) and CsCO3 (600 mg) in DMF (40 mL) was added 2,4-dichloro-benzylchloride (350 mg, 1.8 mmol) at rt. The reaction mixture which resulted was stirred at rt for 72 h. The mixture was cooled to 0° C. and aq. NH4Cl (sat. 10 mL) was added which was followed by extraction with EtOAc (2×100 mL), the combined organic layers were washed with water (3×100 mL), dried (Na2SO4) and the solvent was removed under reduced pressure to provide the crude which was purified by flash chromatography (silica gel, CH2Cl2; EtOAc/hexane=1:8-1:2) to yield I-20 (480 mg, 74% yield) as an yellow solid. MS (ESI+)=416.7 (M). 1H-NMR (500 MHz, CDCl3).

(E)-3-[3-Acetyl-1-(2,4-dichloro-benzyl)-1H-indol-7-yl]-acrylic acid, I-21. To a round bottom flask (50 mL) which contained a solution of NaOH (300 mg, 7.5 mmol) in EtOH (20 mL) and H2O (10 mL) was added I-20 (300 mg, 0.7 mmol) at 5° C. The reaction mixture which resulted was heated to 50° C. and stirred at 50° C. for 5 h. The reaction mixture was cooled to 0° C. and was acidified with addition of aq HCl (10%) until pH=1, which was followed by addition of water (100 mL) and then extracted with dichloromethane-MeOH (10:1, 3×20 mL). The combined organic layers was dried over Na2SO4 and the solvent was removed under vacuo to afford crude which was purified by recrystallization with acetone/EtOAc/Hex to afford the acid I-21 (260 mg, 90% yield) as an yellow solid. MS (ESI$^-$)=386.4 (M−2). LCMS (ESI$^-$)>90%. 1H-NMR (500 MHz).

Synthesis of P085. To a round bottom flask (25 mL) which contained a solution of 2-thiophenesulfonamide, (28 mg, 0.17 mmol), 4-dimethyaminopyridine (DMAP, 23 mg, 0.3 mmol) and 1-[3-(dimethyamino)propyl]-3-ethylcarbodiimide hydrochloride (EDCI, 40 mg, 0.4 mmol) in c (5 mL) was added acrylic acid I-21 (60 mg, 0.16 mmol) at rt. The mixture which resulted was allowed to stir at rt for 72 h, then was cooled to 0° C. After the addition of MeOH (1 mL) and water (5 mL), the reaction mixture was acidified with addition of aq HCl (10%) until pH=1 which was followed by extraction with CH2Cl2/MeOH (9/1, 3×5 mL). The combined organic layers were dried (Na2SO4) and the solvent was removed under reduced pressure to provide the crude product which was purified by flash chromatography (silica gel, CH2Cl2/EtOAc/hexane=1:1:4, EtOAc) to afford desired product P085 (35 mg, 40% yield) as a light yellow solid. ¹H NMR (500 MHz, CDCl3); 2.53 (s, 3H), 5.53 (s, 2H), 6.20 (d, J=15.0 Hz, 1H), 6.42 (d, J=8.5 Hz, 1H), 7.07 (dd, J=8.0, 3.0 Hz, 1H), 7.16 (t, J=4.5 Hz, 1H), 7.26-7.30 (m, 2H), 7.41 (d, J=2.0 Hz, 1H), 7.69 (s, 1H), 7.74 (dd, J=5.5, 1.5 Hz, 1H), 7.91-7.94 (m, 2H), 8.57 (dd, J=7.0, 2.0 Hz, 1H). LC/MS (78%) ESI⁻ Calcd.: 533.5 m/z, found: 535.1 m/z (M).

Example 58

Preparation of P091

(E)-3-[1-(2,4-Dichloro-benzyl)-3-isopropenyl-1H-indol-7-yl]-acrylic acid methyl ester, I-22. To a predried RBF (250 mL) which contained a stirring solution of Ph3PCH3Br (1300 mg, 0.6 mmol) in THF (55 mL) was added BuLi (2.0 mL, 1.6 M in ether) at 0° C. The reaction mixture which resulted was allowed to warm to rt then heated to 40° C. and stir 40° C. for 2 h. The mixture was cooled to 0° C. and I-20 (460 mg, 1.1 mmol) was added at 0° C. The mixture was warmed to rt then heated to 40° C. and stir 40° C. for 3 h. After cooling to 0° C., the reaction was quenched with aq. NH4Cl (sat. 5 mL) which was followed by extraction with EtOAc (2×100 mL), the combined organic layers were washed with water (3×100 mL), dried (Na2SO4) and the solvent was removed under reduced pressure to provide the crude which was purified by flash chromatography (silica gel, EtOAc/hexane=1:8-1:4) to yield the desired I-22 (380 mg, 85% yield)) as a light yellow solid. MS (ESI+): 414.8 (M). 1H-NMR (500 MHz, CDCl3).

3-[1-(2,4-Dichloro-benzyl)-3-isopropyl-1H-indol-7-yl]-propionic acid methyl ester, I-23. To a round bottom flask (50 mL) which contained a solution of I-22 (260 mg, 0.6 mmol) in EtOH (55 mL) was added aq. Pd/C (30 mg) at rt. After it was vacuumed and charged H2 for 3 times, the reaction mixture which resulted and stirred at rt for 16 h. The catalyst was filtered out and washed with EtOAc (3×50 mL) and the filtrate was washed with water (3×50 mL), dried over Na2SO4 and the solvent was removed under vacuo to afford I-23 (240 mg, 95% yield) as an off-white solid. 1H-NMR (500 MHz).

3-[1-(2,4-Dichloro-benzyl)-3-isopropyl-1H-indol-7-yl]-propionic acid, I-24. To a round bottom flask (50 mL) which contained a solution of NaOH (200 mg, 5 mmol) in EtOH (30 mL) and H₂O (20 mL) was added I-23 (180 mg, 0.4 mmol) at 5° C. The reaction mixture which resulted was heated to 50° C. and stirred at 50° C. for 5 h. The reaction mixture was cooled to 0° C. and was acidified with addition of aq HCl (10%) until pH=1, which was followed by addition of water (100 mL) and then extracted with dichloromethane-MeOH (10:1, 3×20 mL). The combined organic layers was dried over Na2SO4 and the solvent was removed under vacuo to afford crude which was purified by recrystallization with acetone/EtOAc/Hex to afford desired I-24 (150 mg, 90% yield) as an yellow solid. MS (ESI⁻)=388.3 (M−1). LCMS(ESI⁻)>85%. 1H-NMR (500 MHz).

Synthesis of P091. To a round bottom flask (25 mL) which contained a solution of 2-thiophenesulfonamide (28 mg, 0.16 mmol), 4-dimethyaminopyridine (DMAP, 30 mg, 0.3 mmol) and 1-[3-(dimethyamino)propyl]-3-ethylcarbodiimide hydrochloride (EDCI, 40 mg, 0.4 mmol) in CH2Cl2 (12 mL) was added propionic acid I-24 (60 mg, 0.15 mmol) at rt. The mixture which resulted was allowed to stir at rt for 48 h, then was cooled to 0° C. After the addition of MeOH (1 mL) and water (5 mL), the reaction mixture was acidified with addition of aq HCl (10%) until pH=1 which was followed by extraction with CH2Cl2 (3×5 mL). The combined organic layers were dried (Na2SO4) and the solvent was removed under reduced pressure to provide the crude product which was purified by flash chromatography (silica gel, CH2Cl2, EtOAc/hexane=1:1, EtOAc) to afford desired target P091 (40 mg, 40% yield) as an off-white solid. MS(ESI⁻) m/z=535.2, (M+); LCMS(ESI⁻)>95%. 1H-NMR (500 MHz).

Example 59

Preparation of P092

To a round bottom flask (25 mL) which contained a solution of 4,5-dichlorothiophenesulfonamide (21 mg, 0.09 mmol), 4-dimethyaminopyridine (DMAP, 15 mg, 0.2 mmol) and 1-[3-(dimethyamino)propyl]-3-ethylcarbodiimide hydrochloride (EDCI, 20 mg, 0.2 mmol) in CH2Cl2 (7 mL) was added acrylic acid I-24 (30 mg, 0.08 mmol) at rt. The mixture which resulted was allowed to stir at rt for 48 h, then was cooled to 0° C. After the addition of MeOH (1 mL) and water (5 mL), the reaction mixture was acidified with addition of aq HCl (10%) until pH=1 which was followed by extraction with CH2Cl2 (3×5 mL). The combined organic layers were dried (Na2SO4) and the solvent was removed under reduced pressure to provide the crude product which was purified by flash chromatography (silica gel, CH2Cl2, EtOAc/hexane=1:1, EtOAc) to afford desired target P092 (15 mg, 32% yield) as an off-white solid. MS(ESI⁻) m/z=603.2, (M−1); LCMS(ESI⁻)>95%. 1H-NMR (500 MHz).

Example 60

Preparation of P093

To a vial (10 mL) which contained a stirring solution of P091 (3 mg, 0.05 mmol) in DMSO-d6 (1 mL) was added HCl (conc. 3 mL) at 0° C. slowly. The mixture which resulted was allowed to warm to it and stir at rt for 4 h then was cooled to 0° C. water (10 mL) was added. The solid which formed was filtered out, washed with water and dried over air and then under vacuo to afford the oxyindole derivative P093 (1.5 mg, 48% yield) as an off-white solid. ¹H NMR (500 MHz, acetone-d6); 0.98 (d, J=7.0 Hz, 3H), 1.06 (d, J=7.0 Hz, 3H), 2.48-2.52 (m, 2H), 2.68-2.71 (m, 2H), 5.15 (m, 2H), 6.94 (d, J=8.0 Hz, 1H), 6.97 (d, J=8.0 Hz, 1H), 7.03 (d, J=7.5 Hz, 1H), 7.18 (t, J=3.5 Hz, 1H), 7.23 (d, J=7.5 Hz, 1H), 7.28 (dd, J=8.0, 3.0 Hz, 1H), 7.45 (d, J=2.5 Hz, 1H), 7.75 (d, J=3.0 Hz, 1H), 7.90 (d, J=5.0 Hz, 1H). LC/MS (97%) ESI⁻ Calcd.: 551.5 m/z, found: 551.2 m/z (M).

Example 61

Preparation of P069

(E)-3-(3-Formyl-1-methyl-1H-indol-7-yl)-acrylic acid ethyl ester, I-23. To a predried round bottom flask (100 mL) which contained a solution of I-2 (2.6 g, 13 mmol) in DMF (5.2 mL) was added POCl3 (1250 uL) at 0-5° C. drop wise. The reaction mixture which resulted was allowed to warm to rt and stir at rt for 20 min and then heated to 40° C. and stirred at 40° C. for 1 h. The reaction mixture was cooled to 0° C. and was poured into ice-water suspension (50 mL) which was followed by the addition of aq NaOH (1.5 g in 20 mL water). The mixture was extracted with EtOAc (3×100 mL), the combined organic layers were washed with water (3×100 mL), dried (Na2SO4) and the solvent was removed under reduced pressure to provide the desired I-23 (2.0 g, 75%) as an yellow solid. MS (ESI⁻): 242.2 (M−1). 1H-NMR (500 MHz, CDCl3).

(E)-3-[1-(2,4-Dichloro-benzyl)-3-formyl-1H-indol-7-yl]-acrylic acid ethyl ester, I-24. To a RBF (250 mL) which contained a stirring suspension of I-23 (480 mg, 2 mmol), KI (500 mg) and CsCO3 (1 g) in DMF (40 mL) was added 2,4-dichloro-benzylchloride (440 mg, 2.4 mmol) at rt. The reaction mixture which resulted was stirred at rt for 72 h. The mixture was cooled to 0° C. and aq. NH4Cl (sat. 10 mL) was added which was followed by extraction with EtOAc (2×100 mL), the combined organic layers were washed with water (3×100 mL), dried (Na2SO4) and the solvent was removed under reduced pressure to provide the crude which was purified by flash chromatography (silica gel, $CH_2Cl_2$; EtOAc/hexane=1:4-1:2) to yield the desired I-24 (400 mg, 50%) as an yellow solid. MS (ESI+): 402.3 (M+1). 1H-NMR (500 MHz, CDCl3).

(E)-3-[1-(2,4-Dichloro-benzyl)-3-formyl-1H-indol-7-yl]-acrylic acid, I-25: To a round bottom flask (50 mL) which contained a solution of NaOH (80 mg, 2 mmol) in EtOH (5 mL) and H2O (3 mL) was added I-24 (80 mg, 0.2 mmol) at 5° C. The reaction mixture which resulted was heated to 50° C. and stirred at 50° C. for 4 h. The reaction mixture was cooled to 0° C. and was acidified with addition of aq HCl (10%) until pH=1, which was followed by addition of water (20 mL) and then extracted with dichloromethane-MeOH (10:1, 3×20 mL). The combined organic layers was dried over Na2SO4 and the solvent was removed under vacuo to afford crude which was purified by recrystallization with acetone/EtOAc/Hex to afford desired I-25 (60 mg, 80% yield) as an yellow solid. MS (ESI⁻): 372.1 (M−2). 1H-NMR (500 MHz).

Synthesis of P069. To a round bottom flask (25 mL) which contained a solution of 2-thiophenesulfonamide (9 mg, 0.05 mmol), 4-dimethyaminopyridine (DMAP, 20 mg, 0.2 mmol) and 1-[3-(dimethyamino)propyl]-3-ethylcarbodiimide hydrochloride (EDCI, 25 mg, 0.3 mmol) in c (5 mL) was added acrylic acid I-25 (9 mg, 0.03 mmol) at rt. The mixture which resulted was allowed to stir at rt for 72 h, then was cooled to 0° C. After the addition of MeOH (1 mL) and water (5 mL), the reaction mixture was acidified with addition of aq HCl (10%) until pH=1 which was followed by extraction with CH2Cl2/MeOH (9/1, 3×5 mL). The combined organic layers were dried (Na2SO4) and the solvent was removed under reduced pressure to provide the crude product which was purified by flash chromatography (silica gel, CH2Cl2/EtOAc/hexane=1:1:4, EtOAc) to afford desired target P069 (6.3 mg, 45% yield) as a light yellow solid. $^1$H NMR (500 MHz, methanol-d4); 5.70 (s, 2H), 6.13 (d, J=15.0 Hz, 1H), 6.36 (d, J=8.5 Hz, 1H), 7.09-7.11 (m, 2H), 7.23 (m, 1H), 7.29-7.35 (m, 2H), 7.60 (m, 1H), 7.70 (m, 1H), 7.89-7.94 (m, 2H), 8.34 (dd, J=9.0, 1.5 Hz, 1H), 9.95 (s, 1H). LC/MS (71%) ESI⁻ Calcd.: 519.4 m/z, found: 517.4 m/z (M−2).

Example 62

Preparation of P062

(E)-3-[1-(2,4-Dichloro-benzyl)-3-hydroxymethyl-1H-indol-7-yl]-acrylic acid ethyl ester, I-26: To a RBF (100 mL) which contained a stirring suspension of I-24 (100 mg, 0.25 mmol) in EtOH (5 mL) was added NaBH4 (100 mg, excess) at 0° C. The reaction mixture which resulted was allowed to warm to rt and stir at rt for 4 h. The mixture was cooled to 0° C. and aq. NH4Cl (sat. 5 mL) was added which was followed by extraction with CH2Cl2 (2×30 mL), the combined organic layers were washed with water (3×30 mL), dried (Na2SO4) and the solvent was removed under reduced pressure to provide the crude which was purified by flash chromatography (silica gel, CH2C2; EtOAc/hexane (1:4 to 1:1 gradient) to yield the alcohol I-26 (85 mg, 84% yield) as an off-white solid. MS (APCI+): 406.2 (M+2). 1H-NMR (500 MHz, CDCl3).

(E)-3-[1-(2,4-Dichloro-benzyl)-3-hydroxymethyl-1H-indol-7-yl]-acrylic acid, I-27. To a round bottom flask (50 mL) which contained a solution of I-26 (80 mg, 0.2 mmol) in MeOH (15 mL) was added aq. NaOH (2N, 0.5 mL) at rt. The reaction mixture which resulted was heated to 80° C. and stirred at 80° C. for 48 h. The reaction mixture was cooled to 0° C. and was acidified with addition of aq HCl (10%) until pH=1, which was followed by addition of water (20 mL) and then extracted with dichloromethane-MeOH (10:1, 3×20 mL). The combined organic layers was dried over Na2SO4 and the solvent was removed under vacuo to afford crude which was purified by flash chromatography (silica gel, CH2Cl2; EtOAc/hexane=1:4-1:1, EtOAc) to yield the acid I-27 (65 mg, 80% yield) as an off-white solid. MS (ESI⁻)= 374.3 (M−2). LCMS(ESI⁻)>90%. 1H-NMR (500 MHz).

Synthesis of P062. To a round bottom flask (25 mL) which contained a solution of 2-thiophenesulfonamide (35 mg, 0.15 mmol), 4-dimethyaminopyridine (DMAP, 45 mg, 0.5 mmol) and 1-[3-(dimethyamino)propyl]-3-ethylcarbodiimide hydrochloride (EDCI, 60 mg, 0.6 mmol) in CH2Cl2 (5 mL) was added acrylic acid I-27 (25 mg, 0.07 mmol) at rt. The resulting mixture was allowed to stir at rt for 48 h, then was cooled to 0° C. After the addition of MeOH (1 mL) and water (5 mL), the reaction mixture was acidified with addition of aq HCl (10%) until pH=1 which was followed by extraction with CH2Cl2 (3×5 mL). The combined organic layers were dried over anhydrous Na2SO4 and the solvent was removed under reduced pressure to provide the crude product which was purified by flash chromatography (silica gel, CH2Cl2, EtOAc/hexane=1:1, EtOAc) to afford P062 (16 mg, 35% yield) as an off-white solid. MS(ESI⁻) m/z=519.3, (M−2); LCMS(ESI⁻)>85%. 1H-NMR (500 MHz).

Example 63

Preparation of P070

(E)-3-[1-(2,4-Dichloro-benzyl)-3-methoxymethyl-1H-indol-7-yl]-acrylic acid ethyl ester, I-28. To a RBF (25 mL) which contained a stirring suspension of NaH (15 mg, 0.25 mmol) in DMF (5 mL) was added I-26 (30 mg, 0.08 mmol) at 0° C. The mixture which resulted was allowed to warm to rt and stir at rt for 90 min. then was cooled to 0° C. and MeI (1 mL) was added. This reaction mixture was allowed to warm to rt and stir at rt for 72 h then was cooled to 0° C. and aq. NH4Cl (sat. 1 mL) was added which was followed by extraction with EtOAc (2×5 mL), the combined organic layers were washed with water (2×5 mL), dried (Na2SO4) and the solvent was removed under reduced pressure to provide the crude which was purified by flash chromatography (silica gel, EtOAc/hexane=1:8) to yield I-28 (17 mg, 50% yield) as an off-white solid. 1H-NMR (500 MHz, CDCl3).

(E)-3-[1-(2,4-Dichloro-benzyl)-3-methoxymethyl-1H-indol-7-yl]-acrylic acid, I-29. To a round bottom flask (50 mL) which contained a solution of NaOH (50 mg, 1.2 mmol) in MeOH (1 mL) and water (2 mL) was added the ester I-28 (17 mg, 0.04 mmol) at rt. The reaction mixture which resulted was heated to 50° C. and stirred at 50° C. for 4 h and then was cooled to 5° C., acidified with addition of aq HCl (10%) until pH=1. After diluted with water (10 mL) the mixture was extracted with dichloromethane-MeOH (1.0:1, 3×5 mL). The combined organic layers was dried over Na2SO4 and the solvent was removed under vacuo to afford crude which was purified purified by flash chromatography (silica gel, CH2Cl2; EtOAc/hexane=1:4-1:1, EtOAc) to yield the acid I-29 (15 mg, 90% yield) as an off-white solid. MS (ESI−)= 388.3 (M−2). 1H-NMR (500 MHz).

Synthesis of P070. To a round bottom flask (25 mL) which contained a solution of 2-thiophenesulfonamide (15 mg, 0.09 mmol), 4-dimethyaminopyridine (DMAP, 20 mg, 0.2 mmol) and 1-[3-(dimethyamino)propyl]-3-ethylcarbodiimide hydrochloride (EDCI, 25 mg, 0.25 mmol) in CH2Cl2 (5 mL) was added acrylic acid I-29 (10 mg, 0.025 mmol) at rt. The resulting mixture was allowed to stir at rt for 48 h, then was cooled to 0° C. After the addition of MeOH (1 mL) and water (5 mL), the reaction mixture was acidified with addition of aq HCl (10%) until pH=1 which was followed by extraction with CH2Cl2 (3×5 mL). The combined organic layers were dried over anhydrous Na2SO4) and the solvent was removed under reduced pressure to provide the crude product which was purified by flash chromatography (silica gel, CH2Cl2, EtOAc/hexane=1:1) to afford P070 (1.5 mg, 10% yield) as an off-white solid. $^{1}$H NMR (500 MHz, methanol-d4); 3.39 (s, 3H), 4.67 (s, 2H), 5.70 (s, 2H), 6.16 (d, J=15.5 Hz, 1H), 6.36 (d, J=9.5 Hz, 1H), 7.05 (dd, J=8.0, 3.0 Hz, 1H), 7.12 (t, J=8.0 Hz, 1H), 7.20 (m, 1H), 7.25 (m, 1H), 7.31 (m, 1H), 7.74 (d, J=7.5 Hz, 1H), 7.84-7.87 (m, 2H), 7.91 (d, J=15.0 Hz, 1H). LC/MS (78%) ESI− Calcd.: 535.5 m/z, found: 535.0 m/z (M−1).

Example 64

Preparation of P060

Synthesis of (E)-3-(5-Fluoro-1H-indol-7-yl)-acrylic acid methyl ester, I-30. To a mixture of 7-Bromo-5-fluoro-1H-indole [which was prepared according to the known method (Dobbs, A., J. Org. Chem., 66, 638-641 (2001)], (400 mg, 1.87 mmol) and methyl acrylate (241 mg, 2.8 mmol) in triethylamine (1.5 ml), palladium(II) acetate (43 mg, 0.19 mmol) and tri-o-tolylphosphine (170 mg, 0.56 mmol) was added under argon at rt The reaction mixture was stirred at 100° C. for 4 hrs in a sealed pressure tube and then cooled to rt The reaction mixture was diluted with CH2Cl2 (50 ml), washed with water (3×30 ml), brine, and dried over sodium sulfate. After removal of solvent, the residue was purified by column chromatography on silica gel with EtOAc/hexane as an eluent to give 300 mg of compound I-30 as a yellow solid. 1H-NMR (500 MHz, CDCl3).

Synthesis of (E)-3-(5-Fluoro-1H-indol-7-yl)-acrylic acid, I-31. To a solution of compound I-30 (219 mg, 1 mmol) in THF (5 ml) and methanol (4 ml), NaOH aq. (4 ml) was added at rt. The reaction mixture was stirred at rt over night and then the pH was adjusted to acidic by adding 2N HCl aq. The reaction mixture was extracted with EtOAc (2×30 ml). The combined organic phase was washed with water, brine and dried over sodium sulfate. After removal of solvent, 180 mg of the acid I-31 was obtained. 1H-NMR (500 MHz, DMSO-d6), MS (ESI−): 204.2 (M−1).

Synthesis of Thiophene-2-sulfonic acid [(E)-3-(5-fluoro-1H-indol-7-yl)-acryloyl]-amide, I-32. A mixture of the acid I-31 (180 mg, 0.88 mmol), 2-thiophenesulfonamide (172 mg, 1.2 mmol), 4-dimethylamino pyridine (215 mg, 1.77 mmol) and EDCI (336 mg, 1.77 mmol) in dichloromethane (20 ml) and DMSO (0.5 ml) was stirred at rt over night. The solution was diluted with dichloromethane, washed with diluted HCl aq., water, brine and dried over sodium sulfate. After removal of solvent, the residue was purified by column chromatography on silica gel with methanol/CH2Cl2 as an eluent to give 150 mg of the sulphonamide I-32. 1H-NMR (500 MHz, DMSO-d6)

Synthesis of P060. To a solution of I-32 (45 mg, 0.13 mmol) in DMF (2 ml), NaH (60% in oil, 16 mg, 0.4 mmol) was added at 0° C. and stirred at rt for 1 hr and then 2-(bromomethyl) naphthalene (57 mg, 0.26 mmol) was added. The reaction mixture was stirred at rt over night and diluted with CH2Cl2 (10 ml). The reaction mixture was washed with diluted HCl aq. (2×8 ml), water (4×8 ml), brine and dried over sodium sulfate. After removal of solvent, the residue was purified by column chromatography on silica gel with methanol/CH2Cl2 as an eluent to give 30 mg of compound P060. $^{1}$H-NMR (500 MHz, DMSO-d6) MS (ESI−): 489.4 (M−1), LC-MS: 80%.

Example 65

Preparation of P061

To a solution of I-32 (45 mg, 0.13 mmol) in DMF (2 ml), NaH (60% in oil, 16 mg, 0.4 mmol) was added at 0° C. and stirred at rt for 1 hr and then 2,4-dichlorobenzyl chloride (51 mg, 0.26 mmol) was added. The reaction mixture was stirred at rt over night and diluted with CH2Cl2 (10 ml). The reaction mixture was washed with diluted HCl aq. (2×8 ml), water (4×8 ml), brine and dried over sodium sulfate. After removal of solvent, the residue was purified by 0.4° column chromatography on silica gel with methanol/CH2Cl2 as an eluent to give 55 mg of compound P061. $^{1}$H-NMR (500 MHz, DMSO-d6) MS (ESI−): 509.3 (M−1), LC-MS: 93%.

Example 66

Preparation of P063

Synthesis of (E)-3-(5-Fluoro-3-methyl-1H-indol-7-yl)-acrylic acid methyl ester, I-33. To a mixture of 7-Bromo-5-fluoro-3-methyl-1H-indole, [which was prepared analogous to I-30, according to the method of Dobbs, A., J. Org. Chem., 66, 638-641 (2001)], (870 mg, 3.8 mmol) and methyl acrylate (819 mg, 9.5 mmol) in triethylamine (4 ml), palladium(II) acetate (112 mg, 0.5 mmol) and tri-o-tolylphosphine (428 mg, 1.42 mmol) was added under argon at rt The reaction mixture was stirred at 100° C. for 3 hrs in a sealed pressure tube and then cooled to rt The reaction mixture was diluted with CH2Cl2 (70 ml), washed with water (3×40 ml), brine, and dried over sodium sulfate. After removal of solvent, the residue purified by column chromatography on silica gel with methanol/dichloromethane as an eluent to give 690 mg of compound I-33 as a solid. 1H-NMR (500 MHz, CDCl3).

Synthesis of (E)-3-(5-Fluoro-3-methyl-1H-indol-7-yl)-acrylic acid, I-34. To a solution of compound I-33 (233 mg, 1 mmol) in THF (5 ml) and methanol (5 ml), NaOH aq. (3 ml) was added at rt. The reaction mixture was stirred at rt over night and then the pH was adjusted to acidic by adding 2N HCl aq. The reaction mixture was extracted with EtOAc (2×40 ml). The combined organic phase was washed with water, brine and dried over sodium sulfate. After removal of solvent, 210 mg of acid I-34 was obtained. 1H-NMR (500 MHz, DMSO-d6).

Synthesis of Thiophene-2-sulfonic acid [(E)-3-(5-fluoro-3-methyl-1H-indol-7-yl)-acryloyl]-amide, I-35. A mixture of the acid I-34 (100 mg, 0.46 mmol), 2-thiophenesulfonamide (90 mg, 0.55 mmol), 4-dimethylamino pyridine (112 mg, 0.92 mmol) and EDCI (176 mg, 0.92 mmol) in dichloromethane (10 ml) was stirred at rt over night. The solution was diluted with dichloromethane, washed with diluted HCl aq. and water. The resulted solid was filtered and solid washed with water, dichloromethane to give 55 mg of compound 4.

The remain dichloromethane mother liquid was purified by column chromatography on silica gel with methanol/CH2Cl2 as an eluent to give 45 mg of acylsulphonamide I-35. Total 100 mg of compound I-35 was obtained. 1H-NMR (500 MHz, DMSO-d6).

Preparation of P063.

To a solution of compound I-35 (45 mg, 0.12 mmol) in DMF (3 ml), NaH (60% in oil, 15 mg, 037 mmol) was added at 0° C. and stirred at rt for 1 hr and then 2,4-dichlorobenzyl chloride (47 mg, 0.24 mmol) was added. The reaction mixture was stirred at rt over night and diluted with CH2Cl2 (12 ml). The reaction mixture was washed with diluted HCl aq. (2×8 ml), water (4×8 ml), brine and dried over sodium sulfate. After removal of solvent, the residue was washed with ether to give 55 mg of compound P063. 1H NMR (DMSO-d6) 2.25 (s, 3H), 5.52 (s, 2H), 6.14 (d, J=8.0 Hz, 1H), 6.25 (d, J=15.0 Hz, 1H), 7.02 (dd, J=10.0, 2.0 Hz, 1H), 7.22 (m, 2H), 7.33 (s, 1H), 7.43 (dd, J=10, 2.0 Hz, 1H), 7.51 (m, 1H), 7.66 (d, J=15.0 Hz, 1H), 7.76 (m, 1H), 8.01 (d, J=5.0 Hz, 1H), 12.4 (bs, 1H). LC/MS (94%) ESI− Calcd. 521.4 m/z Found: 521.6 m/z Example 67

Preparation of P065

To a solution of compound P063 (10 mg, 0.02 mmol) in DMSO (1 ml), concentrated hydrochloride (3 ml) was added drop wise. The reaction mixture was stirred at rt for 5 hrs and then diluted with CH2Cl2, and washed with water (4×10 ml), brine and dried over sodium sulfate. After removal of solvent, the residue was purified by column chromatography on silica gel with EtOAc/hexane as an eluent to give 4 mg of compound P065. 1H-NMR (500 MHz, CDCl3), MS (ESI−): 537.3 (M−1), LC-MS: 77%.

Example 68

Preparation of P064

To a solution of compound I-35 (45 mg, 0.12 mmol) in DMF (3 ml), NaH (60% in oil, 15 mg, 037 mmol) was added at 0° C. and stirred at rt for 1 hr and then 2-(bromomethyl)naphthalene (53 mg, 0.24 mmol) was added. The reaction mixture was stirred at rt over night and diluted with CH2Cl2 (12 ml). The reaction mixture was washed with diluted HCl aq. (2×8 ml), water (4×8 ml), brine and dried over sodium sulfate. After removal of solvent, the residue was washed with ether/hexane to give 55 mg of compound P064. 1H-NMR (500 MHz, DMSO-d6) MS (ESI−): 503.4 (M−1), LC-MS: 95%.

Example 69

Preparation of P066

To a solution of compound P064 (10 mg, 0.02 mmol) in DMSO (1 ml), concentrated hydrochloride (3 ml) was added drop wise. The reaction mixture was stirred at rt for 5 hrs and then diluted with CH2Cl2, and washed with water (4×10 ml), brine and dried over sodium sulfate. After removal of solvent, the residue was purified by column chromatography on silica gel with EtOAc/hexane as an eluent to give 4 mg of compound P066. 1H NMR (CDCl3) 1.61 (d, J=7.5 Hz, 3H), 3.62 (q, J=7.5 Hz, 1H), 5.26 (s, 2H), 6.01 (d, J=15.0 Hz, 1H), 6.83 (dd, J=10, 2.0 Hz, 1H), 7.04 (m, 1H), 7.13 (m, 1H), 7.29 (m, J=8, 2.0 Hz, 1H), 7.43 (m, 2H), 7.69 (m, 3H), 7.76 (m, 2H), 7.91 (m, 1H), 8.01 (d, J=15.0 Hz, 1H). LC/MS (80%) ESI− Calcd. 519.6 m/z Found: 519.4 m/z.

Example 70

Preparation of P067

Synthesis of 4,5-Dichloro-thiophene-2-sulfonic acid [(E)-3-(5-fluoro-3-methyl-1H-indol-7-yl)-acryloyl]-amide, I-36. A mixture of the acid I-34 (100 mg, 0.46 mmol), 4,5-dichloro-2-thiophenesulfonamide (128 mg, 0.55 mmol), 4-dimethylamino pyridine (112 mg, 0.92 mmol) and EDCI (176 mg, 0.92 mmol) in dichloromethane (10 ml) was stirred at rt over night. The solution was diluted with dichloromethane, washed with diluted HCl aq. and water. The resulted solid was filtered and solid washed with water, dichloromethane to give 140 mg of compound I-36. 1H-NMR (500 MHz, DMSO-d6) MS (ESI−): 433.1 (M−1) LC-MS: 97

Synthesis of P067. To a solution of the sulphonamide I-36 (52 mg, 0.12 mmol) in DMF (3 ml), NaH (60% in oil, 15 mg, 037 mmol) was added at 0° C. and stirred at rt for 1 hr and then 2,4-dichlorobenzyl chloride (47 mg, 0.24 mmol) was added. The reaction mixture was stirred at rt over night and diluted with CH2Cl2 (12 ml). The reaction mixture was washed with diluted HCl aq. (2×8 ml), water (4×8 ml), brine and dried over sodium sulfate. After removal of solvent, the residue was purified by column chromatography on silica gel with methanol/dichloromethane as an eluent to give 35 mg of compound P067. 1H NMR (DMSO-d6) 2.25 (s, 3H), 5.54 (s, 2H), 6.13 (d, J=8.0 Hz, 1H), 6.21 (d, J=15.0 Hz, 1H), 7.04 (dd, J=10, 2.0 Hz, 1H), 7.23 (m, 1H), 7.38 (m, 2H), 7.45 (m, 1H), 7.74 (d, J=15.0 Hz, 1H), 7.90 (s, 1H), 12.5(br s, 1H). LC/MS (98%) ESI− Calcd. 591.3 m/z Found: 591.1 m/z Example 71

Preparation of P068

To a solution of compound I-36 (52 mg, 0.12 mmol) in DMF (3 ml), NaH (60% in oil, 15 mg, 037 mmol) was added at 0° C. and stirred at rt for 1 hr and then 2-(bromomethyl)naphthalene (53 mg, 0.24 mmol) was added. The reaction mixture was stirred at rt over night and diluted with CH2Cl2 (12 ml). The reaction mixture was washed with diluted HCl aq. (2×8 ml), water (4×8 ml), brine and dried over sodium sulfate. After removal of solvent, the residue was purified by column chromatography on silica gel with methanol/dichloromethane as an eluent to give 44 mg of compound P068. 1H-NMR (500 MHz, DMSO-d6) MS (ESI−): 571.3 (M−1) LC-MS: 97%.

Example 72

Preparation of P077

A mixture of compound P064 (25 mg, 0.05 mmol) and Pd/C (5%, 50 mg) in methanol (5 ml) and THF (5 ml) was hydrogenated at 40 psi of hydrogen pressure at rt overnight. The reaction mixture was filtered with celite and washed with methanol. After removal of solvent, the residue was washed with ether to give 16 mg of compound P077 as a solid. 1H-NMR (500 MHz, DMSO-d6), MS (ESI−): 505.4 (M−1), LC-MS: 86%.

Example 73

Preparation of P076

To a mixture of compound P068 (10 mg, 0.017 mmol) and Cs2CO3 (17 mg, 0.052 mmol) in DMSO (1 ml), iodomethane (2 drops) was added. The reaction mixture was stirred at rt over night, diluted with EtOAc and then washed with diluted HCl aq. (2×8 ml), water (4×8 ml), brine and dried over sodium sulfate. After removal of solvent, The residue was purified by column chromatography on silica gel with dichloromethane as an eluent to give 5 mg of compound P076. 1H NMR (DMSO-d6) 2.33 (s, 3H), 3.18 (s, 3H), 5.57 (s, 2H), 6.89 (d, 15.0 Hz, 1H), 7.00 (dd, J=10.0, 2.0 Hz, 1H), 7.05 (s, 1H), 7.13 (m, 1H), 7.31 (m, 1H), 7.41 (m, 2H), 7.50 (m, 2H), 7.67 (m, 1H), 7.73 (d, J=8.5 Hz, 1H), 7.76 (m, 1H), 8.27 (d, J=15.0 Hz, 1H).

Example 74

Preparation of P058

To a solution of compound P056 (7 mg, 0.014 mmol) in DMSO (1 ml), concentrated hydrochloride (3 ml) was added drop wise. The reaction mixture was stirred at rt for 2 hrs and then diluted with dichloromethane (10 ml), washed with water (4×6 ml) and dried over sodium sulfate. After removal of solvent, the residue was purified by column chromatography on silica gel with methanol/CH2Cl2 as an eluent to give 6 mg of compound P058. $^1$H-NMR (500 MHz, CDCl$_3$) MS (ESI$^-$): 519.4 (M−1), LC-MS: 76%.

Example 75

Preparation of P059

To a solution of compound P057 (33 mg, 0.067 mmol) in DMSO (5 ml), concentrated hydrochloride (2 ml) was added drop wise. The reaction mixture was stirred at rt for 2 hrs and then diluted with EtOAc (40 ml), washed with water (3×30 ml), brine and dried over sodium sulfate. After removal of solvent, the residue was purified by column chromatography on silica gel with methanol/CH2Cl2 as an eluent to give 15 mg of compound P059. 1H NMR (DMSO-d6) 1.49 (d, J=7.5 Hz, 3H), 3.79 (q, J=7.5 Hz, 1H), 5.22 (m, 2H), 6.18 (d, J=15.0 Hz, 1H), 7.07 (t, J=7.5 Hz, 1H), 7.20 (d, J=7.5 Hz, 1H), 7.27 (m, 2H), 7.46 (m, 3H), 7.66 (m, 2H), 7.73 (d, J=8.5 Hz, 1H), 7.85 (m, 2H), 7.97 (d, J=15.0 Hz, 1H), 8.13 (d, J=5.5 Hz, 1H), 12.3 (bs, 1H). LC/MS (99%) ESI− Calcd. 501.6 m/z Found: 501.4 m/z Example 76

Preparation of P107

Synthesis of (E)-3-[1-(2,4-Dichloro-benzyl)-3-methyl-2-oxo-2,3-dihydro-1H-indol-7-yl]-acrylic acid (I-37): To a solution of compound I-15 (135 mg, 0.375 mmol) in DMSO (3 ml), 40 ml of mixture of AcOH/conc. HCl (4:1) was slowly added at rt. The reaction mixture was stirred at rt for 5 hrs, diluted with EtOAc and then washed with water (4×200 ml), brine, and dried over sodium sulfate. After removal of solvent, residue was washed with ether to give 105 mg of compound I-37. 1H-NMR (500. MHz, DMSO-d6).

Synthesis of P107. A mixture of the acid I-37 (56 mg, 0.15 mmol), 4,5-dichloro-2-thiophenesulfonamide (42 mg, 0.18 mmol), 4-dimethylamino pyridine (37 mg, 0.3 mmol) and EDCI (57 mg, 0.3 mmol) in dichloromethane (8 ml) was stirred at rt over night. The solution was diluted with dichloromethane, washed with diluted HCl aq. (2×10 ml), water (4×10 ml), brine and dried over sodium sulfate. After removal of solvent, the residue was purified by column chromatography on silica gel with dichloromethane and methanol/dichloromethane as eluents to give 40 mg of compound P107. 1H-NMR (500 MHz, DMSO-d6) MS (ESI$^-$): 589.0 (M−1), LC-MS: 87%.

Example 77

Preparation of P112

Synthesis of compound (E)-3-(3-Methyl-1-naphthalen-2-ylmethyl-1H-indol-7-yl)-acrylic acid (I-39): Hydrolysis of I-39. To a solution of acid I-7 (300 mg, 1.5 mmol) in DMF (15 ml), NaH (60% in oil, 180 mg, 4.5 mmol) was added at 0° C. and stirred at rt for 20 min. and then 2-(bromomethyl) naphthalene (365 mg, 1.65 mmol) was added at 0° C. The reaction mixture was stirred at rt over night and diluted with CH2Cl2 (100 ml). The reaction mixture was washed with diluted HCl aq. (2×100 ml), water (4×100 ml), brine and dried over sodium sulfate. After removal of solvent, the solid was washed with CH2Cl2 to 165 mg of compound I-39. Yield: 32%. 1H-NMR (500 MHz, DMSO-d6).

Synthesis of (E)-3-(3-Methyl-1-naphthalen-2-ylmethyl-2-oxo-2,3-dihydro-1H-indol-7-yl)-acrylic acid, (I-40). To a solution of compound I-39 (102 mg, 0.3 mmol) in DMSO (3 ml), 40 ml of mixture of AcOH/conc. HCl (4:1) was slowly added at rt. The reaction mixture was stirred at rt for 4 hrs, diluted with EtOAc and then washed with water (4×200 ml), brine, and dried over sodium sulfate. After removal of solvent, residue was washed with ether to give 80 mg of compound I-40. 1H-NMR (500 MHz, DMSO-d6).

Synthesis of P112. A mixture of the acid I-40 (53 mg, 0.15 mmol), 4,5-dichloro-2-thiophenesulfonamide (42 mg, 0.18 mmol), 4-dimethylamino pyridine (37 mg, 0.3 mmol) and EDCI (57 mg, 0.3 mmol) in dichloromethane (8 ml) was stirred at rt over night. The solution was diluted with dichloromethane, washed with diluted HCl aq. (2×10 ml), water (4×10 ml), brine and dried over sodium sulfate. After removal of solvent, the residue was purified by column chromatography on silica gel with dichloromethane and methanol/dichloromethane as eluents to give 40 mg of compound P112. 1H-NMR (500 MHz, DMSO-d6) MS (ESI$^-$): 569.4 (M−1), LC-MS: 82%.

Example 78

Preparation of P110

To a mixture of compound P057 (160 mg, 0.33 mmol) in THF (15 ml) and 95% t-BuOH/H2O (30 ml), NBS (125 mg, 0.7 mmol) in 95% t-BuOH/H$_2$O (4 ml) and THF (2 ml) was added at rt. The reaction mixture was stirred at rt for 4 hrs, NBS (125 mg, 0.7 mmol) as added and stirred at rt over night. After removal of solvent, the residue was dissolved in EtOAc and washed with water (3×50 ml), brine, and dried over sodium sulfate. After removal of solvent, residue was washed with ether to give 135 mg of compound P110. MS (ESI$^-$): 581.1 (M−1), LC-MS: 82%, 1H-NMR (500 MHz, DMSO-d6).

Example 79

Preparation of P111

To a solution of compound P057 (58 mg, 0.1 mmol) in THF (6 ml) and water (3 ml), NaOH aq. (2N, 0.15 ml) was added at rt. The reaction mixture was stirred at rt over night and then the pH was adjusted to acidic by adding 2N HCl aq. The reaction mixture was extracted with EtOAc. The organic phase was washed with water, brine and dried over sodium sulfate. After removal of solvent, the residue was purified by column chromatography on silica gel with dichloromethane and methanol/dichloromethane as eluents to give 6 mg of compound P111. 1H NMR (CDCl3) 1.73 (s, 3H), 3.01 (s, 1H), 5.21 (s, 2H), 6.02 (d, J=15.0 Hz, 1H), 6.99 (t, J=8.0 Hz, 1H), 7.13 (m, 2H), 7.27 (m, 1H), 7.43 (m, 3H), 7.71 (m, 5H), 7.91 (m, 1H), 8.00 (d, J=15.0 Hz, 1H), 8.39 (s, 1H). LC/MS (81%) ESI+ Calcd. 517.6 m/z Found: 517.4 m/z Example 80

Preparation of P161

Synthesis of (E)-3-(3-Fluoro-3-methyl-1-naphthalen-2-ylmethyl-2-oxo-2,3-dihydro-1H-indol-7-yl)-acrylic acid, (I-41). To a mixture of compound I-39 (160 mg, 0.47 mmol) in acetonitrile (8 ml) and water (3 ml), Select fluor (500 mg, 1.41 mmol) was added and stirred at rt over night, The solution was diluted with EtOAc and then washed with diluted HCl aq. water, brine, and dried over sodium-sulfate. After removal of solvent, the residue was purified by column chromatography on silica gel with dichloromethane and methanol/dichloromethane as eluents to give 65 mg of compound I-41. $^1$H-NMR (500 MHz, CDCl$_3$), $^{19}$F-NMR (400 MHz, CDCl$_3$).

Synthesis of P161. A mixture of the acid I-41 (32 mg, 0.085 mmol), 4,5-dichloro-2-thiophenesulfonamide (23 mg, 0.1 mmol), 4-dimethylamino pyridine (21 mg, 0.17 mmol) and EDCI (33 mg, 0.17 mmol) in dichloromethane (5 ml) was stirred at rt over night. The solution was diluted with dichloromethane, washed with diluted HCl aq. (2×10 ml), water (4×10 ml), brine and dried over sodium sulfate. After removal of solvent, the residue was purified by column chromatography on silica gel with dichloromethane and methanol/dichloromethane as eluents to give 12 mg of compound P161. MS (ESI$^-$): 589.0 (M−1), LC-MS: 91%. $^1$H-NMR (500 MHz, Acetone-d$_6$).

Example 81

Preparation of P160

A mixture of the acid I-41 (32 mg, 0.085 mmol), 2-thiophenesulfonamide (16 mg, 0.1 mmol), 4-dimethylamino pyridine (21 mg, 0.17 mmol) and EDCI (33 mg, 0.17 mmol) in dichloromethane (5 ml) was stirred at rt over night. The solution was diluted with dichloromethane, washed with diluted HCl aq. (2×10 ml), water (4×10 ml), brine and dried over sodium sulfate. After removal of solvent, the residue was purified by column chromatography on silica gel with dichloromethane and methanol/dichloromethane as eluents to give 20 mg of compound P160. 1H NMR (CDCl3) 1.90 (d, J=22 Hz, 3H), 5.20 (d, J=16 Hz, 1H), 5.33 (d, J=16 Hz, 1H), 6.02 (d, J=15.0 Hz, 1H), 7.09 (t, J=8.0 Hz, 1H), 7.15 (m, 1H), 7.23 (d, J=8.0 Hz, 1H), 7.26 (s, 1H), 7.30 (d, J=8.0 Hz, 1H), 7.44 (m, 2H), 7.50 (d, J=7 Hz, 1H), 7.70 (m, 2H), 7.75 (m, 2H), 7.87 (s, 1H), 7.92 (m, 1H), 8.00 (d, J=15.0 Hz, 1H). LC/MS (93%) ESI− Calcd. 519.6 m/z Found: 519.3 m/z Example 82

Preparation of P044

Synthesis of 1-Naphthalen-2-ylmethyl-1H-indole-7-carboxylic acid methyl ester, (I-41). 1H-Indole-7-carboxylic acid methyl ester was prepared according to literature procedure [Batcho B. and Leimgruber, K., Org. Syn. Vol IIV, page 34-40], (1 g, 5.7 mmol) in DMF (10 ml), NaH (60% in oil, 275 mg, 6.9 mmol) was added at 0° C. and stirred at rt for 1 hr and then 2-(bromomethyl)naphthalene (1.26 g, 5.7 mmol) was added. The reaction mixture was stirred at rt over night. The DMF was removed, and diluted with EtOAc (25 mL). The reaction mixture was washed with water (2×15 mL), dried over sodium sulfate, filtered and the solvent removed. The reaction yielded 1.59 g of compound I-41. $^1$H-NMR (500 MHz, DMSO-d$_6$)

Synthesis of (1-Naphthalen-2-ylmethyl-1H-indol-7-yl)-methanol, (I-42). To an ice-cold suspension of LiAlH4 (216 mg, 5.7 mmol) in 15 ml anhydrous THF, under N2 was added drop wise a solution of ester I-41 (940 mg, 2.85 mmol) in 8 mL anhydrous THF. The reaction mixture was stirred at 0° C. for 1 hr, then allowed to warm up to rt. TLC (25% EtOAc/hexane) showed no starting material. Mixture was quenched at 0° C. by slow addition of 1 ml water, 1 ml NaOH 1N, 1.5 ml of water. Mixture was stirred for 10 minute at rt. Suspension was filtered off and the solid was washed several times with THF and EtOAc. Combined organic layers were washed with brine, dried over MgSO4 and concentrated to afford 800 mg crude. Purification by column chromatography using 5%-15% EtOAc/hexane provided 450 mg alcohol I-42. $^1$H NMR (500 MHz, CDCl3).

Synthesis of P044. To a solution of alcohol I-42 (57.8 mg, 0.2 mmol) in 1 ml anhydrous methylene chloride, was added at 0° C. diethoxyphosphinyl isocyanate (34 mg, 0.191 mmol). The reaction mixture was stirred at 0° C. for 2 hours, then at rt for 3 more hours. After an aqueous workup, purification by column chromatography using CH2Cl2 to 2% MeOH/CH2Cl2 provided 79 mg of compound P044. $^1$H NMR (400 MHz, CDCl$_3$) 1.21-1.24 (t, J=7.2 Hz, 6H), 4.01-4.10 (m, 4H), 5.23 (s, 2H), 5.73 (s, 2H), 6.67 (d, J=3.6 Hz, 1H), 7.10 (t, J=7.2 Hz, 1H), 7.17 (m, 2H), 7.2 (d, J=3.6 Hz, 1H), 7.24 (bs, 1H), 7.42-7.45 (m, 3H), 7.65 (m, 1H), 7.72 (dd, J=8.0, 1.2 Hz, 1H), 7.8 (d, J=8.0 Hz, 2H) LC-MS (93%): ESI− Calcd. 466 m/z Found: 465.

Example 83

Preparation of P108

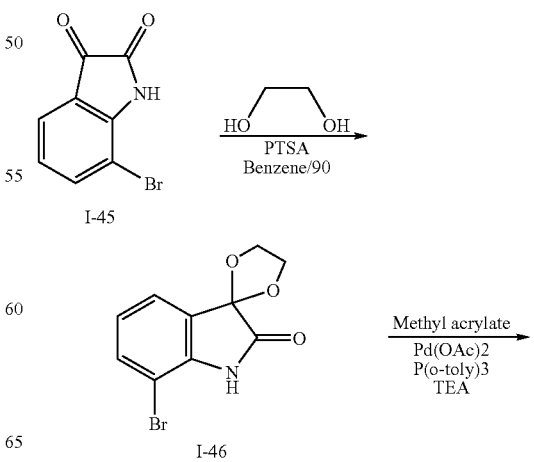

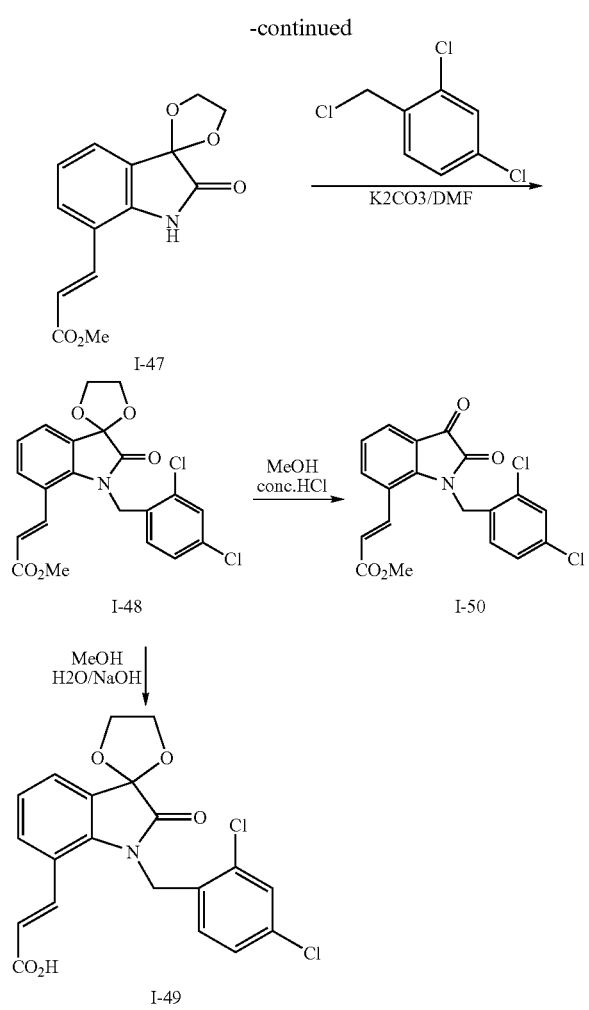

removal of water (Dean-Stark trap). The reaction mixture was allowed to cool to rt, washed with 10% aq NaHCO$_3$ (100 mL) and then water (100 mL). After removal of the solvent, 6 g of crude were obtained which was purified by recrystallization with CH$_2$Cl$_2$/EtOAc/Hex to afford desired acetal, I-46 (5.4 g, 90% yield) as an off-white solid. MS (ESI$^+$): 270 (M+1). $^1$H-NMR (500 MHz, CDCl$_3$).

Synthesis of I-47. To a tube which contained a solution of I-46 (5.4 g, 20 mmol), tri-o-tolylphosphine (2.2, 7 mmol, 0.3 eq.) and palladium acetate (500 mg, 2 mmol, 0.1 eq.) in triethylamine (20 mL) was added methyl acrylate (5 g, 70 mmol, 3.5 eq) at rt. The tube was sealed and the reaction mixture was heated and stirred at 100° C. for 6 h, then cooled to rt, poured into 600 mL stirring ice-water solution, extracted with CH$_2$Cl$_2$ (3×100 mL). The organic layers were washed with water (2×100 mL), brine (100 mL) and dried (Na$_2$SO$_4$). After removal of the solvent, 6 g of crude was obtained which was purified by the combination of recrystallization with CH$_2$Cl$_2$/EtOAc/Hex and flash chromatography (silica gel, CH$_2$Cl$_2$; CH$_2$Cl$_2$/EtOAc/hexane, v/v/v=1:10:20-1:20:10; EtOAc) to yield desired I-47 (total 4.5 g, 81%) as an off-white solid. MS (APCI$^-$): 274 (M−1). $^1$H-NMR (500 MHz, CDCl$_3$).

Synthesis of I-48. To a round-bottomed flask (250 mL) which contained a stirring suspension of I-47 (3 g, 11 mmol) and K$_2$CO$_3$ (10 g, 55 mmol, 5 eq) in DMF (40 mL) was added 2,4-dichloro-benzylchloride (2.4 g, 12 mmol, 1.05 eq). The reaction mixture which resulted was heated to 50° C., stirred at 50° C. for 3 h and then stirred at rt overnight. The mixture was poured into 600 mL stirring ice-water solution. The solid which formed was filtered out, washed with water (3×100 mL) and dried over vacuum at 50° C. to provide the desired I-48 (2.8 g) as off-white solid. Additional 1 g I-48 was obtained from the residue after extraction with EtOAc (2×100 mL) and then and flash chromatography (silica gel, CH$_2$Cl$_2$; CH$_2$Cl$_2$/EtOAc/hexane, v/v/v=1:10:20-1:20:10; EtOAc). Total product I-48, 3.8 g, (80%). MS (APCI$^+$): 434.3 (M), 436.3 (M+2). $^1$H-NMR (500 MHz, CDCl$_3$).

Synthesis of (E)-3-[1-(2,4-Dichloro-benzyl)-2,3-dioxo-2, 3-dihydro-1H-indol-7-yl]-acrylic acid, I-49. To a round bottom flask (200 mL) which contained a solution of NaOH (500 mg, 12 mmol) in MeOH (40 mL) and H$_2$O (40 mL) was added I-48 (450 mg, 10.3 mmol) at 5° C. The reaction mixture which resulted was allowed to warm to rt and stir for 10 min, heated and stirred at 50° C. for 2 h and then at 75° C. for 2 h. The reaction mixture was cooled to 0° C. and was acidified with addition of aq HCl (2N) until pH=1, which was followed by addition of water (150 mL). The solid which formed was filtered out, washed with water (3×60 mL) and dried over vacuum at 50° C. to provide the desired I-49 (430 mg, 95%) as an off-white solid. MS (APCI$^-$): 418.2 (M−2). $^1$H-NMR (500 MHz, CDCl$_3$).

Synthesis of P108. To a round bottom flask (200 mL) which contained a solution of 4,5-dichlorothiophene-2-sulfonamide (243 mg, 1.1 mmol), 4-dimethyaminopyridine (DMAP, 350 mg, 3 mmol) and 1-[3-(dimethyamino)propyl]-3-ethylcarbodiimide hydrochloride (EDCI, 450 mg, 3 mmol) in CH$_2$Cl$_2$ (50 mL) was added acrylic acid I-49 (420 mg, 1.0 mmol) at rt. The mixture which resulted was allowed to stir at rt for 4 days, then was cooled to 0° C. and was acidified with addition of aq HCl (10%) until pH=1, which was followed by extraction with CH$_2$Cl$_2$/MeOH (9/1, 3×100 mL). The combined organic layers were dried (Na$_2$SO$_4$) and the solvent was removed under reduced pressure to provide the crude product which was purified by flash chromatography (silica gel, CH$_2$Cl$_2$; EtOAc/hexane=1:2-1:0) to afford desired target P108 (350 mg, 55%) as a white solid. $^1$H NMR (500 MHz, acetone-d6);

Synthesis of 7-Bromo-1H-indole-2,3-dione, I-45. To a round-bottomed flask (500 mL) which contained a stirring solution chloral hydrate (12 g, 66 mmol) in water (150 mL) was added Na$_2$SO$_4$ (14 g 100 mmol) and a suspension of 2-bromoaniline (9 g, 50 mmol) in 2N aq. HCl (60 mL) at rt. The reaction mixture which resulted was heated to reflux for 30 min., then cooled to rt. The solid which formed was filtered out, washed with water (3×100 mL) and dried over vacuum at 50° C. to provide crude N-(2-Bromo-phenyl)-2-hydroxy-imino-acetamide, (I-44) (9 g) which was directly used for next step without purification. To a RBF (500 mL) which contained a pre-heated (to 50° C.) stirring solution of conc.H$_2$SO$_4$ (80 mL) was added the intermediate I-44 portion wise at 50° C. The reaction mixture which resulted was heated to 80° C. and stirred at 80° C. for 30 min., then cooled to rt, poured into 600 mL stirring ice-water solution. The solid which formed was filtered out, washed with water (3×100 mL) and dried over vacuum at 50° C. to yield the desired I-45 (5.2 g, 44% for two steps) MS (ESI$^+$): 227 (M+1). $^1$H-NMR: (500 MHz, CDCl$_3$)

Synthesis of I-46. To a round-bottomed flask (500 mL) which contained a solution of 7-bromo-indole-2,3-dione I-45 (5 g, 22 mmol) and p-toluenesulphonic acid monohydrate (500 mg, 10 mol. %) in dry benzene (200 mL) was added ethylene glycol (5 g, 82 mmol, 3.8 eq.). The reaction mixture which resulted was heated to reflux for 23 h with azeotropic 4.36-4.38 (m, 2H), 4.48-4.51 (m, 2H), 5.05 (s, 2H), 6.17 (d, J=15.5 Hz, 1H), 6.97 (d, J=8.0 Hz, 1H), 7.11 (t, J=8.0 Hz, 1H), 7.25 (dd, J=8.0, 2.0 Hz, 1H), 7.35-7.45 (m, 2H), 7.45 (dd, J=7.5, 1.0 Hz, 1H), 7.53 (d, J=15.5 Hz, 1H), 7.63 (s, 1H). LC/MS (99.5%) ESI$^-$ Calcd.: 634.3 m/z, found: 633.2 m/z (M−1).

Example 84

Preparation of P113

Synthesis of (E)-3-[1-(2,4-Dichloro-benzyl)-2,3-dioxo-2,3-dihydro-1H-indol-7-yl]-acrylic acid methyl ester, I-50. To a stirring suspension of I-48 (2.1 g, 5 mmol) in MeOH (50 mL) was added conc. HCl (50 mL) at rt. The reaction mixture which resulted was heated to 90° C., stirred at 90° C. for 3 h, cooled to rt and poured into 200 mL stirring ice-water solution. The solid which formed was filtered out, washed with water (3×100 mL) and dried over vacuum at 50° C. to provide 1.7 g (83%) the desired isatin derivative, I-50 as an orange color solid. MS (APCI$^+$): 390.3 (M), 392.2 (M+2). $^1$H-NMR (500 MHz, CDCl$_3$).

Synthesis of (E)-3-[1-(2,4-Dichloro-benzyl)-2,3-dioxo-2,3-dihydro-1H-indol-7-yl]-acrylic acid, I-51. To a round bottom flask (500 mL) which contained a solution of NaOH (1 g, 25 mmol) in MeOH (50 mL) and H$_2$O (50 mL) was added I-50 (1.6 g, 15 mmol) at 5° C. The reaction mixture which resulted was allowed to warm to rt and stir at rt for 10 min, then heated to 50° C. and stirred at 50° C. for 4 h. The reaction mixture was cooled to 5° C. and was acidified with addition of aq HCl (10%) until pH=1, which was followed by addition of water (250 mL). The solid which formed was filtered out, washed with water (3×100 mL) and dried over vacuum at 50° C. to provide the desired acid I-51 (1.34 g, 85%) as orange color solid. MS (APCI$^-$): 374.1(M−2), 376.2 (M). $^1$H-NMR (500 MHz, CDCl$_3$).

Synthesis of P113.

To a round bottom flask (250 mL) which contained a solution of 4,5-dichlorothiophene-2-sulfonamide (1.28 g, 5.5 mmol), 4-dimethyaminopyridine (DMAP, 1.5 g, 15 mmol) and 1-[3-(dimethylamino)propyl]-3-ethylcarbodiimide hydrochloride (EDCI, 1.8 g, 15 mmol) in CH$_2$Cl$_2$ (150 mL) was added acrylic acid I-51 (1.9 g; 5 mmol) at rt. The mixture which resulted was allowed to stir at rt for 72 h, then was cooled to 0° C. and was acidified with addition of aq HCl (10%) until pH=1. After 150 mL ice-water was added, the mixture was allowed to stir vigorously for 30 min. The solid which formed was filtered out, washed with water (3×150 mL) and dried over vacuum at 50° C. to yield the desired product P113 (2.3 g, 77%) as an orange color solid. $^1$H NMR (500 MHz, DMSO-d6); 4.96 (s, 2H), 6.16 (d, J=15.5 Hz, 1H), 7.22 (t, J=7.5 Hz, 1H), 7.30-7.33 (m, 3H), 7.55 (d, J=8.5 Hz, 1H), 7.58 (d, J=8.0 Hz, 1H), 7.70 (d, J=7.5 Hz, 1H), 7.90 (s, 1H). LC/MS (99%) ESI$^-$ Calcd.: 590.3 m/z, found: 589.1 m/z (M−1).

Example 85

Preparation of P128

To a round bottom flask (25 mL) which contained a solution of P113 (50 mg, 0.09 mmol) in acetone (5 mL) Et$_2$NH (0.5 mL) at 0° C. The mixture which resulted was allowed to stir at rt for 72 h, then was cooled to 0° C. and was acidified with addition of aq HCl (2N) until pH=1. After 200 mL ice-water was added, The solid which formed was filtered out, washed with water (3×20 mL) and dried over vacuum at 50° C. to yield the desired product P128 (30 mg, 55%) as a light yellow solid. MS(ESI$^-$)m/z(647, M−1). LCMS(ESI$^-$)>95%. HNMR.

Example 86

Preparation of P134

To a round bottom flask (25 mL) which contained a solution of P113 (50 mg, 0.09 mmol) in CH$_3$NO$_2$ (5 mL) was added Et$_2$NH (0.5 mL) at 0° C. The mixture which resulted was allowed to stir at rt for 72 h, then was cooled to 0° C. and was acidified with addition of aq HCl (2N) until pH=1. After 200 mL ice-water was added, The solid which formed was filtered out, washed with water (3×20 mL) and dried over vacuum at 50° C. to yield the desired product P134 (30 mg, 55%) as a light yellow solid. $^1$H NMR (500 MHz, acetone-d6); 5.08-5.20 (m, 2H), 5.25-5.32, (m, 2H), 6.33 (d, J=15.0 Hz, 1H), 7.17-7.21 (m, 2H), 7.28 (dd, J=8.5, 2.0 Hz, 1H), 7.39 (d, J=2.0 Hz, 1H), 7.42 (d, J=8.0 Hz, 1H), 7.56 (d, J=15.0 Hz, 1H), 7.70 (d, J=7.5 Hz, 1H), 7.78 (d, J=2.0 Hz, 1H). LC/MS (99%) ESI$^-$ Calcd.: 651.3 m/z, found: 650.2 m/z (M−1).

Example 87

Preparation of P129

To a round bottom flask (25 mL) which contained a solution of P113 (50 mg, 0.09 mmol) in EtOH (10 mL) was added NaBH4 (50 mg) at 0° C. The mixture which resulted was allowed to warm to rt and stir at rt for 2 h, then was cooled to 0° C., quenched with 20 mL ice-water and was acidified with addition of aq HCl (2N) until pH=1. The mixture was extracted with dichloromethane (3×30 mL). The combined organic layers was dried over Na$_2$SO$_4$ and the solvent was removed under vacuo to afford a mixture which was separated by flash chromatography (silica gel, CH$_2$Cl$_2$; CH$_2$Cl$_2$/EtOAc/hexane, v/v/v=1:10:20-1:20:10; EtOAc) to provide 6 mg of P129 (10%) as a white solid. MS(ESI$^-$) m/z(559, M−1). LCMS(ESI$^-$)>95%. HNMR.

Example 88

Preparation of P130

To a round bottom flask (25 mL) which contained a solution of P13 (50 mg, 0.09 mmol) in EtOH (10 mL) was added NaBH$_4$ (50 mg) at −78° C. The mixture which resulted was allowed to stir at −78° C. for 6 h, then was quenched with the addition of aq HCl (2N) until pH=1. After diluted with 100 mL, the mixture was extracted with EtOAc(3×30 mL). The combined organic layers was washed with water (2×30 mL), dried over Na$_2$SO$_4$ and the solvent was removed under vacuo to afford a mixture which was purified by flash chromatography (silica gel, CH$_2$Cl$_2$; CH$_2$Cl$_2$/EtOAc/hexane, v/v/v=1:10:20-1:20:10; EtOAc) to provide 20 mg of P130 (70%) as a white solid. $^1$H NMR (500 MHz, acetone-d6); 5.02-5.14 (m, 2H), 5.23 (s, 1H), 6.33 (d, J=15.5 Hz, 1H), 7.07 (d, J=8.5 Hz, 1H), 7.14 (t, J=8.0 Hz, 1H), 7.24 (dd, J=8.5, 2.0 Hz, 1H), 7.34 (d, J=7.5 Hz, 1H), 7.39 (d, J=2.0 Hz, 1H), 7.54 (d, J=7.0 Hz, 1H), 7.58 (d, J=15.5 Hz, 1H),7.79 (s, 1H). LC/MS (96%) ESI$^-$ Calcd.: 592.3 m/z, found: 591.0 m/z (M−1).

Example 89

Preparation of P133

To a round bottom flask (50 mL) which contained a suspension of P113 (50 mg, 0.09 mmol) in THF (10 mL) was added MeMgBr (3N in ether, 0.5 mL) at −78° C. drop wise. The mixture which resulted was allowed to warm to rt and stir at rt for 30 min and then was cooled to 0° C., quenched with the addition of aq HCl (2N) until pH=1. After diluted with 100 mL of water, the mixture was extracted with dichloromethane (3×30 mL). The combined organic layers was dried over $Na_2SO_4$ and the solvent was removed under vacuo to afford a mixture which was separated by flash chromatography (silica gel, $CH_2Cl_2$; $CH_2Cl_2$/EtOAc/hexane, v/v/v=1:10:20-1:20:10; EtOAc) to provide P133 (20 mg, 40%) as a white solid. $^1$H NMR (500 MHz, DMSO-d6); 1.51 (s, 3H), 4.99 (d, J=5.0 Hz, 2H), 6.13 (d, J=15.0 Hz, 1H), 6.98 (d, J=8.5 Hz, 1H), 7.16 (t, J=8.0 Hz, 1H), 7.27 (d, J=8.0 Hz, 1H), 7.32 (dd, J=8.0, 2.0 Hz, 1H), 7.35 (d, J=2.0 Hz, 1H), 7.44 (d, J=15.5 Hz, 1H), 7.51 (d, J=6.0 Hz, 1H), 7.87 (s, 1H). LC/MS (95%) ESI$^-$ Calcd.: 606.3 m/z, found: 605.3 m/z (M−1).

Example 90

Preparation of P132

Synthesis of (E)-3-[1-(2,4-Dichloro-benzyl)-3,3-difluoro-2-oxo-2,3-dihydro-1H-indol-7-yl]-acrylic acid methyl ester, I-52. To a round bottom flask (25 mL) which contained a solution of I-50 (200 mg, 0.5 mmol) in $CH_2Cl_2$ (8 mL) was added diethylaminosulfur trifluoride (DAST, 0.5 mL, excess) at 5° C. The reaction mixture which resulted was allowed to warm to rt and stir for 3d, then was cooled to 5° C. The reaction was quenched with the addition of MeOH (1 mL) at 0° C. and was stirred at 0° C. for 20 min, then at rt for 10 min. The reaction vessel was cooled to 5° C. and water (10 mL) was added at 5° C. and the mixture which resulted was allowed to warm to rt and stir at rt for 30 min which was followed extracted with dichloromethane (2×30 mL). The combined organic layers was washed with water (2×20 mL), dried over $Na_2SO_4$ and the solvent was removed under vacuo to afford crude I-52 (200 mg, 95%) as a light yellow solid which was directly used for next step. MS (APCI$^-$): (410.3, M−2). $^1$H-NMR (400 MHz, CDCl$_3$)

Synthesis of (E)-3-[1-(2,4-Dichloro-benzyl)-3,3-difluoro-2-oxo-2,3-dihydro-1H-indol-7-yl]-acrylic acid, I-53. To a round bottom flask (50 mL) which contained a solution of NaOH (120 mg, 3 mmol) in MeOH (7.5 mL) and $H_2O$ (7.5 mL) was added I-52 (120 mg, 0.3 mmol) at 5° C. The reaction mixture which resulted was allowed to warm to rt and stir at rt for 2 h, then heated to 50° C. and stirred at 50° C. for 2 h. The reaction mixture was cooled to 0° C. and was acidified with addition of aq HCl (10%) until pH=1, which was followed by addition of water (50 mL) and then extracted with dichloromethane-MeOH (10:1, 5×30 mL). The combined organic layers was dried over $Na_2SO_4$ and the solvent was removed under vacuo to afford crude which was purified by recrystallization with acetone/EtOAc/Hex to afford desired acid I-53 (90 mg, 75% yield) as off-white solid. MS (ESI$^-$): (396.1, M−2; 398.0, M). LCMS(ESI$^-$) 95%. $^1$H-NMR (500 MHz, DMSO-d$_6$)).

Synthesis of P132. To a round bottom flask (100 mL) which contained a solution of 4,5-dichlorothiophene-2-sulfonamide (60 mg, 0.26 mmol), 4-dimethyaminopyridine (DMAP, 60 mg, 0.6 mmol) and 1-[3-(dimethyamino)propyl]-3-ethylcarbodiimide hydrochloride (EDCI, 70 mg, 0.6 mmol) in $CH_2Cl_2$ (20 mL) was added acrylic acid I-53 (80 mg, 0.21 mmol) at rt. The mixture which resulted was allowed to stir at rt for 2d, then was cooled to 0° C. After the addition of MeOH (5 mL) and water (20 mL), the reaction mixture was acidified with addition of aq HCl (10%) until pH=1, and stirred at rt for 30 min. The solid which formed was filtered out, washed with water (3×20 mL) and dried over vacuum at 50° C. to yield crude 19 (80 mg) which was purified by flash chromatography (silica gel, $CH_2Cl_2$; EtOAc/hexane=1:4-1:2) to afford desired target P132 (55 mg, 45%) as a white solid. $^1$H NMR (500 MHz, DMSO-d6); 5.05 (s, 2H), 6.13 (d, J=15.5 Hz, 1H), 7.03 (d, J=8.0 Hz, 1H), 7.29-7.35 (m, 3H), 7.41 (d, J=15.0 Hz, 1H), 7.87 (d, J=7.5 Hz, 1H), 7.89 (s, 1H). LC/MS (99%) ESI$^-$ Calcd.: 612.3 m/z, found: 611.0 m/z (M−1).

Example 92

Preparation of P216

To a round bottom flask (25 mL) which contained a solution of thiophene-2-sulfonamide (17 mg, 0.11 mmol), 4-dimethyaminopyridine (DMAP, 20 mg, 0.2 mmol) and 1-[3-(dimethyamino)propyl]-3-ethylcarbodiimide hydrochloride (EDCI, 23 mg, 0.3 mmol) in $CH_2Cl_2$ (2 mL) was added acrylic acid I-53 (40 mg, 0.1 mmol) at rt. The mixture which resulted was allowed to stir at rt for 2d, then was cooled to 0° C. After the addition of MeOH (2 mL) and water (10 mL), the reaction mixture was acidified with addition of aq HCl (10%) until pH=1 which was followed by extraction with $CH_2Cl_2$/MeOH (9/1, 3×10 mL). The combined organic layers were dried (Na2SO4) and the solvent was removed under reduced pressure to provide the crude product which was purified by flash chromatography (silica gel, $CH_2Cl_2$/EtOAc/hexane=1:1:4, EtOAc) to afford desired acylsulphonamide P216 (15 mg, 25%) as a white solid. $^1$H NMR (500 MHz, acetone-d6); 5.04 (s, 2H), 6.15 (d, J=15.0 Hz, 1H), 7.01 (d, J=8.5 Hz, 1H), 7.25-7.27 (m, 2H), 7.33 (t, J=8.6 Hz, 1H), 7.38 (d, J=15.5 Hz, 1H), 7.41 (d, J=2.0 Hz, 1H), 7.53 (d, J=8.0 Hz, 1H), 7.81 (d, J=4.0 Hz, 1H), 7.85 (d, J=8.0 Hz, 1H), 8.10 (d, J=4.0 Hz, 1H). LC/MS (92%) ESI$^-$ Calcd.: 543.4 m/z, found: 541.4 m/z (M−2).

Example 93

Preparation of P127

Synthesis of (E)-3-[1-(2,4-Dichloro-benzyl)-2-oxo-2,3-dihydro-1H-indol-7-yl]-acrylic acid, I-54. To a pressure-resistant flask (350 mL) which contained I-51 (430 mg, 1.2 mmol) was added $NH_2NH_2.H_2O$ (20 mL) at rt. The mixture which resulted was sealed, heated to 130° C. and stirred at 130° C. for 1 h, then was cooled to 0° C. After the addition ice-water (300 mL), the reaction mixture was acidified with addition of aq HCl (10%) until pH=1 and stirred at rt for 30 min. The solid which formed was filtered out, washed with water (3×50 mL) and dried over vacuum at 50° C. to afford desired oxyindole derivative, I-54 (300 mg, 73%) as a white solid. MS(ESI$^-$)m/z=360.1, (M−2); $^1$H-NMR (500 MHz, acetone-d6).

Synthesis of P127. To a round bottom flask (100 mL) which contained a solution of 4,5-dichlorothiophene-2-sulfonamide (130 mg, 0.55 mmol), 4-dimethyaminopyridine (DMAP, 150 mg, 1.5 mmol) and 1-[3-(dimethyamino)propyl]-3-ethylcarbodiimide hydrochloride (EDCI, 180 mg, 1.5 mmol) in $CH_2Cl_2$ (20 mL) was added acrylic acid P-54 (180 mg, 0.5 mmol) at rt. The mixture which resulted was allowed to stir at rt for 2d, then was cooled to 0° C. After the addition of MeOH (5 mL) and water (120 mL), the reaction mixture was acidified with addition of aq HCl (10%) until pH=1, and stirred at rt for 30 min. The solid which formed was filtered out, washed with water (3×50 mL) and dried over vacuum at 50° C. to afford desired product P127 (143 mg, 40%) as a white solid. MS(APCI$^-$) m/z=574.9 (M−1); LCMS(ESI$^-$)>95%. HPLC>95%. $^1$H-NMR (500 MHz, DMSO-d$_6$).

Example 94

Preparation of P219

To a round bottom flask (25 mL) which contained a solution of thiophenesulfonamide (17 mg, 0.11 mmol), 4-dimethylaminopyridine (DMAP, 20 mg, 0.2 mmol) and 1-[3-(dimethyamino)propyl]-3-ethylcarbodiimide hydrochloride (EDCI, 23 mg, 0.3 mmol) in $CH_2Cl_2$ (2 mL) was added acrylic acid I-54 (26 mg, 0.11 mmol) at rt. The mixture which resulted was allowed to stir at rt for 2d, then was cooled to 0° C. After the addition of MeOH (2 mL) and water (10 mL), the reaction mixture was acidified with addition of aq HCl (10%) until pH=1 which was followed by extraction with $CH_2Cl_2$/MeOH (9/1, 3×10 mL). The combined organic layers were dried ($Na_2SO_4$) and the solvent was removed under reduced pressure to provide the crude product which was purified by flash chromatography (silica gel, $CH_2Cl_2$/EtOAc/hexane=1:1:4, EtOAc) to afford desired product P219 (23 mg, 45%) as a white solid. MS(ESI$^-$)m/z(505.2, M−2); LCMS(ESI$^-$)> 95%. $^1$H-NMR (500 MHz, DMSO-d$_6$).

Example 95

Preparation of P131

Synthesis of (E)-3-[1-(2,4-Dichloro-benzyl)-2-oxo-2,3-dihydro-1H-indol-7-yl]-acrylic acid methyl ester, I-55. To a pressure-resistant flask (50 mL) which contained a stirring suspension of I-54 (100 mg, 0.3 mmol) in MeOH (15 mL) was added conc. HCl (0.5 mL) at rt. The reaction mixture which resulted was sealed, heated to 85° C., stirred at 85° C. for 5 h, cooled to 0° C., neutralized with the addition of aq NH$_4$Cl (Sat., 2 mL), diluted with water (30 mL) and extracted with EtOAc (3×20 mL). The combined organic layers were washed with water (2×20 mL), dried (Na$_2$SO$_4$) and the solvent was removed under reduced pressure to provide I-55 (103 mg, 99%) as a white solid. MS (ESI$^-$): (374.2, M−2). $^1$H-NMR (500 MHz, CDCl$_3$).

Synthesis of (E)-3-[1-(2,4-Dichloro-benzyl)-3,3-dimethyl-2-oxo-2,3-dihydro-1H-indol-7-yl]-acrylic acid methyl ester, I-56. To a RBF (20 mL) which contained a stirring suspension of I-55 (45 mg, 0.12 mmol) and K$_2$CO$_3$ (45 mg) in DMF (2 mL) was added methyl iodide (0.5 mL, excess) at 0° C. The reaction mixture which resulted was allowed to warm to rt and stir at rt for 3 d. The mixture was poured into 30 mL stirring ice-water solution and extracted with EtOAc (3×20 mL). The combined organic layers were washed with water (2×20 mL), dried (Na$_2$SO$_4$) and the solvent was removed under reduced pressure to provide the crude 25 which was purified by flash chromatography (silica gel, CH$_2$Cl$_2$; EtOAc/hexane=1:5) to afford desired product I-56 (35 mg, 75%) as a white solid. MS (APCI$^-$): (404.2, M). $^1$H-NMR (500 MHz, CDCl$_3$).

(E)-3-[1-(2,4-Dichloro-benzyl)-3,3-dimethyl-2-oxo-2,3-dihydro-1H-indol-7-yl]-acrylic acid, I-57. To a round bottom flask (50 mL) which contained a solution of NaOH (25 mg, 0.6 mmol) in MeOH (5 mL) and H$_2$O (5 mL) was added I-56 (25 mg, 0.05 mmol) at 5° C. The reaction mixture which resulted was allowed to warm to rt and stir at rt for 16 h. The reaction mixture was cooled to 0° C. and was acidified with addition of aq HCl (10%) until pH=1, which was followed by addition of water (10 mL) and then extracted with dichloromethane (3×20 mL). The combined organic layers was dried over Na$_2$SO$_4$ and the solvent was removed under vacuo to afford crude I-57 (20 mg, 80% yield) as an off-white solid. MS (ESI$^-$): (388, 3, M−2). $^1$H-NMR (500 MHz, CDCl$_3$)

Synthesis of P131. To a round bottom flask (25 mL) which contained a solution of 4,5-dichlorothiophene-2-sulfonamide (7 mg, 0.03 mmol), 4-dimethylaminopyridine (DMAP, 9 mg, 0.9 mmol) and 1-[3-(dimethyamino)propyl]-3-ethylcarbodiimide hydrochloride (EDCI, 12 mg, 0.9 mmol) in CH$_2$Cl$_2$ (3 mL) was added acrylic acid I-57 (10 mg, 0.0.025 mmol) at rt. The mixture which resulted was allowed to stir at rt for 2d, then was cooled to 0° C. After the addition of MeOH (5 mL) and water (20 mL), the reaction mixture was acidified with addition of aq HCl (10%) until pH=1 which was followed by extraction with CH$_2$Cl$_2$/MeOH (9/1, 3×10 mL). The combined organic layers were dried (Na$_2$SO$_4$) and the solvent was removed under reduced pressure to provide the crude product which was purified by flash chromatography (silica gel, CH$_2$Cl$_2$/EtOAc/hexane=1:1:4, EtOAc) to afford P131 (6.5 mg, 45%) as a white solid. $^1$H NMR (500 MHz, DMSO-d6); 1.40 (s, 6H), 5.03 (s, 2H), 6.12 (d, J=15.5 Hz, 1H), 6.81 (d, J=8.5 Hz, 1H), 7.12-7.16 (m, 1H), 7.23 (d, J=8.5 Hz, 1H), 7.28 (dd, J=8.5, 2.0 Hz, 1H), 7.37 (d, J=2.0 Hz, 1H), 7.47 (d, J=15.5 Hz, 1H), 7.51 (d, J=7.0 Hz, 1H), 7.86 (s, 1H). LC/MS (85%) ESI$^-$ Calcd.: 604.4 m/z, found: 603.0 m/z (M−1).

Example 96

Preparation of P019

Synthesis of 5-Nitro-4H-benzo[1,4]oxazin-3-one, I-58. A mixture of 2-amino-3-nitrophenol (1.54 g, 10 mmol), ethyl bromoacetate (1.67 g, 10 mmol), potassium carbonate (1.54 g, 11 mmol) and DMF (5.0 mL) was stirred at room temperature for 20 h. Reaction mixture was diluted with water (100 mL) and extracted with EtOAc (100 mL×3). Combined EtOAc layers were washed with water (50 mL×2), dried (brine, sodium sulphate), concentrated and dried on high vacuum to give 5-Nitro-4H-benzo[1,4]oxazin-3-one, I-58 (1.6 g).

Synthesis of 4-Naphthalen-2-ylmethyl-5-nitro-4H-benzo[1,4]oxazin-3-one, I-59. Sodium hydride (94 mg, 3.0 mmol), was added in portions to a solution of 5-Nitro-4H-benzo[1,4]oxazin-3-one, I-58 (388 mg, 2 mmol) in DMF. After 30 minutes, 2-bromomethyl naphthalene (442 mg, 2 mmol) was added and stirred at room temperature for 20 h. Reaction mixture was diluted with water (100 mL) and extracted with EtOAc (100 mL×3). Combined EtOAc layers were washed with water (50 mL×2), dried (brine, sodium sulphate), concentrated and dried on high vacuum to give 4-Naphthalen-2-ylmethyl-5-nitro-4H-benzo[1,4]oxazin-3-one, I-59 (653 mg).

Synthesis of 5-Amino-4-naphthalen-2-ylmethyl-4H-benzo[1,4]oxazin-3-one, I-60. A solution of 4-naphthalen-2-ylmethyl-5-nitro-4H-benzo[1,4]oxazin-3-one, I-59 (0.65 g) in methanol (30 mL) and dioxane (7.0 mL) was hydrogenated in presence of 10% Pd—C at 45 psi for 22 h. Reaction mixture was filtered and the filtrate was concentrated to give 5-Amino-4-naphthalen-2-ylmethyl-4H-benzo[1,4]oxazin-3-one, I-60 (620 mg).

Synthesis of N-(4-Naphthalen-2-ylmethyl-3-oxo-3,4-dihydro-2H-benzo[1,4]oxazin-5-yl)-oxalamic acid methyl ester, I-61. To a solution of 5-Amino-4-naphthalen-2-ylmethyl-4H-benzo[1,4]oxazin-3-one, I-60 (120 mg, 04 mmol) and ethyl glyoxylylchloride (52 mg, 0.4 mmol) in THF (3.0 mL), triethyl amine (0.11 mL, 1.0 mmol) was added drop wise at room temperature and stirred for 18 h. Reaction mixture was concentrated and the residue was purified over silica gel with chloroform:methanol (97:3) as eluant to afford N-(4-Naphthalen-2-ylmethyl-3-oxo-3,4-dihydro-2H-benzo[1,4]oxazin-5-yl)-oxalamic acid methyl ester, I-61 (102 mg).

Synthesis of N-(4-Naphthalen-2-ylmethyl-3-oxo-3,4-dihydro-2H-benzo[1,4]oxazin-5-yl)-oxalamic acid, I-62. To a suspension of N-(4-Naphthalen-2-ylmethyl-3-oxo-3,4-dihydro-2H-benzo[1,4]oxazin-5-yl)-oxalamic acid methyl ester, I-61 (95 mg,) in methanol (2.0 mL), 1.0 M NaOH (0.5 mL) was added followed by THF (2.0 mL) resulting in a clear solution. Reaction was stirred at room temperature for 30 minutes and then concentrated to remove the solvents. The residue was taken in water (2.0 mL), acidified with 1.0 M HCl and extracted with EtOAc (5.0 mL×4). Combined extracts were washed with water (5.0 mL), dried (brine, $Na_2SO_4$) and concentrated to afford N-(4-Naphthalen-2-ylmethyl-3-oxo-3,4-dihydro-2H-benzo[1,4]oxazin-5-yl)-oxalamic acid, I-62 (69 mg). APCI m/z 375 (M-H)$^+$.

Synthesis of N-(4-Naphthalen-2-ylmethyl-3-oxo-3,4-dihydro-2H-benzo[1,4]oxazin-5-yl)-2-oxo-2-(thiophen-2-sulfonylamino)-acetamide, P019: A mixture of N-(4-Naphthalen-2-ylmethyl-3-oxo-3,4-dihydro-2H-benzo[1,4]oxazin-5-yl)-oxalamic acid, I-62 (52 mg, 0.14 mmol), thiophene sulfonamide (28 mg, 0.17 mmol), EDCI (33 mg, 0.17 mmol), DMAP (22 mg, 0.17 mmol) in methylene chloride was stirred at room temperature for 24 h. Reaction was diluted with chloroform (10 mL) and washed with 6.0 M HCl (3.0 mL×4), water (3.0 mL). Chloroform layer was concentrated and the residue was purified over silica gel with chloroform:methanol (90:10) as eluant to afford N-(4-Naphthalen-2-ylmethyl-3-oxo-3,4-dihydro-2H-benzo[1,4]oxazin-5-yl)-2-oxo-2-(thiophen-2-sulfonylamino)-acetamide, P019 (7.0 mg). 1H NMR (500 MHz, DMSO-d6) 4.59 (s, 2H), 5.35 (s, 2H), 6.84 (dd, J=8.0, 1.5 Hz, 1H), 6.90 (dd, J=8.0, 8.0 Hz, 1H), 7.02 (m, 2H), 7.06 (dd, J=5.0, 3.5 Hz, 1H), 7.44 (m, 1H), 7.56 (s, 1H), 7.61 (dd, J=3.5, 1.5 Hz, 1H), 7.71-7.65 (m, 3H), 7.78 (m, 1H), 10.05 (s, 1H). MS (ESI−) Calcd. (M+) 521.6; Found: 520.7 (M−1).

Example 97

Preparation of P049

Synthesis of (4-naphthalen-2-ylmethyl-3-oxo-3,4-dihydro-2H-benzo[1,4]oxazin-5-ylamino)-acetic acid ethyl ester, I-63: A mixture of 5-Amino-4-naphthalen-2-ylmethyl-4H-benzo[1,4]oxazin-3-one, I-60 (152 mg, 0.5 mmol), ethylgloxylate (50% in toluene, 370 mg), anhydrous $Na_2SO_4$ (520 mg) in toluene (4.0 mL) was heated at 110° C. for 4 h. Reaction mixture was filtered. Filtrate was concentrated and the residue obtained was taken in methanol (4.0 mL) and sodium borohydride (40 mg) was added at room temperature. After stirring for 18 h, methanol was evaporated. Water (10 mL) was added to the residue and extracted with chloroform (10.0 mL×2). Combined organic layers were dried (brine, an $Na_2SO_4$), concentrated and dried to afford (4-naphthalen-2-ylmethyl-3-oxo-3,4-dihydro-2H-benzo[1,4]oxazin-5-ylamino)-acetic acid ethyl ester, I-63 (105 mg).

Synthesis of (4-naphthalen-2-ylmethyl-3-oxo-3,4-dihydro-2H-benzo[1,4]oxazin-5-ylamino)-acetic acid, I-64. A mixture of (4-naphthalen-2-ylmethyl-3-oxo-3,4-dihydro-2H-benzo[1,4]oxazin-5-ylamino)-acetic acid ethyl ester, I-63 (105 mg), methanol (3.0 mL), THF (2.0 mL) and 2.0 M NaOH (0.5 mL) was stirred at room temperature for 18 h. Methanol was evaporated and the residue was taken water (3.0 mL) and acidified to pH 1 with 2.0 M HCl resulting in the precipitation of a white solid. Solid was extracted with chloroform (10 mL×2), and the combined extracts were dried (brine, anhydrous sodium sulfate), concentrated and dried on high vacuum to afford (4-naphthalen-2-ylmethyl-3-oxo-3,4-dihydro-2H-benzo[1,4]oxazin-5-ylamino)-acetic acid, I-64 (102 mg).

Synthesis of P049. Thiophen-2-sulfonic acid[2-(4-naphthalen-2-ylmethyl-3-oxo-3,4-dihydro-2H-benzo[1,4]oxazin-5-ylamino)-acetyl]-amide. A solution of (4-naphthalen-2-ylmethyl-3-oxo-3,4-dihydro-2H-benzo[1,4]oxazin-5-ylamino)-acetic acid, I-64 (102 mg, 0.281 mmol), thiophen-2-sulfonamide (46 mg, 0.281 mmol), EDCI (40 mg, 0.33 mmol), DMAP (40 mg, 0.33 mmol) in $CH_2Cl_2$ was stirred at room temperature for 48 h. Reaction mixture was diluted with $CH_2Cl_2$ (30.0 mL) and washed with 6N HCl (5 mL×3), water (5 mL), dried (brine, $Na_2SO_4$) concentrated and the residue obtained was purified over silica gel with Chloroform:methanol (95:5) as eluant to afford thiophen-2-sulfonic acid[2-(4-naphthalen-2-ylmethyl-3-oxo-3,4-dihydro-2H-benzo[1,4]oxazin-5-ylamino)-acetyl]-amide, P049 (16 mg). 1H NMR (500 MHz, DMSO-d6) 3.76 (s, 2H), 4.48 (s, 2H), 5.39 (s, 2H), 5.52 (br s, 1H), 6.11 (dd, J=8.5, 1.0 Hz, 1H), 6.32 (dd, J=8.5, 1.0 Hz, 1H), 6.74 (t, J=8.5 Hz, 1H), 7.12 (m, 2H), 7.44 (m, 2H), 7.60 (s, 1H), 7.73-7.67 (m, 2H), 7.79 (m, 1H), 7.90 (d, J=4.5 Hz, 1H), 12.45 (br s, 1H). LC/MS=93.8% purity, MS (ESI−) Calcd. (M+) 511.6; Found: 511.5 (M−1).

Example 98

Preparation of P018

Synthesis of (3-Methoxycarbonylmethoxy-2-nitro-phenoxy)-acetic acid methyl ester, I-65. Methyl bromoacetate (23 g, 150 mmol) was added to a stirred mixture of 2-Nitrobenzene-1,3-diol (9.3 g, 60 mmol), $K_2CO_3$ (24.8 g, 180 mmol) in acetone (250 ml) and water (5 ml) at room temperature. The reaction mixture was stirred at rt over weekend. Solvent was removed under vacuum and then partitioned between EtOAc (200 ml) and water (200 ml). Solid was filtered and washed with water, EtOAc and ether. After drying, 9.5 g of compound 2 was obtained as a white solid. Water layer was extracted with EtOAc (2×100 ml). The combined organic phase was washed with water, brine and dried over sodium sulfate. After removal of solvent, the residue was washed with EtOAc to give 4 g of compound I-65. Total 13.5 g of compound 2 was obtained. $^1$H-NMR (500 MHz, DMSO-$d_6$).

Synthesis of 2-(3-Oxo-3,4-dihydro-2H-benzo[1,4]oxazin-5-yloxy)-propionic acid methyl ester, I-66. A mixture of compound I-65 (3.9 g, 13 mmol) and 1.4 g of Pd/C (5%) in THF (300 ml and methanol (100 ml) was hydrogenated at rt over 2 days. The reaction mixture was filtered with celite and the celite was washed with EtOAc, and methanol. After removal of solvent under vacuum, solid was washed with ether to give 3.07 g of compound I-66 as white solid. $^1$H-NMR (500 MHz, $CDCl_3$).

Synthesis of 2-(4-Naphthalen-2-ylmethyl-3-oxo-3,4-dihydro-2H-benzo[1,4]oxazin-5-yloxy)-propionic acid methyl ester, I-67. A mixture of compound I-66 (350 mg, 1.5 mmol), 2-(bromomethyl) naphthalene (500 mg, 2.25 mmol), KI (374 mg, 2.25 mmol) and $K_2CO_3$ (310 mg, 2.25 mmol) in DMF (8 ml) and water (10 drops) was stirred at rt over night and then partitioned between dichloromethane and water. Water layer was extracted with dichloromethane (3×30 ml). The combined organic phase was washed with water (4×30 ml), brine and dried over sodium sulfate. After removal of solvent, the residue was purified by column chromatography on silica gel with EtOAc/hexane as the eluant to give 300 mg of compound I-67. $^1$H-NMR (500 MHz, $CDCl_3$).

Synthesis of 2-(4-Naphthalen-2-ylmethyl-3-oxo-3,4-dihydro-2H-benzo[1,4]oxazin-5-yloxy)-propionic acid, I-68. To a solution of compound I-67 (300 mg, 0.8 mmol) in EtOH (5 ml) and THF (5 ml), NaOH aq. (2N, 5 ml) was added at rt. The reaction mixture was stirred at rt over night and then the pH was adjusted to acidic by adding 2N HCl aq. The reaction mixture was extracted with EtOAc (2×30 ml). The combined organic phase was washed with water, brine, and dried over sodium sulfate. After removal of solvent, the residue dissolved in ether and filtered off solid. After re-moval of ether, 140 mg of compound I-68 was obtained. $^1$H-NMR (500 MHz, DMSO-d$_6$).

Synthesis of P018. To a mixture of the acid I-68 (140 mg, 0.38 mmol), 2-thiophenesulfonamide (76 mg, 0.45 mmol), 4-dimethylamino pyridine (94 mg, 0.77 mmol) in dichloromethane (8 ml), was added EDCI (147 mg, 0.77 mmol). The reaction mixture was stirred at rt over night. The solution was diluted with dichloromethane, washed with diluted HCl aq., water, brine and dried over sodium sulfate. After removal of solvent, the solid was washed with ether to give 135 mg of compound P018. MS (ESI$^-$): 507.5 (M−1), LC-MS: 83%, $^1$H-NMR (500 MHz, DMSO-d$_6$).

Example 99

Preparation of P020

Synthesis of 3-Oxo-3,4-dihydro-2H-benzo[1,4]oxazin-5-yloxy)-acetic acid, I-69. To a solution of compound I-66: (1.5 g, 6.3 mmol) in EtOH (15 ml) and THF (35 ml), NaOH aq. (2N, 10 ml) was added at rt. The reaction mixture was stirred at rt over weekend and then the pH was adjusted to acidic by adding 2N HCl aq. The resulted solid was filtered and washed with water, EtOAc and ether. After drying, 1.3 g of compound I-69 was obtained as a white solid. $^1$H-NMR (500 MHz, DMSO-d$_6$).

Synthesis of Thiophene-2-sulfonic acid [2-(3-oxo-3,4-dihydro-2H-benzo[1,4]oxazin-5-yloxy)-acetyl]-amide, I-70. To a mixture of the acid I-69 (1.11 g, 5 mmol), 2-thiophenesulfonamide (913 mg, 5.5 mmol), 4-dimethylamino pyridine (1.22 g, 10 mmol) in dichloromethane (200 ml), was added EDCI (1.91 g, 10 mmol). The reaction mixture was stirred at rt over night. The solution was diluted with water and adjusted pH to acidic by adding HCl aq. (2N). The resulted solid was filtered and washed with diluted HCl aq. water, CH2Cl2 and ether. After drying, 1.6 g of compound I-70 was obtained as a white solid. $^1$H-NMR (500 MHz, DMSO-d$_6$). MS (ESI$^-$): 367.2 (M−1), LC-MS: 96%.

General Synthetic Procedure (A-3) for N-alkylation of I-70.

A mixture of compound I-70 (50 mg, 0.136 mmol), substituted benzyl bromide (or chloride) (0.27 mmol), KI (45 mg, 0.27 mmol) and K$_2$CO$_3$ (38 mg, 0.27 mmol) in DMF (3 ml) and water (3 drops) was stirred at rt for 5 days. The solution was diluted with water and adjusted pH to acidic by adding HCl aq. (2N). The resulted solid was filtered and washed with diluted HCl aq. and water. Solid was dissolved in CH2Cl2 and filtered off insoluble solid. After removal of solvent, the residue was washed with ether to give product.

Synthesis of P020. General procedure (A-3) was used to alkylate thiophene-2-sulfonic acid [2-(3-oxo-3,4-dihydro-2H-benzo[1,4]oxazin-5-yloxy)-acetyl]-amide, I-70 with 3,4-dimethyl benzyl bromide to provide compound P020. $^1$H-NMR (500 MHz, DMSO-d$_6$), MS (ESI$^-$): 485.4 (M−1) LC-MS: 85%.

Example 100

Preparation of P021

General procedure (A-3) was used to alkylate thiophene-2-sulfonic acid [2-(3-oxo-3,4-dihydro-2H-benzo[1,4]oxazin-5-yloxy)-acetyl]-amide, I-70 with 2,5-dimethyl benzyl bromide to provide compound P021. $^1$H-NMR (500 MHz, DMSO-d$_6$) MS (ESI$^-$): 485.4 (M−1), LC-MS: 95%

Example 101

Preparation of P022

General procedure (A-3) was used to alkylate thiophene-2-sulfonic acid [2-(3-oxo-3,4-dihydro-2H-benzo[1,4]oxazin-5-yloxy)-acetyl]-amide, I-70 with benzyl bromide to provide compound P022. $^1$H-NMR (500 MHz, DMSO-d$_6$), MS (ESI$^-$): 457.4 (M−1), LC-MS: 93%.

Example 102

Preparation of P023

General procedure (A-3) was used to alkylate thiophene-2-sulfonic acid [2-(3-oxo-3,4-dihydro-2H-benzo[1,4]oxazin-5-yloxy)-acetyl]-amide, I-70 with 4-methyl benzyl bromide to provide compound P023. $^1$H-NMR (500 MHz, DMSO-d$_6$) MS (ESI$^-$): 471.4 (M−1), LC-MS: 87%.

Example 103

Preparation of P024

General procedure (A-3) was used to alkylate thiophene-2-sulfonic acid [2-(3-oxo-3,4-dihydro-2H-benzo[1,4]oxazin-5-yloxy)-acetyl]-amide, I-70 with 4-fluorobenzyl bromide to provide compound P024. $^1$H-NMR (500 MHz, DMSO-d$_6$) MS (ESI$^-$): 475.2 (M−1), LC-MS: 87%.

Example 104

Preparation of P025

General procedure (A-3) was used to alkylate thiophene-2-sulfonic acid [2-(3-oxo-3,4-dihydro-2H-benzo[1,4]oxazin-5-yloxy)-acetyl]-amide, I-70 with 4-chlorobenzyl chloride to provide compound P025. $^1$H-NMR (500 MHz, DMSO-d$_6$), MS (ESI$^-$): 491.3 (M−1), LC-MS: 90%.

Example 105

Preparation of P026

General procedure (A-3) was used to alkylate thiophene-2-sulfonic acid [2-(3-oxo-3,4-dihydro-2H-benzo[1,4]oxazin-5-yloxy)-acetyl]-amide, I-70 with 1-bromomethyl-4-difluoromethoxy-benzene to provide compound P026. 1H NMR (DMSO-d6) 4.57 (s, 2H), 4.59 (s, 2H), 5.35 (s, 2H), 6.45 (d, J=8.5 Hz, 1H), 6.67 (d, J=0.5 Hz, 1H), 6.91 (t, J=8.0 Hz, 1H), 6.99 (m, 2H), 7.02 (m, 2H), 7.14 (s, 1H), 7.20 (m, 1H), 7.79 (s, 1H), 8.02 (s, 1H), 12.5 (bs, 1H). LC/MS (91%) ESI− Calcd. 523.5 m/z Found: 523.4 m/z

Example 106

Preparation of P027

General procedure (A-3) was used to alkylate thiophene-2-sulfonic acid [2-(3-oxo-3,4-dihydro-2H-benzo[1,4]oxazin-5-yloxy)-acetyl]-amide, I-70 with 4-trifluoromethoxy benzyl bromide to provide compound P027. $^1$H-NMR (500 MHz, DMSO-$d_6$), MS (ESI$^-$): 541.5 (M−1), LC-MS: 90%.

Example 107

Preparation of P028

General procedure (A-3) was used to alkylate thiophene-2-sulfonic acid [2-(3-oxo-3,4-dihydro-2H-benzo[1,4]oxazin-5-yloxy)-acetyl]-amide, I-70 with 3-trifluoromethoxybenzyl bromide to provide compound P028. $^1$H-NMR (500 MHz, DMSO-$d_6$), MS (ESI$^-$): 542.9 (M−1), LC-MS: 81%.

Example 108

Preparation of P029

General procedure (A-3) was used to alkylate thiophene-2-sulfonic acid [2-(3-oxo-3,4-dihydro-2H-benzo[1,4]oxazin-5-yloxy)-acetyl]-amide, I-70 with 3-trifluoromethyl benzyl bromide to provide compound P029. $^1$H-NMR (500 MHz, DMSO-$d_6$), MS (ESI$^-$): 526.9 (M−1), LC-MS: 83%.

Example 109

Preparation of P030

General procedure (A-3) was used to alkylate thiophene-2-sulfonic acid [2-(3-oxo-3,4-dihydro-2H-benzo[1,4]oxazin-5-yloxy)-acetyl]-amide, I-70 with 3-methoxybenzyl bromide to provide compound P030. $^1$H-NMR (500 MHz, DMSO-$d_6$), MS (ESI$^-$): 487.4 (M−1), LC-MS: 83%

Example 110

Preparation of P031

General procedure (A-3) was used to alkylate thiophene-2-sulfonic acid [2-(3-oxo-3,4-dihydro-2H-benzo[1,4]oxazin-5-yloxy)-acetyl]-amide, I-70 with 2-trifluoromethylbenzyl bromide to provide compound P301. $^1$H-NMR (500 MHz, DMSO-$d_6$), MS (ESI$^-$): 525.5 (M−1), LC-MS: 90%.

Example 111

Preparation of P032

General procedure (A-3) was used to alkylate thiophene-2-sulfonic acid [2-(3-oxo-3,4-dihydro-2H-benzo[1,4]oxazin-5-yloxy)-acetyl]-amide, I-70 with 4-methylsulphonebenzyl bromide to provide compound P032. 1H NMR (DMSO-d6) 3.15 (s, 3H), 4.53 (s, 2H), 4.65 (s, 2H), 5.40 (s, 2H), 6.46 (d, J=8.5 Hz, 1H), 6.71 (d, J=8.0 Hz, 1H), 6.93 (t, J=8.5 Hz, 1H), 7.21 (t, J=4 Hz, 1H), 7.29 (d, J=8.5 Hz, 2H), 7.75 (d, J=8.5 Hz, 2H), 7.79 (m, 1H), 8.04 (m, 1H). LC/MS (98%) ESI− Calcd. 535.6 m/z Found: 535.3 m/z

Example 112

Preparation of P039

General procedure (A-3) was used to alkylate thiophene-2-sulfonic acid [2-(3-oxo-3,4-dihydro-2H-benzo[1,4]oxazin-5-yloxy)-acetyl]-amide, I-70 with 3,4-dichlorobenzyl bromide to provide compound P039. $^1$H-NMR (500 MHz, DMSO-$d_6$), MS (ESI$^-$): 525.5 (M−1), LC-MS: 90%.

Example 113

Preparation of P040

General procedure (A-3) was used to alkylate thiophene-2-sulfonic acid [2-(3-oxo-3,4-dihydro-2H-benzo[1,4]oxazin-5-yloxy)-acetyl]-amide, I-70 with 2,4-dichlorobenzyl bromide to provide compound P040. $^1$H-NMR (500 MHz, DMSO-$d_6$), MS (ESI$^-$): 525.4 (M−1), LC-MS: 78%;

Example 114

Preparation of P041

General procedure (A-3) was used to alkylate thiophene-2-sulfonic acid [2-(3-oxo-3,4-dihydro-2H-benzo[1,4]oxazin-5-yloxy)-acetyl]-amide, I-70 with 3,5-dimethoxybenzyl bromide to provide compound P041. $^1$H-NMR (500 MHz, DMSO-$d_6$), MS (ESI$^-$): 517.5 (M−1), LC-MS: 94%.

Example 115

Preparation of P042

General procedure (A-3) was used to alkylate thiophene-2-sulfonic acid [2-(3-oxo-3,4-dihydro-2H-benzo[1,4]oxazin-5-yloxy)-acetyl]-amide, I-70 with 5-bromomethyl-benzo[1,2,5]oxadiazole to provide compound P042. 1H NMR (DMSO-d6) 4.55 (s, 2H), 4.69 (s, 2H), 5.35 (s, 2H), 6.48 (d, J=8.5 Hz, 1H), 6.74 (d, J=8.0 Hz, 1H), 6.94 (t, J=8.0 Hz, 1H), 7.21 (t, J=4.0 Hz, 1H), 7.30 (d, J=9.0 Hz, 1H), 7.60 (s, 1H), 7.77 (m, 1H), 7.90 (d, J=9.0 Hz, 1H), 8.07 (d, J=5.0 Hz, 1H), 12.5 (bs, 1H). LC/MS (92%) ESI− Calcd. 499.5 m/z Found: 499.8 m/z

Example 116

Preparation of P004

Synthesis of (2-Oxo-1,2-dihydro-quinolin-8-yloxy)-acetic acid methyl ester, I-71. Methyl bromoacetate (367 mg, 2.4 mmol) was added to a stirred mixture of 8-hydroxy-1H-quinolin-2-one [which was prepared according to literature procedure (Wang, T. C. et al, *Synthesis*, 1997, 87-90)], (322 mg, 2 mmol), $K_2CO_3$ (414 mg, 3 mmol) in DMF (10 ml) at room temperature. The reaction mixture was stirred at rt over night and then partitioned between dichloromethane and water. Water layer was extracted with dichloromethane (2×50 ml). The combined organic phase was washed with water (3×50 ml), brine and dried over sodium sulfate. After removal of solvent, the residue was washed with ether to give 250 mg of compound I-71.

Synthesis of (1-Naphthalen-2-ylmethyl-2-oxo-1,2-dihydro-quinolin-8-yloxy)-acetic acid methyl ester, I-72. A mixture of compound I-71 (233 mg, 1 mmol), 2-(bromomethyl) naphthalene (332 mg, 1.5 mmol), KI (250 mg, 1.5 mmol) and $K_2CO_3$ (207 mg, 1.5 mmol) in DMF (8 ml) and water (2 drops) was stirred at rt over weekend and then partitioned between dichloromethane and water. Water layer was extracted with dichloromethane (2×50 ml). The combined organic phase was washed with water (4×50 ml), brine and dried over sodium sulfate. After removal of solvent, the residue was purified by column chromatography on silica gel with 2% methanol in dichloromethane as the eluant to give 120 mg of compound I-72, and 50 mg O-alkylated byproduct, (1-Naphthalen-2-ylmethyl-2-oxo-1,2-dihydro-quinolin-8-yloxy)-acetic acid methyl ester. For compound I-72: $^1$H-NMR (500 MHz, CDCl$_3$), $^{13}$C-NMR (125 MHz, CDCl$_3$)

Synthesis of (1-Naphthalen-2-ylmethyl-2-oxo-1,2-dihydro-quinolin-8-yloxy)-acetic acid, I-73. To a solution of compound I-72 (120 mg, 0.32 mmol) in EtOH (8 ml), NaOH aq. (2N, 5 ml) was added at r.t. The reaction mixture was stirred at r.t. over night and then the pH was adjusted to acidic by adding 2N HCl aq. The reaction mixture was extracted with EtOAc (2×10 ml). The combined organic phase was washed with water, brine, and dried over sodium sulfate. After removal of solvent, the residue was washed with ether to give 100 mg of compound I-73. $^1$H-NMR (500 MHz, DMSO-d$_6$)

Synthesis of P004. To a mixture of the acid I-73 (36 mg, 0.1 mmol), 2-thiophenesulfonamide (20 mg, 0.12 mmol), 4-dimethylamino pyridine (25 mg, 0.2 mmol) in dichloromethane (5 ml), was added EDCI (38 mg, 0.2 mmol). The reaction mixture was stirred at r.t. over night. The solution was diluted with dichloromethane, washed with diluted HCl aq., water, brine and dried over sodium sulfate. After removal of solvent, the solid was washed with ether to give 35 mg of compound P004. 1H NMR (DMSO-d6) 4.36 (s, 2H), 6.06 (s, 2H), 6.74 (d, J=9 Hz, 1H), 6.92 (d, J=8.0 Hz, 1H), 7.11 (t, J=7.5 Hz, 1H), 7.16 (m, 2H), 7.34 (d, J=7 Hz, 1H), 7.38-7.42 (m, 3H), 7.63-7.72 (m, 3H), 7.81 (m, 1H), 7.95 (m, 2H). LC/MS (90%) ESI− Calcd. 503.6 m/z Found: 503.4 m/z Example 117

Preparation of P012

Synthesis of 8-(Naphthalen-2-ylmethoxy)-1H-quinolin-2-one, I-74. 2-(bromomethyl) naphthalene (530 mg, 2.4 mmol) was added to a stirred mixture of 8-(Naphthalen-2-ylmethoxy)-1H-quinolin-2-one (322 mg, 2 mmol), K$_2$CO$_3$ (414 mg, 3 mmol) in DMF (10 ml) at room temperature. The reaction mixture was stirred at rt over night and then partitioned between dichloromethane and water. Water layer was extracted with dichloromethane (2×50 ml). The combined organic phase was washed with water (3×50 ml), brine and dried over sodium sulfate. After removal of solvent, the residue was washed with ether to give 470 mg of compound I-74. $^1$H-NMR (500 MHz, CDCl$_3$).

Synthesis of [8-(Naphthalen-2-ylmethoxy)-2-oxo-2H-quinolin-1-yl]-acetic acid methyl ester, I-75. A mixture of compound I-74 (210 mg, 0.7 mmol), Methyl bromoacetate (230 mg, 1.5 mmol), KI (250 mg, 1.5 mmol) and K$_2$CO$_3$ (207 mg, 1.5 mmol) in DMF (8 ml) and water (2 drops) was stirred at rt over night and then partitioned between dichloromethane and water. Water layer was extracted with dichloromethane (2×50 ml). The combined organic phase was washed with water (4×50 ml), brine and dried over sodium sulfate. After removal of solvent, the residue was purified by column chromatography on silica gel with Hexane, Hexane/dichloromethane (1:1), dichloromethane, 1% methanol in dichloromethane as the eluant to give 160 mg of compound I-75, and 30 mg O-alkyl byproduct [8-(Naphthalen-2-ylmethoxy)-quinolin-2-yloxy]-acetic acid methyl ester. For compound I-75: $^1$H-NMR (500 MHz, CDCl$_3$); $^{13}$C-NMR (125 MHz, CDCl$_3$).

Synthesis of [8-(Naphthalen-2-ylmethoxy)-2-oxo-2H-quinolin-1-yl]-acetic acid, I-76. To a solution of compound I-75 (30 mg, 0.08 mmol) in THF (3 ml) and MeOH (3 ml), NaOH aq. (2N, 3 ml) was added at rt. The reaction mixture was stirred at rt over night and then the pH was adjusted to acidic by adding 2N HCl aq. The reaction mixture was extracted with EtOAc (2×15 ml). The combined organic phase was washed with water, brine, and dried over sodium sulfate. After removal of solvent, the residue was washed with ether to give 25 mg of acid I-76. $^1$H-NMR (500 MHz, DMSO-d$_6$).

Synthesis of P012. To a mixture of the acid I-76 (25 mg, 0.07 mmol), 2-thiophenesulfonamide (14 mg, 0.084 mmol), 4-dimethylamino pyridine (18 mg, 0.15 mmol) in dichloromethane (5 ml) and DMSO (0.5 ml) was added EDCI (29 mg, 0.15 mmol). The reaction mixture was stirred at rt over night. The solution was diluted with dichloromethane, washed with diluted HCl aq., water, brine and dried over sodium sulfate. After removal of solvent, the solid was washed with ether to give 30 mg of compound P-12. $^1$H-NMR (500 MHz, DMSO-d$_6$), MS (ESI−): 503.3 (M−1), LC-MS: 91%.

Example 119

Preparation of P015

Synthesis of 8-(Naphthalen-2-ylmethoxy)-quinoline, I-81. 2-(bromomethyl) naphthalene (663 mg, 3 mmol) was added to a stirred mixture of 8-hydroxy quinoline (435 mg, 3 mmol), K$_2$CO$_3$ (621 mg, 4.5 mmol) in acetone (20 ml) at room temperature. The reaction mixture was stirred at rt over weekend and then partitioned between EtOAc and water. Water layer was extracted with EtOAc (2×100 ml). The combined organic phase was washed with water (2×100 ml), brine and dried over sodium sulfate. After removal of solvent, the residue was washed with ether to give 650 mg of compound I-81. $^1$H-NMR (500 MHz, CDCl$_3$).

Synthesis of 8-(Naphthalen-2-ylmethoxy)-1,2,3,4-tetrahydro-quinoline, I-82. To a solution of compound I-81 (285 mg, 1 mmol) in AcOH (15 ml), NaCNBH$_3$ (252 mg, 4 mmol) was added at rt. The reaction mixture was stirred at rt for 1 hr and then 60° C. for 1 hr. The reaction mixture was stirred at rt over night and solvent was removed under vacuum. The residue was partitioned in dichloromethane and water and the pH was adjusted to 8-8 by adding NH$_4$OH aq. Water phase was extracted with dichloromethane (3×50 ml). The combined organic phase was washed with brine and dried over sodium sulfate. After removal of solvent, the residue was purified by column chromatography on silica gel with dichloromethane and 2% methanol/dichloromethane as the eluant to give 200 mg of compound I-82. $^1$H-NMR (500 MHz, CDCl$_3$).

Synthesis of [8-(Naphthalen-2-ylmethoxy)-3,4-dihydro-2H-quinolin-1-yl]-acetic acid methyl ester, I-83. A mixture of compound I-82 (200 mg, 0.7 mmol), Methyl bromoacetate (153 mg, 1 mmol), KI (233 mg, 1.4 mmol) and K$_2$CO$_3$ (193 mg, 1.4 mmol) in DMF (10 ml) and water (0.2 ml) was stirred at rt over night and then partitioned between dichloromethane and water. Water layer was extracted with dichloromethane (2×50 ml). The combined organic phase was washed with water (4×50 ml), brine and dried over sodium sulfate. After removal of solvent, 250 mg of crude compound I-83 was obtained. $^1$H-NMR (500 MHz, CDCl$_3$).

Synthesis of [8-(Naphthalen-2-ylmethoxy)-3,4-dihydro-2H-quinolin-1-yl]-acetic acid, I-84. To a solution of compound I-83 (250 mg, 0.7 mmol) in THF (3 ml) and EtOH (6 ml), NaOH aq. (2N, 4 ml) was added at rt. The reaction mixture was stirred at rt over night and then the pH was adjusted to acidic by adding 2N HCl aq. The reaction mixture was extracted with EtOAc (2×15 ml). The combined organic phase was washed with water, brine, and dried over sodium sulfate. After removal of solvent, the residue was washed with ether to give 120 mg of compound I-84. $^1$H-NMR (500 MHz, DMSO-d$_6$).

Synthesis of compound P015. To a mixture of the acid I-84 (25 mg, 0.07 mmol), 2-thiophenesulfonamide (16 mg, 0.1 mmol), 4-dimethylamino pyridine (24 mg, 0.2 mmol) in dichloromethane (6 ml) and DMSO (0.5 ml) was added EDCI (38 mg, 0.2 mmol). The reaction mixture was stirred at rt over night. The solution was diluted with dichloromethane, washed with diluted HCl aq., water, brine and dried over sodium sulfate. After removal of solvent, the residue was purified by column chromatography on silica gel with dichloromethane and 2% methanol/dichloromethane as the eluant to give 7 mg of P015. 1H NMR (DMSO-d6) 1.81 (m, 2H), 2.78 (t, J=6.5 Hz, 2H), 3.03 (m, 2H), 3.62 (s, 2H), 5.12 (s, 2H), 6.66 (d, J=7.5 Hz, 1H), 6.72 (d, J=7.5 Hz, 1H), 6.79 (m, 1H), 6.87 (m, 1H), 7.19 (m, 1H), 7.35 (m, 1H), 7.43 (m, 1H), 7.49 (m, 2H), 7.62 (m, 1H), 7.72 (m, 2H), 7.82 (m, 3H). LC/MS (97%) ESI– Calcd. 491.6 m/z Found: 491.2 m/z Example 120

Preparation of P046

Synthesis of 2-Amino-benzene-1,3-diol, I-85. A mixture of 2-nitrobenzene-1,3-diol (3.1 g, 20 mmol) and 1 g of Pd/C (5%) in methanol (100 ml) was hydrogenated at 30 psi of H$_2$ at rt for 2 days. The reaction mixture was filtered with celite and the celite was washed with ethanol, water and methanol. After removal of solvent under vacuum, 2.6 g of compound I-85 was obtained as white solid. $^1$H-NMR (500 MHz, DMSO-d$_6$).

Synthesis of 2-[(Naphthalen-2-ylmethyl)-amino]-benzene-1,3-diol, I-86. A mixture of compound I-85 (250 mg, 2 mmol) and 2-naphthaldehyde (343 mg, 2.2 mmol) in methanol (20 ml) was stirred at rt for 2 hrs and then cooled to –10° C. NaBH$_4$ (304 mg, 8 mmol) was slowly added to reaction mixture at –10 to 0° C. After stirring at 0° C. for 30 min and rt for 2 hrs, the reaction mixture was cooled to 0° C. and quenched with water. The reaction mixture was adjusted to pH ~4 and extracted with EtOAc (2×100 ml). Sodium chloride was added to water layer, and extracted with dichloromethane. Solid was formed from water/CH2Cl2. Solid was filtered and washed with water and CH2Cl2 to give 140 mg of compound I-86. $^1$H-NMR (500 MHz, DMSO-d$_6$).

Synthesis of 4-Hydroxy-3-naphthalen-2-ylmethyl-3H-benzooxazol-2-one, I-87. A mixture of compound I-86 (140 mg, 0.46 mmol), triethylamine (46 mg, 0.46 mmol) and 1,1'-carbonyldiimidazole (80 mg, 0.5 mmol) in THF (20 ml) was refluxed over night and then partitioned between EtOAc and water. Water layer was extracted with EtOAc. The combined organic phase was washed with diluted HCl aq., water, brine and dried over sodium sulfate. After removal of solvent, 140 mg of compound I-87 was obtained as a white solid. $^1$H-NMR (500 MHz, DMSO-d$_6$). $^{13}$C-NMR (125 MHz, DMSO-d$_6$).

Synthesis of (3-Naphthalen-2-ylmethyl-2-oxo-2,3-dihydro-benzooxazol-4-yloxy)-acetic acid tert-butyl ester, I-88. A mixture of compound I-87 (140 mg, 0.48 mmol), tert-butyl bromoacetate (136 mg, 0.7 mmol) and K2CO3 (95 mg, 0.7 mmol) in acetone (10 ml) and DMF (5 ml) was stirred at rt over night and then partitioned between EtOAc and water. Water layer was extracted with EtOAc. The combined organic phase was washed with water, brine and dried over sodium sulfate. After removal of solvent, 160 mg of compound I-88 was obtained. 1H-NMR (500 MHz, CDCl3).

Synthesis of (3-Naphthalen-2-ylmethyl-2-oxo-2,3-dihydro-benzooxazol-4-yloxy)-acetic acid, I-89. To a solution of compound I-88 (150 mg, 0.37 mmol) in dichloromethane (5 ml), TFA (10 ml) was added at rt The reaction mixture was stirred at rt for 2 hrs and solvent was removed under vacuum. The residue was washed with ether to give 130 mg of compound I-89. MS (ESI): 348.2 (M–1), LC-MS: 99%, 1H-NMR (500 MHz, DMSO-d6).

Synthesis of Compound P046. A mixture of the acid I-89 (35 mg, 0.1 mmol), 2-thiophenesulfonamide (20 mg, 0.12 mmol), 4-dimethylamino pyridine (25 mg, 0.2 mmol) and EDCI (38 mg, 0.2 mmol) in dichloromethane (5 ml) and DMSO (0.5 ml) was stirred at rt over night. The solution was diluted with dichloromethane, washed with diluted HCl aq., water, brine and dried over sodium sulfate. After removal of solvent, the solid was washed with ether to give 30 mg of compound P046. MS (ESI–): 493.4 (M–1), LC-MS: 81%, 1H-NMR (500 MHz, DMSO-d6).

Example 121

Preparation of P047

A mixture of the acid I-89 (35 mg, 0.1 mmol), 2-methoxy-5-bromo-phenylsulfonamide (32 mg, 0.12 mmol), 4-dimethylamino pyridine (25 mg, 0.2 mmol) and EDCI (38 mg, 0.2 mmol) in dichloromethane (5 ml) and DMSO (0.5 ml) was stirred at rt over night. The solution was diluted with dichloromethane, washed with diluted HCl aq., water, brine and dried over sodium sulfate. After removal of solvent, the residue was purified by column chromatography on silica gel with methanol/dichloromethane as the eluent to give 24 mg of compound P047. MS (ESI–): 597.2 (M–1), LC-MS: 94%, 1H-NMR (500 MHz, DMSO-d6).

Example 122

Preparation of P048

A mixture of the acid I-89 (35 mg, 0.1 mmol), trifluoromethylsulfonamide (18 mg, 0.12 mmol), 4-dimethylamino pyridine (25 mg, 0.2 mmol) and EDCI (38 mg, 0.2 mmol) in dichloromethane (5 ml) and DMSO (0.5 ml) was stirred at rt over night. The solution was diluted with dichloromethane, washed with diluted HCl aq., water, brine and dried over sodium sulfate. After removal of solvent, 30 mg of compound P048 was obtained as DMAP salt. MS (ESI–): 479.3 (M–1), LC-MS: 96%, 1H-NMR (500 MHz, DMSO-d6).

Example 123

Preparation of P050

Synthesis of 4-Hydroxy-3H-benzooxazol-2-one, I-90. A mixture of 2-amin-benzne-1,3-diol (2.03 g, 16.2 mmol) and 1,1'-carbonyldiimidazole (2.63 g, 16.2 mmol) in THF (200 ml) was refluxed over night. After removal of THF under vacuum, residue was dissolved in EtOAc and washed with diluted HCl aq., water, brine and dried over sodium sulfate. After removal of solvent, solid was washed with ether to give 1.9 g of compound I-90. $^1$H-NMR (500 MHz, DMSO-d$_6$).

Synthesis of Carbonic acid tert-butyl ester 2-oxo-2,3-dihydro-benzooxazol-4-yl ester, I-91. To a solution of compound I-90 (1 g, 6.6 mmol) in THF (20 ml), water (8 ml) and NaOH aq. (2N, 13 ml), di-tert-butyl dicarbonate (3.16 g, 14.5 mmol) in THF (15 ml) was added at rt. After stirring at rt over night, reaction mixture was diluted with water and EtOAc and cooled with ice, and then adjusting pH to about 2-3 by addition of HCl aq. (2N). Water layer was extracted with EtOAc (2×100 ml). The combined organic phase was washed with water, brine and dried over sodium sulfate. After removal of solvent, 2.3 g of compound I-91 was obtained. $^1$H-NMR (500 MHz, DMSO-$d_6$).

Synthesis of 3-Benzo[1,3]dioxol-5-ylmethyl-4-hydroxy-3H-benzooxazol-2-one, I-92. A mixture of compound I-91 (251 mg, 1 mmol), 3,4-methylenedioxy benzyl chloride (255 mg, 1.5 mmol), K2CO3 (207 mg, 1.5 mmol) and KI (249 mg, 1.5 mmol) in acetone (10 ml) and water (5 drops) was stirred at rt over night and then partitioned between EtOAc and water. Water layer was extracted with EtOAc. The combined organic phase was washed with water, brine and dried over sodium sulfate. After removal of solvent, the intermediate O-BOC compound (carbonic acid 3-benzo[1,3]dioxol-5-yl-methyl-2-oxo-2,3-dihydro-benzooxazol-4-yl ester tert-butyl ester) was dissolved in dichloromethane (6 ml), and then TFA (3 ml) was added at rt The reaction mixture was stirred at rt for 15 min and solvent was removed under vacuum. The residue was washed with ether to give 100 mg of compound I-92. $^1$H-NMR (500 MHz, DMSO-$d_6$).

Synthesis of (3-Benzo[1,3]dioxol-5-ylmethyl-2-oxo-2,3-dihydro-benzooxazol-4-yloxy)-acetic acid tert-butyl ester, I-93. A mixture of compound I-92 (100 mg, 0.35 mmol), tert-butyl bromoacetate (136 mg, 0.7 mmol) and K2CO3 (95 mg, 0.7 mmol) in acetone (8 ml) and DMSO (2 ml) was stirred at rt over night and then partitioned between EtOAc and water. Water layer was extracted with EtOAc. The combined organic phase was washed with water, brine and dried over sodium sulfate. After removal of solvent, 100 mg of compound I-93 was obtained. $^1$H-NMR (500 MHz, CDCl$_3$).

Synthesis of (3-Benzo[1,3]dioxol-5-ylmethyl-2-oxo-2,3-dihydro-benzooxazol-4-yloxy)-acetic acid, I-94. To a solution of compound I-93 (100 mg, 0.25 mmol) in dichloromethane (4 ml), TFA (8 ml) was added at rt The reaction mixture was stirred at rt for 3 hrs and solvent was removed under vacuum. The residue was washed with ether to give 80 mg of compound I-94. $^1$H-NMR (500 MHz, DMSO-$d_6$), MS (ESI$^-$): 342.2 (M–1), LC-MS: >90%.

Synthesis of P050. A mixture of the acid I-94 (35 mg, 0.1 mmol), 2-thiophenesulfonamide (20 mg, 0.12 mmol), 4-dimethylamino pyridine (25 mg, 0.2 mmol) and EDCI (38 mg, 0.2 mmol) in dichloromethane (5 ml) and DMSO (0.5 ml) was stirred at rt over night. The solution was diluted with dichloromethane, washed with diluted HCl aq., water, brine and dried over sodium sulfate. After removal of solvent, the residue was purified by column chromatography on silica gel with methanol/dichloromethane as the eluent to give 35 mg of P050. MS (ESI$^-$): 487.4 (M–1), LC-MS: 87%, $^1$H-NMR (500 MHz, DMSO-$d_6$).

Example 124

Preparation of P051

Synthesis of 3-(3,4-Dichloro-benzyl)-4-hydroxy-3H-benzooxazol-2-one, I-95. A mixture of compound I-91 (251 mg, 1 mmol), 3,4-dichlorobenzyl chloride (292 mg, 1.5 mmol), K2CO$_3$ (207 mg, 1.5 mmol) and KI (249 mg, 1.5 mmol) in acetone (10 ml) and water (5 drops) was stirred at rt over night and then partitioned between EtOAc and water. Water layer was extracted with EtOAc. The combined organic phase was washed with water, brine and dried over sodium sulfate. After removal of solvent, the O-BOC prodcut (Carbonic acid tert-butyl ester 3-(3,4-dichloro-benzyl)-2-oxo-2,3-dihydro-benzooxazol-4-yl ester) was dissolved in dichloromethane (6 ml), and then TFA (3 ml) was added at rt The reaction mixture was stirred at rt for 15 min and solvent was removed under vacuum. The residue was washed with ether to give 80 mg of compound I-95. $^1$H-NMR (500 MHz, DMSO-$d_6$).

Synthesis of [3-(3,4-Dichloro-benzyl)-2-oxo-2,3-dihydro-benzooxazol-4-yloxy]-acetic acid tert-butyl ester, I-96. A mixture of compound I-95 (80 mg, 0.26 mmol), tert-butyl bromoacetate (136 mg, 0.7 mmol) and K2CO3 (95 mg, 0.7 mmol) in acetone (8 ml) and DMSO (2 ml) was stirred at rt over night and then partitioned between EtOAc and water. Water layer was extracted with EtOAc. The combined organic phase was washed with water, brine and dried over sodium sulfate. After removal of solvent, 90 mg of compound I-96 was obtained. $^1$H-NMR (500 MHz, CDCl$_3$).

Synthesis of [3-(3,4-Dichloro-benzyl)-2-oxo-2,3-dihydro-benzooxazol-4-yloxy]-acetic acid, I-97:20. To a solution of compound I-96 (90 mg, 0.21 mmol) in dichloromethane (4 ml), TFA (8 ml) was added at rt The reaction mixture was stirred at rt for 3 hrs and solvent was removed under vacuum. The residue was washed with ether to give 70 mg of acid I-97. MS (ESI$^-$): 367.9 (M–1), LC-MS: >90%, $^1$H-NMR (500 MHz, DMSO-$d_6$).

Synthesis of P051. A mixture of the acid I-97 (37 mg, 0.1 mmol), 2-thiophenesulfonamide (20 mg, 0.12 mmol), 4-dimethylamino pyridine (25 mg, 0.2 mmol) and EDCI (38 mg, 0.2 mmol) in dichloromethane (5 ml) and DMSO (0.5 ml) was stirred at rt over night. The solution was diluted with dichloromethane, washed with diluted HCl aq., water, brine and dried over sodium sulfate. After removal of solvent, the residue was purified by column chromatography on silica gel with methanol/dichloromethane as the eluent to give 32 mg of compound P051. MS (ESI$^-$): 511.4 (M–1), LC-MS: 89%, $^1$H-NMR (500 MHz, DMSO-$d_6$).

Example 125

Preparation of P052

Synthesis of 3-(2,4-Dichloro-benzyl)-4-hydroxy-3H-benzooxazol-2-one, I-98. A mixture of compound I-91 (251 mg, 1 mmol), 2,4-dichlorobenzyl chloride (292 mg, 1.5 mmol), K2CO$_3$ (207 mg, 1.5 mmol) and KI (249 mg, 1.5 mmol) in acetone (10 ml) and water (5 drops) was stirred at rt over night and then partitioned between EtOAc and water. Water layer was extracted with EtOAc. The combined organic phase was washed with water, brine and dried over sodium sulfate. After removal of solvent, the O-BOC derivative (carbonic acid tert-butyl ester 3-(2,4-dichloro-benzyl)-2-oxo-2,3-dihydro-benzooxazol-4-yl ester), was dissolved in dichloromethane (6 ml), and then TFA (3 ml) was added at rt The reaction mixture was stirred at rt for 15 min and solvent was removed under vacuum. The residue was washed with ether to give 110 mg of compound I-98. $^1$H-NMR (500 MHz, DMSO-$d_6$).

Synthesis of 3-(2,4-Dichloro-benzyl)-2-oxo-2,3-dihydro-benzooxazol-4-yloxy]-acetic acid tert-butyl ester, I-99. A mixture of compound I-98 (80 mg, 0.26 mmol), tert-butyl bromoacetate (136 mg, 0.7 mmol) and K2CO3 (95 mg, 0.7 mmol) in acetone (8 ml) and DMSO (2 ml) was stirred at rt over night and then partitioned between EtOAc and water. Water layer was extracted with EtOAc. The combined organic phase was washed with water, brine and dried over sodium sulfate. After removal of solvent, 140 mg of compound I-99 was obtained. $^1$H-NMR (500 MHz, CDCl$_3$).

Synthesis of 3-(2,4-Dichloro-benzyl)-2-oxo-2,3-dihydro-benzooxazol-4-yloxy]-acetic acid, I-100. To a solution of compound I-99 (90 mg, 0.33 mmol) in dichloromethane (4 ml), TFA (8 ml) was added at rt The reaction mixture was stirred at rt for 3 hrs and solvent was removed under vacuum. The residue was washed with ether to give 105 mg of compound I-100. MS (ESI⁻): 366.2 (M−1), LC-MS: >90%, ¹H-NMR (500 MHz, DMSO-d₆).

Synthesis of P052. A mixture of the acid I-100 (37 mg, 0.1 mmol), 2-thiophenesulfonamide (20 mg, 0.12 mmol), 4-dimethylamino pyridine (25 mg, 0.2 mmol) and EDCI (38 mg, 0.2 mmol) in dichloromethane (5 ml) and DMSO (0.5 ml) was stirred at rt over night. The solution was diluted with dichloromethane, washed with diluted HCl aq., water, brine and dried over sodium sulfate. After removal of solvent, the residue was purified by column chromatography on silica gel with methanol/dichloromethane as the eluent to give 34 mg of compound P052. MS (ESI⁻): 511.4 (M−1), LC-MS: 89%, ¹H-NMR (500 MHz, DMSO-d₆).

Example 126

Preparation of P053

Synthesis of 3-(2,5-Dimethyl-benzyl)-4-hydroxy-3H-benzooxazol-2-one, I-101. A mixture of compound I-91 (251 mg, 1 mmol), 2,5-dimethylbenzyl chloride (233 mg, 1.5 mmol), K2CO3 (207 mg, 1.5 mmol) and KI (249 mg, 1.5 mmol) in acetone (10 ml) and water (5 drops) was stirred at rt over night and then partitioned between EtOAc and water. Water layer was extracted with EtOAc. The combined organic phase was washed with water, brine and dried over sodium sulfate. After removal of solvent, the O-BOC derivative (Carbonic acid tert-butyl ester 3-(2,5-dimethyl-benzyl)-2-oxo-2,3-dihydro-benzooxazol-4-yl ester), was dissolved in dichloromethane (6 ml), and then TFA (3 ml) was added at rt The reaction mixture was stirred at rt for 15 min and solvent was removed under vacuum. The residue was washed with ether to give 110 mg of compound I-101.

Synthesis of 3-(2,5-Dimethyl-benzyl)-2-oxo-2,3-dihydro-benzooxazol-4-yloxy]-acetic acid tert-butyl ester, I-102. A mixture of compound I-101 (110 mg, 0.4 mmol), tert-butyl bromoacetate (136 mg, 0.7 mmol) and K2CO3 (95 mg, 0.7 mmol) in acetone (8 ml) and DMSO (2 ml) was stirred at rt over night and then partitioned between EtOAc and water. Water layer was extracted with EtOAc. The combined organic phase was washed with water, brine and dried over sodium sulfate. After removal of solvent, 150 mg of compound I-102 was obtained. ¹H-NMR (500 MHz, CDCl₃).

Synthesis of [3-(2,5-Dimethyl-benzyl)-2-oxo-2,3-dihydro-benzooxazol-4-yloxy]-acetic acid, I-103. To a solution of compound I-102 (150 mg, 0.39 mmol) in dichloromethane (4 ml), TFA (8 ml) was added at rt The reaction mixture was stirred at rt for 3 hrs and solvent was removed under vacuum. The residue was washed with ether to give 120 mg of compound I-103. MS (ESI⁻): 326.4 (M−1), LC-MS: >90%, ¹H-NMR (500 MHz, DMSO-d₆).

Synthesis of P053. A mixture of the acid I-103 (33 mg, 0.1 mmol), 2-thiophenesulfonamide (20 mg, 0.12 mmol), 4-dimethylamino pyridine (25 mg, 0.2 mmol) and EDCI (38 mg, 0.2 mmol) in dichloromethane (5 ml) and DMSO (0.5 ml) was stirred at rt over night. The solution was diluted with dichloromethane, washed with diluted HCl aq., water, brine and dried over sodium sulfate. After removal of solvent, the residue was purified by column chromatography on silica gel with methanol/dichloromethane as the eluent to give 37 mg of compound P053. 1H NMR (DMSO-d6) 2.11 (s, 3H), 2.24 (s, 3H), 4.58 (s, 2H), 5.13 (s, 2H), 6.69 (m, 2H), 6.92 (d, J=8.0 Hz, 1H), 7.01 (d, J=8.0 Hz, 1H), 7.04 (m, 2H), 7.18 (m, 1H), 7.73 (m, 1H), 8.01 (m, 1H), 12.5 (bs, 1H). LC/MS (88%) ESI− Calcd. 471.5 m/z Found: 471.4 m/z Example 127

Preparation of P083

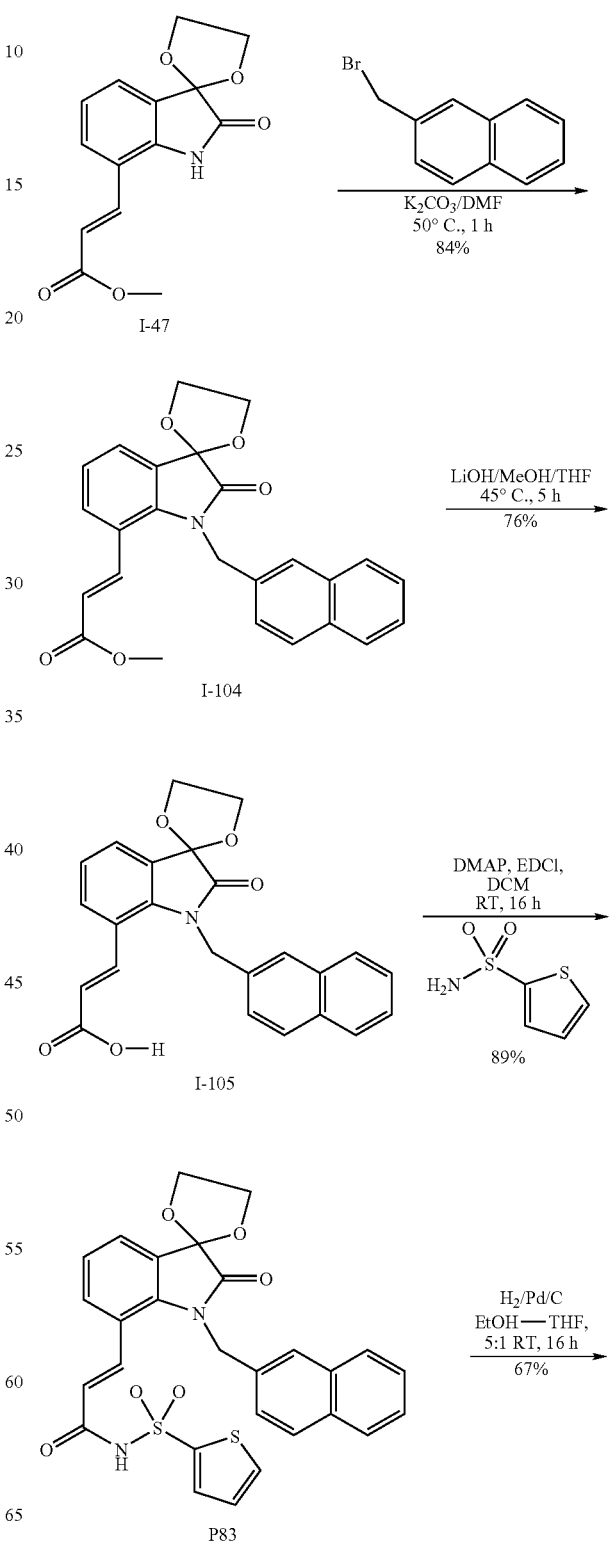

-continued

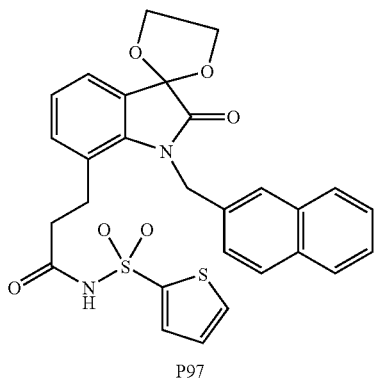

P97

Synthesis of I-104. A mixture of I-47 (0.7 g, 2.54 mmol, 1 equiv.), 2-bromomethylnaphthalene (0.59 g, 2.67 mmol, 1.05 equiv.) and $K_2CO_3$ (1.76 g, 12.72 mmol, 5 equiv.) in DMF (10 mL) was heated at 50° C. for 1 h. A suspension was filtered, washed with water, brine, dried over $MgSO_4$ to afford product I-104, 0.89 g (84%) as yellow solid. MS (ESI$^+$): 416 (M+1). $^1$H-NMR (500 MHz, CDCl$_3$) confirmed the structure Synthesis of I-105. A solution of ester I-104 (600 mg, 1.44 mmol, 1 equiv.), LiOH.H$_2$O (70 mg, 1.66 mmol, 1.15 equiv.) in THF/MeOH/H$_2$O (3:1:1, 22 mL) was stirred at 45° C. for 5 h. A reaction was concentrated in vacuo and sat. NH$_4$Cl (10 mL) was added to the residue. Precipitate was extracted with CH2Cl2. A solution was washed with sat. NH$_4$Cl, brine, dried over MgSO$_4$ and concentrated in vacuo. The residue was triturated with ether (8 mL) to afford the acid I-105 [362 mg (62%)] as white solid. MS (ESI$^-$): 400 (M−1). $^1$H-NMR (500 MHz, CDCl$_3$) confirmed the structure.

Synthesis of P083. To a mixture of the acid, I-105 (71 mg, 0.177 mmol, 1 equiv.) in 2 mL dichloromethane were added DMAP (43 mg, 0.354 mmol, 2 equiv.), 2-thiophenesulfonamide (37 mg, 0.225 mmol), and EDCI (82 mg, 0.425 mmol). The mixture was stirred at room temperature for 16 hours and then quenched with NH$_4$Cl (6 mL). The mixture was then extracted with EtOAc (6 mL). The extract was washed with brine, and then dried over MgSO$_4$. The solvent was removed in vacuo. Trituration of the residue with ether (2 mL) afforded 86 mg (86%) of sulfonamide P083 as off-white solid. LC-MS (ESI$^-$): 545 (M−1) (81%). $^1$H-NMR (500 MHz, CDCl$_3$) confirmed the structure.

Example 128

Preparation of P097

Sulfonamide P083 (57 mg, 0.104 mmol) was dissolved in EtOH-THF (24 mL, 5:1) and the solution was saturated by hydrogen. Balloon with hydrogen was attached to the apparatus and the reaction mixture was stirred at RT for 20 h, followed by stirring at 60° C. for 22 h. The resulting solution was filtered through Whatman 0.45 µm filter. The solvent was removed in vacuo. Trituration of the residue with ether (2×2 mL) afforded 44 mg (67%) of sulfonamide P097 as off-white solid. LC-MS (ESI$^-$): 547 (M−1) (95%). $^1$H-NMR (500 MHz, CDCl$_3$) confirmed the structure.

Example 129

Preparation of P096

Synthesis of (E)-3-(1-Naphthalen-2-ylmethyl-2,3-dioxo-2,3-dihydro-1H-indol-7-yl)-acrylic acid, I-106. A solution of I-105 (48 mg, 0.12 mmol) in a mixture of conc. HCl and i-PrOH (1:1, 4 mL) was heated at 100° C. for 30 min. The reaction mixture was cooled to RT, filtered and washed with water to afford isatin derivative I-106, 28 mg (66%) as bright orange solid which is insoluble in ether, EtOAc or CH2Cl2. MS(ESI−) 356 (M−1).

Synthesis of P096. To a mixture of I-106 (21 mg, 0.059 mmol, 1 equiv.) in 0.5 mL dichloromethane were added DMAP (19 mg, 0.157 mmol, 2.6 equiv.), 2-thiophenesulfonamide (13 mg, 0.078 mmol, 1.3 equiv.), and EDCI (30 mg, 0.157 mmol, 2.6 equiv.). The mixture was stirred at room temperature for 16 hours and then quenched with 10% HCl and extracted with EtOAc-CH2Cl2. The extract was washed with water, brine, and then dried over MgSO$_4$. The solvent was removed in vacuo. The residue was dissolved in CH2Cl2 (2 mL) and filtered. Chromatography on SiO$_2$ (5 g) with EtOAc/Hex (1:1) afforded 10 mg (33%) of sulfonamide P096 as off-white solid. LC-MS (ESI$^-$): 501 (M−1) (98%). $^1$H-NMR (500 MHz, CDCl$_3$) confirmed the structure.

Example 130

Preparation of P126

A solution of isatin analog P113 (64 mg, 0.108 mmol, 1 equiv.), 2-mercaptoethyleneamine (8.3 mg, 0.108 mmol, 1 equiv.) in AcOH (1 mL) was heated to 100° C. for 20 min. Another portion of 2-mercaptoethyleneamine (4.3 mg, 0.056 mmol, 0.5 equiv.) was added and heating continued for another 10 min. The reaction mixture was evaporated, the resulted oil was triturated with THF-ether, 1:3 and a solution was filtered off to afford the thiazolidine derivative P126 (28.3 mg, 40%) as red solid. $^1$H NMR (DMSO-d$_6$) 3.5-3.7 (m, 3H), 3.99 (dd, J=11, 8.0 Hz, 1H), 4.93 (d, J=18.0 Hz, 1H), 5.01 (d, J=18.0 Hz, 1H), 6.03 (d, J=15.2 Hz, 1H), 6.85 (d, J=8.4 Hz, 2H), 7.11 (t, J=4.0 Hz, 1H), 7.19 (d, J=15.0 Hz, 2H), 7.30-7.34 (m, 2H), 7.36 (s, 1H), 7.36 (d, J=2.0 Hz, 1H), 7.51 (dd, J=7.2, 1.2 Hz, 1H). LC-MS (99%): ESI$^-$ Calcd. 547 m/z Found: 547

Example 131

Preparation of P037

Synthesis of 2-Benzyloxy-6-nitro-phenylamine, I-107: A mixture of 2-amino-3-nitro-phenol (1.54 g, 0.01 mol), benzyl bromide (1.71 g, 0.01 mol) and K$_2$CO$_3$ (1.54 g, 0.011 mol) in DMF (5.0 mL) was stirred at room temperature. After 20 h, reaction mixture was diluted with water (100 mL) and extracted with EtOAc (100 mL×3). Combined organic layers were washed with 2N NaOH (20 mL×3), water (100 mL), brine (100 mL), dried over anhydrous sodium sulfate and concentrated to afford 2-Benzyloxy-6-nitro-phenylamine, I-107 (2.01 g).

Synthesis of N-(2-benzyloxy-6-nitro-phenyl)acetamide, I-108. To a solution of 2-Benzyloxy-6-nitro-phenylamine (I-107, 1.52 g, 0.0062 mol) in acetic anhydride (1.27 g, 0.0125 mol), 4 drops of conc. H$_2$SO$_4$ was added at room temperature and stirred for one minute and then the reaction flak was immersed in an oil bath maintained at 90° C. After 2 minutes, the solidified reaction mixture was taken in water (20 mL) and filtered the solid. Solid was further washed with water (20 mL×2) and dried under high vacuum to afford N-(2-benzyloxy-6-nitro-phenyl)acetamide, I-108 (1.59 g).

Synthesis of N-(2-benzyloxy-6-nitro-phenyl)-N-naphthalene-2-ylmethyl-acetamide, I-109 To a solution of N-(2-benzyloxy-6-nitro-phenyl)acetamide (0.576 g, 2.0 mmol) in DMF (2.0 mL), NaH in 60% dispersion in mineral oil (160 mg, 4.0 mmol) was added in small portions over a period of 10 minutes at room temperature. 2-(bromomethyl)naphthalene (442 mg, 2.0 mmol) was added to the reaction mixture and stirred at room temperature for 1.5 h. DMF was removed under high vacuum and the residue was taken in $CH_2Cl_2$ (60 mL) and washed with water (20 mL) brine (20 mL), dried over anhydrous sodium sulfate and concentrated. The dark brown oily syrup obtained was 40 mL of ether/hexane (1:1) and stirred for 1 h, resulting in the precipitation of solid, which was filtered and dried to afford N-(2-benzyloxy-6-nitro-phenyl)-N-naphthalene-2-ylmethyl-acetamide, I-109 (478 mg).

Synthesis of 7-Benzyloxy-2-methyl-1-naphthalen-2-ylmethyl-1H-benzoimidazole, I-110. Fe (470 mg) was added in portions to a stirred suspension of N-(2-benzyloxy-6-nitro-phenyl)-N-naphthalene-2-ylmethyl-acetamide (517 mg) in MeOH (15 mL) and conc. HCl (1.5 mL). The reaction mixture was heated to reflux for 17 h and then filtered to remove the solids. Filtrate was concentrated and the residue obtained was taken in water (5 mL) and adjusted the pH to 14 with 6 N NaOH and then extracted with methylene chloride (10 mL×3). The combined fractions were washed with water (10 mL), brine (10 mL), dried over anhydrous sodium sulfate and concentrated. The residue obtained was purified over silica gel, eluting with chloroform/methanol (97:3 v/v) to give 7-Benzyloxy-2-methyl-1-naphthalen-2-ylmethyl-1H-benzoimidazole, I-110 (212 mg).

Synthesis of 2-methyl-3-naphthalen-2-ylmethyl-1H-benzoimidazol-4-ol, I-111. 7-Benzyloxy-2-methyl-1-naphthalen-2-ylmethyl-1H-benzoimidazole (211 mg) in methanol (12 mL) and acetic acid (1.0 mL) was hydrogenated in presence of 10% Pd—C at 45 psi for 20 h. Reaction mixture was filtered through a pad of celite. The filtrate was concentrated to afford 2-methyl-3-naphthalen-2-ylmethyl-1H-benzoimidazol-4-ol, I-111 (211 mg).

Synthesis of 2-methyl-3-naphthalen-2-ylmethyl-1H-benzoimidazol-4-yloxy)-acetic acid, I-112. A mixture of 2-methyl-3-naphthalen-2-ylmethyl-1H-benzoimidazol-4-ol (200 mg), methyl bromoacetate (162 mg) potassium carbonate (530 mg) and acetone (20 mL) was heated to reflux for 36 h. Reaction mixture was filtered. The filtrate obtained was concentrated and the residue obtained was taken in methanol (1.0 mL), THF (10 mL) and 2N NaOH (1.0 mL) and stirred at room temperature 48 h. Reaction mixture was concentrated and the residue was taken in water (5.0 mL) and acidified to pH-1 with 1.0 N HCl. It was extracted with Ethyl acetate (10 mL×4), and the combined organic were dried (brine, sodium sulfate), concentrated and dried to give 2-methyl-3-naphthalen-2-ylmethyl-1H-benzoimidazol-4-yloxy)-acetic acid, I-112 (77 mg).

Synthesis of Thiophen-2-sulfonic acid [2-(2-methyl-3-naphthalen-2-ylmethyl-3H-benzoimidazol-4-yloxy)-acetyl] amide, P037. 2-Methyl-3-naphthalen-2-ylmethyl-1H-benzoimidazol-4-yloxy)-acetic acid (77 mg, 2 mmol), thiophen-2-sulfonamide (36 mg, 2.2 mmol), EDCI (47 mg, 0.25 mmol), DMAP (30 mg, 2.5 mmol) in methylene chloride (2.0 mL) was stirred at room temperature for 48 h. Reaction mixture was concentrated and the residue was purified over silica gel with chloroform:methanol (97:3) as eluant to afford thiophen-2-sulfonic acid [2-(2-methyl-3-naphthalen-2-ylmethyl-3H-benzoimidazol-4-yloxy)-acetyl] amide, P037 (5.2 mg). 1H NMR (500 MHz, CD3OD) 2.47 (s, 3H), 4.50 (s, 2H), 5.86 (s, 2H), 6.60 (d, J=8.0 Hz. 1H), 6.91 (dd, J=5.0, 4.0 Hz, 1H), 7.06 (dd, J=8.5, 8.0 Hz, 1H), 7.26 (m, 2H), 7.32 (s, 1H), 7.36 (dd, J=5.0, 1.0 Hz, 1H), 7.45-7.40 (m, 3H), 7.51 (dd, J=3.5, 1.0 Hz, 1H), 7.68 (m, 1H), 7.72 (d, J=8.5 Hz, 1H), 7.70 (m, 1H). LC/MS=95.7% purity, MS (ESI−) Calcd. (M+) 491.5; Found: 490.5 (M−1).

Example 132

Preparation of P149

Synthesis of 2,4-Dichloro-benzoic acid 2-amino-3-nitrophenyl ester, I-113. To a 500 mL, round-bottomed, one-necked flask equipped with a magnetic stir bar and a septum was added 2-amino-3-nitrophenol (4.25 g, 27.6 mmol), anhydrous $CH_2Cl_2$ (140 mL), 4-(dimethylamino)pyridine (3.37 g, 27.6 mmol) and 2,4-dichlorobenzoyl chloride (5.78 g, 3.87 mL, 27.6 mmol). The reaction mixture was allowed to stir at room temperature overnight. TLC analysis indicated the complete consumption of starting material. The reaction mixture was diluted with $CH_2Cl_2$ (300 mL) and the mixture was washed with $H_2O$ (2×200 mL), dried ($Na_2SO_4$), and concentrated to give 8.91 g (98.7%) of a yellow-orange solid. $^1H$ NMR analysis indicated the material, I-113 was pure enough to carry on to the next step. $^1H$ NMR (500 MHz, $CDCl_3$).

Synthesis of 2,4-Dichloro-N-(2-hydroxy-6-nitro-phenyl)-benzamide, I-114. To a 500 mL, round-bottomed, one-necked flask containing I-113 (8.91 g, 27.2 mmol) was added a magnetic stir bar and anhydrous THF (300 mL) and the reaction vessel was placed under a $N_2$ atmosphere. Sodium hydride (1.08 g, 44.9 mmol, 60% in oil dispersion) was added in portions cautiously to the stirring reaction mixture over a period of 2 min. After an additional 2 min, $H_2$ gas evolution occurs (fairly rapidly) and a slight exotherm was observed. The mixture was stirred at room temperature for 1 h. TLC analysis at this time shows reaction complete. The mixture was allowed to stir at room temperature overnight. The mixture was cautiously quenched through the slow addition of water (50 ml) dropwise and then in small portions. The mixture was poured into EtOAc (1 L) and water (200 mL). The aqueous layer was acidified to a pH ~1 with 1N HCl and extracted. The layers were separated and the aqueous layer extracted with EtOAc (100 mL). The combined organic extracts were dried ($Na_2SO_4$), filtered and concentrated to give I-114, (9.36 g) as a tan solid. 1H NMR (500 MHz, $CDCl_3$).

Synthesis of N-(2-Amino-6-hydroxy-phenyl)-2,4-dichloro-benzamide I-115. To a 250 mL hydrogenation vessel was added an aqueous slurry of Raney nickel (700 mg) and it was cautiously diluted with EtOH (60 mL). Compound I-114 (700 mg, 2.14 mmol) was added as a solid. The sides of the vessel were rinsed with EtOH (10 mL) and the mixture was subjected to hydrogenation in a Parr shaker at 50 psi of $H_2$ gas at room temperature overnight. The reaction mixture was filtered through a pad of Celite and the pad was rinsed with EtOH (400 mL). The filtrate was concentrated to give a quantitative yield of a dark brown solid, I-115. 1H NMR (400 MHz, DMSO-$d_6$).

Synthesis of 3-Amino-2-(2,4-dichloro-benzylamino)-phenol, I-116. To a 250 mL round bottomed, one-necked flask equipped with a magnetic stir bar, a reflux condenser and placed under a $N_2$ atmosphere was added compound I-115

(635 mg, 2.14 mmol). Anhydrous THF (31 mL) was added followed by dropwise addition of 1M BH$_3$ in THF (8.6 mL, 8.6 mmol). The reaction mixture was heated at reflux overnight. The cooled reaction mixture was cautiously quenched through the dropwise addition of methanol (50 mL). The resulting mixture was concentrated on a rotary evaporator. The residue was again dissolved in methanol (50 mL) and reconcentrated. This redissolution of the residue in methanol and reconcentration was repeated two more times to give a quantitative yield of a brown oil, I-116. 1H NMR (500 MHz, DMSO-d$_6$).

Synthesis of 3-(2,4-Dichloro-benzyl)-3H-benzoimidazol-4-ol, I-117. To a 20 mL vial containing a magnetic stir bar was added compound I-116 (980 mg, 3.46 mmol) and absolute EtOH (8 mL). To this stirring suspension was added triethyl orthoformate (0.634 mL, 3.81 mmol) and p-toluenesulfonic acid monohydrate (33 mg, 0.173 mmol). The vial was capped and placed in an oil bath at 75° C. for 1 h. At this time the cap was removed from the vial and the oil bath temperature was increased to 95-100° C., boiling off the solvent. The last traces of solvent were removed under high vacuum. The residue was triturated twice with 1:1 hexanes/acetone (6 ml each time) and resulting dark brown solid was filtered and dried to give I-117, 570 mg (56%). 1H NMR (500 MHz, DMSO-d$_6$).

Synthesis of [3-(2,4-Dichloro-benzyl)-3H-benzoimidazol-4-yloxy]-acetic acid methyl ester, I-118. To a 5 mL vial containing a magnetic stir bar and compound I-117 (60 mg, 0.204 mmol) was added anhydrous DMF (0.8 mL), anhydrous potassium carbonate (34 mg, 0.246 mmol) and methyl bromoacetate (24 mL, 0.246 mmol). The reaction mixture was stirred at room temperature overnight. The reaction mixture was concentrated to give a residue which was dissolved in 1:1 hexanes/acetone (1 mL) and was purified by column chromatography on flash silica gel (6 g) utilizing 4:1 hexanes/acetone followed by 7:3 hexanes/acetone as eluent to give I-118, 40 mg (54%) of a semisolid. 1H NMR (500 MHz, CDCl$_3$).

Synthesis of [3-(2,4-Dichloro-benzyl)-3H-benzoimidazol-4-yloxy]-acetic acid, I-119. To a 50 mL round bottomed, one-necked flask containing compound I-118 (32 mg, 0.088 mmol) was added absolute ethanol (0.5 mL), water (0.5 mL) and 15% aqueous sodium hydroxide (0.025 mL, 0.093 mmol). The reaction mixture was allowed to stir at room temperature overnight. The mixture was concentrated to give a solid. The solid was dissolved in water (3 mL) and made acidic through the addition of 1 N HCl (0.25 mL). pH of the solution was 2-3 by litmus paper. The resulting precipitate was filtered and dried. The aqueous filtrate was extracted with EtOAc (3×1 mL) and the organic extracts were concentrated to give a solid. This solid was combined with the isolated precipitate to give 28 mg (91%), I-119, as an off-white solid. 1H NMR (500 MHz, DMSO-d$_6$), LC/MS=96%, ESI/− 349.2.

Synthesis of P149. To a 3 mL vial containing a magnetic stir bar and compound I-119 (21 mg, 0.060 mmol) was added anhydrous CH$_2$Cl$_2$ (2 mL) followed by DMAP (14.7 mg, 0.120 mmol) which made the solution homogenous. 4,5-Dichlorothiophene-2-sulfonamide (15.5 mg, 0.66 mmol) was added followed by EDCI (23 mg, 0.12 mmol). The reaction was stirred at room temperature for 4 h and then diluted with CH$_2$Cl$_2$ and water (5 mL each). The aqueous layer was made acidic through the addition of 1 N HCl until a pH of 2-3 was reached (litmus paper). The layers were separated and the aqueous layer was extracted with CH$_2$Cl$_2$ (5 mL). The combined organic layers were concentrated and dried under vacuum. The resulting solid was triturated with hot CH$_2$Cl$_2$ (3 mL) and the cooled solution was filtered and dried to give 26 mg (71%) of P149 as an off-white solid. 1H NMR (500 MHz, DMSO-d6) 4.59 (s, 2H), 5.91 (s, 2H), 6.85 (d, J=8.0 Hz, 1H), 7.04 (d, J=8.5 Hz, 1H), 7.30 (t, J=8.0 Hz, 1H), 7.33 (dd, J=8.5, 2.0 Hz, 1H), 7.36 (d, J=8.0 Hz, 1H), 7.54 (s, 1H), 7.65 (d, J=2.0 Hz, 1H), 8.98 (s, 1H). LC/MS=97.8% purity, MS (ESI+) Calcd. (M+H) 564.4; Found: 564.4.

Example 133

Preparation of P152

Synthesis of Naphthalene-2-carboxylic acid 2-amino-3-nitro-phenyl ester, I-120. Compound I-119 was synthesized from 2-amino-3-nitrophenol (99%) in a manner analogous to that of the synthesis of compound I-113. $^1$H NMR (500 MHz, CDCl$_3$)

Synthesis of Naphthalene-2-carboxylic acid (2-hydroxy-6-nitro-phenyl)-amide, I-121. Compound I-121 was synthesized from compound I-120 (quantitative yield) in a manner analogous to that of the synthesis of compound I-114 from compound I-113. $^1$H NMR (500 MHz, CDCl$_3$).

Synthesis of Naphthalene-2-carboxylic acid (2-amino-6-hydroxy-phenyl)-amide, I-122. To a 50 mL round-bottomed, one-necked flask equipped with a magnetic stir bar, a condenser and a N$_2$ inlet/outlet adapter was added compound I-121 (100.7 mg, 0.327 mmol) and absolute ethanol (5 mL). The reaction mixture was placed in an oil bath at 70° C. and under a N2 atmosphere. Tin(II) chloride dihydrate (738 mg, 3.27 mmol) was added followed by the dropwise addition of 6 N HCl (2.18 mL, 13.1 mmol). After heating at 70° C. for 1 h the reaction mixture was cooled to room temperature, diluted with water and EtOAc (50 mL each) and made basic (pH~8) through the cautious addition of saturated aqueous NaHCO$_3$. The solution was filtered to remove the precipitated tin salts and the organic layer was separated, dried (Na2SO4), filtered and concentrated to give, I-122, 81 mg (89%). 1H NMR (500 MHz, DMSO-d$_6$), MS; AP− 277.0.

Synthesis of 3-Amino-2-[(naphthalen-2-ylmethyl)-amino]-phenol, I-123. Compound I-122 was synthesized from compound I-121 (quantitative yield) in a manner analogous to that of the synthesis of compound I-116 from compound I-115. $^1$H NMR (500 MHz,. DMSO-d$_6$).

Synthesis of 3-Naphthalen-2-ylmethyl-3H-benzoimidazol-4-ol, I-124. Compound I-124 was synthesized from compound I-123 (35%) in a manner analogous to that of the synthesis of compound I-117 from compound I-116. $^1$H NMR (500 MHz, DMSO-d$_6$).

Synthesis of (3-Naphthalen-2-ylmethyl-3H-benzoimidazol-4-yloxy)-acetic acid methyl ester, I-125. Compound I-125 was synthesized from compound I-124 (55%) in a manner analogous to that of the synthesis of compound I-118 from compound I-117. $^1$H NMR (500 MHz, DMSO-d$_6$).

Synthesis of (3-Naphthalen-2-ylmethyl-3H-benzoimidazol-4-yloxy)-acetic acid, I-126. Compound I-126 was synthesized from compound I-125 (55%) in a manner analogous to that of the synthesis of compound I-119 from compound I-118. LC/MS=95.7%, ESI/− 331.1, $^1$H NMR (500 MHz, DMSO-d$_6$).

Synthesis of P152. Compound P152 was synthesized from compound I-126 (52%) in a manner analogous to that of the synthesis of compound P149 from compound I-119. 1H NMR (500 MHz, DMSO-d6) 4.65 (s, 2H), 6.00 (s, 2H), 6.86 (m, 1H), 7.31 (m, 2H), 7.54-7.44 (m, 3H), 7.60 (dd, J=9.0, 2.0 Hz, 1H), 7.79 (dd, J=9.0, 2.0 Hz, 1H), 7.88-7.82 (m, 2H), 8.09 (s, 1H), 9.36 (br s, 1H). LC/MS=96% purity, MS (ESI+). Calcd. (M+H) 546.5; Found: 546.7.

Example 134

Preparation of P253

General Synthesis of Hexahydro 2-oxyindole Derivatives:

Synthesis of 2-Methyl-2-allylcyclohexanone, I-127: To a solution of sodium hydride (1 eq.; 60% dispersion in mineral oil) in dimethoxyethylene glycol at 5° C. under nitrogen atmosphere, add 2-methylcyclohexanone dropwise. The solution was allowed to warm to room temperature, after which it was heated to 80° C. for 1.5 hours. The solution was then cooled to room temperature, and then to 5° C. Allyl bromide (1 eq.) was added dropwise, after which, the reaction mixture was heated to 80° C. for 1.5 hours. The reaction was cooled to room temperature, and water (~14 eq.) was added dropwise. Aqueous layer was extracted twice with ethyl ether, and dried over sodium sulfate. After concentration, the crude product was purified via silica gel chromatography using 2.5% ethyl ether in hexanes to obtain compound I-127 in 35% yield. $^1$H NMR(CDCl$_3$) confirms structure Synthesis of(1-Methyl-2-oxo-cyclohexyl)-acetic acid, I-128: To biphasic solution of 1-methyl-1-allylcyclohexanone, I-127, in H$_2$O/AcN/CCl$_4$ under nitrogen atmosphere was added NaIO4 (20 eq), followed by RuCl3.H2O. The reaction was stirred at room temperature overnight. 2-propanol (~88 eq) was added dropwise, causing the reaction mixture to blacken. The mixture was diluted with water and ethyl ether, and filtered through a Celite pad, and washed with ethyl ether. The aqueous layer was extracted with dichloromethane and EtOAc. The combined organics were dried over sodium sulfate, and concentrated in vacuo to give compound I-128 in quantitative yield. $^1$H NMR(CDCl$_3$) confirms structure.

General procedure (A-4) for preparation of hexahydroindol-2-ones, I-129x. A solution of (1-methyl-2-oxo-cyclohexyl)-acetic acid, I-128 (1 eq), and the appropriate aryl amine (1 eq) in m-xylene was heated under reflux at 145° C. for 3 hours. The reaction was concentrated in vacuo, and the residue either taken through crude, or purified via silica gel chromatography, using hexanes in dichloromethane (10-20%) as eluent to obtain the desired product, I-129x. Product structure was verified by $^1$H NMR.

General procedure (A-5) for bromination of hexahydroindol-2-ones, I-129x to provide vinyl bromides I-130x: To a solution of the appropriate hexahydro-indol-2-one, I-129 in dichloromethane at 0° C. was added bromine (1 eq) dropwise. The reaction mixture was stirred until bromine color disappeared, and then for an additional 5 minutes. Triethylamine (3 eq) was added in one portion, and stirred at room temperature for 10 minutes. The reaction was washed with water (3x), and dried over magnesium sulfate. The dichloromethane solution was concentrated in vacuo. The residue was either taken through to the next step crude, or purified via silica gel chromatography, using dichloromethane as the eluent, to obtain the appropriate vinyl bromide, I-130x. Product structure was verified by $^1$H NMR.

General procedure (A-6) for Heck couplings of I-130x to provide acrylate ester I-131x: In a round bottom flask equipped with a reflux condenser, and nitrogen inlet/outlet, was placed a solution of the appropriate 7-bromo-hexahydro-indol-2-one and triethylamine (10 eq) in DMF. To the solution was added, in order, methyl acrylate (1.1 eq), palladium (II) acetate (0.1 eq), and tri-o-tolyl phosphine (0.3 eq) were added. The reaction was heated at 100° C. for 16 hours, and then allowed to cool to room temperature. The reaction mixture was filtered through Celite, and washed with dichloromethane, and then diluted with dichloromethane and water, and the layers separated. The organics were washed with water (2x), and brine, and dried over magnesium sulfate. The organics were then concentrated in vacuo. The residue was either taken through crude, or purified via silica gel chromatography, using 15% hexanes in dichloromethane as eluent, to obtain acrylate ester I-131x. Product structure was verified by $^1$H NMR.

General procedure (A-7) for hydrolysis of methyl esters to provide acrylic acid, I-132x: To a solution of the appropriate methyl ester, I-131x in THF/MeOH (2:1), was added aqueous NaOH (3 eq), and the reaction stirred for 24-72 hours at room temperature. The mixture was washed with 2 portions of diethyl ether, diluted with EtOAc, and the pH adjusted to 2-3 with 1 N HCl. The organics were washed with brine, dried over magnesium sulfate, and concentrated to obtain acid I-132x compound. Product structure was verified by $^1$H NMR.

General procedure (A-8) for coupling of I-132x to provide acylsulfonamides: To a solution of the appropriate acid, I-132x, the appropriate sulfonamide (1.2 eq) and DMAP (2.4 eq) in CH2Cl2, was added EDCI (2 eq). The reaction mixture was stirred at room temperature overnight. The reaction was washed with 1N HCl$_{(aq)}$, water, and brine, dried over magnesium sulfate, and concentrated in vacuo. The residue was purified either via chromatography on silica gel, using methanol(0-3%) in dichloromethane as eluent, or via trituration with dichloromethane/hexanes to obtain the desired acyl sulphonamide product. Product structure was verified via $^1$H NMR, and purity determined via ESI LC/MS.

Synthesis of P253. Synthesis of 3a-Methyl-1-naphthalen-2-ylmethyl-1,3,3a,4,5,6-hexahydro-indol-2-one, I-129A: Following the general procedure A-4, (1-methyl-2-oxo-cyclohexyl)-acetic acid, I-128 was converted to I-129A. Consistent with 1H-NMR.

Synthesis of 7-Bromo-3a-methyl-1-naphthalen-2-ylmethyl-1,3,3a,4,5,6-hexahydro-indol-2-one, I-130A: Following the general procedure A-5, 3a-methyl-1-naphthalen-2-ylmethyl-1,3,3a,4,5,6-hexahydro-indol-2-one, I-129A was converted to I-130A. Consistent with 1H-NMR Synthesis of (E)-3-(3a-Methyl-1-naphthalen-2-ylmethyl-2-oxo-2,3,3a,4,5,6-hexahydro-1H-indol-7-yl)-acrylic acid methyl ester, I-131A: Following the general procedure A-6, 7-bromo-3a-methyl-1-naphthalen-2-ylmethyl-1,3,3a,4,5,6-hexahydro-indol-2-one, I-130A was converted to I-131A. Consistent with 1H-NMR Synthesis of (E)-3-(3a-Methyl-1-naphthalen-2-ylmethyl-2-oxo-2,3,3a,4,5,6-hexahydro-1H-indol-7-yl)-acrylic acid, I-132A: Following the general procedure A-7, (E)-3-(3a-methyl-1-naphthalen-2-ylmethyl-2-oxo-2,3,3a,4,5,6-hexahydro-1H-indol-7-yl)-acrylic acid methyl ester, I-131A was converted to I-132A. Consistent with 1H-NMR; LCMS (M−1=362.6)

Synthesis of P253.

Following the general procedure A-8, (E)-3-(3a-methyl-1-naphthalen-2-ylmethyl-2-oxo-2,3,3a,4,5,6-hexahydro-1H-indol-7-yl)-acrylic acid, I-132A was converted to P253. Consistent with 1H-NMR; LC-MS (M−1=575.2)

Example 135

Preparation of P269

To a round bottom flask containing I-132A dissolved in pyridine (1 eq.) and dichloromethane under nitrogen protection was added cyanuric fluoride (8 eq.). The resultant mixture was heated to reflux for 2 hours. The reaction mixture was washed with cold (0° C.) water, and dried over sodium sulfate. The solution was filtered and concentrated in vacuo. The residue was dissolved in dichloromethane, and to it was added 4-dimethylamino pyridine(1.4 eq.), and the 4-trifluoromethoxybenzene sulfonamide (1.7 eq.), and the resultant solution was stirred at room temperature overnight. The reaction mixture was washed with 1N HCl, water, and brine, and dried over magnesium sulfate. The solution was filtered, and concentrated, and the residue purified via silica gel chromatography, using methanol/dichloromethane as eluent to afford a residue, which was dissolved in acetic acid, and precipitated with water, and filtered to afford P269. Consistent with 1H-NMR; LC-MS (M−1=583.5)

Example 136

Preparation of P262

Synthesis of 1-(3-Fluoro-benzyl)-3a-methyl-1,3,3a,4,5,6-hexahydro-indol-2-one, I-129B: Following the general procedure A-4, (1-methyl-2-oxo-cyclohexyl)-acetic acid, I-128 was converted to I-129B. Consistent with 1H-NMR Synthesis of 7-Bromo-1-(3-Fluoro-benzyl)-3a-methyl-1,3,3a,4,5,6-hexahydro-indol-2-one, I-130B: Following the general procedure A-5,1-(3-fluoro-benzyl)-3a-methyl-1,3,3a,4,5,6-hexahydro-indol-2-one, I-129B was converted to I-130B. Consistent with 1H-NMR.

Synthesis of (E)-3-[1-(3-Fluoro-benzyl)-3a-methyl-2-oxo-2,3,3a,4,5,6-hexahydro-1H-indol-7-yl]-acrylic acid methyl ester, I-131B: Following the general procedure A-6, 7-bromo-1-(3-fluoro-benzyl)-3a-methyl-1,3,3a,4,5,6-hexahydro-indol-2-one, I-130B was converted to I-131B. Consistent with 1H-NMR.

Synthesis of (E)-3-[1-(3-Fluoro-benzyl)-3a-methyl-2-oxo-2,3,3a,4,5,6-hexahydro-1H-indol-7-yl]-acrylic acid, I-132B: Following the general procedure A-7, (E)-3-[1-(3-fluoro-benzyl)-3a-methyl-2-oxo-2,3,3a,4,5,6-hexahydro-1H-indol-7-yl]-acrylic acid methyl ester, I-131B was converted to I-132B. Consistent with 1H-NMR; LCMS (M−1=330.6).

Synthesis of P262. Following the general procedure A-8, (E)-3-[1-(3-fluoro-benzyl)-3a-methyl-2-oxo-2,3,3a,4,5,6-hexahydro-1H-indol-7-yl]-acrylic acid, I-132B was converted to P262. Consistent with 1H-NMR; LC-MS (M−1=541.5).

Example 137

Preparation of P263

Synthesis of 1-(4-Fluoro-benzyl)-3a-methyl-1,3,3a,4,5,6-hexahydro-indol-2-one, I-129C: Following the general procedure A-4, (1-methyl-2-oxo-cyclohexyl)-acetic acid, I-128 was converted to I-129C. Consistent with 1H-NMR.

Synthesis of 7-Bromo-1-(4-Fluoro-benzyl)-3a-methyl-1,3,3a,4,5,6-hexahydro-indol-2-one, I-130C: Following the general procedure A-5,1-(4-fluoro-benzyl)-3a-methyl-1,3,3a,4,5,6-hexahydro-indol-2-one, I-129C was converted to I-130C. Consistent with 1H-NMR.

Synthesis of (E)-3-[1-(4-Fluoro-benzyl)-3a-methyl-2-oxo-2,3,3a,4,5,6-hexahydro-1H-indol-7-yl]-acrylic acid methyl ester, I-131C: Following the general procedure A-6, 7-bromo-1-(4-fluoro-benzyl)-3a-methyl-1,3,3a,4,5,6-hexahydro-indol-2-one, I-130C was converted to I-131C. Consistent with 1H-NMR.

Synthesis of (E)-3-[1-(4-Fluoro-benzyl)-3a-methyl-2-oxo-2,3,3a,4,5,6-hexahydro-1H-indol-7-yl]-acrylic acid, I-132C: Following the general procedure A-7, (E)-3-[1-(4-fluoro-benzyl)-3a-methyl-2-oxo-2,3,3a,4,5,6-hexahydro-1H-indol-7-yl]-acrylic acid methyl ester, I-131C was converted to I-132C. Consistent with 1H-NMR; LCMS (M−1=330.5).

Synthesis of P263. Following the general procedure A-8, (E)-3-[1-(4-Fluoro-benzyl)-3a-methyl-2-oxo-2,3,3a,4,5,6-hexahydro-1H-indol-7-yl]-acrylic acid, I-132C was converted to P263. Consistent with 1H-NMR; LC-MS (M−1=543.3)

Example 138

Preparation of P294

Following the general procedure A-8, (E)-3-[1-(4-fluoro-benzyl)-3a-methyl-2-oxo-2,3,3a,4,5,6-hexahydro-1H-indol-7-yl]-acrylic acid, I-132C was converted to P294. Consistent with 1H-NMR; LC-MS (M−1=503.7).

Example 139

Preparation of P295

Following the general procedure A-8, (E)-3-[1-(4-fluoro-benzyl)-3a-methyl-2-oxo-2,3,3a,4,5,6-hexahydro-1H-indol-7-yl]-acrylic acid, I-132C was converted to P295. $^1$H NMR (CDCl$_3$) 1.18 (s, 3H), 1.84 (m, 3H), 2.18 (m, 3H), 2.44 (s, 2H), 4.74 (d, J=16.4 Hz, 1H), 5.26 (d, J=16.0 Hz, 1H), 5.52 (d, J=14.8 Hz, 1H), 6.97 (t, J=8.8 Hz, 2H), 7.11 (m, 1H), 7.18 (dd, J=8.8, 5.6 Hz, 2H), 7.62 (m, 2H), 7.77 (d, J=15.2 Hz, 1H). LC/MS (98%) ESI− Calcd. 504.5 m/z Found: 503.7 m/z

Example 140

Preparation of P300

Following the general procedure A-8, (E)-3-[1-(4-fluoro-benzyl)-3a-methyl-2-oxo-2,3,3a,4,5,6-hexahydro-1H-indol-7-yl]-acrylic acid, I-132C was converted to P300. Consistent with 1H-NMR; LC-MS (M−1=521.8).

Example 141

Preparation of P264

Synthesis of 1-(3,4-Difluoro-benzyl)-3a-methyl-1,3,3a,4,5,6-hexahydro-indol-2-one, I-129D: Following the general procedure A-4, (1-methyl-2-oxo-cyclohexyl)-acetic acid, I-128 was converted to I-129D. Consistent with 1H-NMR.

Synthesis of 7-Bromo-1-(3,4-Difluoro-benzyl)-3a-methyl-1,3,3a,4,5,6-hexahydro-indol-2-one, I-130D: Following the general procedure A-5,1-(3,4-difluoro-benzyl)-3a-methyl-1,3,3a,4,5,6-hexahydro-indol-2-one, I-129D was converted to I-130D. Consistent with 1H-NMR.

Synthesis of (E)-3-[1-(3,4-Difluoro-benzyl)-3a-methyl-2-oxo-2,3,3a,4,5,6-hexahydro-1H-indol-7-yl]-acrylic acid methyl ester, I-131D: Following the general procedure A-6, 7-bromo-1-(3,4-difluoro-benzyl)-3a-methyl-1,3,3a,4,5,6-hexahydro-indol-2-one, I-130D was converted to I-131D. Consistent with 1H-NMR.

Synthesis of (E)-3-[1-(3,4-Difluoro-benzyl)-3a-methyl-2-oxo-2,3,3a,4,5,6-hexahydro-1H-indol-7-yl]-acrylic acid, I-132D: Following the general procedure A-7, (E)-3-[1-(3,4-difluoro-benzyl)-3a-methyl-2-oxo-2,3,3a,4,5,6-hexahydro-1H-indol-7-yl]-acrylic acid methyl ester, I-131D was converted to I-132D. Consistent with 1H-NMR; LCMS (M−1=348.5).

Synthesis of P264. Following the general procedure A-8, (E)-3-[1-(3,4-difluoro-benzyl)-3a-methyl-2-oxo-2,3,3a,4,5,6-hexahydro-1H-indol-7-yl]-acrylic acid, I-132D was converted to P264. Consistent with 1H-NMR; LC-MS (M−1=561.3).

Example 142

Preparation of P266

Following the general procedure A-8, (E)-3-[1-(3,4-Difluoro-benzyl)-3a-methyl-2-oxo-2,3,3a,4,5,6-hexahydro-1H-indol-7-yl]-acrylic acid, I-132D was converted to P266. Consistent with 1H-NMR; LC-MS (M+1=557.0).

Example 143

Preparation of P267

Following the general procedure A-8, (E)-3-[1-(3,4-difluoro-benzyl)-3a-methyl-2-oxo-2,3,3a,4,5,6-hexahydro-1H-indol-7-yl]-acrylic acid, I-132D was converted to P267. Consistent with 1H-NMR; LC-MS (M+1=541.9).

Example 144

Preparation of P304

Following the general procedure A-8, (E)-3-[1-(3,4-difluoro-benzyl)-3a-methyl-2-oxo-2,3,3a,4,5,6-hexahydro-1H-indol-7-yl]-acrylic acid, I-132D was converted to P304. $^1$H NMR (CDCl$_3$) 1.19 (s, 3H), 1.57 (m, 1H), 1.87 (m, 3H), 2.19 (d, J=6.8 Hz, 2H), 2.44 (d, J=1.2 Hz, 2H), 4.75 (d, J=16.4 Hz, 1H), 5.17 (d, J=16.0 Hz, 1H), 5.53 (d, J=14.8 Hz, 1H), 7.04 (m, 3H), 7.35 (ddd, J=16.8, 9.2, 7.6 Hz, 1H), 7.72 (d, J=14.8 Hz, 1H), 7.88 (m, 2H), 7.93 (ddd, J=9.2, 7.2, 2.4 Hz, 1H). LC/MS (95%) ESI− Calcd. 522.5 m/z Found: 521.6 m/z

Example 145

Preparation of P305

Following the general procedure A-8, (E)-3-[1-(3,4-difluoro-benzyl)-3a-methyl-2-oxo-2,3,3a,4,5,6-hexahydro-1H-indol-7-yl]-acrylic acid, I-132D was converted to P305. Consistent with 1H-NMR.

Example 146

Preparation of P274

Synthesis of 1-(2,4-Dichloro-benzyl)-3a-methyl-1,3,3a,4,5,6-hexahydro-indol-2-one, I-129E: Following the general procedure A-4, (1-methyl-2-oxo-cyclohexyl)-acetic acid, I-128 was converted to I-129E. Consistent with 1H-NMR.
Synthesis of 7-Bromo-1-(2,4-Dichloro-benzyl)-3a-methyl-1,3,3a,4,5,6-hexahydro-indol-2-one, I-130E: Following the general procedure A-5,1-(2,4-dichloro-benzyl)-3a-methyl-1,3,3a,4,5,6-hexahydro-indol-2-one, I-129E was converted to I-130E. Consistent with 1H-NMR.
Synthesis of (E)-3-[1-(2,4-Dichloro-benzyl)-3a-methyl-2-oxo-2,3,3a,4,5,6-hexahydro-1H-indol-7-yl]-acrylic acid methyl ester, I-131E: Following the general procedure A-6, 7-bromo-1-(2,4-dichloro-benzyl)-3a-methyl-1,3,3a,4,5,6-hexahydro-indol-2-one, I-130E was converted to I-131 E. Consistent with 1H-NMR.
Synthesis of (E)-3-[1-(2,4-Dichloro-benzyl)-3a-methyl-2-oxo-2,3,3a,4,5,6-hexahydro-1H-indol-7-yl]-acrylic acid, I-132E: Following the general procedure A-7, (E)-3-[1-(2,4-dichloro-benzyl)-3a-methyl-2-oxo-2,3,3a,4,5,6-hexahydro-1H-indol-7-yl]-acrylic acid methyl ester, I-131E was converted to I-132E. Consistent with 1H-NMR; LC-MS (M−1=380.3).
Synthesis of P274. Following the general procedure A-8, (E)-3-[1-(2,4-Dichloro-benzyl)-3a-methyl-2-oxo-2,3,3a,4,5,6-hexahydro-1H-indol-7-yl]-acrylic acid, I-132E was converted to P274. Consistent with 1H-NMR; LC-MS (M−1=536.4).

Example 147

Preparation of P275

Following the general procedure A-8, (E)-3-[1-(2,4-Dichloro-benzyl)-3a-methyl-2-oxo-2,3,3a,4,5,6-hexahydro-1H-indol-7-yl]-acrylic acid, I-132E was converted to P275. Consistent with 1H-NMR; LC-MS (M−1=573.3).

Example 148

Preparation of P276

Following the general procedure A-8, (E)-3-[1-(2,4-dichloro-benzyl)-3a-methyl-2-oxo-2,3,3a,4,5,6-hexahydro-1H-indol-7-yl]-acrylic acid, I-132E was converted to P276. $^1$H NMR (DMSO-d6) 1.20 (s, 3H), 1.61 (m, 1H), 1.80 (m, 3H), 2.11 (m, 1H), 2.19 (m, 1H), 2.34 (d, J=16.0 Hz, 1H), 2.65 (d, J=16.4 Hz, 1H), 4.75 (d, J=17.6 Hz, 1H), 4.91 (d, J=17.6 Hz, 1H), 5.73 (d, J=14.8 Hz, 1H), 7.01 (d, J=8 Hz, 1H), 7.19 (d, J=14.8 Hz, 1H), 7.19 (dd, J=4.8, 3.6 Hz, 1H), 7.30 (dd, J=8.0, 2.4 Hz, 1H), 7.67 (d, J=2.4 Hz, 1H), 7.70 (dd, J=4.0, 2.4 Hz, 1H), 8.03 (dd, J=4.8,1.2 Hz, 1H), 12.0 (s, 1H). LC/MS (93%) ESI− Calcd. 525.5 m/z Found: 525.5 m/z

Example 149

Preparation of P278

Following the general procedure A-8, (E)-3-[1-(2,4-dichloro-benzyl)-3a-methyl-2-oxo-2,3,3a,4,5,6-hexahydro-1H-indol-7-yl]-acrylic acid, I-132E was converted to P278.

Example 150

Preparation of P279

Following the general procedure A-8, (E)-3-[1-(2,4-dichloro-benzyl)-3a-methyl-2-oxo-2,3,3a,4,5,6-hexahydro-1H-indol-7-yl]-acrylic acid, I-132E was converted to P279. $^1$H NMR (CDCl$_3$) 1.26 (s, 3H), 1.59 (m, 1H), 1.81 (m, 2H), 1.89 (dd, J=10.4, 2.4 Hz, 1H), 2.18 (m, 1H), 2.29 (m, 1H), 2.45 (s, 2H), 4.99 (d, J=4 Hz, 2H), 5.67 (d, J=14.8 Hz, 1H), 6.94 (dd, J=4.0, 0.4 Hz, 1H), 6.97 (d, J=8.4 Hz, 1H), 7.16 (dd, J=8.4, 2.4 Hz, 1H), 7.34 (d, J=14.8, 1H), 7.46 (d, J=2.0 Hz, 1H), 7.62 (d, J=4.0 Hz, 1H). LC/MS (96%) ESI− Calcd. 559.9 m/z Found: 559.3 m/z

Example 151

Preparation of P280

Following the general procedure A-8, (E)-3-[1-(2,4-dichloro-benzyl)-3a-methyl-2-oxo-2,3,3a,4,5,6-hexahydro-

141

1H-indol-7-yl]-acrylic acid, I-132E was converted to P280. Consistent with 1H-NMR; LC-MS (M−1=587.1).

Example 152

Preparation of P281

Following the general procedure A-8, (E)-3-[1-(2,4-dichloro-benzyl)-3a-methyl-2-oxo-2,3,3a,4,5,6-hexahydro-1H-indol-7-yl]-acrylic acid, I-132E was converted to P281. Consistent with 1H-NMR; LC-MS (M−1=553.3).

Example 153

Preparation of P282

Following the general procedure A-8, (E)-3-[1-(2,4-dichloro-benzyl)-3a-methyl-2-oxo-2,3,3a,4,5,6-hexahydro-1H-indol-7-yl]-acrylic acid, I-132E was converted to P282.
1H NMR (400 MHz, CDCL3) 1.26 (s, 3H), 1.61 (m, 2H), 1.89 (m, 2H), 2.18 (m, 2H), 2.46 (s, 2H), 4.95 (m, 2H), 5.58 (d, J=15.2 Hz, 1H), 6.92 (m, 1H), 7.06 (m, 1H), 7.10 (m, 1H), 7.16 (m, 1H), 7.28 (m, 1H), 7.58 (m, 2H). LC/MS=99% purity, MS (ESI−) Calcd. (M/Z) 555; Found: 555.

Example 154

Preparation of P283

Following the general procedure A-8, (E)-3-[1-(2,4-dichloro-benzyl)-3a-methyl-2-oxo-2,3,3a,4,5,6-hexahydro-1H-indol-7-yl]-acrylic acid, I-132E was converted to P283. Consistent with 1H-NMR; LC-MS (M−1=555.3).

Example 155

Preparation of P285

Synthesis of 1-(3-Chloro-benzyl)-3a-methyl-1,3,3a,4,5,6-hexahydro-indol-2-one, I-129F: Following the general procedure A-4, (1-methyl-2-oxo-cyclohexyl)-acetic acid, I-128 was converted to I-129F. Consistent with 1H-NMR.
Synthesis of 7-Bromo-1-(3-Chloro-benzyl)-3a-methyl-1,3,3a,4,5,6-hexahydro-indol-2-one, I-130F: Following the general procedure A-5,1-(3-chloro-benzyl)-3a-methyl-1,3,3a,4,5,6-hexahydro-indol-2-one, I-129F was converted to I-130F. Consistent with 1H-NMR.
Synthesis of (E)-3-[1-(3-Chloro-benzyl)-3a-methyl-2-oxo-2,3,3a,4,5,6-hexahydro-1H-indol-7-yl]-acrylic acid methyl ester, I-131F: Following the general procedure A-6, 7-bromo-1-(3-chloro-benzyl)-3a-methyl-1,3,3a,4,5,6-hexahydro-indol-2-one, I-130F was converted to I-131F. Consistent with 1H-NMR.
Synthesis of (E)-3-[1-(3-Chloro-benzyl)-3a-methyl-2-oxo-2,3,3a,4,5,6-hexahydro-1H-indol-7-yl]-acrylic acid, I-132F: Following the general procedure A-7, (E)-3-[1-(3-chloro-benzyl)-3a-methyl-2-oxo-2,3,3a,4,5,6-hexahydro-1H-indol-7-yl]-acrylic acid methyl ester, I-131F was converted to I-132F. Consistent with 1H-NMR; LC-MS
Synthesis of P285. Following the general procedure A-8, (E)-3-[1-(3-chloro-benzyl)-3a-methyl-2-oxo-2,3,3a,4,5,6-hexahydro-1H-indol-7-yl]-acrylic acid, I-132F was converted to P285. 1H NMR (DMSO-d6) 1.24 (s, 1H), 1.7 (m, 5H),2.14 (m, 2H), 2.32 (m, 1H), 2.56 (m, 1H), 4.73 (d, J=16.4, 1H), 5.12 (d, J=41.6, 1H), 5.65 (d, J=14.8, 1H), 7.16 (m, 1H), 7.29 (m, 3H). 7.57 (d, J=15.5, 1H), 7.65 (s, 1H). LC/MS (96%) ESI− Calcd: 559.91 Found: 559.3 m/z

142

Example 156

Preparation of P296

Synthesis of 1-(2,3-Dichloro-benzyl)-3a-methyl-1,3,3a,4,5,6-hexahydro-indol-2-one, I-129G: Following the general procedure A-4, (1-methyl-2-oxo-cyclohexyl)-acetic acid, I-128 was converted to I-129G. Consistent with 1H-NMR.
Synthesis of 7-Bromo-1-(2,3-Dichloro-benzyl)-3a-methyl-1,3,3a,4,5,6-hexahydro-indol-2-one, I-130G: Following the general procedure A-5,1-(2,3-dichloro-benzyl)-3a-methyl-1,3,3a,4,5,6-hexahydro-indol-2-one, I-129G was converted to I-130G. Consistent with 1H-NMR.
Synthesis of (E)-3-[1-(2,3-Dichloro-benzyl)-3a-methyl-2-oxo-2,3,3a,4,5,6-hexahydro-1H-indol-7-yl]-acrylic acid methyl ester, I-131G: Following the general procedure A-6, 7-bromo-1-(2,3-dichloro-benzyl)-3a-methyl-1,3,3a,4,5,6-hexahydro-indol-2-one, I-130G was converted to I-131G. Consistent with 1H-NMR.
Synthesis of (E)-3-[1-(2,3-Dichloro-benzyl)-3a-methyl-2-oxo-2,3,3a,4,5,6-hexahydro-1H-indol-7-yl]-acrylic acid, I-132G: Following the general procedure A-7, (E)-3-[1-(2,3-dichloro-benzyl)-3a-methyl-2-oxo-2,3,3a,4,5,6-hexahydro-1H-indol-7-yl]-acrylic acid methyl ester, I-131G was converted to I-132G. Consistent with 1H-NMR; LC-MS
Synthesis of P296: Following the general procedure A-8, (E)-3-[1-(2,3-dichloro-benzyl)-3a-methyl-2-oxo-2,3,3a,4,5,6-hexahydro-1H-indol-7-yl]-acrylic acid, I-132G was converted to P296. Consistent with 1H-NMR; LC-MS (M−1=573.3).

Example 157

Preparation of P297

Following the general procedure A-8, (E)-3-[1-(2,3-dichloro-benzyl)-3a-methyl-2-oxo-2,3,3a,4,5,6-hexahydro-1H-indol-7-yl]-acrylic acid, I-132G was converted to P297. Consistent with 1H-NMR; LC-MS (M−1=553.4)

Example 158

Preparation of P298

Following the general procedure A-8, (E)-3-[1-(2,3-dichloro-benzyl)-3a-methyl-2-oxo-2,3,3a,4,5,6-hexahydro-1H-indol-7-yl]-acrylic acid, I-132G was converted to P298. Consistent with 1H-NMR; LC-MS (M−1=553.4).

Example 159

Preparation of P299

Following the general procedure A-8, (E)-3-[1-(2,3-dichloro-benzyl)-3a-methyl-2-oxo-2,3,3a,4,5,6-hexahydro-1H-indol-7-yl]-acrylic acid, I-132G was converted to P299. Consistent with 1H-NMR; LC-MS (M−1=593.3)

Example 160

Preparation of P306

Synthesis of 1-(3-Methoxy-benzyl)-3a-methyl-1,3,3a,4,5,6-hexahydro-indol-2-one, I-129H: Following the general procedure A-4, (1-methyl-2-oxo-cyclohexyl)-acetic acid, I-128 was converted to I-129H. Consistent with 1H-NMR Synthesis of 7-Bromo-1-(3-Methoxy-benzyl)-3a-methyl-1,3,3a,4,5,6-hexahydro-indol-2-one, I-130H: Following the general procedure A-5,1-(3-methoxy-benzyl)-3a-methyl-1,3,3a,4,5,6-hexahydro-indol-2-one, I-129H was converted to I-130H. Consistent with 1H-NMR.

Synthesis of (E)-3-[1-(3-Methoxy-benzyl)-3a-methyl-2-oxo-2,3,3a,4,5,6-hexahydro-1H-indol-7-yl]-acrylic acid methyl ester, I-131H: Following the general procedure A-6, 7-bromo-1-(3-methoxy-benzyl)-3a-methyl-1,3,3a,4,5,6-hexahydro-indol-2-one, I-130H was converted to I-131H. Consistent with 1H-NMR.

Synthesis of(E)-3-[1-(3-Methoxy-benzyl)-3a-methyl-2-oxo-2,3,3a,4,5,6-hexahydro-1H-indol-7-yl]-acrylic acid, I-132H. Following the general procedure A-7, (E)-3-[1-(3-methoxy-benzyl)-3a-methyl-2-oxo-2,3,3a,4,5,6-hexahydro-1H-indol-7-yl]-acrylic acid methyl ester, I-131H was converted to I-132H. Consistent with 1H-NMR.

Synthesis of P306. Following the general procedure A-8, (E)-3-[1-(3-methoxy-benzyl)-3a-methyl-2-oxo-2,3,3a,4,5,6-hexahydro-1H-indol-7-yl]-acrylic acid, I-132H was converted to P306. Consistent with 1H-NMR.

Example 161

Preparation of P307

Following the general procedure A-8, (E)-3-[1-(3-methoxy-benzyl)-3a-methyl-2-oxo-2,3,3a,4,5,6-hexahydro-1H-indol-7-yl]-acrylic acid, I-132H was converted to P307. 1H NMR (400 MHz, CDCL3) 1.23 (s, 3H), 1.59 (m, 2H), 1.87 (m, 2H), 2.16 (m, 2H), 2.45 (s, 2H), 3.77 (s, 3H), 4.75 (d, J=16.4 Hz, 1H), 5.24 (d, J=16.4 Hz, 1H), 5.52 (d, J=15.2 Hz, 1H), 6.79 (m, 3H), 7.07 (m, 1H), 7.23 (m, 1H), 7.58 (m, 2H), 7.71 (d, J=15.2 Hz, 1H). LC/MS=96% purity, MS (ESI−) Calcd. (M/Z) 516; Found: 515.

Example 162

Preparation of P308

Following the general procedure A-8, (E)-3-[1-(3-methoxy-benzyl)-3a-methyl-2-oxo-2,3,3a,4,5,6-hexahydro-1H-indol-7-yl]-acrylic acid, I-132H was converted to P308. Consistent with 1H-NMR.

Example 163

Preparation of P260

Following the general procedure A-8, (E)-3-[1-(3-methoxy-benzyl)-3a-methyl-2-oxo-2,3,3a,4,5,6-hexahydro-1H-indol-7-yl]-acrylic acid, I-132H was converted to P260. Consistent with 1H-NMR; LC-MS (M−1=553.4).

Example 164

Preparation of P151

Synthesis of(1H-Indol-4-yloxy)-acetic acid methyl ester, I-138. To a mixture of 4-hydroxy-indole (1.33 g, 10 mmol) and K$_2$CO$_3$ (2.07 g, 15 mmol) in acetone (50 ml), methyl bromoacetate (1.84 g, 12 mmol) was added at rt The reaction mixture was stirred at r.t over night and solid was removed by filtration. After removal of solvent under vacuum, the residue was dissolved in EtOAc and washed with diluted HCl aq.,
water, brine and dried over sodium sulfate. After removal of solvent, solid was washed with ether/hexane to give 2.02 g of I-138. Consistent with 1H-NMR.

Synthesis of(1H-Indol-4-yloxy)-acetic acid, I-139. To a solution of I-138 (410 mg, 2 mmol) in THF (6 ml) and methanol (6 ml), NaOH aq. (2N, 3 ml) was added at rt. The reaction mixture was stirred at rt for 4 hrs and then the pH was adjusted to acidic by adding 2N HCl aq. The reaction mixture was extracted with EtOAc (2×30 ml). The combined organic phase was washed with water, brine and dried over sodium sulfate. After removal of solvent, 370 mg of I-139 was obtained. Consistent with 1H-NMR.

General Procedure (A-9) for the Coupling of I-139 with Sulfonamides.

A mixture of the acid I-139 (250 mg, 1.3 mmol), the appropriate sulfonamide (1.57 mmol), 4-dimethylamino pyridine (317 mg, 2.6 mmol) and EDCI (497 mg, 2.6 mmol) in dichloromethane (20 ml) and DMSO (8 ml) was stirred at r.t. over weekend. The solution was diluted with dichloromethane, washed with diluted HCl aq., water and dried over sodium sulfate. After removal of solvent, the residue was purified by column chromatography on silica gel with EtOAc as an eluent to give compound I-140x.

General Procedure (A-10) for the Production of Sufides.

To a mixture of compound 140x (0.12 mmol) and the appropriate thiol (0.18 mmol) in ethanol (5 ml) and water (2 ml), 0.25 ml of iodine-potassium iodide (1N in ethanol/H$_2$O, 1:1) was added and stirred at r.t. over weekend. The solution was diluted with EtOAc, washed with diluted HCl aq., water, brine and dried over sodium sulfate. After removal of solvent, the solid was washed with CH2Cl2/hexane (1:1) to give the desired sufide.

General Procedure (A-11) for the Production of Sulphone.

To a mixture of sulfide [from general procedure (A-10)] (0.07 mmol) in methanol (2 ml) and ethanol (2 ml), OXONE (44 mg, 0.07 mmol in 0.5 ml of water) was added and stirred at r.t. for 6 hrs. The reaction mixture was diluted with EtOAc, washed with diluted HCl aq., water, brine and dried over sodium sulfate. After removal of solvent, the residue was purified by column chromatography on silica gel with dichloromethane, EtOAc/Hexane as an eluent to give the target sulphone compound.

Synthesis of 4,5-Dichloro-thiophene-2-sulfonic acid [2-(1H-indol-4-yloxy)-acetyl]-amide, I-140A: Following the general procedure A-9, I-139, was reacted with sulphonamide 4,5-dichloro-thiophene-2-sulfonic acid amide to provide compound I-140A. Consistent with 1H-NMR.

Synthesis of P151. Following the general procedure A-10, the sulphonamide I-140A, was reacted with Naphthalene-2-thiol to provide compound P151. Consistent with 1H-NMR.

Example 165

Preparation of P150

Following the general procedure A-11, the sulfide P151 was oxidized to the sulphone P150. Consistent with 1H-NMR.

Example 166

Preparation of P164

Following the general procedure A-10, the sulphonamide I-140A, was reacted with Quinoline-2-thiol to provide compound P164. 1H NMR (500 MHz, DMSO-d6) 4.26 (s, 2H), 6.28 (d, J=8.0 Hz, 1H), 7.03 (m, 3H), 7.10 (d, J=8.0 Hz, 1H), 7.46 (m, 2H), 7.66 (m, 2H), 7.81 (m, 2H), 8.02 (d, J=8.5 Hz, 1H), 11.74 (s, 1H). LC/MS=95% purity, MS (ESI–) Calcd. (M/Z) 564; Found: 562.

Example 167

Preparation of P169

Following the general procedure A-11, the sulfide P164 was oxidized to the sulphone P169. 1H NMR (500 MHz, DMSO-$d_6$) 4.31 (s, 2H), 6.34 (s, 2H), 7.07 (m, 2H), 7.49 (s, 1H), 7.71 (m, 1H), 7.80 (m, 1H), 7.90 (m, 1H), 8.04 (m, 1H), 8.23 (s, 1H), 8.21 (s, 1H), 8.60 (s, 1H), 12.21 (s, 1H). LC/MS=95% purity, MS (ESI–) Calcd. (M/Z) 596; Found: 594.

Example 168

Preparation of P165

Following the general procedure A-10, the sulphonamide I-140A, was reacted with 2,4-dimethyl-benzenethiol to provide compound P165. Consistent with 1H-NMR.

Example 169

Preparation of P172

Following the general procedure A-11, the sulfide P165 was oxidized to the sulphone P172. Consistent with 1H-NMR.

Example 170

Preparation of P167

Following the general procedure A-10, the sulphonamide I-140A, was reacted with 3,4-dimethoxy-benzenethiol to provide compound P167. Consistent with 1H-NMR.

Example 171

Preparation of P170

Following the general procedure A-11, the sulfide P167 was oxidized to the sulphone P170. Consistent with 1H-NMR.

Example 172

Preparation of P168

Following the general procedure A-10, the sulphonamide I-140A, was reacted with 2-chloro-4-fluoro-benzenethiol to provide compound P168. Consistent with 1H-NMR.

Example 173

Preparation of P234

Following the general procedure A-11, the sulfide P168 was oxidized to the sulphone P234. Consistent with 1H-NMR.

Example 174

Preparation of P173

Following the general procedure A-10, the sulphonamide I-140A, was reacted with 4-chloro-benzenethiol to provide compound P173. Consistent with 1H-NMR.

Example 175

Preparation of P190

Following the general procedure A-11, the sulfide P173 was oxidized to the sulphone P190. Consistent with 1H-NMR.

Example 176

Preparation of P178

Following the general procedure A-10, the sulphonamide I-140A, was reacted with 3,4-dichloro-benzenethiol to provide compound P178. Consistent with 1H-NMR.

Example 177

Preparation of P204

Following the general procedure A-1, the sulfide P178 was oxidized to the sulphone P204. Consistent with 1H-NMR.

Example 178

Preparation of P181

Following the general procedure A-10, the sulphonamide I-140A, was reacted with benzooxazole-2-thiol to provide compound P181. Consistent with 1H-NMR.

Example 179

Preparation of P182

Following the general procedure A-10, the sulphonamide I-140A, was reacted with benzothiazole-2-thiol to provide compound P182. Consistent with 1H-NMR.

Example 180

Preparation of P196

Following the general procedure A-11, the sulfide P182 was oxidized to the sulphone P196. 1H NMR (DMSO-d6) 4.54 (s, 2H), 6.51 (d, J=7.0, 1H), 7.14 (m, J=7.5 2H), 7.58 (m, J=6.0, 3H), 7.96 (m, J=3.5, 1H), 8.35 (d, J=5.0, 1H), 12.58 LC/MS (80%) ESI– Calcd: 602.52 Found: 602.0 m/z

Example 181

Preparation of P194

Following the general procedure A-10, the sulphonamide I-140A, was reacted with 2,5-dimethoxy-benzenethiol to provide compound P194. Consistent with 1H-NMR.

Example 182

Preparation of P202

Following the general procedure A-11, the sulfide P194 was oxidized to the sulphone P202. 1H NMR (500 MHz, DMSO-d6) 3.60 (s, 3H), 3.69 (s, 3H), 4.67 (s, 2H), 6.46 (d, J=7.5 Hz, 1H), 6.98 (d, J=9.0 Hz, 1H), 7.06 (m, 2H), 7.11 (d, J=8.0 Hz, 1H), 7.48 (d, J=3.0 Hz, 1H), 7.83 (s, 1H), 8.07 (d, J=3.0 Hz, 1H), 12.19 (s, 1H). LC/MS=97% purity, MS (ESI−) Calcd. (M+) 605.5; Found: 605.2.

Example 183

Preparation of P195

Following the general procedure A-10, the sulphonamide I-140A, was reacted with 1-methyl-1H-benzoimidazole-2-thiol to provide compound P195. Consistent with 1H-NMR.

Example 184

Preparation of P197

Following the general procedure A-10, the sulphonamide I-140A, was reacted with 2,4-difluoro-benzenethiol to provide compound P197. Consistent with 1H-NMR.

Example 185

Preparation of P206

Following the general procedure A-11, the sulfide P197 was oxidized to the sulphone P206. Consistent with 1H-NMR.

Example 186

Preparation of P198

Following the general procedure A-10, the sulphonamide I-140A, was reacted with benzenethiol to provide compound P198. Consistent with 1H-NMR.

Example 187

Preparation of P207

Following the general procedure A-11, the sulfide P198 was oxidized to the sulphone P207. Consistent with 1H-NMR.

Example 188

Preparation of P200

Following the general procedure A-10, the sulphonamide I-140A, was reacted with 4-methoxy-benzenethiol to provide compound P200. Consistent with 1H-NMR.

Example 189

Preparation of P210

Following the general procedure A-11, the sulfide P200 was oxidized to the sulphone P210. Consistent with 1H-NMR.

Example 190

Preparation of P201

Following the general procedure A-10, the sulphonamide I-140A, was reacted with pyridine-2-thiol to provide compound P201. Consistent with 1H-NMR.

Example 191

Preparation of P221

Following the general procedure A-11, the sulfide P201 was oxidized to the sulphone P221. 1H NMR (500 MHz, DMSO-d6) 4.58 (s, 2H), 6.48 (d, J=7.5 Hz, 1H), 7.09 (m, 1H), 7.13 (m, 1H), 7.54 (m, 1H), 7.82 (s, 1H), 8.0 (m, 1H), 8.13 (m, 1H), 8.17 (m, 1H), 8.52, (m, 1H), 12.35 (s, 1H). LC/MS=96% purity, MS (ESI−) Calcd. (M/Z) 546; Found: 544.

Example 192

Preparation of P205

Following the general procedure A-10, the sulphonamide I-140A, was reacted with 2,4-dichloro-benzenethiol to provide compound P205. Consistent with 1H-NMR.

Example 193

Preparation of P238

Following the general procedure A-11, the sulfide P205 was oxidized to the sulphone P238. Consistent with 1H-NMR.

Example 194

Preparation of P208

Following the general procedure A-10, the sulphonamide I-140A, was reacted with 3-methoxy-benzenethiol to provide compound P208. Consistent with 1H-NMR.

Example 195

Preparation of P209

Following the general procedure A-10, the sulphonamide I-140A, was reacted with 3,4-difluoro-benzenethiol to provide compound P209. Consistent with 1H-NMR.

Example 196

Preparation of P211

Following the general procedure A-10, the sulphonamide I-140A, was reacted with pyrimidine-2-thiol to provide compound P211. 1H NMR (500 MHz, DMSO-d6) 4.45 (s, 2H), 6.27 (d, J=8.0 Hz, 1H), 6.98 (t, J=8.0 Hz, 2H), 7.08 (m, 2H), 7.54 (s, 1H), 7.84 (s, 1H), 8.46 (s, 2H), 11.59 (s, 1H). LC/MS=95% purity, MS (ESI−) Calcd. (M/Z) 515; Found: 513.

Example 197

Preparation of P212

Following the general procedure A-10, the sulphonamide I-140A, was reacted with 2-methoxy-benzenethiol to provide compound P212. Consistent with 1H-NMR.

Example 198

Preparation of P222

Following the general procedure A-11, the sulfide P212 was oxidized to the sulphone P222. Consistent with 1H-NMR.

Example 199

Preparation of P213

Following the general procedure A-10, the sulphonamide I-140A, was reacted with 2-chloro-benzenethioll to provide compound P213. Consistent with 1H-NMR.

Example 200

Preparation of P232

Following the general procedure A-11, the sulfide P213 was oxidized to the sulphone P232. Consistent with 1H-NMR.

Example 201

Preparation of P233

Following the general procedure A-10, the sulphonamide I-140A, was reacted with N-(4-mercapto-phenyl)-acetamide to provide compound P233. Consistent with 1H-NMR.

Example 202

Preparation of P235

Following the general procedure A-11, the sulfide P233 was oxidized to the sulphone P235. 1H NMR (500 MHz, DMSO-d6) 2.05 (s, 3H), 4.72 (s, 2H), 6.47 (d, J=7.5 Hz, 1H), 7.08 (d, J=8.0 Hz, 1H), 7.12 (d, J=8.5 Hz, 1H), 7.67 (d, J=9.0 Hz, 2H), 7.82 (d, J=9.0 Hz, 2H), 10.25 (s, 1H), 12.24 (s, 1H). LC/MS=90% purity, MS (ESI−) Calcd. (M/Z) 602; Found: 600.

Example 203

Preparation of P220

Following the general procedure A-10, the sulphonamide I-140A, was reacted with 1H-imidazole-2-thiol to provide compound P220. Consistent with 1H-NMR.

Example 204

Preparation of P227

Following the general procedure A-10, the sulphonamide I-140A, was reacted with 1-methyl-1H-tetrazole-5-thiol to provide compound P227. Consistent with 1H-NMR.

Example 205

Preparation of P239

Following the general procedure A-11, the sulfide P227 was oxidized to the sulphone P239. 1H NMR (DMSO-d6) 4.26 (s, 3H), 4.58 (s, 2H), 6.53 (d, J=7.5, 1H), 7.17 (m, 2H), 7.80 (s, 1H), 8.45 (s, 1H), 12.74 (s, 1H) LC/MS (89%) ESI− Calcd: 551.41 Found: 549.2 m/z

Example 206

Preparation of P228

Following the general procedure A-10, the sulphonamide I-140A, was reacted with 4H-[1,2,4]triazole-3-thiol to provide compound P228. 1H NMR (DMSO-d6) 4.65 (s, 2H), 6.34 (d, J=8.0), 6.97 (t, J=8.0, 1H), 7.05 (d, J=3.0, 1H), 7.58 (d, J=3.0, 1H), 7.81 (s, 1H), 8.25 (s, 1H), and 11.60 (s, 1H). LC/MS (94%) ESI+ Calcd: 504.40 Found: 506.1 m/z.

Example 207

Preparation of P240

Following the general procedure A-11, the sulfide P228 was oxidized to the sulphone: P240. Consistent with 1H-NMR.

Example 208

Preparation of P230

Following the general procedure A-10, the sulphonamide I-140A, was reacted with 5-methyl-[1,3,4]thiadiazole-2-thiol to provide compound P230. Consistent with 1H-NMR.

Example 209

Preparation of P231

Following the general procedure A-11, the sulfide P230 was oxidized to the sulphone P231. 1H NMR (500 MHz, DMSO-d6) 2.71 (s, 3H), 4.67 (s, 2H), 6.53 (m, 1H), 7.16 (m, 2H), 7.83 (s, 1H), 8.35 (d, J=3.5 Hz, 1H), 12.62 (s, 1H). LC/MS=96% purity, MS (ESI−) Calcd. (M/Z) 567; Found: 567.

Example 210

Preparation of P166

Synthesis of Thiophene-2-sulfonic acid [2-(1H-indol-4-yloxy)-acetyl]-amide, I-140B: Following the general procedure A-9, I-139, was reacted with thiophene-2-sulfonic acid amide to provide compound I-140B. Consistent with 1H-NMR.

Synthesis of P166. Following the general procedure A-10, the sulphonamide I-140B, was reacted with naphthalene-2-thiol to provide compound P166. Consistent with 1H-NMR.

Example 211

Preparation of P163

Following the general procedure A-11, the sulfide P166 was oxidized to the sulphone P163. Consistent with 1H-NMR.

Example 212

Preparation of P174

Synthesis of 5-Chloro-thiophene-2-sulfonic acid [2-(1H-indol-4-yloxy)-acetyl]-amide, I-140C. Following the general procedure A-9, I-139, was reacted with 5-chloro-thiophene-2-sulfonic acid amide to provide compound I-140C. Consistent with 1H-NMR.

Synthesis of P174. Following the general procedure A-10, the sulphonamide I-140C, was reacted with Naphthalene-2-thiol to provide compound P174. Consistent with 1H-NMR.

Example 213

Preparation of P187

Following the general procedure A-11, the sulfide P174 was oxidized to the sulphone P187. Consistent with 1H-NMR.

Example 214

Preparation of P175

Synthesis of N-[2-(1H-Indol-4-yloxy)-acetyl]-benzenesulfonamide, I-140D. Following the general procedure A-9, I-139, was reacted with benzenesulfonamide to provide compound I-140D. Consistent with 1H-NMR.

Synthesis of P175. Following the general procedure A-10, the sulphonamide I-140D, was reacted with naphthalene-2-thiol to provide compound P175. Consistent with 1H-NMR.

Example 215

Preparation of P188

Following the general procedure A-11, the sulfide P175 was oxidized to the sulphone P188. Consistent with 1H-NMR.

Example 216

Preparation of P176

Synthesis of N-[2-(1H-Indol-4-yloxy)-acetyl]-2,5-dimethoxy-benzenesulfonamide, I-140E: Following the general procedure A-9, I-139, was reacted with 2,5-dimethoxy-benzenesulfonamide to provide compound I-140E. Consistent with 1H-NMR.

Synthesis of P176. Following the general procedure A-10, the sulphonamide I-140E, was reacted with naphthalene-2-thiol to provide compound P176. Consistent with 1H-NMR.

Example 217

Preparation of P189

Following the general procedure A-11, the sulfide P176 was oxidized to the sulphone P189. 1H NMR (DMSO-$d_6$) 3.75 (s, 3H), 3.84 (s, 3H), 4.71 (s, 2H), 6.32 (d, J=7.5 Hz, 1H), 7.04 (t, J=8.0 Hz, 1H), 7.10 (d, J=8.0 Hz, 1H), 7.25 (m, 2H), 7.35 (m, 1H), 7.59 (t, J=7.0 Hz, 1H), 7.66 (t, J=7.5 Hz, 1H), 7.82 (d, J=8.0 Hz, 1H), 7.94 (m, 2H), 8.03 (d, J=8.0 Hz, 1H), 8.17 (d, J=3.0 Hz, 1H), 8.65 (s, 1H), 12.05 (s, 1H), 12.29 (s, 1H). LC/MS (95%) ESI– Calcd. 579.6 m/z Found: 579.5 m/z

Example 218

Preparation of P177

Synthesis of 3,5-Dichloro-N-[2-(1H-indol-4-yloxy)-acetyl]-benzenesulfonamide, I-140F: Following the general procedure A-9, I-139, was reacted with 3,5-dichloro-benzenesulfonamide to provide compound I-140F. Consistent with 1H-NMR.

Synthesis of P177. Following the general procedure A-10, the sulphonamide I-140F, was reacted with naphthalene-2-thiol to provide compound P177. Consistent with 1H-NMR.

Example 219

Preparation of P186

Following the general procedure A-11, the sulfide P177 was oxidized to the sulphone P186. Consistent with 1H-NMR.

Example 220

Preparation of P183

Synthesis of 2-Chloro-N-[2-(1H-indol-4-yloxy)-acetyl]-benzenesulfonamide, I-140G. Following the general procedure A-9, I-139, was reacted with sulphonamide 2-chloro-benzenesulfonamide to provide compound I-140G. Consistent with 1H-NMR.

Synthesis of P183. Following the general procedure A-10, the sulphonamide I-140G, was reacted with naphthalene-2-thiol to provide compound P183. Consistent with 1H-NMR.

Example 221

Preparation of P191

Following the general procedure A-11, the sulfide P183 was oxidized to the sulphone P191. Consistent with 1H-NMR.

Example 222

Preparation of P184

Synthesis of 3-Chloro-N-[2-(1H-indol-4-yloxy)-acetyl]benzenesulfonamide, I-140H: Following the general procedure A-9, I-139, was reacted with 3-chloro-benzenesulfonamide to provide compound I-140H. Consistent with 1H-NMR.

Synthesis of P184. Following the general procedure A-10, the sulphonamide I-140H, was reacted with naphthalene-2-thiol to provide compound P184. Consistent with 1H-NMR.

Example 223

Preparation of P192

Following the general procedure A-11, the sulfide P184 was oxidized to the sulphone P192. Consistent with 1H-NMR.

Example 224

Preparation of P185

Synthesis of N-[2-(1H-Indol-4-yloxy)-acetyl]-4-methoxy-benzenesulfonamide, I-140I: Following the general procedure A-9, I-139, was reacted with 4-methoxy-benzenesulfonamide to provide compound I-140I. Consistent with 1H-NMR.

Synthesis of P185. Following the general procedure A-10, the sulphonamide I-140I, was reacted with naphthalene-2-thiol to provide compound P185. Consistent with 1H-NMR.

Example 225

Preparation of P193

Following the general procedure A-11, the sulfide P185 was oxidized to the sulphone P193. Consistent with 1H-NMR.

Example 226

Preparation of P199

Synthesis of 3,5-Dimethyl-isoxazole-4-sulfonic acid [2-(1H-indol-4-yloxy)-acetyl]-amide, I-140J: Following the general procedure A-9, I-139, was reacted with 3,5-dimethyl-isoxazole-4-sulfonic acid amide to provide compound I-140J. Consistent with 1H-NMR.

Synthesis of P199. Following the general procedure A-10, the sulphonamide I-140J, was reacted with naphthalene-2-thiol to provide compound P199. Consistent with 1H-NMR.

Example 227

Preparation of P203

Following the general procedure A-11, the sulfide P199 was oxidized to the sulphone P203. Consistent with 1H-NMR

Example 228

Preparation of P214

Synthesis of 3,5-Difluoro-N-[2-(1H-indol-4-yloxy)-acetyl]-benzenesulfonamide, I-140K. Following the general procedure A-9, I-139, was reacted with sulphonamide 3,5-difluoro-benzenesulfonamide to provide compound I-140K. Consistent with 1H-NMR.

Synthesis of P214. Following the general procedure A-10, the sulphonamide I-140K, was reacted with naphthalene-2-thiol to provide compound P214. Consistent with 1H-NMR.

Example 229

Preparation of P223

Following the general procedure A-11, the sulfide P214 was oxidized to the sulphone P223. Consistent with 1H-NMR.

Example 230

Preparation of P215

Synthesis of 3,4-Difluoro-N-[2-(1H-indol-4-yloxy)-acetyl]-benzenesulfonamide, I-140L: Following the general procedure A-9, I-139, was reacted with 3,4-difluoro-benzenesulfonamide to provide compound I-140L. Consistent with 1H-NMR.

Synthesis of P215. Following the general procedure A-10, the sulphonamide I-140L, was reacted with naphthalene-2-thiol to provide compound P215. Consistent with 1H-NMR.

Example 231

Preparation of P224

Following the general procedure A-11, the sulfide P215 was oxidized to the sulphone P224. Consistent with 1H-NMR.

Example 232

Preparation of P225

Synthesis of 4-Fluoro-N-[2-(1H-indol-4-yloxy)-acetyl]-benzenesulfonamide, I-140M: Following the general procedure A-9, I-139, was reacted with 4-fluoro-benzenesulfonamide to provide compound I-140M. Consistent with 1H-NMR.

Synthesis of P225. Following the general procedure A-10, the sulphonamide I-140M, was reacted with naphthalene-2-thiol to provide compound P225. Consistent with 1H-NMR.

Example 233

Preparation of P236

Following the general procedure A-11, the sulfide P225 was oxidized to the sulphone P236. Consistent with 1H-NMR.

Example 234

Preparation of P226

Synthesis of 2,4,5-Trifluoro-N-[2-(1H-indol-4-yloxy)-acetyl]-benzenesulfonamide, I-140N: Following the general procedure A-9, I-139, was reacted with 2,4,5-trifluoro-benzenesulfonamide to provide compound I-140N. Consistent with 1H-NMR.

Synthesis of P226. Following the general Procedure A-10, the sulphonamide I-140N, was reacted with naphthalene-2-thiol to provide compound P226. Consistent with 1H-NMR.

Example 235

Preparation of P237

Following the general procedure A-11, the sulfide P226 was oxidized to the sulphone P237. Consistent with 1H-NMR.

Example 236

Preparation of P243

Synthesis of [3-(Naphthalen-2-ylsulfanyl)-1H-indol-4-yloxy]-acetic acid methyl ester, I-141: To a mixture of I-138 (102 mg, 0.5 mmol) and naphthalene-2-thiol (160 mg, 1 mmol) in ethanol (10 ml) and water (5 ml), 1 ml of iodine-potassium iodide (1N in ethanol/$H_2O$, 1:1) was added and stirred at rt over weekend. Water (~5 ml) was added to reaction mixture and stirred at rt for 30 min. Solid was filtered and washed with water, water/ethanol (1:1), CH2Cl2/hexane (5 ml/5 ml) to give 50 mg of compound I-141. Consistent with 1H-NMR.

Synthesis of [3-(Naphthalen-2-ylsulfanyl)-1H-indol-4-yloxy]-acetic acid, I-142. To a solution of I-141 (50 mg, 13 mmol) in THF (3 ml) and methanol (3 ml), NaOH aq. (2N, 1.5 ml) was added at rt The reaction mixture was stirred at rt over night and then the pH was adjusted to acidic by adding 2N HCl aq. The reaction mixture was extracted with EtOAc (2×20 ml). The combined organic phase was washed with water, brine and dried over sodium sulfate. After removal of solvent, 35 mg of compound I-142 was obtained. Consistent with 1H-NMR.

Synthesis of P243. A mixture of the acid I-142 (35 mg, 0.1 mmol), trifluoromethylsulfonamide (30 mg, 0.2 mmol), 4-dimethylamino pyridine (25 mg, 0.2 mmol) and EDCI (38 mg, 0.2 mmol) in dichloromethane (5 ml) and DMSO (1 ml) was stirred at rt over night. The solution was diluted with dichloromethane, washed with diluted HCl aq., water and dried over sodium sulfate. After removal of solvent, the residue was purified by column chromatography on silica gel with EtOAc/hexane as an eluent to give 23 mg of compound P243. MS (ESI⁻): 479.2 (M−1), LC-MS: 94% pure, ¹H-NMR (500 MHz, DMSO-d$_6$) RP-HPLC: 92% pure.

Example 237

Preparation of P277

Synthesis of 4-Bromo-1-methyl-1H-indole, I-133. To a solution of NaH (60% in oil, 600 mg, 15 mmol) in DMF (20 ml), 4-bromoindole (1.96 g, 10 mmol) was added at −10° C. and stirred at rt for 10 min. and then iodomethane (6.7 g, 50 mmol) was added at −10° C. The reaction mixture was stirred at rt for 3 hrs and diluted with CH2Cl2 (200 ml). The reaction mixture was washed with water (3×200 ml), brine and dried over sodium sulfate. After removal of solvent, 3 g of crude I-133 was obtained. Without further purification I-133 directly used in next step reaction. Consistent with 1H-NMR.

General Procedure (A-12), coupling of 4-bromoindole with phenol.

A mixture of I-133 (420 mg, 2 mmol), CuI (38 mg, 0.2 mmol, 0.1 eq.), N,N-dimethylglycine HCl salt (84 mg, 0.6 mmol, 0.3 eq.), phenol (3 mmol, 1.5 eq) and Cs$_2$CO$_3$ (1.3 g, 4 mmol, 2 e.q.) in dioxane (4 ml) was stirred under Ar at 105° C. for 3 days. The reaction mixture was diluted with EtOAc and washed with water, brine and dried over sodium sulfate. After removal of solvent, the residue was purified by column chromatography on silica gel with EtOAc/hexane as an eluent to give I-134.

Synthesis of 1-Methyl-4-(naphthalen-2-yloxy)-1H-indole, I-134A. Following the general procedure A-12, I-133, was reacted with naphthalen-2-ol to provide compound I-134A. Consistent with 1H-NMR.

Synthesis of 1-Methyl-4-(naphthalen-2-yloxy)-1H-indole-3-carbaldehyde, I-135A. General Procedure (A-13), conversion of indole to 3-formaldehyde indole. To a solution of I-134 (1.6 mmol) in DMF (8 ml), POCl$_3$ (1.8 mmol, 1.1 e.q.) was added dropwise at rt The reaction mixture was stirred at 50° C. for 1 hr, poured into ice-water. The pH of the resulting mixture was adjusted to 8-9 by addition of NaOH aq (2N) and then stirred at rt for 30 min. The reaction mixture was extracted with EtOAc (2×40 ml). The organic phase was washed with water (3×50 ml), brine, and dried over sodium sulfate. After removal of solvent, I-135 was obtained as a solid.

Following the general procedure A-13, I-134A, was converted to formaldehyde I-135A. Consistent with 1H-NMR.

Synthesis of (E)-3-[1-Methyl-4-(naphthalen-2-yloxy)-1H-indol-3-yl]-acrylic acid ethyl ester, I-136A. General Procedure (A-14), conversion of 3-formaldehyde indole to 3-acrylic acid ethyl ester indole. To a solution of NaH (60% in oil, 100 mg, 2.5 mmol, 2.5 eq.) in THF (20 ml), triethyl phosphonoacetate (493 mg, 2.2 mmol, 2.2 e.q.) was added at −10° C. and stirred at rt for 10 min. and then I-135 (1 mmol) dissolved in THF (10 ml) was added at −10° C. The reaction mixture was stirred at 60° C. over night. The reaction mixture was diluted with EtOAc and washed with NH$_4$Cl aq. water (2×100 ml), brine and dried over sodium sulfate. After removal of solvent, crude product I-136 was obtained. Without further purification I-136 directly used in next step reaction.

Following the general Procedure A-14, I-135A, was converted to acrylic acid ethyl ester I-136A. Consistent with 1H-NMR.

Synthesis of (E)-3-[1-Methyl-4-(naphthalen-2-yloxy)-1H-indol-3-yl]-acrylic acid, I-137A.

General Procedure (A-7A). Hydrolysis of 3-acrylic acid ethyl ester to 3-acrylic acid.

A mixture of crude I-136 (1 mmol) in THF (10 ml), MeOH (10 ml) and NaOH aq. (2N, 10 ml) was stirred at 50° C. for 3 hrs. After removal of THF and MeOH, the reaction mixture was diluted with water (~20 ml), adjusted pH to acidic by addition of HCl aq. (2N) and extracted with EtOAc (2×30 ml). The combined organic phase was washed with water (2×30 ml), brine and dried over sodium sulfate. After removal of solvent, residue washed with ether to give I-137.

Following the general procedure A-7A, I-136A, was hydrolyzed to acrylic acid I-137A. Consistent with 1H-NMR.

General Procedure (A-8A), coupling of acid to arylsulfonamide. A mixture of the acid I-137 (0.16 mmol), sulfonamide (0.20 mmol, 1.2 e.q.), 4-dimethylamino pyridine (41 mg, 0.33 mmol, 2 e.q.) and EDCI (63 mg, 0.33 mmol, 2 e.q.) in dichloromethane (10 ml) was stirred at rt over night. The reaction mixture washed with diluted HCl aq., water and dried over sodium sulfate. After removal of solvent, the residue was purified by column chromatography on silica gel with methanol/dichloromethane as an eluent to give product.

Synthesis of P277. Following the general procedure A-8A, the acrylic acid I-137A, was reacted with 4,5-Dichloro-thiophene-2-sulfonic acid amide to provide compound P277. Consistent with 1H-NMR.

Example 238

Preparation of P343

Following the general Procedure A-8A, the acrylic acid I-137A, was reacted with 2,4,5-Trifluoro-benzenesulfonamide to provide compound P343. 1H NMR (DMSO-d6) 3.89 (s, 3H), 6.43 (d, J=15.0 Hz, 1H), 6.70 (d, J=7.5 Hz, 1H), 7.23 (t, J=8.0 Hz, 1H), 7.27 (m, 1H), 7.35-7.48 (m, 4H), 7.73 (d, J=8.0 Hz, 1H), 7.83-7.98 (m, 5H), 7.97 (d, J=15.0 Hz, 1H), 12.6 (s, 1H). HPLC (97%) MS ESI− Calcd. 535.5 m/z Found: 535.7 m/z.

Example 239

Preparation of P334

Following the general Procedure A-8A, the acrylic acid I-137A, was reacted with 3,4-Difluoro-benzenesulfonamide to provide compound P334. 1H NMR (DMSO-d6) 3.89 (s, 3H), 6.39 (d, J=15.0 Hz, 1H), 6.70 (d, J=7 Hz, 1H), 7.23 (t, J=8.0 Hz, 1H), 7.30 (m, 1H), 7.35 (m, 1H), 17.37 (d, J=8.0 Hz, 1H), 7.44 (m, 2H), 7.6-7.8 (m, 3H), 7.89-7.97 (m, 4H), 7.96 (d, J=15.0 Hz, 1H), 12.2 (s, 1H). HPLC (99%) MS ESI− Calcd. 517.5 m/z Found: 517.7 m/z.

Example 240

Preparation of P290

Synthesis of 4-(3,4-Dichloro-phenoxy)-1-methyl-1H-indole, I-134B: Following the general Procedure A-12, I-133, was reacted with 3,4-Dichloro-phenol to provide compound I-134B. Consistent with 1H-NMR.

Synthesis of 4-(3,4-Dichloro-phenoxy)-1-methyl-1H-indole-3-carbaldehyde, I-135B: Following the general Procedure A-13, I-134B, was converted to formaldehyde I-135B. Consistent with 1H-NMR.

Synthesis of (E)-3-[4-(3,4-Dichloro-phenoxy)-1-methyl-1H-indol-3-yl]-acrylic acid ethyl ester, I-136B: Following the general Procedure A-14, I-135B, was converted to acrylic acid ethyl ester I-136B. Consistent with 1H-NMR.

Synthesis of (E)-3-[4-(3,4-Dichloro-phenoxy)-1-methyl-1H-indol-3-yl]-acrylic acid, I-137B. Following the general Procedure A-7A, I-136B, was hydrolyzed to acrylic acid I-137B. Consistent with 1H-NMR.

Synthesis of P290. Following the general Procedure A-8A, the acrylic acid I-137B, was reacted with 4,5-Dichloro-thiophene-2-sulfonic acid amide to provide compound P290. Consistent with 1H-NMR.

Example 241

Preparation of P292

Following the general Procedure A-8A, the acrylic acid I-137B, was reacted with 2,4,5-Trifluoro-benzenesulfonamide to provide compound P292. Consistent with 1H-NMR.

Example 242

Preparation of P293

Following the general Procedure A-8A, the acrylic acid I-137B, was reacted with 3,4-Difluoro-benzenesulfonamide to provide compound P293. Consistent with 1H-NMR.

Example 243

Preparation of P291

Synthesis of 4-(2,3-Dichloro-phenoxy)-1-methyl-1H-indole, I-134C. Following the general Procedure A-12, I-133, was reacted with 2,3-Dichloro-phenol to provide compound I-134C. Consistent with 1H-NMR.

Synthesis of 4-(2,3-Dichloro-phenoxy)-1-methyl-1H-indole-3-carbaldehyde, I-135C. Following the general Procedure A-13, I-134C, was converted to formaldehyde I-135C. Consistent with 1H-NMR.

Synthesis of (E)-3-[4-(2,3-Dichloro-phenoxy)-1-methyl-1H-indol-3-yl]-acrylic acid ethyl ester, I-136C. Following the general Procedure A-14, I-135C, was converted to acrylic acid ethyl ester I-136C. Consistent with 1H-NMR.

Synthesis of (E)-3-[4-(2,3-Dichloro-phenoxy)-1-methyl-1H-indol-3-yl]-acrylic acid, I-137C. Following the general Procedure A-7A, I-136C, was hydrolyzed to acrylic acid I-137C. Consistent with 1H-NMR.

Synthesis of P291. Following the general Procedure A-8A, the acrylic acid I-137C, was reacted with 4,5-Dichloro-thiophene-2-sulfonic acid amide to provide compound P291. Consistent with 1H-NMR.

Example 244

Preparation of P303

Synthesis of 4-(2,4-Dichloro-phenoxy)-1-methyl-1H-indole, I-134D: Following the general Procedure A-12, I-133, was reacted with 2,4-Dichloro-phenol to provide compound I-134D. Consistent with 1H-NMR.

Synthesis of 4-(2,4-Dichloro-phenoxy)-1-methyl-1H-indole-3-carbaldehyde, I-135D: Following the general Procedure A-13, I-134D, was converted to formaldehyde I-135D. Consistent with 1H-NMR.

Synthesis of (E)-3-[4-(2,4-Dichloro-phenoxy)-1-methyl-1H-indol-3-yl]-acrylic acid ethyl ester, I-136D. Following the general Procedure A-14, I-135D, was converted to acrylic acid ethyl ester I-136D. Consistent with 1H-NMR.

Synthesis of (E)-3-[4-(2,4-Dichloro-phenoxy)-1-methyl-1H-indol-3-yl]-acrylic acid, I-137D. Following the general Procedure A-7A, I-136D, was hydrolyzed to acrylic acid I-137D. Consistent with 1H-NMR.

Synthesis of P303. Following the general Procedure A-8A, the acrylic acid I-137D, was reacted with 4,5-Dichloro-thiophene-2-sulfonic acid amide to provide compound P303. Consistent with 1H-NMR.

Example 245

Preparation of P301

Following the general Procedure A-8A, the acrylic acid I-137D, was reacted with 2,4,5-Trifluoro-benzenesulfonamide to provide compound P301. Consistent with 1H-NMR.

Example 246

Preparation of P302

Following the general Procedure A-8A, the acrylic acid I-137D, was reacted with 3,4-Difluoro-benzenesulfonamide to provide compound P302. Consistent with 1H-NMR.

Example 247

Preparation of P311

Synthesis of 4-(4-Chloro-phenoxy)-1-methyl-1H-indole, I-134E: Following the general Procedure A-12, I-133, was reacted with 4-Chloro-phenol to provide compound I-134E. Consistent with 1H-NMR.

Synthesis of 4-(4-Chloro-phenoxy)-1-methyl-1H-indole-3-carbaldehyde, I-135E: Following the general Procedure A-13, I-134E, was converted to formaldehyde I-135E. Consistent with 1H-NMR.

Synthesis of (E)-3-[4-(4-Chloro-phenoxy)-1-methyl-1H-indol-3-yl]-acrylic acid ethyl ester, I-136E. Following the general Procedure A-14, I-135E, was converted to acrylic acid ethyl ester I-136E. Consistent with 1H-NMR.

Synthesis of (E)-3-[4-(4-Chloro-phenoxy)-1-methyl-1H-indol-3-yl]-acrylic acid, I-137E. Following the general Procedure A-7A, I-136E, was hydrolyzed to acrylic acid I-137E. Consistent with 1H-NMR.

Synthesis of P311. Following the general Procedure A-8A, the acrylic acid I-137E, was reacted with 4,5-Dichloro-thiophene-2-sulfonic acid amide to provide compound P311. 1H NMR (DMSO-d6) 3.87 (s, 3H), 6.36 (d, J=15.0 Hz, 1H), 6.69 (d, J=8.0 Hz, 1H), 6.99 (d, J=7 Hz, 2H), 7.23 (d, J=7 Hz, 1H), 7.38 (m, 1H), 7.39 (d, J=7 Hz, 2H), 7.86 (s, 1H), 7.94 (d, J=15.0 Hz, 1H), 7.99 (s, 1H), 12.5 (bs, 1H). HPLC (97%) MS ESI– Calcd. 541.8 m/z Found: 541.4 m/z

Example 248

Preparation of P309

Following the general Procedure A-8A, the acrylic acid I-137E, was reacted with 2,4,5-Trifluoro-benzenesulfonamide to provide compound P309. Consistent with 1H-NMR.

Example 249

Preparation of P310

Following the general Procedure A-8A, the acrylic acid I-137E, was reacted with 3,4-Difluoro-benzenesulfonamide to provide compound P310. Consistent with 1H-NMR.

Example 250

Preparation of P320

Synthesis of 4-(3,4-Difluoro-phenoxy)-1-methyl-1H-indole, I-134F: Following the general Procedure A-12, I-133, was reacted with 3,4-Difluoro-phenol to provide compound I-134F. Consistent with 1H-NMR.

Synthesis of 4-(3,4-Difluoro-phenoxy)-1-methyl-1H-indole-3-carbaldehyde, I-135F: Following the general Procedure A-13, I-134F, was converted to formaldehyde I-135F. Consistent with 1H-NMR.

Synthesis of (E)-3-[4-(3,4-Difluoro-phenoxy)-1-methyl-1H-indol-3-yl]-acrylic acid ethyl ester, I-136F: Following the general Procedure A-14, I-135F, was converted to acrylic acid ethyl ester I-136F. Consistent with 1H-NMR.

Synthesis of (E)-3-[4-(3,4-Difluoro-phenoxy)-1-methyl-1H-indol-3-yl]-acrylic acid, I-137F. Following the general Procedure A-7A, I-136F, was hydrolyzed to acrylic acid I-137F. Consistent with 1H-NMR.

Synthesis of P320. Following the general Procedure A-8A, the acrylic acid I-37F, was reacted with 4,5-Dichlorothiophene-2-sulfonic acid amide to provide compound P320. Consistent with 1H-NMR.

Example 251

Preparation of P318

Following the general Procedure A-8A, the acrylic acid I-137F, was reacted with 2,4,5-Trifluoro-benzenesulfonamide to provide compound P318. Consistent with 1H-NMR.

Example 252

Preparation of P319

Following the general Procedure A-8A, the acrylic acid I-137F, was reacted with 3,4-Difluoro-benzenesulfonamide to provide compound P319. Consistent with 1H-NMR.

Example 253

Preparation of P326

Synthesis of 4-(2,4-Difluoro-phenoxy)-1-methyl-1H-indole, I-134G: Following the general Procedure A-12, I-133, was reacted with 2,4-Difluoro-phenol to provide compound I-134G. Consistent with 1H-NMR.

Synthesis of 4-(2,4-Difluoro-phenoxy)-1-methyl-1H-indole-3-carbaldehyde, I-135G. Following the general Procedure A-13, I-134G, was converted to formaldehyde I-135G. Consistent with 1H-NMR.

Synthesis of (E)-3-[4-(2,4-Difluoro-phenoxy)-1-methyl-1H-indol-3-yl]-acrylic acid ethyl ester, I-136G. Following the general Procedure A-14, I-135G, was converted to acrylic acid ethyl ester I-136G. Consistent with 1H-NMR.

Synthesis of (E)-3-[4-(2,4-Difluoro-phenoxy)-1-methyl-1H-indol-3-yl]-acrylic acid, I-137G. Following the general Procedure A-7A, I-136G, was hydrolyzed to acrylic acid I-137G. Consistent with 1H-NMR.

Synthesis of P326. Following the general Procedure A-8A, the acrylic acid I-137G, was reacted with 4,5-Dichlorothiophene-2-sulfonic acid amide to provide compound P326. Consistent with 1H-NMR.

Example 254

Preparation of P324

Following the general Procedure A-8A, the acrylic acid I-137G, was reacted with 2,4,5-Trifluoro-benzenesulfonamide to provide compound P324. Consistent with 1H-NMR.

Example 255

Preparation of P325

Following the general Procedure A-8A, the acrylic acid I-137G, was reacted with 3,4-Difluoro-benzenesulfonamide to provide compound P325. $^1$HNMR (DMSO-$d_6$) 6.12 (d, J=8.0 Hz, 1H), 6.21 (d, J=15.2 Hz, 1H), 7.04 (dd, J=10.0, 2.4 Hz, 1H), 7.23 (dd, J=8.0, 2.4 Hz, 1H), 7.36 (s, 1H), 7.39 (d, J=2.4 Hz, 1H), 7.45 (dd, J=9.2, 2.4 Hz, 1H), 7.72 (d, J=15.2 Hz, 1H), 7.88 (s, 1H) LC/MS (96%) (ESI−) Calcd. 594.34 m/z Found 593.3 m/z.

Example 256

Preparation of P330

Synthesis of 4-(3-Chloro-4-fluoro-phenoxy)-1-methyl-1H-indole, I-134H: Following the general Procedure A-12, I-133, was reacted with 3-Chloro-4-fluoro-phenol to provide compound I-134H. Consistent with 1H-NMR.

Synthesis of 4-(3-Chloro-4-fluoro-phenoxy)-1-methyl-1H-indole-3-carbaldehyde, I-135H. Following the general Procedure A-13, I-134H, was converted to formaldehyde I-135H. Consistent with 1H-NMR.

Synthesis of (E)-3-[4-(3-Chloro-4-fluoro-phenoxy)-1-methyl-1H-indol-3-yl]-acrylic acid ethyl ester, I-136H. Following the general Procedure A-14, I-135H, was converted to acrylic acid ethyl ester I-136H. Consistent with 1H-NMR.

Synthesis of (E)-3-[4-(3-Chloro-4-fluoro-phenoxy)-1-methyl-1H-indol-3-yl]-acrylic acid, I-137H. Following the general Procedure A-7A, I-136H, was hydrolyzed to acrylic acid I-137H. Consistent with 1H-NMR.

Synthesis of P330. Following the general Procedure A-8A, the acrylic acid I-137H, was reacted with 4,5-Dichloro-thiophene-2-sulfonic acid amide to provide compound P330. Consistent with 1H-NMR.

Example 257

Preparation of P328

Following the general Procedure A-8A, the acrylic acid I-137H, was reacted with 2,4,5-Trifluoro-benzenesulfonamide to provide compound P328. Consistent with 1H-NMR.

Example 258

Preparation of P329

Following the general Procedure A-8A, the acrylic acid I-137H, was reacted with 3,4-Difluoro-benzenesulfonamide to provide compound P329. Consistent with 1H-NMR.

Example 259

Preparation of P333

Synthesis of 4-(4-Chloro-3-fluoro-phenoxy)-1-methyl-1H-indole, I-134I. Following the general Procedure A-12, I-133, was reacted with 4-Chloro-3-fluoro-phenol to provide compound I-134I. Consistent with 1H-NMR.
Synthesis of 4-(4-Chloro-3-fluoro-phenoxy)-1-methyl-1H-indole-3-carbaldehyde, I-135I. Following the general Procedure A-13, I-134I, was converted to formaldehyde I-135I. Consistent with 1H-NMR.
Synthesis of (E)-3-[4-(4-Chloro-3-fluoro-phenoxy)-1-methyl-1H-indol-3-yl]-acrylic acid ethyl ester, I-136I. Following the general Procedure A-14, I-135I, was converted to acrylic acid ethyl ester I-136I. Consistent with 1H-NMR.
Synthesis of (E)-3-[4-(4-Chloro-3-fluoro-phenoxy)-1-methyl-1H-indol-3-yl]-acrylic acid, I-137I. Following the general Procedure A-7A, I-136I, was hydrolyzed to acrylic acid I-137I. Consistent with 1H-NMR.
Synthesis of P333. Following the general Procedure A-8A, the acrylic acid I-137I, was reacted with 4,5-Dichloro-thiophene-2-sulfonic acid amide to provide compound P333. Consistent with 1H-NMR.

Example 260

Preparation of P331

Following the general Procedure A-8A, the acrylic acid I-137I, was reacted with 2,4,5-trifluoro-benzenesulfonamide to provide compound P331. 1H NMR (DMSO-d6) 3.88 (s, 3H), 6.38 (d, J=15.0 Hz, 1H), 6.72 (m, 1H), 6.78 (d, J=7 Hz, 1H), 7.09 (dd, J=10 and 3 Hz, 1H), 7.26 (t, J=8.0 Hz, 1H), 7.42 (d, J=8.0 Hz, 1H), 7.50 (t, J=9 Hz, 1H), 7.80 (d, J=15.0 Hz, 1H), 7.88 (m, 1H), 7.98 (m, 2H), 12.6 (s, 1H). HPLC (93%) MS ESI− Calcd. 537.9 m/z Found: 537.4 m/z Example 261

Preparation of P332

Following the general Procedure A-8A, the acrylic acid I-137I, was reacted with 3,4-difluoro-benzenesulfonamide to provide compound P332. Consistent with 1H-NMR.

Example 262

Preparation of P339

Synthesis of 4-(4-Chloro-2-fluoro-phenoxy)-1-methyl-1H-indole, I-134J. Following the general Procedure A-12, I-133, was reacted with 4-Chloro-2-fluoro-phenol to provide compound I-134J. Consistent with 1H-NMR.
Synthesis of 4-(4-Chloro-2-fluoro-phenoxy)-1-methyl-1H-indole-3-carbaldehyde, I-135J. Following the general Procedure A-13, I-134J, was converted to formaldehyde I-135J. Consistent with 1H-NMR.
Synthesis of (E)-3-[4-(4-Chloro-2-fluoro-phenoxy)-1-methyl-1H-indol-3-yl]-acrylic acid ethyl ester, I-136J. Following the general Procedure A-14, I-135J, was converted to acrylic acid ethyl ester I-136J. Consistent with 1H-NMR.
Synthesis of (E)-3-[4-(4-Chloro-2-fluoro-phenoxy)-1-methyl-1H-indol-3-yl]-acrylic acid, I-137J. Following the general Procedure A-7A, I-136J, was hydrolyzed to acrylic acid I-137J. Consistent with 1H-NMR.
Synthesis of P339. Following the general Procedure A-8A, the acrylic acid I-137J, was reacted with 4,5-Dichloro-thiophene-2-sulfonic acid amide to provide compound P339. 1H NMR (DMSO-d6) 3.87 (s, 3H), 6.40 (d, J=15.0 Hz, 1H), 6.49 (d, J=8.0 Hz, 1H), 7.17 (m, 2H), 7.32 (m, 2H), 7.65 (dd, J=10 and 2 Hz, 1H), 7.86 (s, 1H), 8.02 (s, 1H), 8.04 (d, J=15.0 Hz, 1H), 12.5 (bs, 1H). HPLC (89%) MS ESI− Calcd. 558.8 m/z Found: 559.1 m/z Example 263

Preparation of P337

Following the general Procedure A-8A, the acrylic acid I-137J, was reacted with 2,4,5-trifluoro-benzenesulfonamide to provide compound P337. Consistent with 1H-NMR.

Example 264

Preparation of P338

Following the general Procedure A-8A, the acrylic acid I-137J, was reacted with 3,4-difluoro-benzenesulfonamide to provide compound P338. Consistent with 1H-NMR.

Example 265

Preparation of P342

Synthesis of 4-(2-Chloro-4-fluoro-phenoxy)-1-methyl-1H-indole, I-134K. Following the general Procedure A-12, I-133, was reacted with 2-chloro-4-fluoro-phenol to provide compound I-134K. Consistent with 1H-NMR.
Synthesis of 4-(2-Chloro-4-fluoro-phenoxy)-1-methyl-1H-indole-3-carbaldehyde, I-135K. Following the general Procedure A-13, I-134K, was converted to formaldehyde I-135K. Consistent with 1H-NMR.
Synthesis of (E)-3-[4-(2-Chloro-4-fluoro-phenoxy)-1-methyl-1H-indol-3-yl]-acrylic acid ethyl ester, I-136K. Following the general Procedure A-14, I-135K, was converted to acrylic acid ethyl ester I-136K. Consistent with 1H-NMR.
Synthesis of (E)-3-[4-(2-Chloro-4-fluoro-phenoxy)-1-methyl-1H-indol-3-yl]-acrylic acid, I-137K. Following the general Procedure A-7A, I-136K, was hydrolyzed to acrylic acid I-137K. Consistent with 1H-NMR.
Synthesis of P342. Following the general Procedure A-8A, the acrylic acid I-137K, was reacted with 4,5-dichlorothiophene-2-sulfonic acid amide to provide compound P342. 1H NMR (DMSO-d6) 3.87 (s, 3H), 6.31 (d, J=8.0 Hz, 1H), 6.41 (d, J=15.0 Hz, 1H), 7.13 (t, J=8.0 Hz, 1H), 7.25-7.30 (m, 3H), 7.64 (dd, J=8 and 2 Hz, 1H), 7.86 (s, 1H), 8.01 (s, 1H), 8.11 (d, J=15.0 Hz, 1H), 12.5 (bs, 1H). HPLC (86%) MS ESI– Calcd. 558.8 m/z Found: 559.1

Example 266

Preparation of P340

Following the general Procedure A-8A, the acrylic acid I-137K, was reacted with 2,4,5-trifluoro-benzenesulfonamide to provide compound P340. Consistent with 1H-NMR.

Example 267

Preparation of P341

Following the general Procedure A-8A, the acrylic acid I-137K, was reacted with 3,4-Difluoro-benzenesulfonamide to provide compound P341. Consistent with 1H-NMR.

Example 268

Preparation of P034

Synthesis of 5-Amino-1-(2,2-diethoxy-ethyl)-1H-pyrazole-4-carboxylic acid ethyl ester, I-141. To a solution of hydrazine hydrate (17.5 ml, 0.355 moles) in 60 ml absolute ethanol stirred at reflux temperature, bromoacetaldehyde diethylacetal (20 g, 0.101 moles) was added dropwise. Mixture was refluxed overnight. The cooled reaction mixture was concentrated in vacuo, 25 ml of 35% NaOH solution mixed with 3 g NaCl was added and this was extracted with ether (2×100 ml). Combined organics were dried over $MgSO_4$ and concentrated in vacuum to afford 12.3 g of an oil (I-138). This was used for next step without purification. To a solution of I-138 (2,2-diethoxy-ethyl)-hydrazine, 12.3 g, 0.0831 moles) in 25 ml absolute ethanol was added a solution of ethyl ethoxymethylene cyanoacetate (14 g, 0.0831 moles) in 75 ml absolute ethanol. Mixture was stirred at room temperature for 3 days. The solvent was removed to give an oily residue (5-amino-1-(2,2-diethoxy-ethyl)-1H-pyrazole-4-carboxylic acid ethyl ester, I-141) which was used without purification for next step.

Synthesis of 1H-Imidazo[1,2-b]pyrazole-7-carboxylic acid ethyl ester, I-142 To a solution of crude I-141 (2 g in 10 ml absolute ethanol) was added aqueous 20% sulfuric acid solution (12 ml). Mixture was refluxed for 1 hour. The reaction mixture was cooled, the solvent was removed and the mixture was poured into ice and adjusted to pH=8 with sodium bicarbonate. The insoluble material was filtered off and filtrate was extracted with methylene chloride (2×60 ml). Combined organic layers were dried over MgSO4. Filtering of the mixture and evaporation of the solvent gave 1.2 g of a residue. This residue was purified by column chromatography using CH2Cl2 to 2% MeOH/CH2Cl2 to afford 280 mg product I-142. H nmr.

Synthesis of 1-Naphthalen-2-ylmethyl-1H-imidazo[1,2-b] pyrazole-7-carboxylic acid, I-143. To a suspension of NaH (60% in mineral oil, 65 mg, 1.6 mmol) in 5 ml DMF, at 0° C. was added compound I-142 (240 mg, 1.34 mmol). Mixture was stirred at 0° C. for 30 min., then at rt for 2 hrs. The reaction mixture was cooled to 0° C. and the 2-bromomethylnaphthalene was added. The mixture was stirred at rt overnight. The reaction was quenched through the addition of a saturated solution of NH4Cl (10 ml) to the mixture and this solution was extracted with CH2Cl2 (2×50 ml). The combined organic extracts were washed with brine and dried over MgSO4. 300 mg crude was obtained after solvent evaporation. Purification by column chromatography using 5%-20% ethylacetate/hexane afforded 208 mg compound I-143. H nmr.

Synthesis of (1-Naphthalen-2-ylmethyl-1H-imidazo[1,2-b]pyrazol-7-yl)-methanol, I-144. To a stirred solution of compound I-143 (100 mg, 0.313 mmol) in anhydrous methylene chloride (5 mL) cooled to −70° C. was added dropwise DIBAL (1M solution in CH2Cl2, 0.94 ml, 3 eq.) The reaction mixture was stirred at this temperature for 4 hours. Mixture was quenched with MeOH, then a 50% saturated solution of sodium, potassium tartrate and allowed to warm to room temperature. The mixture was extracted with CH2Cl2 (2×20 ml) and the combined organic layers were washed with brine and dried over MgSO4. After solvent removal, 70 mg crude alcohol, I-144 was obtained. This was used without purification for next step.

Synthesis of 1-Naphthalen-2-ylmethyl-1H-imidazo[1,2-b]pyrazole-7-carbaldehyde, I-145 Activated MnO2 (110 mg, 1.26 mmol) was added to a suspension of alcohol (70 mg, 0.25 mmol) in 10 ml anhydrous methylene chloride. The reaction mixture was stirred at rt overnight. TLC shows some unreacted alcohol and the reaction was continued one more day. After workup, the mixture was purified by column chromatography using CH2Cl2 to 5% MeOH/CH2Cl2 to afford 70 mg compound I-145.

Synthesis of 3-(1-Naphthalen-2-ylmethyl-1H-imidazo[1,2-b]pyrazol-7-yl)-acrylic acid ethyl ester, I-146. To a suspension of NaH (60% in mineral oil, 21 mg, 0.525 mmol) in anhydrous THF (3 mL), at 0° C. triethylphosphonoacetate (92 µl, 0.462 mmol) was added. The reaction mixture was warmed up to rt. After 1 h at rt, the mixture was cooled to 0° C. and a solution of compound I-145 (60 mg, 0.21 mmol) in 2 ml anhydrous THF was added. Mixture was allowed to warm up to rt and stirred for 1 hour, then it was heated up to 70° C. and stirred at this temperature overnight. The reaction mixture was cooled to rt, the solvent was removed, and 10 ml of CH2Cl2 was added and mixture was quenched with 1 ml saturated solution of NH4Cl. Organic layer was washed with brine and dried over MgSO4. Solvent was removed to afford 70 mg crude compound I-146, by 1H NMR. This was used for hydrolysis without purification.

Synthesis of 3-(1-Naphthalen-2-ylmethyl-1H-imidazo[1,2-b]pyrazol-7-yl)$_7$-acrylic acid, I-147 To a solution of compound I-146 (70 mg, 0.2 mmol) in MeOH/THF (2 mL/mL) was added 1 ml of 1N NaOH solution. The reaction mixture was stirred at rt for 3 days. The solvent was removed, 1 ml of 10% aqueous HCl solution was added to the residue and mixture was extracted with EtOAc (3×10 ml). Combined organic layers were washed with brine and dried over MgSO4. After solvent was removed, 50 mg crude acid was obtained. A short silica gel plug to was done to purify the compound I-147 (25 mg).

Synthesis of 3-(1-Naphthalen-2-ylmethyl-1H-imidazo[1,2-b]pyrazol-7-yl)-acrylic acid, P034. To a suspension of the acid I-147 (18.6 mg, 0.0586 mmol) in anhydrous methylene chloride (1.5 mL), were added DMAP (14.3 mg, 0.117 mmol), 2-thiophene sulfonylamide (9.6 mg, 0.0586 mmol) and EDCI (22.5 mg, 0.117 mmol). The reaction mixture was stirred at rt for 2 days. The mixture was quenched through the addition of 10% aqueous HCl solution (1 mL) and the mixture was extracted with EtOAc. Organic layer was dried over MgSO4 and after the solvent was removed, 10 mg of crude residue was purified by column chromatography using CH2Cl2 to 3% MeOH/CH₂Cl to afford 5 mg compound P034. ¹H NMR (500 MHz, CDCl₃) 5.4 (s, 2H), 5.98 (d, J=14.5 Hz, 1H), 6.78 (s, 1H), 7.05 (t, 1H), 7.30 (dd, J=8.0, 1.0 Hz, 1H), 7.5-7.53 (m, 3H), 7.62 (m, 1H), 7.68 (bs, 1H), 7.70 (m, 1H), 7.76 (d, J=14.5 Hz, 1H), 7.82-7.85 (m, 2H), 7.89 (s, 1H). LC-MS (92%): APCI⁻ Calcd. 462 m/z Found: 461 (M−1).

Example 269

Preparation of P013

Synthesis of 1-Naphthalen-2-ylmethyl-1H-imidazo[1,2-b]pyrazole-7-carboxylic acid, I-148. To a solution of compound I-145 (24 mg, 0.075 mmol) in 1,4-dioxane (1 mL) 1M aqueous LiOH (0.4 ml) was added. The reaction mixture was heated to 80° C. and stirred at this temperature until starting material disappeared (about 5 h). The solvent was removed and the residue was taken up to EtOAc (10 mL). 10% Aqueous HCl was added until pH=3. The suspension was filtered off and the solid was triturated with ether to afford 20 mg of the acid, I-148. LCMS (95%).

Synthesis of P013. To a suspension of acid I-148 (20 mg, 0.668 mmol) in methylene chloride (2 mL), was added DMAP (17 mg, 0.137 mmol). Turning the suspension into a homogenous solution. To this solution thiophene-5-sulfonylamide (11 mg, 0.068 mmol), then EDCI (26 mg, 0.137 mmol) were added. Reaction mixture was stirred at rt overnight. The solvent was removed and the residue was dissolved in EtOAc (5 mL) and washed with 10% aqueous HCl solution (1 mL). The organic layer was washed with brine and dried over MgSO4. 20 mg crude product was obtained after solvent evaporation. Purification by column chromatography using methylene chloride to 3% methanol/methylene chloride afforded 10 mg compound P013.

Example 270

Preparation of P033

To a solution of p-toluene sulfonylisocyanate (27 mg, 0.135 mmol) in anhydrous THF (1 mL) was added at 0° C. a solution of alcohol I-144 (25 mg, 0.09 mmol) in THF (1 mL). The mixture was stirred at 20° C. for 3 hours. The solvent was removed and the residue was purified by column chromatography using CH2Cl2 and 3% MeOH/CH2Cl2 to afford 5 mg of P033. ¹H NMR (500 MHz, CDCl₃) 2.38 (s, 3H), 3.96 (d, 6.0 Hz, 1H), 4.27 (t, J=6.0 Hz, 1H), 5.35 (s, 2H), 6.78 (d, J=3.5 Hz, 1H), 7.24-7.31 (m, 5H), 7.49-7.51 (m, 2H), 7.66-7.68 (m, 3H), 7.80-7.84 (m, 3H). LC-MS (95%): APCI⁻ Calcd. 430 m/z Found: 429 (M−1).

Example 271

Preparation of P116

5-(2,4-Dichloro-phenyl)-2,4-dioxo-pentanoic acid methyl ester, I-149. A methanolic 25 wt. % solution of sodium methoxide (11 mL, 48 mol, 2 equiv.) was gradually (in 4 min) added to a solution of 2,4-dichlorophenylacetone (4.88 g, 24 mmol, 1 equiv.) and dimethyl oxalate (4.8 g, 40 mmol, 1.7 equiv.) in methanol (55 mL). The reaction mixture was stirred at room temperature overnight. 10% Aqueous HCl solution was added, a precipitated oil was separated, washed with water. The oil crystallized by addition of hexane. The precipitate was filtered and recrystallized from MTBE (12 mL) to afford 0.78 g (11%) of I-149. MS (AP−): 288 (M−1). ¹H-NMR (500 MHz, CDCl₃) confirmed the structure.

(E)-3-{3-[2-(2,4-Dichloro-phenyl)-acetyl]-4-hydroxy-1-methyl-5-oxo-2,5-dihydro-1H-pyrrol-2-yl}-acrylic acid ethyl ester, I-150. A 40% aqueous solution of methylamine (28 mg, 0.363 mmol, 1.1 equiv.) was added to a solution of pyruvate I-149 (96 mg, 0.33 mmol, 1 equiv.) and (E)-4-oxobutenoic acid ethyl ester (45 mg, 0.35 mmol, 10.05 equiv.) in AcOH-dioxane, 1:1 (0.4 mL). The reaction mixture was stirred at rt overnight. Ether was added and the resulting mixture was filtered. The mother liquor was concentrated in vacuo to afford crude pyrroledione I-150 (117 mg, 87%) as an oil. LC-MS (ESI−): 397 (M−1) (87%). ¹H-NMR (500 MHz, CDCl₃) confirmed the structure.

(E)-3-[3-(2,4-Dichloro-benzyl)-5-methyl-6-oxo-1,4,5,6-tetrahydro-pyrrolo[3,4-c]pyrazol-4-yl]-acrylic acid ethyl ester, I-151. Hydrazine hydrate (18 mg, 0.35 mmol, 1.2 equiv.) was added in one portion to solution of pyrroledione I-150 (117 mg, 0.294 mmol, 1 equiv.) in AcOH (1.2 mL) and the reaction mixture was heated at 80° C. for 2 h. The reaction mixture was quenched with saturated aqueous NaHCO₃ followed by extraction with EtOAc. The organic phase was washed with brine, dried over MgSO₄, filtered and concentrated to afford a residue (120 mg). This residue was chromatographed on SiO₂ (5 g) using EtOAc as eluent to afford pyrrazolepyrroledione I-151 (20 mg, 17%) as yellow oil. MS(ESI−): 392 (M−1). ¹H-NMR (500 MHz, CDCl₃) confirmed the structure.

(E)-3-[3-(2,4-Dichloro-benzyl)-5-methyl-6-oxo-1,4,5,6-tetrahydro-pyrrolo[3,4-c]pyrazol-4-yl]-acrylic acid, I-152. LiOH.H₂O (6.2 mg, 0.146 mmol, 1.2 equiv.) was added to a solution of pyrrazolepyrroledione I-151 (48 mg, 0.122 mmol, 1 equiv.) in MeOH-water-THF, 1:1:1 (1.2 mL). The reaction mixture was stirred overnight at room temperature. Aqueous saturated NH₄Cl (4 mL) was added and the reaction mixture was extracted with CH2Cl2. The organic phase was washed with brine, dried over MgSO₄, filtered and concentrated to afford acid I-152 (18.5 mg, 42%) as an oil. MS (ESI+): 367 (M+1).

Synthesis of P116. To a mixture of acid I-152 (18.5 mg, 0.0505 mmol, 1 equiv.) in dichloromethane (0.5 mL) were added DMAP (12.4 mg, 0.01010 mmol, 2 equiv.), 4,5-dichloro-2-thiophenesulfonamide (11.7 mg, 0.0505 mmol, 1 equiv.), and EDCI (19.4 mg, 0.1010 mmol, 2 equiv.). The mixture was stirred at room temperature for 3 days and then quenched with 10% aqueous HCl. The mixture was then extracted with EtOAc. The extract was washed with brine, and then dried over MgSO₄. The solvent was removed in vacuo and the residue was chromatographed on SiO₂ (1 g) with MeOH-EtOAc, 19:1. to afford 2 mg (7%) of sulfonamide P116 as an oil. LC-MS (ESI⁻): 579 (M−1) (86%). ¹H-NMR (500 MHz, DMSO) confirmed the structure.

Example 272

Preparation of P117

3-{3-[2-(2,4-Dichloro-phenyl)-acetyl]-4-hydroxy-1-methyl-5-oxo-2,5-dihydro-1H-pyrrol-2-yl}-propionic acid, I-153. A 2.0 M THF solution of methylamine (0.2 mL, 0.4 mmol, 1.1 equiv.) was added to a solution of pyruvate I-149 (100 mg, 0.35 mmol, 1 equiv.) and 15% aqueous succinic semialdehyde (250 mg, 2.42 mmol, 7 equiv.) in AcOH (0.5 mL). The reaction mixture was stirred at 80° C. for 30 min, then another portion of methylamine (0.1 mL, 0.2 mmol, 0.55 equiv.) was added and the reaction mixture was stirred at 80° C. for 30 min. The reaction mixture was concentrated, the residue was dissolved in EtOAc, a solution was washed with water, brine, dried over MgSO$_4$, filtered and concentrated to afford pyrroledione I-153 (147 mg, 114%) as yellow oil. This oil was converted to a beige solid (104 mg, 81%) by trituration with MTBE-Hexane, 1:1. MS (ESI–): 371 (M–1). $^1$H-NMR (500 MHz, DMSO) confirmed the structure.

3-[3-(2,4-Dichloro-benzyl)-5-methyl-6-oxo-1,4,5,6-tetrahydro-pyrrolo[3,4-c]pyrazol-4-yl]-propionic acid, I-154. Hydrazine hydrate (23 mg, 0.46 mmol, 3.4 equiv.) was added in one portion to solution of pyrroledione I-153 (50 mg, 0.134 mmol, 1 equiv.) in AcOH (0.5 mL) and the reaction mixture was heated at 80° C. for 2.5 h. The reaction mixture was diluted with water followed by extraction with EtOAc. The organic layer was washed with brine and then dried over MgSO$_4$, filtered and concentrated to afford crude product (60 mg) as oil. It was triturated with ether to afford pyrrazolepyrroledione I-154 (40 mg, 80%) as yellow solid. MS(AP–): 366 (M–1). $^1$H-NMR (500 MHz, DMSO) confirmed the structure.

Synthesis of P117. To a mixture of pyrrazolepyrroledione I-154 (30 mg, 0.0815 mmol, 1 equiv.) in dichloromethane (0.8 mL) were added DMAP (20 mg, 0.163 mmol, 2 equiv.), 2-thiophenesulfonamide (19 mg, 0.0815 mmol, 1 equiv.), and EDCI (31 mg, 0.163 mmol, 2 equiv.). The mixture was stirred at room temperature for 3 h and then quenched with 10% aqueous HCl. The mixture was then extracted with EtOAc. The extract was washed with brine, and then dried over MgSO$_4$, filtered and concentrated to afford 6.5 mg (14%) of sulfonamide P117 as white solid. $^1$H NMR (DMSO-d$_6$) 1.4-2.0 (m, 4H), 2.77 (s, 3H), 4.08 (s, 2H), 4.26 (s, 1H), 7.37 (s, 2H), 7.49 (s, 1H), 7.81 (s, 1H), 12.4 (bs, 1H), 13.3 (bs, 1H). LC-MS (89%): ESI– Calcd. 580 m/z Found: 580.

Example 273

Preparation of P344

1-Allyl-2-oxo-cyclohexane carboxylic acid ethyl ester, I-155: To a 1 L round-bottom flask equipped with a condenser, magnetic stir bar and under a nitrogen atmosphere was added 2-oxo-cyclohexane carboxylic acid ethyl ester (19.0 g, 112 mmol), allyl bromide (14.2 g, 117 mmol), THF (223 mL) and potassium tert-butoxide (13.2 g, 117 mmol). The mixture was brought to reflux in an oil bath (67° C.) and reacted for 18 hours. The reaction was cooled and the solvent was removed via rotary evaporation. 1M Aqueous HCl was added until the mixture turned from a paste to a cloudy solution. The mixture was extracted with CH2Cl2 (3×250 mL). The combined extracts were washed with water (2×250 mL) and brine (250 mL), dried (MgSO4) and concentrated under reduced pressure to produce 21.8 g (93%) of I-155 as a pale yellow oil. $^1$H NMR analysis indicated the material was pure enough to carry on to the next step. $^1$H NMR (400 MHz, CDCl$_3$)

1-Carboxymethyl-2-oxo-cyclohexane carboxylic acid ethyl ester, I-156: To a 2 L, three-neck round-bottom flask equipped with an overhead stirrer and two loose caps was placed compound I-155 (21.8 g, 104 mmol). In a 1 L Erlenmeyer flask equipped with a stir bar was added sodium periodate (182 g, 850 mmol), potassium permanganate (3.28 g, 20.7 mmol), potassium carbonate (10.9 g, 78.8 mmol) and water (430 mL) at room temperature. The oxidizing mixture was stirred for 5 min and then added to the flask containing olefin I-155 in one portion. The mixture was allowed to stir at room temperature for a period of 24 h. After this reaction period, additional potassium permanganate (0.820 g, 5.19 mmol) was added to the reaction mixture. The contents of the flask were stirred for an additional 2.5 hours. The reaction was quenched by the slow addition of aqueous sodium hydrogensulfite, until the mixture turned from a dark brown mixture to clear yellow solution. The aqueous mixture was extracted with CH2Cl2 (3×250 mL). The combined extracts were washed with water (2×250 mL) and brine (250 mL), dried (MgSO$_4$) and concentrated under reduced pressure to produce 18.6 g (79%) of I-156 as a pale yellow oil. $^1$H NMR analysis indicated the material was pure enough to carry on to the next step. $^1$H NMR (400 MHz, CDCl$_3$)

1-(2,4-Dichloro-benzyl)-2,4-dioxo-1,2,3,4,5,6-hexahydro-indole-3a-carboxylic acid ethyl ester, I-157. To a 250 mL round-bottom flask equipped with a condenser and stir bar was placed compound I-156 (5.00 g, 21.9 mmol), m-xylene (45 mL) and 2,4-dichlorobenzylamine (2.95 mL, 21.9 mmol). The mixture was brought to reflux in an oil bath (138° C.) and reacted for 6 hours. The reaction was then cooled to room temperature. The solvent was removed by evaporation to yield 7.92 g (98%) of compound I-157 as reddish-orange oil. $^1$H NMR analysis indicated the material was pure enough to carry on to the next step. $^1$H NMR (400 MHz, CDCl$_3$)

7-Bromo-1-(2,4-dichloro-benzyl)-2-oxo-1,2,3,4,5,6-hexahydro-indole-3a-carboxylic acid ethyl ester, I-158: To a 40 mL vial equipped with a stir bar and cap was placed compound I-157 (600 mg, 1.63 mmol) which was dissolved in CH2Cl2 (16 mL). The solution was cooled to 0° C. in an ice bath and bromine (416 µL, 8.15 mmol) was added. The mixture was stirred for 2 hours while gradually warming to room temperature and then triethylamine (750 µL, 5.38 mmol) was added. The mixture was allowed to stir an additional 45 minutes and then the reaction was quenched with water (15 mL). After stirring for 30 min, the organic portion was extracted and then dried with MgSO$_4$. The solvent was removed by evaporation and yielded a brown oil which was purified by silica gel column chromatography. The solvent system that was employed was composed of 20% EtOAc/Hex. After purification, 431 mg of compound I-158 was isolated as a tan solid (59%). $^1$H NMR analysis indicated the material was pure enough to carry on to the next step. $^1$H NMR (400 MHz, CDCl$_3$).

7-((E)-2-Carboxy-vinyl)-1-(2,4-dichloro-benzyl)-2-oxo-1,2,3,4,5,6-hexahydro-indole-3a-carboxylic acid ethyl ester I-159: To an 18 mL vial equipped with a stir bar and cap was placed compound I-158 (431 mg, 0.964 mmol), anhydrous DMF (4.8 mL) and triethylamine (1.34 mL, 9.64 mmol). The mixture was stirred while being degassed with nitrogen for 10 min. After degassing, tert-butyl acrylate (423 µL, 2.89 mmol), palladium acetate (21.6 mg, 0.0964 mmol) and tri(o-tolyl) phosphine (88.0 mg, 0.289 mmol) were added. After addition, the mixture was degassed with nitrogen for an additional 3 min and then the vial was sealed with a cap. The vial was heated in an oil bath to 100° C. for a period of 22 h. The reaction was then cooled and filtered through celite. The mixture was diluted with CH2Cl2 (75 mL) and then washed with water (2×75 mL) and brine (75 mL). The organic portion was dried with MgSO$_4$ and concentrated under reduced pressure to produce the t-butyl ester product as a brown oil. The crude material was dissolved in CH2Cl2 (4.4 mL) and cooled to 0° C. To this solution was added trifluoroacetic acid (440 µL, 5.9 eq) and the mixture was allowed to stir at room temperature. After stirring for 4.5 hour, an additional portion of trifluoroacetic acid (440 µL, 5.9 eq) was introduced and the mixture was stirred for 20 min. The solvent was removed by a stream of nitrogen and the material was dissolved in ether and washed with saturated aqueous NaHCO$_3$ (4×30 mL). During the second washing with NaHCO$_3$, a small portion of 3M NaOH (20 mL) was added in order to better separate the layers. The aqueous layers were combined and acidified to pH 1 with 3M aqueous HCl. The aqueous layer was extracted with CH2Cl2 (3×100 mL). The organic portions were combined, dried (MgSO$_4$) and concentrated via rotary evaporation to yield 182 mg of I-159 as a pale yellow solid (43% yield from I-158 to I-159). $^1$H NMR analysis indicated the material was pure enough to carry on to the next step. $^1$H NMR (400 MHz, CDCl$_3$) LC/MS purity=81.0%

Synthesis of P344. In an 8 mL vial equipped with a stir bar was placed acid I-159 (50.0 mg, 0.114 mmol), CH2Cl2 (2.4 mL), 2,4,5-trifluorophenyl sulfonamide (28.9 mg, 0.137 mmol), DMAP (33.5 mg, 0.274 mmol) and EDCI (54.6 mg, 0.285 mmol). The mixture was stirred at room temperature for 18 hours. The mixture was diluted with CH2Cl2 (30 mL) and the organic portion was washed with 1M aqueous HCl (30 mL), water (3×30 mL) and brine (30 mL). The organic portion was dried (MgSO$_4$) and concentrated via rotary evaporation to yield a light yellow solid. After drying, the reaction yielded 40.2 mg of P344 as a pale yellow solid (56%). $^1$H NMR (400 MHz, CDCl$_3$) 1.26 (t, J=7.2 Hz, 3H), 1.53-1.68 (m, 2H), 1.92 (m, 1H), 2.20-2.26 (m, 2H), 2.54 (m, 1H), 2.78 (AB q, J=16.8 Hz, 2H), 4.19 (q, J=7.2 Hz, 2H), 4.95 (AB q, J=17.2, 17.6 Hz, 2H), 5.68 (d, J=15.2 Hz, 1H), 7.03-7.08 (m, 2H), 7.10 (d, J=8.0 Hz, 1H), 7.17 (dd, J=8.4, 2.0 Hz, 1H), 7.22 (s, 1H), 7.94 (m, 1H). LC/MS (95%), MS (ESI–) Calcd.: 630.5 m/z, Found: 631.3 m/z

Example 274

Preparation of P345

Synthesis of P345. Following the procedure outlined for the synthesis of P344, acid I-159 (50.0 mg, 0.114 mmol), CH2Cl2 (2.4 mL), 4,5-dichlorothiophene-2-sulfonamide (31.8 mg, 0.137 mmol), DMAP (33.5 mg, 0.274 mmol), and EDCI (54.6 mg, 0.285 mmol) yielded 49.0 mg of P345 as a pale yellow solid (66%). $^1$H NMR (400 MHz, CDCl$_3$) 1.27 (t, J=6.8 Hz, 3H), 1.53-1.65 (m, 2H), 1.92 (m, 1H), 2.20-2.29 (m, 2H), 2.54 (m, 1H), 2.79 (AB q, J=16.8 Hz, 2H), 4.20 (q, J=7.2 Hz, 2H), 4.99 (AB q, J=17.2, 17.6 Hz, 2H), 5.65 (d, J=15.2 Hz, 1H), 7.12 (d, J=8.4 Hz, 2H), 7.20 (dd, J=8.4, 2.0 Hz, 1H), 7.29 (s, 1H), 7.49 (d, J=2.0 Hz, 1H), 7.62 (s, 1H). The sulfonamide proton was not observed. LC/MS (95%), MS (ESI–) Calcd.: 651.4 m/z, Found: 651.4 m/z

Example 275

Preparation of P346

Synthesis of P346. Following the procedure outlined for the synthesis of P344, acid I-159 (35.0 mg, 0.0799 mmol), CH2Cl2 (1.7 mL), 3,4-difluorophenyl sulfonamide (18.5 mg, 0.0959 mmol), DMAP (23.5 mg, 0.192 mmol), and EDCI (38.3 mg, 0.200 mmol) yielded 30.8 mg of P346 as a pale yellow solid (63%). $^1$H NMR (400 MHz, CDCl$_3$) LC/MS purity=86.5%.

Example 276

Preparation of P075

Acetic acid 1H-indol-4-yl ester, I-160. Acetic anhydride (16.75 mL, 169 mmol, 1.5 equiv.) was added slowly (over 7 min) to a solution of 4-hydroxy indole (15 g, 113 mmol, 1 equiv.) in pyridine (113 mL) at rt (temperature rose from 25 to 32° C.). After stirring for an additional 5 min, the reaction mixture was cooled by ice-water- and 10% aqueous HCl (340 mL) was added, followed by EtOAc (565 mL). the organic solution was separated and the aqueous layer was extracted with EtOAc (100 mL). the combined organic layers were washed with 10% aqueous HCl (2×50 mL), water (2×300 mL), brine (300 mL) and dried over MgSO$_4$. Filtration and evaporation of the solvent afforded 19.3 g (98%) of I-160 as light-brown solid. $^1$H-NMR (500 MHz, CDCl$_3$) confirmed the structure. $^1$H NMR (500 MHz, CDCl$_3$) 2.39 ppm (s, 3H), 6.43 ppm (br. s, 1H), 6.86 (d, 1H, J=16.0 Hz), 7.14 (m, 2H), 7.24 (m, 1H), 8.20 (br. s, 1H)

Acetic acid 3-(naphthalene-2-carbonyl)-1H-indol-4-yl ester, I-161. Methyl magnesium bromide (26 mL, 78 mmol, 1.05 equiv., 3.0 M solution in ether) was added slowly (over 10 min) via syringe to a solution of acetate I-160 (13 g, 74 mmol, 1 equiv.) in anhydrous CH2Cl2 (260 mL) at rt. After 5 min stirring at rt, zinc chloride (223 mL, 3.0 equiv., 1.0 M solution in ether) was added via syringe in 5 min at rt. After 10 min stirring at rt, a solution of 2-naphthoyl chloride (14.85 g, 1.05 equiv.) in anhydrous CH2Cl2 (87 mL) was added over 3 min. The reaction mixture was stirred for 3 h at rt and then was poured into saturated aqueous NH$_4$Cl (866 mL) and the mixture was diluted with CH$_2$Cl$_2$ (200 mL). The aqueous layer was extracted with CH2Cl2 (100 mL). the combined organic layers were washed with water (500 mL×2), brine (500 mL), dried over MgSO$_4$, filtered and concentrated to afford 24.4 g (100%) as brown solid. MTBE (100 mL) was added to the solid, heated to reflux, cooled down to 30-40° C. and filtered, the residue was washed on filter with MTBE (50 mL, 25 mL, 5 mL×2), then with ether (5 mL×2) to afford 16.0 g (65%) of I-161 as light-brown solid. MS (ESI–): 329. $^1$H-NMR (500 MHz, CDCl$_3$) confirmed the structure. $^1$H-NMR (500 MHz, CDCl$_3$) 2.41 (s, 3H), 6.89 (d, 1H), 7.03 (dd, 1H, J=16.5 Hz), 7.09 (m, 2H), 7.52 (t, J=15.0 Hz, 1H), 7.56 (t, 1H, J=15.0 Hz), 7.79 (m, 3H), 7.88 (d, 1H, J=16.0 Hz), 8.12 (br. s, 1H), 9.35 (br. s, 1H)

3-Naphthalen-2-ylmethyl-1H-indol-4-ol, I-162 BH$_3$THF (1M in THF, 120 mL, 120 mmol, 3.3 equiv.) was added slowly to a solution of I-161 (12.0 g, 36.4 mmol, 1 equiv.) at 0° C. under a nitrogen atmosphere. The reaction mixture was allowed to warm to room temperature and stirred overnight. The reaction mixture was quenched by slow addition of methanol (120 mL), evaporated and co-evaporated with MeOH (3×120 mL). The residue was purified by silica gel chromatography (150 g, CH2Cl2) to afford I-162 (6.2 g, 62%). MS (ESI$^-$): 271(M-1). $^1$H-NMR (500 MHz, CDCl$_3$) confirmed the structure.

(3-Naphthalen-2-ylmethyl-1H-indol-4-yloxy)-acetic acid methyl ester, I-163. A solution of methyl bromoacetate (3.10 g, 1.9 mL, 20.3 mmol, 1.05 equiv.) in DMF (20 mL) was added slowly to the mixture of I-162 (5.29 g, 19.4 mmol, 1 equiv.) and K$_2$CO$_3$ (3.21 g, 23.2 mmol, 1.2 equiv.) in DMF (51 mL). Reaction mixture was stirred at rt overnight (17 h). Water-brine (5:1, 180 mL) was added and the resulting solution was extracted with EtOAc (180 mL, 140 mL, 70 mL). The organic layer was washed with brine (2×210 mL), dried over MgSO$_4$, filtered and concentrated to afford 7.8 g as solid. This residue was washed with ether (20 ml) and filtered to afford 5.0 g (75%) of I-163 as off-white solid. MS (ESI): 346 (M+1). $^1$H-NMR (500 MHz, CDCl$_3$) confirmed the structure.

(3-Naphthalen-2-ylmethyl-1H-indol-4-yloxy)-acetic acid, I-164. A solution 2N NaOH (9.5 mL, 19 mmol, 2 equiv.) was added to a solution of I-163 (3.3 g, 9.55 mmol, 1 equiv.) in THF-MeOH, 2:1 (132 mL). The reaction mixture was stirred at rt for 1 h. The reaction was concentrated to ~20 mL, 10% aqueous HCl (10 mL) was added followed by water (50 mL). The mixture was extracted with EtOAc (250 ml) and the organic phase was dried over MgSO$_4$, filtered and concentrated to afford I-164 (2.95 g, 92%) as off-white solid. $^1$H-NMR (500 MHz, DMSO) confirmed the structure.

Synthesis of P075. To the solution of I-164 (2.87 g, 8.65 mmol, 1 equiv.) in dichloromethane (80 mL) was added DMAP (2.11 g, 17.30 mmol, 2 equiv.), 4,5-dichloro-2-thiophenesulfonamide (2.11 mg, 9.08 mmol, 1.05 equiv.), and EDCI (3.22 g, 17.30 mmol, 2 equiv.). The mixture was stirred at room temperature for 16 hours and then quenched with 10% aqueous HCl (5 mL) followed by EtOAc (100 mL). The aqueous layer was extracted with EtOAc (2×50 mL). The combined organic layers were washed with saturated aqueous $NH_4Cl$ (100 mL), brine (2×100 mL), and then dried over $MgSO_4$, filtered and concentrated to afford a residue (3.31 g, 63%). This residue was triturated with MeOH (12 mL), heated to reflux, then cooled down to 0° C. and filtered off to give 2.97 g (71%) as semi crude sulfonamide 4. HPLC: 96.2%.: ESI$^-$ Calcd. 544 m/z Found: 544. $^1$H NMR (DMSO-$d_6$) confirmed the structure. $^1$H NMR (DMSO-$d_6$) 4.32 (s, 2H), 4.68 (s, 2H), 6.18 (d, J=7.5 Hz, 1H), 6.87 (t, J=8.0 Hz, 1H), 6.94 (d, J=8.5 Hz, 1H), 7.01 (d, J=3.5 Hz, 1H), 7.41 (m, 2H), 7.46 (dd, J=8.5, 1.5 Hz, 1H), 7.72 (d, J=8.5 Hz, 2H), 7.79-7.81 (m, 2H), 7.89 (s, 1H), 10.9 (br s, 1H).

Example 277

Preparation of P162

2-(3-Naphthalen-2-ylmethyl-1H-indol-4-yloxy)-propionic acid methyl ester, I-165. A solution of indole I-162 (125 mg, 0.46 mmol, 1 equiv), methyl bromopropionate (80 mg, 0.48 mmol, 1.05 equiv.), and $K_2CO_3$ (76 mg, 0.55 mmol, 1.2 equiv.) in DMF (1.7 mL) was stirred and heated at 50° C. for 16 h. Water-brine, 5:1 was added, the suspension was extracted with EtOAc, the organic layer was washed with water, brine, dried over $MgSO_4$, filtered and concentrated to afford ester I-165 (150 mg, 91%) as green oil. MS (AP$^+$): 360 (M+1). $^1$H-NMR (500 MHz, CDCl$_3$) confirmed the structure.

2-(3-Naphthalen-2-ylmethyl-1H-indol-4-yloxy)-propionic acid, I-166. 2N NaOH (0.44 mL, 0.88 mmol, 2.1 equiv.) solution was added dropwise to a solution of ester I-165 (150 mg, 0.42 mmol, 1 equiv.) in THF-MeOH (2:1, 6 mL). The reaction mixture was stirred for 2 h at rt. The reaction was concentrated in vacuo and 10% aqueous HCl (4 mL) followed with water (6 mL) was added to the residue. Precipitate was extracted with EtOAc (6 mL, 4 mL). A solution was washed with brine, dried over $MgSO_4$ to afford acid I-166 (149 mg) as an oil. MS (ESI$^-$): 344 (M−1). $^1$H-NMR (500 MHz, CDCl$_3$) confirmed the structure.

Synthesis of P162. To the acid I-166 (134 mg, 0.39 mmol, 1 equiv.) in dichloromethane (4 mL) was added DMAP (95 mg, 0.77 mmol, 2 equiv.), 4,5-dichloro-2-thiophenesulfonamide (94 mg, 0.41 mmol, 1.05 equiv.), and EDCI (148 mg, 0.77 mmol, 2 equiv.). The mixture was stirred at room temperature for 2 hours and then quenched with 10% aqueous HCl (1 mL) followed by water (4 mL). The aqueous layer was extracted with EtOAc (4 mL). The combined organic layers were washed with brine, and then dried over $MgSO_4$. Chromatography of the resulting residue on $SiO_2$ (5 g) with CH2Cl2 afforded sulfonamide P162 (101 mg, 47%) as greenish solid. LC-MS (ESI$^-$): 558 (M−1) (99%). $^1$H-NMR (500 MHz, DMSO) confirmed the structure.

Example 278

Preparation of P171

2-Methyl-2-(3-naphthalen-2-ylmethyl-1H-indol-4-yloxy)-propionic acid methyl ester, I-167. A solution of indole I-162 (300 mg, 1.1 mmol, 1 equiv), methyl bromoisobutyrate (609 mg, 3.29 mmol, 3 equiv.), $K_2CO_3$ (607 mg, 4.39 mmol, 4 equiv.), and $MgSO_4$ (132 mg, 1.1 equiv.) in DMF (13.3 mL) was stirred and heated at 75° C. for 24 h. The reaction mixture was filtered, concentrated to afford ~0.4 g. Chromatography on $SiO_2$ (20 g) with EtOAc/Hex, 1:4 afforded I-167 (96 mg, 23%) as oil. R$_f$=0.31 (EtOAc/Hex, 1:3). $^1$H-NMR (500 MHz, CDCl$_3$) confirmed the structure.

2-Methyl-2-(3-naphthalen-2-ylmethyl-1H-indol-4-yloxy)-propionic acid, I-168. 2N NaOH (0.53 mL, 1.06 mmol, 4.1 equiv.) solution was added drop-wise to a solution of ester I-167 (96 mg, 0.26 mmol, 1 equiv.) in THF-MeOH (2:1, 3 mL). The reaction mixture was stirred at 75° C. for 1.5 h. Reaction was concentrated in vacuo and 10% HCl (0.5 mL) was added to the residue. Mixture was extracted with EtOAc (6 mL). A solution was washed with brine, dried over $MgSO_4$ to afford acid I-168 (92 mg, 100%) as oil. R$_f$=0.61 (MeOH/CH2Cl2, 1:7). MS (ESI$^+$): 358 (M+1). $^1$H-NMR (500 MHz, CDCl$_3$) confirmed the structure.

Synthesis of P171. To the acid I-168 (88 mg, 0.24 mmol, 1 equiv.) in 4 mL dichloromethane were added DMAP (60 mg, 0.49 mmol, 2 equiv.), 4,5-dichloro-2-thiophenesulfonamide (60 mg, 0.26 mmol, 1.05 equiv.), and EDCI (94 mg, 0.49 mmol, 2 equiv.). The mixture was stirred at room temperature for 3 days and then quenched with 10% HCl (1 mL) followed by water (4 mL). Aqueous layer was extracted with EtOAc (4 mL). Combined organic layers were washed with brine, and then dried over $MgSO_4$. The solution was concentrated and the residue was extracted with ether to afford sulfonamide P171 (120 mg, 87%) as yellow solid. R$_f$=0.56 (MeOH/CH2Cl2, 1:7). $^1$H NMR (CDCl$_3$) 1.34 (s, 6H), 4.42 (s, 2H), 5.89 (d, J=8.0 Hz, 1H), 6.81 (t, J=8.0 Hz, 1H), 6.86 (d, J=2.0 Hz, 1H), 7.06 (d, J=8.0 Hz, 1H), 7.33 (dd, J 8.0, 3.0 Hz, 1H), 7.39 (s, 1H), 7.40-7.46 (m, 2H), 7.57 (bs, 1H), 7.70-7.83 (m, 2H), 7.79 (d, 8.5 Hz, 1H), 8.09 (bs, 1H), 8.51 (bs, 1H). LC-MS (99%): ESI$^-$ Calcd. 572 m/z Found: 572

Example 279

Preparation of P259

3-(1-Ethyl-1H-benzoimidazol-2-ylsulfanyl)-benzofuran-4-ol, I-169. A solution of 2.0 M HCl in ether (3.75 mL, 7.5 mmol, 5 equiv.) was added to a preheated (40° C.) suspension of 4-hydroxybenzofuran (225 mg, 1.5 mmol, 1 equiv.) and 1-methyl-1H-benzimidazole-2-thiol (Aldrich, 246 mg, 1.5 mmol, 1 equiv.) in ethanol (3.75 mL). A solution was stirred at RT overnight, then concentrated to ~0.5 mL. EtOAc/dichloromethane (8 mL, 1:1) was added, washed with water (8 ml×2), brine (6 mL), dried over over $MgSO_4$, concentrated. Ether (4 mL) was added, solid was filtered off and mother liquor was concentrated to afford 277 mg of a crude material as red oil. The material was triturated with MTBE (methyl t-butyl ether) and filtered off to give 260 mg. The oil was chromatographed on $SiO_2$ (10 g) with 3:7 dichloromethane/Hex, 1:1 dichloromethane/Hex, 100% dichloromethane to afford sulfide I-169 (52 mg, 11%) as yellow oil. R$_f$0.28 (dichloromethane). MS (AP$^-$): 309 (M−1). $^1$H-NMR (500 MHz, CDCl$_3$) confirmed the structure.

[3-(1-Ethyl-1H-benzoimidazol-2-ylsulfanyl)-benzofuran-4-yloxy]-acetic acid methyl ester, I-170. Solution of methyl bromoacetate (27 mg, 0.173 mmol, 1.2 equiv.) in acetone (0.2 mL) was added to a suspension of sulfide I-169 (45 mg, 0.1445 mmol, 1 equiv.) and $K_2CO_3$ (30 mg, 0.217 mmol, 1.5 equiv.) in acetone (0.2 mL). Reaction mixture was sealed in a 4 mL vial and heated at 50° C. for 5 h. Water was added followed by EtOAc, and emulsion was quenched with 10%

HCl to pH=2. Organic layer was separated, washed with water, brine, dried over MgSO$_4$ to give 50 mg as orange oil which partly crystallized upon staying. The material was triturated with MTBE (, followed by MTBE/Hex, 1:1 to afford ester I-170 (36 mg, 65%) as orange solid. R$_f$0.49 (dichloromethane). MS (ESI$^-$): 381 (M−1). $^1$H-NMR (500 MHz, CDCl$_3$) confirmed the structure.

[3-(1-Ethyl-1H-benzoimidazol-2-ylsulfanyl)-benzofuran-4-yloxy]-acetic acid, I-171. A solution 2N NaOH (0.1 mL, 0.21 mmol, 2.5 equiv.) was added drop-wise to a solution of ester I-170 (32 mg, 0.084 mmol, 1 equiv.) in THF-MeOH (1:1, 0.5 mL). The reaction mixture was stirred at rt for 15 min. Reaction was concentrated in vacuo, water was added followed by EtOAc. A suspension was quenched with 10% HCl. Organic layer was washed with water, brine, dried over MgSO$_4$ to afford acid I-171 (27 mg, 88%) as off-white solid. R$_f$=0.37 (MeOH/dichloromethane, 1:4). MS (ESI$^-$): 367 (M−1). $^1$H-NMR (500 MHz, CDCl$_3$) confirmed the structure.

Synthesis of P259. To the acid I-171 (24 mg, 0.065 mmol, 1 equiv.) in 0.5 mL dichloromethane were added DMAP (16 mg, 0.130 mmol, 2 equiv.), 4,5-dichloro-2-thiophenesulfonamide (15 mg, 0.065 mmol, 1.05 equiv.), and EDCI (25 mg, 0.130 mmol, 2 equiv.). The mixture was stirred at room temperature overnight and then quenched with 10% HCl followed by water. Aqueous layer was extracted with EtOAc. Combined organic layers were washed with brine, and then dried over MgSO$_4$. The solution was concentrated and the solid residue was extracted with MTBE/Hexane, 1:1, then with ether. A solution was concentrated to give 24.5 mg as yellow oil. Oil was chromatographed on SiO$_2$ (with EtOAc/Hex, 1:3, 2:3) to afford sulfonamide P259 (10 mg, 26%) as yellow oil. R$_f$=0.28 (EtOAc). $^1$H NMR (CDCl$_3$) 1.47 (t, J=7.2 Hz, 3H), 4.29 (q, J=7.2 Hz, 2H), 4.76 (s, 2H), 6.71 (dd, J=6.4, 1.8 Hz, 1H), 6.91 (dd, J=11.6, 0.4 Hz, 1H), 7.16 (dd, J=11.6, 0.4 Hz, 1H), 7.26-7.32 (m, 3H), 7.73 (m, 1H), 8.20 (d, J=4.8 Hz, 2H). LC-MS (94%): ESI$^-$ Calcd. 581 m/z Found: 581.

Example 280

Preparation of P153

Compound I-162 (0.50 g, 0.0018 mol) was dissolved in DMF (8 mL). Potassium carbonate (1.00 g, 0.0072 mol) was added and the mixture was stirred for 15 min. Ethyl bromodifluoroacetate (2.5 mL, 0.087 mol) was added and the resulting mixture was stirred at 70° C. overnight, concentrated, and partitioned between CH2Cl2 and water. The CH2Cl2 layer was washed with brine, dried over anh. Na2SO4, filtered, concentrated, and chromatographed on silica gel (EtOAc/hexane gradient) to afford a fraction enriched in difluoro-(3-naphthalen-2-ylmethyl-1H-indol-4-yloxy)-acetic acid ethyl ester (ca. 30%, HNMR, LC-MS), which was used as such in the next step. The difluoroester with an actual content of (ca. 30 mg) was treated with 7M NH3/MeOH (2 mL) at rt, overnight, in closed vial. RP-chromatography (C18 silica gel; MeCN/water gradient) afforded compound P153, 5.8 mg. 1H NMR (400 MHz, DMSO-d6) 4.29 (s, 2H), 6.83 (d, J=8.0 Hz, 1H), 7.03 (d, J=8.0 Hz, 1H), 7.06 (m, 1H), 7.27 (dd, J=8.0, 0.8 Hz, 1H), 7.39-7.48 (m, 3H), 7.72 (s, 1H), 7.76-7.86 (m, 3H), 8.24 (bs, 1H), 8.48 (bs, 1H), 11.15 (bs, 1H). LC/MS (86.3%) ESI− Calcd. M=366.4 Found: 365.3 m/z Example 281

Preparation of P159

Synthesis of 5-Bromo-4-oxo-pentanoic acid ethyl ester, I-171 Bromine (22 g, 7.2 ml, 138.8 mmol) was added to a solution of ethyllevulinate (20 g, 138.8 mmol) in 250 ml EtOH at RT under a flow of N2 for a period of ½ hr. After the addition was complete, the reaction mixture was stirred at RT for another ½ hr., and then refluxed for 1.5 hr. A H NMR sample analysis shows a ratio SM: monobromo: dibromo=1: 2.5:0.5. The reaction mixture was cooled to RT and concentrated in vacuo. The residue was taken into ether, washed with sat. solution of NaHCO3 (3×50 ml), water, brine, dried over MgSO4 and concentrated to give 20.3 g of I-171 as a dark brown oil. This was used without purification for next step. 1H NMR Synthesis of ethyl 2-amino-4-thiazolyl-3-propionate, I-172. A solution of crude bromide I-171 (8 g, 35.8 mmol) in 50 ml ethanol was added to a solution of thiourea (2.85 g, 37.59 mmol) in 20 ml ethanol. The reaction mixture was stirred at RT for 1 hr., and then refluxed for 4 hrs. Solvent was removed; the residue was taken into 100 ml EtOAc, washed with water, saturated sol. of NaHCO3, brine, dried over MgSO4 and concentrated to give the oily crude. The crude was purified by column chromatography using methylene chloride to 5% MeOH/methylene chloride to afford 3.75 g product I-172. 1H NMR, MS Synthesis of 3-imidazo[2,1-b]thiazol-3-yl-propionic acid ethyl ester, I-173. Bromoacetaldehyde diethylacetal (8 g, 40.31 mmol) in 60 ml aqueous 3N HCl was refluxed 1 hr. The solution was cooled to RT and extracted with ether (3×30 ml). The combined organic layers were dried over MgSO4 and then added dropwise to a refluxing solution of 3.75 g ethyl 2-amino-4 thiazolyl-3-propionate, I-172 in 100 ml EtOH. The distilling ether was collected. After ether collection finished, the reaction mixture was refluxed for 8 hrs. The solvent was removed and the residue was washed with saturated sol. of NaHCO3. Mixture was extracted with methylene chloride (3×50 ml). The combined organic layers were washed with water, brine, dried over MgSO4, concentrated to afford 3 g crude. Column chromatography using 20% to 50% EtOAc/Hexane gave 1 g pure product I-173. 1H NMR 3-(5-Formyl-imidazo[2,1-b]thiazol-3-yl)-propionic acid ethyl ester, I-174. The Vilsmeier reagent was prepared at 0° C.-5° C. by dropping POCl$_3$ (0.085 ml, 0.892 mmol) into a stirred solution of 0.1 ml DMF. Mixture was stirred at 0° C. for ½ hr., then imidazothiazole I-173 (100 mg, 0.446 mmol) in 2 ml CHCl3 was added dropwise. The reaction mixture was stirred at RT for 2 hrs. then refluxed for 24 hrs. Mixture was cooled to rt and quenched with water, stirred for ½ hr, then extracted with methylene chloride. The organic layer was dried over MgSO4 and concentrated to afford 30 mg product, I-174. 1H NMR.

3-[5-((E)-2-Naphthalen-2-yl-vinyl)-imidazo[2,1-b]thiazol-3-yl]-propionic acid ethyl ester, I-175. To a suspension of NaH, 60% dispersion in mineral oil, (10 mg, 0.25 mmol) in 3 ml anhydrous THF, (2-naphthyl)methyl triphenylphosphonium bromide (80 mg, 0.158 mmol) was added. Mixture was heated to 60° C. for 1 hr., then the aldehyde, I-174 (40 mg, 0.158 mmol) in 2 ml THF was added. The reaction mixture was stirred at 60° C. overnight. Mixture was cooled to RT, quenched with sat. sol. NH4Cl and extracted with methylene chloride. The organic layer was dried over MgSO4, concentrated and the crude was purified by column chromatography with 20% to 50% EtOAc/hexane to afford 30 mg pure product, I-175. 1H NMR.

3-[5-((E)-2-Naphthalen-2-yl-vinyl)-imidazo[2,1-b]thiazol-3-yl]-propionic acid, I-176. To a solution of ethyl ester, I-175 (30 mg, 0.079 mmol) in a mixture of THF: MeOH (1.5 ml/0.5 ml) was added 0.16 ml of LiOH, 1N. Mixture was stirred at 40° C. for 2 hrs. TLC (5% MeOH/CH2Cl2) indicated the reaction completion. The reaction mixture was concentrated in vacuo and to this residue a solution of 10% HCl was added to pH=5-6. The mixture was extracted with CH2Cl2 (2×5 ml). The combined organic layers were washed with brine, dried (MgSO4), and concentrated to give 20 mg crude product, I-176 1H NMR (500 MHz, CD3OD) confirmed structure, LCMS (ESI$^-$): 348 (M−1), 90%.

Synthesis of P159. To a suspension of acid I-176 (10 mg, 0.028 mmol) in CH$_2$Cl$_2$ (0.5 ml) was subsequently added 2,3-dichlorothiophene-5-sulfonamide (7 mg, 0.028 mmol), DMAP (7 mg, 0.057 mmol) and EDCI (11 mg, 0.057 mmol). The mixture was stirred at rt overnight. The solution was acidified with 10% HCl to pH=5-6 and extracted with EtOAc (2×5 ml). The organic layer was washed with water, dried over MgSO$_4$ and concentrated in vacuum to afford 20 mg crude. Purification by column chromatography using CH2Cl2 gave 7 mg pure product, P153. 1H NMR (500 MHz, CDCl$_3$) confirmed structure, LCMS (ESI$^-$): 562 (M−1), 60%.

Example 282

Preparation of P244

Synthesis of 4-Bromo-1H-indole-2,3-dione (I-177) and 6-Bromo-1H-indole-2,3-dione (I-178) (2a). To a solution chloral hydrate (50.0 g, 0.247 mol) in water (237 mL) were successively added Na2SO$_4$ (69.0 g, 0.486 mol), 3-bromoaniline (40.0 g, 0.233 mol) in a mixture of 37% HCl (25 ml, 0.302 mol) and water (632 ml) with vigorous stirring. After the addition was completed, the resulting reaction mixture was heated to reflux for 10 min, and allowed to cool to room temperature. The precipitate formed was collected by filtration, washed with water (3×100 ml) and dried in vacuo to yield the crude isonitrosoacetanilide. This product was added portion-wise to rapidly stirred concentrated H$_2$SO$_4$ (790 ml) at a rate to keep the reaction temperature between 50 and 70° C. The reaction mixture was heated to 80° C. for 20 min and allowed to cool to room temperature. The cooled mixture was poured into crushed ice (ca. 3200 g). The mixture was allowed to stand for 1 h. The orange precipitate was collected by a filtration, washed with water and dried to yield a mixture of I-177 and I-178 (40 g, 83%). MS (ESI$^+$): 227 (M+1). $^1$H-NMR (DMSO-d$_6$).

Synthesis of Eethlyene ketal of I-179. To a mixture of I-177 and I-178 (25.0 g, 0.111 mol), ethylene glycol (27.5 g, 0.442 mol) and p-toluenesulfonic acid monohydrate (2.5 g, 11.3 mmol) in benzene (500 ml) was heated to reflux with Dean-Stark trap to remove the water generated. The reaction mixture was allowed to cool to room temperature, washed with 10% aq NaHCO$_3$ and then water. After concentrated, the crude product (25 g) was obtained and purified by recrystallization in EtOAc/Hex to afford 4-Bromoisotin-3-ethylene ketal, I-179 (8.2 g, 27% yield) as off-white solid. MS (ESI$^+$): 270 (M+1). $^1$H-NMR (DMSO-d$_6$).

Synthesis of Ethlyene Acetal I-180 (N—H derivative). A mixture of I-179 (5.4 g, 20 mmol), tri-o-tolylphosphine (2.2 g, 7 mmol) and palladium acetate (0.5 g, 2 mmol) in triethylamine (20 ml) and methyl acrylate (5 g, 70 mmol) in a sealed tube was heated to 100° C. and stirred at 100° C. for 6 h, then cooled. The reaction mixture was poured into 600 ml of stirring ice-water solution, extracted with CH$_2$Cl$_2$. The organic layers were washed with water, brine (100 ml) and dried over Na$_2$SO$_4$. After removal of the solvent, the crude product was purified by a chromatography on silica gel to afford I-180 (total 4.5 g, 81%) as off-white solid. $^1$H-NMR (DMSO-d$_6$).

Synthesis of Eethlyene Acetal I-181 (N—CH3 drivative): A mixture of the ketal I-180 (3 g, 11 mmol), methyliodide (g, mmol) and K$_2$CO$_3$ (10 g, 55 mmol) in DMF (40 ml) was stirred at rt overnight. The mixture was poured into 600 mL ice-water solution with stirring. The product was isolated by extraction with ethyla actetate and the crude product was purified by a chromatography on silica gel to afford N-methyl compound. I-181, as off-white solid (2.8 g, 80%). $^1$H-NMR (DMSO-d$_6$).

Hydrolysis to I-182 (N—H drivative). To a solution of the ester I-180 (2.0 g, 5.58 mmol) in MeOH (20 ml) was added a solution of NaOH (0.45 g, 11.2 mmol) in water, and then stirred at room temperature for 16 h. After the methanol was removed, the aqueous residue was cooled to −5° C. and acidified with 10% HCl to pH~2. The precipitate was collected by a filtration, washed with water and dried to yield I-182 (1.8 g, 86%). $^1$H-NMR (DMSO-d$_6$).

Hydrolysis to I-183 (N—CH3 drivative). Compound I-183 was prepared from I-181 similar to the preparation of compound I-182, in 95% yield. $^1$H-NMR (DMSO-d$_6$).

(E)-3-(2,3-Dioxo-2,3-dihydro-1H-indol-4-yl)-acrylic acid, I-184. To a stirring suspension of I-182 (2.1 g, 5 mmol) in MeOH (50 ml) was added conc. HCl (50 ml) at rt. The resulting reaction mixture was heated to 50° C. for 3 h, cooled to RT and poured into 200 ml of a stirring ice-water solution. The precipitate formed was collected by a filtration, washed with water and dried to yield a mixture of I-184, as orange color solid (1.6 g, 90%). $^1$H-NMR (DMSO-d$_6$).

(E)-3-(1-Methyl-2,3-dioxo-2,3-dihydro-1H-indol-4-yl)-acrylic acid, I-185. The preparation of compound I-185 was prepared from I-183 similar to the preparation of compd. I-184, in 90% yield. $^1$H-NMR (DMSO-d$_6$).

4,5-Dichloro-thiophene-2-sulfonic acid [(E)-3-(2,3-di-oxo-2,3-dihydro-1H-indol-4-yl)-acryloyl]-amide, I-186. To a mixture of the acid I-184 (1.4 g, 6.06 mmol) in CH$_2$Cl$_2$ (28 ml) was successively added 4-dimethyaminopyridine (1.48 g, 12.11 mmol), 3,4-dichlorothiophenesulfonamide (1.56 g, 6.67 mmol) and 1-[3-(dimethyamino)propyl]-3-ethylcarbodiimide hydrochloride (2.32 g, 12.11 mmol) rt, and stirred for 20 h. After the solvent was removed, the residue was dissolved in acetic acid (1 g/1 ml) and diluted with water (10 ml). The precipitate formed was collected by filtration, washed with water and dried under vacuo to yield compound. I-186 (2.1 g, 78%). $^1$H-NMR (DMSO-d$_6$).

4,5-Dichloro-thiophene-2-sulfonic acid [(E)-3-(1-methyl-2,3-dioxo-2,3-dihydro-1H-indol-4-yl)-acryloyl]-amide, I-187. The preparation of Compd. I-187 was prepared from I-185 similar to the preparation of Compd. I-186, in 79% yield. $^1$H-NMR (DMSO-d$_6$).

General Procedure for Preparation of "3-amino Oxyindole" Analogs.

General procedure A-15. A mixture of the I-187 (1 eq), the aniline (1.2 eq) and p-TsA monohydrate (0.05eq) in MeOH was heated to 65 C for 6 h and allowed to cool to room temperature. After concentration in vacuo, the residue was purified by a chromatography on silica gel to afford the imine. To a solution of the imine (1 eq) in glacial acetic acid was added sodium cyanoborohydride (3 eq) at room temperature, and continued to stir for 2 h. The resulting reaction was quenched with water. The mixture was stirred for 30 min at room temperature. The precipitate was collected by a filtration, washed with water and dried to yield the 3-amino-2-oxyindole derivatives.

General procedure A-16. A mixture of the I-187 (1 eq), the aniline (1.2 eq) and p-TsA monohydrate (0.05 eq) in toluene was heated to reflux for 16 h and allowed to cool to room temperature. The reaction was diluted with methylene chloride. To this mixture was added Na(CN)BH3 in portions. After stirred at room temperature for 2 h, the reaction was quenched with water. The precipitate formed was collected by a filtration, washed with water and dried to yield the 3-amino-2-oxyindole derivatives.

Synthesis of P244. Using Method A-15, I-186 was reacted with 2-naphthyl amine to provide P244 in 76% yield. $^1$HNMR (DMSO-$d_6$) 6.78 (d, J=16.0 Hz, 1H), 6.94 (d, J=8.0 Hz, 1H), 7.22 (dd, J=9.0, 2.5 Hz, 1H), 7.37 (d, J=29.0 Hz, 1H), 7.4-7.5 (m, 4H), 7.80-7.90 (m, 5H), 8.66 (d, J=16.0 Hz, 1H), 11.00 (s, 1H) LC/MS (78%) (ESI–) Calcd. 556.46 m/z Found 556.0 m/z.

Example 283

Preparation of P241

Using Method A-16, I-186 was reacted with 2-naphthyl amine to provide P241 in 82%. $^1$HNMR (DMSO-$d_6$) 5.40 (s, 1H), 6.54 (d, J=16 Hz, 1H), 6.96 (dd, J=20.5, 8.0 Hz, 2H), 7.12 (t, J=7.5 Hz, 1H), 7.21-7.37 (m, 5H), 7.61 (dd, J=26.5, 8.5 Hz, 2H), 7.85 (s, 1H), 7.94 (d, J=16.5 Hz, 1H), 10.74 (s, 1H) LC/MS (82%) (ESI–) Calcd. 558.46 m/z Found 558.0 m/z.

Example 284

Preparation of P245

Using Method A-15, I-186 was reacted with 2-naphthyl amine to provide P245 in 71%; LC/MS 94%. $^1$HNMR (DMSO-$d_6$) 3.17 (s, 3H), 6.77 (d, J=16 Hz, 1H), 6.93 (d, J=8 Hz, 1H), 7.24 (dd, J=9.0, 2.5 Hz, 1H), 7.40 (d, J=29.0 Hz, 1H), 7.40-7.50 (m, 4H), 7.80-7.90 (m, 5H), 8.68 (d, J=16.0 Hz, 1H), 11.03 (s, 1H) LC/MS (71%) (ESI–) Calcd. 570.48 m/z Found 568.5 m/z.

Example 285

Preparation of P242

Using Method A-16, I-187 was reacted with 2-naphthyl amine to provide P242 in 94% yield. 1H-NMR (DMSO-d6).

Example 286

Preparation of P252

Using Method A-16, I-187 was reacted with 2,4-dicholoroaniline to provide P252 in 99% yield. $^1$HNMR (DMSO-$d_6$) 3.18 (s, 3H), 5.52 (d, J=8.4 Hz, 1H), 6.18 (s, 1H), 6.51 (d, J=15.6 Hz, 2H), 7.01 (dd, J=8.8, 2.8 Hz, 1H), 7.24 (d, J=8.4 Hz, 1H), 7.29 (d, J=2.4 Hz, 2H), 7.42 (t, J=8 Hz, 1H), 7.84 (d, J=16 Hz, 1H), 7.88 (s, 1H) LC/MS (99%) (APCI–) Calcd. 589 m/z Found 588 m/z.

Example 287

Preparation of P268

Using Method A-16, I-186 was reacted with 2,4-dicholoroaniline to provide P268 in 99% yield. 1H-NMR (DMSO-d6).

Example 288

Preparation of P270

Using Method A-16, I-186 was reacted with 3,4-difloroaniline to provide P270 in 99% yield. $^1$HNMR (DMSO-$d_6$) 3.15 (s, 3H), 5.48 (d, J=8.0 Hz, 1H), 6.24 (br d, J=8.8 Hz, 1H), 6.48 (m, 1H), 6.57 (d, J=16 Hz, 1H), 6.71 (br d, J=9.6 Hz, 1H), 7.07 (q, J=9.2 Hz, 1H), 7.14 (d, J=8.0 Hz, 1H), 7.30 (d, J=8.0 Hz, 1H), 7.45 (t, J=8.0 Hz, 1H), 7.83 (d, J=16 Hz, 1H), 7.87 (s, 1H) LC/MS (95%) (ESI–) Calcd. 558.41 m/z Found 557 m/z Example 289

Preparation of P247

4,5-Dichloro-thiophene-2-sulfonic acid [(E)-3-(3-amino-1-methyl-2-oxo-2,3-dihydro-1H-indol-4-yl)-acryloyl]-amide, I-188. To a solution of the isatin derivative I-187 (350 mg, 0.8 mmol) in MeOH (8 mL) was added NH4OH (1 mL) at ~5° C. The reaction mixture was allowed to stir at RT for 16 h and then diluted with 50 mL water. The precipitate formed was collected by a filtration, dried over air and then suspended in glacial acetic acid (8 mL). To this mixture was added sodium cyanoborohydride (150 mg) at room temperature, and continued to stir for 2 h. The resulting reaction was quenched with water. The mixture was stirred for 30 min at room temperature. The precipitate was collected by a filtration, washed with water and dried to yield the amino derivative I-188 (300 mg, 85%). 1H-NMR; MS.

Synthesis of P247. To a solution of the amine I-188 (45 mg 0.1 mmol) and DMAP (45 mg) in CH2Cl2 (5 mL) was added a Naphthalene-2-carbonyl chloride (21 mg, 0.12 mmol)) at 0° C. The reaction mixture was allowed to stir at rt for 24 h. After the solvent was removed, the residue was dissolved in acetic acid (3 mL) and diluted with ice-water (50 mL). The precipitate formed was collected by a filtration, washed with water and dried to yield the crude (60 mg) A which was purified by a chromatography on silica gel to afford P247 (25 mg, 40%) as off-white solid. $^1$H NMR (500 MHz, DMSO-d6); 3.20 (s, 3H), 6.40 (s, 1H), 6.46 (d, J=16.0 Hz, 1H), 7.04 (d, J=7.5 Hz, 1H), 7.31-7.39 (m, 2H), 7.52 (d, J=16.0 Hz, 1H), 7.59 (t, J=7.0 Hz, 1H), 7.67 (t, J=7.0 Hz, 1H), 7.92 (d, J=7.5 Hz, 1H), 7.99 (d, J=9.0 Hz, 1H), 8.14 (d, J=8.0 Hz, 1H), 8.63 (s, 1H). LC/MS (97%) ESI⁻ Calcd.: 600.5 m/z, found: 599.3 m/z (M–1).

Example 290

Preparation of P265

4,5-Dichloro-thiophene-2-sulfonic acid [(E)-3-(3-amino-1-methyl-2-oxo-2,3-dihydro-1H-indol-4-yl)-acryloyl]-amide I-188 (0.110 g, 0.25 mmol) was dissolved in chloroform (3 mL). Glacial acetic acid (0.043 mL, 0.75 mmol) was added, followed by isoamyl nitrite (0.34 mL, 0.2525 mmol). The mixture was stirred at 60° C. for 30 min and allowed to cool to room temp. over 1 h, after which it was concentrated under nitrogen, washed 3× with water via decanting (no scrapping) and dried under nitrogen to afford the diazonium salt. It was used as such in the next step. IR (neat) reveals a strong absorbtion at 2100 cm⁻¹.

2-Naphthol (0.0540 g, 0.375 mmol) was dissolved in 3 mL dry toluene. Dirhodium (II) tetraacetate (0.0055 g, 0.0125 mmol) was added and the mixture was heated under nitrogen to 65° C., at which point a solution of 4-[(E)-3-(4,5-Dichlorothiophene-2-sulfonylamino)-3-oxo-propenyl]-1-methyl-2-oxo-2,3-dihydro-1H-indole-3-diazonium (assumed 0.250 mmol) in 1 mL anhydrous toluene was added. The resulting mixture was stirred for 30 min more at 65° C., after which it was cooled to room temperature over 1 h, concentrated, and chromatographed on silica gel (gradient MeOH/CH2Cl2).

Fraction 81 contained 4,5-dichloro-thiophene-2-sulfonic acid {(E)-3-[1-methyl-3-(naphthalen-2-yloxy)-2-oxo-2,3-dihydro-1H-indol-4-yl]-acryloyl}-amide P265, 6.5 mg. 1H NMR (500 MHz, DMSO-d6) 3.30 (s, 3H), 5.75 (s, 1H), 6.23 (d, J=16.0 Hz, 1H), 6.57 (d, J=8.4 Hz, 1H), 6.69 (d, J=16.0 Hz, 1H), 6.9-7.8 (m, 9H), 8.05 (d, J=16.0 Hz, 1H), 10.44 (s, 1H). LC/MS (87.3%) ESI– Calcd. M=573.5 Found: 573.3 m/z Example 291

Preparation of P284

Synthesis of 2-Fluoro-6-(naphthalen-2-yloxy)-benzonitrile, I-189. To a 20 mL vial containing a magnetic stir bar was added sodium hydride (103.7 mg, 4.32 mmol, 60% in mineral oil) followed by anhydrous DMF (2 mL) resulting in gas evolution. To this stirring reaction mixture was added 2-naphthol (623 mg, 4.32 mmol) as a solid in small portions over 5 min. The mixture was stirred at room temperature for 3 min and then 2,6-difluorobenzonitrile (601 mg, 4.32 mmol) in anhydrous DMF was added in one portion. The reaction mixture was heated in an oil bath at 100° C. for a total of 2 h and allowed to cool to room temperature. The reaction mixture was diluted with water (15 mL) and the resulting mixture was extracted with EtOAc (2×20 mL). The combined organic extracts were washed with water (3×20 mL), dried ($Na_2SO_4$), filtered and concentrated to give I-189 as brown solid (1.216 g) of sufficient purity (contains 2-naphthol) to be used in the subsequent step. 1H NMR.

Synthesis of 1-Methyl-4-(naphthalen-2-yloxy)-1H-indazol-3-ylamine, I-190. To a 20 mL vial containing 2-fluoro-6-(naphthalen-2-yloxy)-benzonitrile (966 mg, 3.67 mmol) and a magnetic stir bar was added anhydrous N,N-dimethylacetamide and the mixture was stirred until solution was achieved. Methyl hydrazine (390 uL, 7.34 mmol) was added, the vial was capped, the reaction mixture was placed in an oil bath at 120° C. and stirred at that temperature overnight. The reaction mixture was heated at 130° C. for an additional 3 h. The cooled reaction mixture was diluted with water (20 mL) and extracted with EtOAc (2×30 mL). The combined organics were washed with water (3×15 mL), dried ($Na_2SO_4$), filtered and concentrated to give 1.03 g of a tan solid. This residue was purified via flash chromatography on silica gel (120 g) utilizing $CH_2Cl_2$ and then 9:1 $CH_2Cl_2$/EtOAc as eluent to give 770 mg of I-190 an off-white solid. This material was deemed of sufficient purity to be utilized in subsequent reactions. 1H NMR, MS.

Synthesis of 4,5-Dichloro-thiophene-2-sulfonic acid [1-methyl-4-(naphthalen-2-yloxy)-1H-indazol-3-yl]-amide, P284. To a 5 mL vial equipped with a magnetic stir bar was added I-190 (37 mg, 0.13 mmol), anhydrous $CH_2Cl_2$ (1 mL), N,N-dimethylaminopyridine (17.2 mg, 0.141 mmol) and 4,5-dichlorothiophene-2-sulfonyl chloride. The reaction mixture was stirred at room temperature for 36 h and the resulting solid was filtered and rinsed with $CH_2Cl_2$ to give, after drying, 18.5 mg of P284 as a white solid. 1H NMR (400 MHz, DMSO-d6) 4.16 (s, 3H), 6.46 (d, J=7.6 Hz, 1H), 7.08 (dd, J=8.8, 2.4 Hz, 1H), 7.41-7.35 (m, 2H), 7.47 (d, J=8.0 Hz, 1H), 7.53 (m, 2H), 7.87 (br d, J=8.4 Hz, 1H), 8.01-7.95 (m, 3H). MS (ESI+) Calcd. (M+H) 504.4; Found: 504.4

Example 292

Preparation of P056

General procedure (A-2) was used to alkylate thiophene-2-sulfonic acid [(E)-3-(3-methyl-1H-indol-7-yl)-acryloyl]-amide (I-8) with 2,4-dicholoro benzyl bromide to provide compound P056. $^1$H-NMR (500 MHz, DMSO-$d_6$). MS (ESI$^-$): 505.1 (M–1), LC-MS: 96% pure.

Example 293

Preparation of P347

Following the general Procedure A-8, the acrylic acid I-137B, was reacted with 4,5-Dichlorothiophene-2-sulfonamide to provide compound P347. Consistent with 1H-NMR.

Example 294

Preparation of P350

Synthesis of 7-Bromo-1-(2,4-dichloro-benzyl)-5-fluoro-3-methyl-1H-indole, I-191. NaH (60% in oil, 526 mg, 13.15 mmol, 1.5 equiv.) was added to a solution of 7-bromo-5-fluoro-3-methyl-1H-indole, [which was prepared analogous to I-30, according to the method of Dobbs, A., J. Org. Chem., 66, 638-641 (2001)], (2 g, 8.77 mmol, 1 equiv.) in DMF (30 mL) at –10° C. Reaction mixture was warmed to rt and stirred for 30 min. A solution of 2,4-dichlorobenzyl chloride (2.06 g, 10.52 mmol, 1.2 equiv.) in DMF (10 mL) was added gradually over 2.5 min at –10° C. The reaction mixture was allowed to warm to rt and stirred for 1 h. The reaction mixture was poured into a stirred solution of 10% HCl/water/ether (1:1:2, 40 mL) mixture, and the aqueous layer was extracted with ether (2×10 mL). The combined organic layers were washed with water (3×75 mL), brine (75 mL), dried over $MgSO_4$, filtered, and concentrated to afford crude product as brown solid. Ether (4 mL) was added to the crude product, cooled down to –78° C. and filtered to afford I-191 (2.49 g, 73%) as off-white solid. $^1$H-NMR (500 MHz, $CDCl_3$) confirmed the structure.

Synthesis of 1-(2,4-Dichloro-benzyl)-5-fluoro-3-methyl-1H-indole-7-carboxylic acid ethyl ester, I-192. BuLi (1.6 M in hexanes, 0.97 mL, 1.55 mmol, 1.5 equiv.) was slowly over 7 min, added to a solution of I-191 (400 mg, 1.03 mmol, 1 equiv.) in ether (7 mL) at –78° C. under Ar atmosphere. The reaction mixture was stirred at –78° C. for additional 30 min. Ethyl chloroformate (0.2 mL, 2.07 mmol, 2 equiv.) was added slowly to the reaction mixture and it was allowed to warm to and stirred at rt for 30 min. The reaction mixture was quenched through the addition of 10% aqueous HCl (5 mL). The organic layer was washed with water (2×10 mL), brine (10 mL), dried over $MgSO_4$, filtered, and concentrated to afford I-192 mg, 98%) as brown oil. MS (AP$^+$): 380, 382 (M+1). $^1$H-NMR (500 MHz, $CDCl_3$) confirmed the structure.

Synthesis of 1-(2,4-Dichloro-benzyl)-5-fluoro-3-methyl-1H-indole-7-carboxylic acid, I-193. A 2N aqueous NaOH solution (2.5 mL, 5 mmol, 5 equiv.) was added to a solution of ester I-192 (381 mg, 1 mmol, 1 equiv.) in MeOH/THF (1:1, 4 mL). The reaction mixture was stirred and heated to 75° C. for 1 h. The reaction mixture was concentrated, cooled to –70° C., quenched through the addition of 10% aqueous HCl (6 mL), and extracted with EtOAc (4 mL). The organic layer was washed with water (2×4 mL), brine (4 mL), dried over $MgSO_4$, filtered, and concentrated. The resulting material was triturated with hexane (2×2 mL) and dried to afford I-193 (262 mg, 74%) as off-white solid. $^1$H-NMR (500 MHz, $CDCl_3$) confirmed the structure.

Synthesis of P350. 4,5-Dichloro-2-thiophenesulfone amide (23.2 mg, 0.1 mmol, 1 equiv.) was added at rt to a solution of I-193 (35 mg, 0.1 mmol, 1 equiv.) and DMAP (24.5 mg, 0.2 mmol, 2 equiv.) in anhydrous CH2Cl2 (0.5 mL)

followed by EDCI (38 mg, 0.2 mmol, 2 equiv.). The reaction mixture was stirred at rt for 1 hour and then left at 0° C. for 2 days. The reaction mixture was warmed to rt, quenched by addition of 10% HCl$_{(aq.)}$ (1 mL) and extracted with EtOAc (1 mL). The organic layer was washed with water-brine, 1:1 (3×1 mL), dried over MgSO$_4$, filtered, and concentrated to afford crude product (51 mg) as light-brown solid. The crude material was triturated with hexane (2×1 mL), followed by hexane-MeOH, 30:1 (1 mL) to afford P350 (45 mg, 79%) as off-white solid. LC-MS (95%): ESI$^-$ $^{Calcd.}$ 564 m/z Found: 564. $^1$H NMR (DMSO-d$_6$) 2.24 (d, J=0.8 Hz, 3H), 5.39 (s, 2H), 6.01 (d, J=8.4 Hz, 1H), 7.15 (dd, J=8.4, 2.4 Hz, 1H), 7.28 (dd, J=8.4, 2.4 Hz, 1H), 7.29 (s, 1H), 7.25 (d, J=2.4 Hz, 1H), 7.60-7.64 (m, 1H), 7.64 (s, 1H), 7.95 (br s, 1H).

Example 295

Preparation of P417

3,4-Difluorobenzenesulfone amide (19.3 mg, 0.1 mmol, 1 equiv.) was added at rt to a solution of I-193 (35 mg, 0.1 mmol, 1 equiv.) and DMAP (24.5 mg, 0.2 mmol, 2 equiv.) in anhydrous CH2CL2 (Aldrich, 0.5 mL) followed by EDCI (38 mg, 0.2 mmol, 2 equiv.) analogous to the procedure described for the preparation of P350 to afford P417 (42 mg, 79%) as beige solid. LC-MS (98%): ESI$^-$ Calcd. 526 m/z Found: 526. $^1$H NMR (DMSO-d$_6$) 2.22 (d, J=1.2 Hz, 3H), 5.22 (s, 2H), 5.96 (d, J=8.4 Hz, 1H), 7.14 (dd, J=8.2, 1.8 Hz, 1H), 7.24 (s, 1H), 7.29 (dd, J=9.6, 2.4 Hz, 1H), 7.36 (d, J=2.4 Hz, 1H), 7.54 (br s, 1H), 7.61-7.66 (m, 2H), 7.67-7.70 (m, 1H), 7.76-7.81 (m, 1H).

Example 296

Preparation of P354

Synthesis of [1-(2,4-Dichloro-benzyl)-5-fluoro-3-methyl-1H-indol-7-yl]-oxo-acetic acid ethyl ester, I-194. A solution of n-BuLi (2.5 M in hexanes, 0.31 mL, 0.78 mmol, 1.5 equiv.) was slowly added over 7 min to a solution of bromide I-191 (200 mg, 0.517 mmol, 1 equiv.) in anhydrous Et2O (4 mL) at −78° C. under an argon atmosphere. The reaction mixture was stirred at −78° C. for 20 min. Ethyl oxalate (0.146 mL, 1.034 mmol, 2.0 equiv.) was slowly added over 2 min at −78° C. and the reaction mixture was warmed up to 0° C. in the water-ice bath. The reaction mixture was warmed to rt, quenched by addition of 10% HCL$_{(aq.)}$ (3 mL) and extracted by ether (3 mL). Organic layer was washed with water (2×6 mL), brine (6 mL), dried over MgSO$_4$, filtered, and concentrated to afford I-194 (215 mg, 100%) as orange oil. $^1$H-NMR (500 MHz, CDCl$_3$) confirmed the structure.

Synthesis of [1-(2,4-Dichloro-benzyl)-5-fluoro-3-methyl-1H-indol-7-yl]-oxo-acetic acid, I-195. An aqueous solution of 2N NaOH (0.29 mL, 0.58 mmol, 1.1 equiv.) was slowly added over 2 min to a solution of I-194 (215 mg, 0.53 mmol, 1 equiv.) in THF-MeOH, 1:1 (4 mL) at 0° C. The reaction mixture was stirred at 0° C. for 30 min and then warmed up to rt. 2N Aqueous NaOH (0.24 mL, 0.48 mmol, 0.9 equiv.) was added in one portion and the reaction mixture was stirred for 15 min. The reaction mixture was concentrated, 10% HCl$_{(aq.)}$ (1 mL) was added, followed by extraction with ether (2 mL). The organic layer was washed with water (3×2 mL), brine (2 mL), dried over MgSO$_4$, filtered, and concentrated to afford I-195 (141 mg, 95%) as yellow solid. LC-MS (98%): ESI$^-$ Calcd. 380.2 m/z Found: 380.2. $^1$H-NMR (500 MHz, CDCl$_3$) confirmed the structure.

Synthesis of P354. 2,4,5-Trifluorobenzenesulfone amide (22 mg, 0.11 mmol, 1 equiv.) was added at rt to a solution of I-195 (40 mg, 0.111 mmol, 1 equiv.) and DMAP (26 mg, 0.2 mmol, 2 equiv.) in anhydrous CH2Cl2 (0.6 mL) followed by EDCI (40 mg, 0.2 mmol, 2 equiv.) analogous to the procedure described for the preparation of P350 to afford crude product as yellow solid. The crude material was triturated with MTBE (2 mL), boiled for one minute, and the solution was filtered and washed with MTBE (2×0.5 mL), hexane (2 mL) at rt to afford P354 (28 mg, 46%) as yellow solid. LC-MS (100%): AP$^-$ Calcd. 572 m/z Found: 572. $^1$H NMR (DMSO-d$_6$) 2.27 (d, J=0.8 Hz, 3H), 5.57 (s, 2H), 6.14 (d, J=8.4 Hz, 1H), 7.15-7.19 (m, 2H), 7.35 (s, 1H), 7.54 (d, J=2.0 Hz, 1H), 7.73 (dd, J=8.6, 2.6 Hz, 1H), 7.76-7.82 (m, 2H).

Example 297

Preparation of P351

Following the general Procedure A-8, the acrylic acid I-137A, was reacted with 4-Fluoro-benzenesulfonamide to provide compound P351. Consistent with 1H-NMR.

Example 298

Preparation of P352

Following the general Procedure A-8, the acrylic acid I-137A, was reacted with 2-Chloro-benzenesulfonamide to provide compound P352. Consistent with 1H-NMR.

Example 299

Preparation of P353

Following the general Procedure A-8, the acrylic acid I-137A, was reacted with 3-Chloro-benzenesulfonamide to provide compound P353. Consistent with 1H-NMR.

Example 300

Preparation of P355

Following the general Procedure A-8, the acrylic acid I-137A, was reacted with 3,4-Dichloro-benzenesulfonamide to provide compound P355. Consistent with 1H-NMR.

Example 301

Preparation of P356

Following the general Procedure A-8, the acrylic acid I-137A, was reacted with 2,4-Dichloro-benzenesulfonamide to provide compound P356. Consistent with 1H-NMR.

Example 302

Preparation of P357

Following the general Procedure A-8, the acrylic acid I-137A, was reacted with 3,5-Dichloro-benzenesulfonamide to provide compound P357. Consistent with 1H-NMR.

Example 303

Preparation of P358

Following the general Procedure A-8, the acrylic acid I-137A, was reacted with 2,4-Difluoro-benzenesulfonamide to provide compound P358. Consistent with 1H-NMR.

Example 304

Preparation of P359

Following the general Procedure A-8, the acrylic acid I-137A, was reacted with 2,5-Difluoro-benzenesulfonamide to provide compound P359. Consistent with 1H-NMR.

Example 305

Preparation of P360

Following the general Procedure A-8, the acrylic acid I-137A, was reacted with 2,6-Difluoro-benzenesulfonamide to provide compound P360. Consistent with 1H-NMR.

Example 306

Preparation of P361

Following the general Procedure A-8, the acrylic acid I-137A, was reacted with 3,5-Difluoro-benzenesulfonamide to provide compound P361. Consistent with 1H-NMR.

Example 307

Preparation of P363

Following the general Procedure A-8, the acrylic acid I-137A, was reacted with 3-Fluoro-benzenesulfonamide to provide compound P363. Consistent with 1H-NMR.

Example 308

Preparation of P364

Following the general Procedure A-8, the acrylic acid I-137A, was reacted with 2-Fluoro-benzenesulfonamide to provide compound P364. Consistent with 1H-NMR.

Example 309

Preparation of P365

Following the general Procedure A-8, the acrylic acid I-137A, was reacted with 4-Chloro-benzenesulfonamide to provide compound P365. Consistent with 1H-NMR.

Example 310

Preparation of P366

Following the general Procedure A-8, the acrylic acid I-137A, was reacted with 4-Methoxy-benzenesulfonamide to provide compound P366. Consistent with 1H-NMR.

Example 311

Preparation of P373

Following the general Procedure A-8, the acrylic acid I-137A, was reacted with 2,3,4,5,6-Pentafluoro-benzenesulfonamide to provide compound P373. Consistent with 1H-NMR.

Example 312

Preparation of P367

Synthesis of 2,4,5-Trifluoro-N-[(E)-3-(5-fluoro-3-methyl-1H-indol-7-yl)-acryloyl]-benzenesulfonamide, I-196. In an 8 mL vial equipped with a stir bar was placed acid I-34 (300 mg, 1.37 mmol), anhydrous CH2CL2 (4 mL), 2,4,5-trifluorobenzenesulfonamide (346 mg, 1.64 mmol), DMAP (200 mg, 1.64 mmol) and EDCI (314 mg, 1.64 mmol) at room temperature. The vial was sealed with a cap and allowed to react for 17 hours at room temperature. The contents of the vial were transferred to a separatory funnel and diluted with CH2CL2 (20 mL). Then, water (20 mL) and 1M HCl (20 mL) were added to the funnel and the organic portion was removed. The aqueous layer was extracted with EtOAc (2×20 mL). The organic portions were combined, dried (MgSO$_4$) and concentrated to produce a brown oil. The crude product was triturated with ice cold CH2CL2 (2 mL), which produced an insoluble solid. The solid was collected via suction filtration and washed with ice cold CH2CL2 (4 mL) to produce 135 mg of I-196 as a yellow solid (24%). $^1$H NMR (400 MHz, DMSO-d6) LC/MS (87%)

General Procedure (A-17) for Alkylation of Acylsulfonamides

To a solution of acylsulfonamide in THF at room temperature was added 3 eq. of potassium t-butoxide. The corresponding aryl halide was added, and the mixture stirred at room temperature overnight. The reaction mixture was diluted with EtOAc, and acidified with 10% HCl. The organics were washed with water (3×), brine, and dried over Na$_2$SO$_4$. The solution was filtered, concentrated, and the residue purified via trituration with dichloromethane at 40° C. or silica gel chromatography, using methanol/dichloromethane as eluent.

Synthesis of P367. Following the general procedure (A-17) acylsulfonamide I-196 was alkylated with 3-methoxybenzyl bromide to provide P367 (30%). LC/MS (95%) ESI− Calcd. 532.5 m/z Found: 531.5 m/z $^1$H NMR(DMSO-d$_6$)

Example 313

Preparation of P368

Synthesis of 3,4-Difluoro-N-[(E)-3-(5-fluoro-3-methyl-1H-indol-7-yl)-acryloyl]-benzenesulfonamide, I-197. Following the procedure described for the I-196, I-34 was reacted with 3,4-difluorobenzenesulfonamide to give I-197. After filtration, 223 mg of I-197 was isolated as a yellow solid (41%). $^1$H NMR (400 MHz, DMSO-d6) LC/MS (99%)

Following the general procedure (A-17) acylsulfonamide I-197 was alkylated with 3-methoxybenzyl bromide to provide P368 (19%). LC/MS (97%) ESI− Calcd. 514.5 m/z Found: 513.7 m/z $^1$H NMR(DMSO-d$_6$)

Example 314

Preparation of P369

Following the general procedure (A-17) acylsulfonamide I-197 was alkylated with 4-(chloromethyl)-3,5-dimethyl-isoxazole to provide P369 (31%) LC/MS (92%) ESI− Calcd. 503.5 m/z Found: 502.4 m/z $^1$H NMR(DMSO-d$_6$)

Example 315

Preparation of P370

Following the general procedure (A-17) acylsulfonamide I-196 was alkylated with 4-(chloromethyl)-3,5-dimethyl-isoxazole to provide P370 (18%) LC/MS-(96%) ESI− Calcd. 521.5 m/z Found: 520.6 m/z $^1$H NMR (DMSO-d6) 1.68 (s, 3H), 1.75 (s, 3H), 2.21 (s, 3H), 5.29 (s, 2H), 6.40 (d, J=15.6

Hz, 2H), 7.09 (dd, J=10.4, 2.4 Hz, 1H), 7.21 (s, 1H), 7.44 (dd, J=8.8, 2.4 Hz, 1H), 7.93 (ddd, J=10.0, 10.0, 6.0 Hz, 1H), 8.02 (d, J=14.8 Hz, 1H), 8.03 (dd, J=18.0, 6.4 Hz, 1H), 12.8 (s, 1H)

Example 316

Preparation of P374

Following the general procedure (A-17) acylsulfonamide I-197 was alkylated with 3,5-dimethoxybenzyl bromide to provide P374 (20%). LC/MS (97%) ESI– Calcd. 544.6 m/z Found: 543.6 m/z $^1$H NMR(DMSO-d$_6$)

Example 317

Preparation of P375

Following the general procedure (A-17) acylsulfonamide I-196 was alkylated with 3,5-dimethoxybenzyl bromide to provide P375 (37%). LC/MS (98%) ESI– Calcd. 562.5 m/z Found: 561.5 m/z $^1$H NMR(DMSO-d$_6$)

Example 318

Preparation of P378

Synthesis of (5-Fluoro-3-methyl-7-(naphthalen-2-yloxy)-1H-indole (I-198A). General Method A-18: In a 40 mL vial equipped with a stir bar was placed 7-bromo-5-fluoro-3-methyl-1H-indole, [which was prepared analogous to I-30, according to the method of Dobbs, A., J. Org. Chem., 66, 638-641 (2001)], (1.10 g, 4.78 mmol), anhydrous dioxane (9.5 ml), 2-naphthol (1.03 g, 7.17 mmol), CuI (91.0 mg, 0.478 mmol), N,N-dimethylglycine hydrochloride (200 mg, 1.43 mmol) and Cs$_2$CO$_3$ (3.12 g, 9.56 mmol) at room temperature. The mixture was degassed with argon for 15 minutes, sealed with a cap and then placed in an oil bath at 100° C. for a period of 65 hours. The reaction was quenched with water (50 mL) and extracted with EtOAc (3×50 mL). The organic portions were combined, washed with water (2×50 mL), brine (50 mL), dried (MgSO$_4$) and concentrated to produce a dark brown oil. The oil was purified by silica gel column chromatography using a solvent system of 5% EtOAc/hexanes as eluent to produce 791 mg of I-198A as a yellow solid (57%). $^1$H NMR (400 MHz, CDCl$_3$)

Synthesis of 3-[5-Fluoro-3-methyl-7-(naphthalen-2-yloxy)-indol-1-yl]-propionic acid (I-200A): General Method A-19. In an 18 mL vial equipped with a stir bar was placed compound Ib-1 (500 mg, 1.72 mmol), methyl acrylate (3.10 mL, 34.4 mmol) and DBU (257 uL, 1.72 mmol) at room temperature. The vial was purged with N$_2$ for 1 minute, sealed with a cap and reacted for 18 hours at room temperature. The reaction was quenched with 1 M aqueous HCl (8 mL) and stirred for 10 minutes. After transferring to a separatory funnel, additional 1 M aqueous HCl (50 mL) was added followed by an extraction with CH2Cl2 (2×100 mL). The organic portions were combined, washed with water (60 mL) and brine (60 mL), dried (MgSO$_4$) and concentrated to produce 749 mg of I-199A as a yellow oil. In a 40 mL vial equipped with a stir bar was placed crude compound Ib-2 (600 mg, 1.59 mmol), THF (7.40 mL), MeOH (3.70 mL) and 50% aqueous NaOH (3.34 mL, 1.67 mmol) at room temperature. After 10 minutes, the reaction was quenched with a saturated NaHCO$_3$ solution (75 mL) and extracted with Et$_2$O (100 mL). The Et$_2$O layer was washed with a saturated NaHCO$_3$ solution (2×75 mL). The aqueous portions were combined, acidified to pH 1 with 3M HCl and extracted with CH2Cl2 (3×80 mL). The organic portions were combined, washed with water (100 mL), brine (100 mL), dried (MgSO$_4$) and concentrated to produce 338 mg of I-200A as an orange oil (54% yield from I-198A to I-200A). $^1$H NMR (400 MHz, CDCl$_3$)

Synthesis of P378. 2,4,5-Trifluoro-N-{3-[5-fluoro-3-methyl-7-(naphthalen-2-yloxy)-indol-1-yl]-propionyl}-benzenesulfonamide General Method A-20. In an 8 mL vial equipped with a stir bar was placed I-200A (65.0 mg, 0.179 mmol), CH2Cl2 (1.2 mL), 2,4,5-trifluorophenyl sulfonamide (45.4 mg, 0.215 mmol), DMAP (52.5 mg, 0.430 mmol) and EDCI (85.9 mg, 0.448 mmol). The mixture was stirred at room temperature for 18 hours. The reaction was quenched with 1 M aqueous HCl (3 mL) and stirred for 10 minutes. After transferring to a separatory funnel, additional 1 M aqueous HCl (30 mL) was added followed by an extraction with CH2Cl2 (2×30 mL). The organic portions were combined, washed with water (35 mL), brine (35 mL), dried (MgSO$_4$) and concentrated to produce 78.3 mg of P378 as a white solid (79%). $^1$H NMR (400 MHz, CDCl$_3$) LC/MS purity (92%)

Example 319

Preparation of P380

Compound I-200A (65.0 mg, 0.179 mmol) was reacted with 4,5-dichlorothiophene-2-sulfonamide (49.9 mg, 0.215 mmol), DMAP (52.5 mg, 0.430 mmol), and EDCI (85.9 mg, 0.448 mmol) in anhydrous CH2Cl2 (1.2 mL) analogous to the procedure described for the preparation of P378. The crude product was purified by silica gel column chromatography utilizing a solvent system of 20% EtOAc/Hexanes, 1% AcOH. After concentration and a toluene azeotrope (3×75 mL), 64.5 mg of P380 was isolated as a white solid (63%). $^1$H NMR (400 MHz, DMSO-d6) 2.16 (s, 3H), 2.78 (t, J=6.8 Hz, 2H), 4.36 (t, J=6.8 Hz, 2H), 6.54 (dd, J=10.4, 2.4 Hz, 1H), 7.00 (s, 1H), 7.10 (dd, J=9.2, 2.4 Hz, 1H), 7.32 (dd, J=8.8, 2.4 Hz, 1H), 7.38 (d, J=2.4 Hz, 1H), 7.44-7.52 (m, 2H), 7.80 (br s, 1H), 7.81 (d, J=9.6 Hz, 1H), 7.93 (d, J=8.0 Hz, 1H), 7.96 (d, J=8.8 Hz, 1H). HPLC purity (99%), MS (ESI$^-$) Calcd.: 576.5 m/z, Found: 577.1 m/z Example 320

Preparation of P379

Compound I-200A (65.0 mg, 0.179 mmol) was reacted with 3,4-difluorophenyl sulfonamide (49.9 mg, 0.215 mmol), DMAP (52.5 mg, 0.430 mmol), and EDCI (85.9 mg, 0.448 mmol) in anhydrous CH2Cl2 (1.2 mL) analogous to the procedure described for the preparation of P378. The crude product was purified by silica gel column chromatography utilizing a solvent system of 30% EtOAc/hexanes, 1% AcOH. After concentration and a toluene azeotrope (3×75 mL), 48.3 mg of P379 was isolated as a white solid (50%). $^1$H NMR (400 MHz, DMSO-d6), HPLC purity (97%).

Example 321

Preparation of P381

Compound I-200A (65.0 mg, 0.179 mmol) was reacted with 3-chlorophenyl sulfonamide (49.9 mg, 0.215 mmol), DMAP (52.5 mg, 0.430 mmol), and EDCI (85.9 mg, 0.448 mmol) in anhydrous CH2Cl2 (1.2 mL) analogous to the procedure described for the preparation of P378. The crude product was purified by silica gel column chromatography utilizing a solvent system of 30% EtOAc/Hexanes, 1% AcOH.

After concentration and a toluene azeotrope (3×75 mL), 86.7 mg of P381 was isolated as a white solid (90%). $^1$H NMR (400 MHz, DMSO-d6) HPLC purity (95%), MS: Theoretical (537.0), Found (535.3)

Example 322

Preparation of P382

Synthesis of 7-(2,4-Dichloro-phenoxy)-5-fluoro-3-methyl-1H-indole, I-198B. Following general method A-18, 7-Bromo-5-fluoro-3-methyl-1H-indole (1.60 g, 7.02 mmol) was reacted with 2,4-dichlorophenol (1.72 g, 10.5 mmol), CuI (134 mg, 0.702 mmol), N,N-dimethylglycine hydrochloride (293 mg, 2.10 mmol), and $Cs_2CO_3$ (4.57 g, 14.0 mmol) in anhydrous dioxane (14 mL). The crude product was purified by silica gel column chromatography utilizing a solvent system of 5% EtOAc/Hexanes to yield 746 mg of I-198B as a yellow oil (34%). $^1$H NMR (400 MHz, $CDCl_3$)

Synthesis of 3-[7-(2,4-Dichloro-phenoxy)-5-fluoro-3-methyl-indol-1-yl]-propionic acid (I-200B): Following general method A-19, I-198B (690 mg, 2.22 mmol) was reacted with methyl acrylate (4.00 mL, 44.4 mmol), and DBU (348 µL, 2.33 mmol). After concentration, 882 mg of I-199B was isolated as an orange oil. Crude I-199B (880 mg, 2.22 mmol) was saponified using THF (10.3 mL), MeOH (5.17 mL) and 50% aqueous NaOH (4.66 mL, 2.33 mmol). The first workup yielded 320 mg of I-200B as a white solid. The ether layer was reduced in volume, washed with 1 M aqueous HCl (35 mL) and extracted with CH2Cl2 (2×60 mL). The organic portions were combined, washed with water (40 mL), brine (40 mL) and dried ($MgSO_4$). After concentration, 279 mg of I-200B was isolated as a light orange solid. The two portions of compound I-200B were identical by 1H NMR and were combined to yield 599 mg of I-200B (70% from I-198B to I-200B). $^1$H NMR (400 MHz, $CDCl_3$)

Synthesis of P382. Compound I-200B (70.0 mg, 0.183 mmol) was reacted with 2,4,5-trifluorophenyl sulfonamide (46.5 mg, 0.220 mmol), DMAP (53.6 mg, 0.439 mmol), and EDCI (87.8 mg, 0.458 mmol) in anhydrous $CH_2Cl_2$ (1.2 mL) analogous to the procedure described for the preparation of P378. The crude product was purified by silica gel column chromatography utilizing a solvent system of 30% EtOAc/Hexanes, 1% AcOH. After concentration and a toluene azeotrope (3×75 mL), 73.0 mg of P382 was isolated as a yellow oil (70%). $^1$H NMR (400 MHz, DMSO-d6) HPLC purity (85%)

Example 323

Preparation of P384

Compound I-200B (70.0 mg, 0.183 mmol) was reacted with 4,5-dichlorothiophene-2-sulfonamide (51.1 mg, 0.220 mmol), DMAP (53.6 mg, 0.439 mmol), and EDCI (87.8 mg, 0.458 mmol) in anhydrous CH2Cl2 (1.2 mL) analogous to the procedure described for the preparation of P378. The crude product was purified by silica gel column chromatography utilizing a solvent system of 30% EtOAc/Hexanes, 1% AcOH. After concentration and a toluene azeotrope (3×75 mL), 84.8 mg of P384 was isolated as a tan solid (78%). $^1$H NMR (400 MHz, DMSO-d6) HPLC purity (94%)

Example 324

Preparation of P383

Compound I-200B (70.0 mg, 0.183 mmol) was reacted with 3,4-difluorophenyl sulfonamide (42.5 mg, 0.220 mmol), DMAP (53.6 mg, 0.439 mmol), and EDCI (87.8 mg, 0.458 mmol) in anhydrous CH2Cl2 (1.2 mL) analogous to the procedure described for the preparation of P378. The crude product was purified by silica gel column chromatography utilizing a solvent system of 30% EtOAc/Hexanes, 1% AcOH. After concentration and a toluene azeotrope (3×75 mL), 66.5 mg of P383 was isolated as a white solid (65%). $^1$H NMR (400 MHz, DMSO-d6) 2.13 (s, 3H), 2.74 (t, J=6.8 Hz, 2H), 4.32 (t, J=6.8 Hz, 2H), 6.38 (dd, J=10.4, 2.4 Hz, 1H), 6.97 (s, 1H), 7.07 (dd, J=9.2, 2.4 Hz, 1H), 7.11 (d, J=8.8 Hz, 1H), 7.44 (dd, J=9.2, 2.8 Hz, 1H), 7.67-7.78 (m, 3H), 7.87 (m, 1H), 12.25 (br s, 1H)HPLC purity (88%), MS (ESI–) Calcd.: 556.4 m/z, Found: 555.1 m/z.

Example 325

Preparation of P385

Compound I-200B (70.0 mg, 0.183 mmol) was reacted with 3-chlorophenyl sulfonamide (42.2 mg, 0.220 mmol), DMAP (53.6 mg, 0.439 mmol), and EDCI (87.8 mg, 0.458 mmol) in anhydrous CH2Cl2 (1.2 mL) analogous to the procedure described for the preparation of P378. The crude product was purified by silica gel column chromatography utilizing a solvent system of 30% EtOAc/Hexanes, 1% AcOH. After concentration and a toluene azeotrope (3×75 mL), 72.2 mg of P385 was isolated as a white solid (71%). $^1$H NMR (400 MHz, DMSO-d6) HPLC purity (90%)

Example 326

Preparation of P386

Synthesis of 7-(3,4-Dichloro-phenoxy)-5-fluoro-3-methyl-1H-indole (–198C): Following general method A-18, 7-Bromo-5-fluoro-3-methyl-1H-indole (727 mg, 3.19 mmol) was reacted with 3,4-dichlorophenol (779 mg, 4.78 mmol), CuI (60.8 mg, 0.319 mmol), N,N-dimethylglycine hydrochloride (134 mg, 0.957 mmol), and $Cs_2CO_3$ (2.07 g, 6.38 mmol) in anhydrous dioxane (6.4 mL). The crude product was purified by silica gel column chromatography utilizing a solvent system of 5% EtOAc/Hexanes to yield 506 mg of I-198C as a yellow oil (34%). $^1$H NMR (400 MHz, $CDCl_3$).

Synthesis of 3-[7-(3,4-Dichloro-phenoxy)-5-fluoro-3-methyl-indol-1-yl]-propionic acid (I-200C): Following general method A-19, I-198C (450 mg, 1.45 mmol) was reacted with methyl acrylate (2.61 mL, 29.0 mmol), and DBU (227 µL, 1.52 mmol). After concentration, 584 mg of I-199C was isolated as an orange oil. Crude I-199C (580 mg, 1.46 mmol) was saponified using THF (6.80 mL), MeOH (3.40 mL) and 50% aqueous NaOH (3.07 mL, 1.53 mmol). The ether layer was reduced in volume, washed with 1 M aqueous HCl (35 mL) and extracted with CH2Cl2 (2×60 mL). The organic portions were combined, washed with water (40 mL), brine (40 mL) and dried ($MgSO_4$). After concentration, 240 mg of I-200C was isolated as a yellow oil (43% yield from I-198C to I-200C). $^1$H NMR (400 MHz, $CDCl_3$)

Synthesis of P386. Compound I-200C (65.0 mg, 0.170 mmol) was reacted with 2,4,5-trifluorophenyl sulfonamide (43.1 mg, 0.204 mmol), DMAP (49.8 mg, 0.408 mmol), and EDCI (81.5 mg, 0.425 mmol) in anhydrous CH2Cl2 (1.2 mL) analogous to the procedure described for the preparation of P378. The crude product was purified by silica gel column chromatography utilizing a solvent system of 30% EtOAc/Hexanes, 1% AcOH. After concentration and a toluene azeotrope (3×75 mL), 80.6 mg of P386 was isolated as a green solid (82%). $^1$H NMR (400 MHz, DMSO-d6) HPLC purity (93%)

Example 327

Preparation of P388

Compound I-200C (75.0 mg, 0.196 mmol) was reacted with 4,5-dichlorothiophene-2-sulfonamide (54.5 mg, 0.235 mmol), DMAP (57.4 mg, 0.470 mmol), and EDCI (93.9 mg, 0.490 mmol) in anhydrous CH2Cl2 (1.2 mL) analogous to the procedure described for the preparation of P378. The crude product was purified by silica gel column chromatography utilizing a solvent system of 20% EtOAc/Hexanes, 1% AcOH. After concentration and a toluene azeotrope (3×75 mL), 93.0 mg of P388 was isolated as a green solid (79%). $^1$H NMR (400 MHz, DMSO-d6) HPLC purity (93%).

Example 328

Preparation of P387

Compound I-200C (65.0 mg, 0.170 mmol) was reacted with 3,4-difluorophenyl sulfonamide (39.4 mg, 0.204 mmol), DMAP (49.8 mg, 0.408 mmol), and EDCI (81.5 mg, 0.425 mmol) in anhydrous CH2Cl2 (1.2 mL) analogous to the procedure described for the preparation of P378. The crude product was purified by silica gel column chromatography utilizing a solvent system of 30% EtOAc/Hexanes, 1% AcOH. After concentration and a toluene azeotrope (3×75 mL), 62.7 mg of P387 was isolated as a green solid (66%). $^1$H NMR (400 MHz, DMSO-d6) 2.13 (s, 3H), 2.69 (t, J=6.8 Hz, 2H), 4.27 (t, J=6.8 Hz, 2H), 6.58 (dd, J=10.4, 2.4 Hz, 1H), 6.95 (br s, 1H), 7.00 (dd, J=8.8, 2.8 Hz, 1H), 7.10 (dd, J=9.2, 2.4 Hz, 1H), 7.31 (d, J=2.8 Hz, 1H), 7.63 (d, J=8.8 Hz, 1H), 7.65-7.76 (m, 2H), 7.86 (m, 1H), 12.24 (br s, 1H). HPLC purity (95%), MS (ESI–) Calcd.: 556.4 m/z, Found: 556.9 m/z

Example 329

Preparation of P389

In an 8 mL vial equipped with a stir bar was placed I-36 (250 mg, 0.576 mmol) and anhydrous THF (2.8 mL) at room temperature. The yellow solution was cooled to 0° C. using an ice bath and then NaH (60%) (69.2 mg, 1.73 mmol) was added slowly and in portions. The solution turned from yellow to bright red. The mixture was allowed to warm to room temperature and then re-cooled to 0° C. upon which 2-(bromomethyl)benzonitrile (192 mg, 0.981 mmol) was added. The contents of the vial were allowed to react for a period of 18 hours. The reaction was cautiously quenched with water (1 mL) and 1 M aqueous HCl (3 mL) and allowed to stir for 10 minutes. After the material was transferred to a separatory funnel, water (15 mL) and 1 M aqueous HCl (15 mL) were added followed by extraction with EtOAc (3×40 mL). The organic portions were combined, washed with water (40 mL) and brine (40 mL), dried (MgSO4) and concentrated to produce a yellow solid. The crude material was triturated with ice cold CH2CL2 (30 mL) and the solid was collected by suction filtration followed by washing with additional ice cold CH2CL2 (2×30 mL). After filtration, 193 mg of P389 was isolated as a pale yellow solid (61%). $^1$H NMR (400 MHz, d6-DMSO)HPLC purity (95%)

Example 330

Preparation of P390

4,5-Dichloro-thiophene-2-sulfonic acid {(E)-3-[1-(3-cyano-benzyl)-5-fluoro-3-methyl-1H-indol-7-yl]-acryloyl}-amide. Compound I-36 (250 mg, 0.576 mmol) was alkylated using NaH (60%) (69.2 mg, 1.73 mmol) and 3-(bromomethyl)benzonitrile (192 mg, 0.981 mmol) in anhydrous THF (2.8 mL) in a manner analogous to the preparation of P389. After filtration, 186 mg of P390 was isolated as a lime green solid (59%). $^1$H NMR (400 MHz, DMSO-d6) 2.26 (s, 3H), 5.59 (s, 2H), 6.32 (d, J=15.6 Hz, 1H), 7.05 (dd, J=10.0, 2.4 Hz, 1H), 7.22 (d, J=7.6 Hz, 1H), 7.37 (br s, 1H), 7.40-7.47 (m, 3H), 7.69 (d, J=7.6 Hz, 1H), 7.90 (s, 1H), 7.94 (d, J=15.6 Hz, 1H). HPLC purity (87%), MS (ESI–) Calcd.: 547.5 m/z, Found: 546.2 m/z.

Example 331

Preparation of P391

Compound I-36 (250 mg, 0.576 mmol) was alkylated using NaH (60%) (69.2 mg, 1.73 mmol) and 4-(bromomethyl)benzonitrile (192 mg, 0.981 mmol) in anhydrous THF (2.8 mL) in a manner analogous to the preparation of P389. After filtration, 90.8 mg of P391 was isolated as a lime green solid (29%). $^1$H NMR (400 MHz, d6-DMSO)HPLC purity (95%)

Example 332

Preparation of P396

To a solution of P067 (4.0 g, 6.75 mmol) in THF (32 mL), was added water (1.6 mL). 2,3-Dichloro-5,6-dicyano-1,4-benzoquinone (4.6 g, 20.3 mmol) was added in one portion, and the resultant solution stirred overnight at room temperature. The mixture was concentrated in vacuo to remove organic solvents, and ethanol (60 mL) was added. The resulting mixture was heated to reflux for 1 hour, and allowed to cool naturally to room temperature overnight. The resulting suspension was filtered, and washed with ethanol until the washings were colorless. The resulting solid was refluxed with acetonitrile to remove residual P067, and allowed to cool to room temperature overnight. The resulting solid was treated with refluxing ethanol, cooled to room temperature, filtered and dried at 55° C. in vacuo overnight to give 1.72 g of P396 (42%). MS ESI– Calcd. 606.3 m/z Found: 605.1 m/z. H NMR (DMSO-d6)

Example 333

Preparation of P397

To a solution of P396 (1.3 g, 2.16 mmol) in THF (66 mL) was added water (0.52 mL), and the solution cooled to 0-5° C. Sodium borohydride (409 mg, 10.8 mmol) was added in portions over 5 min, and the mixture stirred for 30 min. The reaction mixture was diluted with EtOAc (75 mL), and washed with a half-saturated solution of aqueous ammonium chloride (2×80 mL), water (2×40 mL), and brine (50 mL). The solution was concentrated in vacuo, and the resulting solid was triturated with EtOAc, filtered, and dried in vacuo. The resulting solid was triturated twice with diethyl ether, and dried in vacuo to give 1.07 g (82%) of P397. $^1$H NMR (DMSO-d6).

Example 334

Preparation of P398

To a solution of P396 (300 mg, 0.495 mmol) and 2-methyl-2-butene (495 uL, 0.99 mmol) in THF (15 mL), was added, over 5 minutes, a solution of sodium chlorite (246 mg, 2.72 mmol) and monobasic sodium phosphate (416 mg, 3.46 mmol) in water (3.6 mL). The mixture was stirred at room temperature for 2 hours, and additional sodium chlorite (246 mg, 2.72 mmol) and monobasic sodium phosphate (416 mg, 3.46 mmol) in water (3.6 mL) was added, and the reaction stirred at room temperature for an additional 2 hours. The layers were separated, and the organics were washed with 1 N aqueous hydrochloric acid (15 mL), water (2×15 mL), and brine (15 mL). The resultant solution was concentrated in vacuo, and the resulting solid was treated with dichloromethane at 40° C. for 2 hours, and allowed to cool naturally to room temperature overnight. The resultant suspension was filtered, and the solid washed with dichloromethane, and dried at 35° C. in vacuo to afford 151 mg of P398 (50%). $^1$H NMR(DMSO-d$_6$) LC/MS (93%) ESI– Calcd. 622.3 m/z Found: 621.3 m/z Example 335

Preparation of P402

Synthesis of P402. In an 8 mL vial equipped with a stir bar was placed compound I-196 (100 mg, 0.243 mmol) and anhydrous DMF (500 µL) at room temperature. The yellow solution was cooled to 0° C. in an ice bath and then NaH (60%) (29.2 mg, 0.729 mmol) was added. The red mixture was warmed to room temperature and then re-cooled to 0° C., upon which 2-chloromethyl-imidazo[1,2-a]pyridine (48.7 mg, 0.292 mmol) was added. The mixture was warmed to room temperature and allowed to react for a period of 17 hours. The reaction was quenched with water (2 mL) and 1M HCl (4 mL). The resulting solid was collected via suction filtration, washed with ice cold CH2Cl2 (4 mL) and dried in a high vacuum oven at 70° C. for 5 hours. After drying, 14.3 mg of P402 was isolated as a tan solid (11%). $^1$H NMR (400 MHz, DMSO-d6) LC/MS (74%)

Example 336

Preparation of P395

Compound I-36 (250 mg, 0.576 mmol) was reacted with 2-chloromethyl-imidazo[1,2-a]pyridine (115 mg, 0.692 mmol) and NaH (60%) (138 mg, 3.46 mmol) in anhydrous DMF (2.8 mL) analogous to the procedure described for the preparation of P402. After drying, 233 mg of P395 was isolated as a tan solid (72%). $^1$H NMR (400 MHz, DMSO-d$_6$) 2.22 (s, 3H), 5.49 (s, 2H), 6.24 (d, J=15.6 Hz, 1H), 6.87 (m, 1H), 7.04 (dd, J=10.8, 2.8 Hz, 1H), 7.19-7.26 (m, 2H), 7.36 (br s, 1H), 7.47 (s, 1H), 7.48 (d, J=8.4 Hz, 1H), 8.22 (d, J=15.2 Hz, 1H), 8.27 (s, 1H), 8.43 (d, J=6.8 Hz, 1H). HPLC purity (89%), MS (ESI–) Calcd.: 562.5 m/z, Found: 563.1 m/z Example 337

Preparation of P399

Compound I-197 (100 mg, 0.254 mmol) was reacted with 2-chloromethyl-imidazo[1,2-a]pyridine (50.8 mg, 0.305 mmol) and NaH (60%) (30.5 mg, 0.762 mmol) in anhydrous DMF (500 µL) analogous to the procedure described for the preparation of P402. After drying, 16.2 mg of P399 was isolated as a tan solid (12%). $^1$H NMR (400 MHz, DMSO-d6) LC/MS (94%)

Example 338

Preparation of P400

Synthesis of 3-Chloro-N-[(E)-3-(5-fluoro-3-methyl-1H-indol-7-yl)-acryloyl]-benzenesulfonamide, I-201. I-201 was synthesized following the method for preparation of I-196 using I-34 (300 mg, 1.37 mmol), anhydrous CH2Cl2 (4 mL), 3-chlorobenzenesulfonamide (314 mg, 1.64 mmol), DMAP (200 mg, 1.64 mmol) and EDCI (314 mg, 1.64 mmol). After filtration, 286 mg of I-201 was isolated as a yellow solid (53%). $^1$H NMR (400 MHz, DMSO-d6) LC/MS (98%)

Synthesis of P400. Compound I-201 (100 mg, 0.255 mmol) was reacted with 2-chloromethyl-imidazo[1,2-a]pyridine (51.0 mg, 0.306 mmol) and NaH (60%) (30.7 mg, 0.765 mmol) in anhydrous DMF (500 µL) analogous to the procedure described for the preparation of P402. After drying, 83.0 mg of P400 was isolated as a yellow solid (62%). $^1$H NMR (400 MHz, DMSO-d6) 2.24 (s, 3H), 5.73 (s, 2H), 6.40 (d, J=15.2 Hz, 1H), 7.08 (dd, J=2.4, 10.0 Hz, 1H), 7.26-7.32 (m, 1H), 7.38 (s, 1H), 7.46 (dd, J=2.4, 9.2 Hz, 1H), 7.68-7.74 (m, 3H), 7.80 (s, 1H), 7.82-7.85 (m, 1H), 7.89-7.94 (m, 2H), 8.10 (d, J=15.2 Hz, 1H), 8.60 (d, J=6.8 Hz, 1H). LC/MS (95%), MS (ESI–) Calcd.: 522.0 m/z, Found: 521.5 m/z Example 339

Preparation of P401

Synthesis of 3-Fluoro-N-[(E)-3-(5-fluoro-3-methyl-1H-indol-7-yl)-acryloyl]-benzenesulfonamide, I-202. I-202 was synthesized following the method for preparation of I-196 using I-34 (300 mg, 1.37 mmol), anhydrous CH2Cl2 (4 mL), 3-fluorobenzenesulfonamide (287 mg, 1.64 mmol), DMAP (200 mg, 1.64 mmol) and EDCI (314 mg, 1.64 mmol). After filtration, 212 mg of I-202 was isolated as a yellow solid (41%). $^1$H NMR (400 MHz, DMSO-d6) LC/MS (97%)

Synthesis of P401. Compound I-202 (100 mg, 0.266 mmol) was reacted with 2-chloromethyl-imidazo[1,2-a]pyridine (53.1 mg, 0.319 mmol) and NaH (60%) (32.0 mg, 0.798 mmol) in anhydrous DMF (500 µL) analogous to the procedure described for the preparation of P402. After drying, 74.9 mg of P401 was isolated as a tan solid (55%). $^1$H NMR (400 MHz, DMSO-d6) LC/MS (97%)

Example 340

Preparation of P413

Synthesis of 2,4-Difluoro-N-[(E)-3-(5-fluoro-3-methyl-1H-indol-7-yl)-acryloyl]-benzenesulfonamide, I-203. I-203 was synthesized following the method for preparation of I-196 using I-34 (300 mg, 1.37 mmol), anhydrous CH2Cl2 (4 mL), 2,4-difluorobenzenesulfonamide (317 mg, 1.64 mmol), DMAP (200 mg, 1.64 mmol) and EDCI (314 mg, 1.64 mmol). After filtration, 297 mg of I-203 was isolated as a yellow solid (55%). $^1$H NMR (400 MHz, DMSO-d6) LC/MS (97%)

Synthesis of P413. Compound I-203 (100 mg, 0.254 mmol)) was reacted with 2-chloromethyl-imidazo[1,2-a]pyridine (50.8 mg, 0.305 mmol) and NaH (60%) (30.5 mg, 0.762 mmol) in anhydrous DMF (500 µL) analogous to the procedure described for the preparation of P402. After dry-

Example 341

Preparation of P403

Synthesis of 4-Fluoro-N-[(E)-3-(5-fluoro-3-methyl-1H-indol-7-yl)-acryloyl]-benzenesulfonamide, I-204. I-204 was synthesized following the method for preparation of I-196 using I-34 (300 mg, 1.37 mmol), anhydrous CH2Cl2 (4 mL), 4-fluorobenzenesulfonamide (287 mg, 1.64 mmol), DMAP (200 mg, 1.64 mmol) and EDCI (314 mg, 1.64 mmol). After filtration, 273 mg of I-204 was isolated as a yellow solid (53%). $^1$H NMR (400 MHz, DMSO-d6) LC/MS (96%)

Synthesis of P403. Compound I-204 (100 mg, 0.266 mmol) was reacted with 2-chloromethyl-imidazo[1,2-a]pyridine (53.1 mg, 0.319 mmol) and NaH (60%) (32.0 mg, 0.798 mmol) in anhydrous DMF (500 μL) analogous to the procedure described for the preparation of P402. After drying, 90.9 mg of P403 was isolated as a tan solid (67%). $^1$H NMR (400 MHz, DMSO-d6) LC/MS (95%)

Example 342

Preparation of P404

Synthesis of 3,5-Difluoro-N-[(E)-3-(5-fluoro-3-methyl-1H-indol-7-yl)-acryloyl]-benzenesulfonamide, I-205. I-205 was synthesized following the method for preparation of I-196 using I-34 (300 mg, 1.37 mmol), anhydrous $CH_2Cl_2$ (4 mL), 3,5-difluorobenzenesulfonamide (317 mg, 1.64 mmol), DMAP (200 mg, 1.64 mmol) and EDCI (314 mg, 1.64 mmol). After filtration, 278 mg of I-205 was isolated as a yellow solid (51%). $^1$H NMR (400 MHz, DMSO-d6) LC/MS (98%)

Synthesis of P404. Compound I-205 (100 mg, 0.254 mmol) was reacted with 2-chloromethyl-imidazo[1,2-a]pyridine (50.8 mg, 0.305 mmol) and NaH (60%) (30.5 mg, 0.762 mmol) in anhydrous DMF (500 μL) analogous to the procedure described for the preparation of P402. After drying, 90.2 mg of P404 was isolated as a tan solid (68%). $^1$H NMR (400 MHz, DMSO-d6) 2.24 (s, 3H), 5.77 (s, 2H), 6.44 (d, J=15.2 Hz, 1H), 7.09 (dd, J=2.8, 10.4 Hz, 1H), 7.34-7.37 (m, 1H), 7.40 (s, 1H), 7.47 (dd, J=2.4, 8.8 Hz, 1H), 7.62-7.65 (m, 2H), 7.72-7.80 (m, 3H), 7.86 (s, 1H), 8.07 (d, J=14.8 Hz, 1H), 8.66 (d, J=6.8 Hz, 1H). LC/MS (95%), MS (ESI−) Calcd.: 523.5 m/z, Found: 523.6 m/z.

Example 343

Preparation of P405

Synthesis of 4-Chloro-N-[(E)-3-(5-fluoro-3-methyl-1H-indol-7-yl)-acryloyl]-benzenesulfonamide, I-206. I-206 was synthesized following the method for preparation of I-196 using I-34 (300 mg, 1.37 mmol), anhydrous CH2Cl2 (4 mL), 4-chlorobenzenesulfonamide (314 mg, 1.64 mmol), DMAP (200 mg, 1.64 mmol) and EDCI (314 mg, 1.64 mmol). After filtration, 213 mg of I-206 was isolated as a yellow solid (40%). $^1$H NMR (400 MHz, DMSO-d6) LC/MS (98%)

Synthesis of P405. Compound I-206 (100 mg, 0.255 mmol)) was reacted with 2-chloromethyl-imidazo[1,2-a]pyridine (51.0 mg, 0.306 mmol) and NaH (60%) (30.7 mg, 0.765 mmol) in anhydrous DMF (500 μL) analogous to the procedure described for the preparation of P402. After drying, 110 mg of P405 was isolated as a tan solid (83%). $^1$H NMR (400 MHz, DMSO-d6) LC/MS (96%)

Example 344

Preparation of P406

3,4-Dichloro-N-[(E)-3-(5-fluoro-3-methyl-1H-indol-7-yl)-acryloyl]-benzenesulfonamide, I-207. I-207 was synthesized following the method for preparation of I-196 using I-34 (300 mg, 1.37 mmol), anhydrous $CH_2Cl2$ (4 mL), 3,4-dichlorobenzenesulfonamide (371 mg, 1.64 mmol), DMAP (200 mg, 1.64 mmol) and EDCI (314 mg, 1.64 mmol). After filtration, 321 mg of I-207 was isolated as a yellow solid (55%). $^1$H NMR (400 MHz, DMSO-d6) LC/MS (99%)

Synthesis of P406. Compound I-207 (100 mg, 0.234 mmol) was reacted with 2-chloromethyl-imidazo[1,2-a]pyridine (46.8 mg, 0.281 mmol) and NaH (60%) (28.0 mg, 0.702 mmol) in anhydrous DMF (500 μL) analogous to the procedure described for the preparation of P402. After drying, 95.1 mg of P406 was isolated as a yellow solid (73%). $^1$H NMR (400 MHz, DMSO-d6) LC/MS (95%)

Example 345

Preparation of P407

Synthesis of 2,5-Difluoro-N-[(E)-3-(5-fluoro-3-methyl-1H-indol-7-yl)-acryloyl]-benzenesulfonamide, I-208. I-208 was synthesized following the method for preparation of I-196 using I-34 (300 mg, 1.37 mmol), anhydrous CH2Cl2 (4 mL), 2,5-difluorobenzenesulfonamide (317 mg, 1.64 mmol), DMAP (200 mg, 1.64 mmol) and EDCI (314 mg, 1.64 mmol). After filtration, 284 mg of I-208 was isolated as a yellow solid (53%). $^1$H NMR (400 MHz, DMSO-d6) LC/MS (99%)

Synthesis of P407. Compound I-208 (100 mg, 0.254 mmol) was reacted with 2-chloromethyl-imidazo[1,2-a]pyridine (50.8 mg, 0.305 mmol) and NaH (60%) (30.5 mg, 0.762 mmol) in anhydrous DMF (500 μL) analogous to the procedure described for the preparation of P402. After drying, 106 mg of P407 was isolated as a yellow solid (80%). $^1$H NMR (400 MHz, DMSO-d6) LC/MS (97%).

Example 346

Preparation of P408

Synthesis of 3,5-Dichloro-N-[(E)-3-(5-fluoro-3-methyl-1H-indol-7-yl)-acryloyl]-benzenesulfonamide, I-209. I-209 was synthesized following the method for preparation of I-196 using I-34 (300 mg, 1.37 mmol), anhydrous CH2Cl2 (4 mL), 3,5-dichlorobenzenesulfonamide (371 mg, 1.64 mmol), DMAP (200 mg, 1.64 mmol) and EDCI (314 mg, 1.64 mmol). After filtration, 215 mg of I-209 was isolated as a yellow solid (37%). $^1$H NMR (400 MHz, DMSO-d6) LC/MS (98%).

Synthesis of P408. Compound I-209 (100 mg, 0.234 mmol) was reacted with 2-chloromethyl-imidazo[1,2-a]pyridine (46.8 mg, 0.281 mmol) and NaH (60%) (28.0 mg, 0.702 mmol) in anhydrous DMF (500 μL) analogous to the procedure described for the preparation of P402. After drying, 117 mg of P408 was isolated as a tan solid (90%). $^1$H NMR (400 MHz, DMSO-d6) LC/MS (96%)

Example 347

Preparation of P409

Synthesis of 2-Fluoro-N-[(E)-3-(5-fluoro-3-methyl-1H-indol-7-yl)-acryloyl]-benzenesulfonamide, I-210. I-210 was synthesized following the method for preparation of I-196 using I-34 (300 mg, 1.37 mmol), anhydrous CH2Cl2 (4 mL), 2-fluorobenzenesulfonamide (287 mg, 1.64 mmol), DMAP (200 mg, 1.64 mmol) and EDCI (314 mg, 1.64 mmol). After filtration, 275 mg of I-210 was isolated as a yellow solid (53%). $^1$H NMR (400 MHz, DMSO-d6) LC/MS (99%)

Synthesis of P409. Compound I-210 (100 mg, 0.266 mmol) was reacted with 2-chloromethyl-imidazo[1,2-a]pyridine (53.1 mg, 0.319 mmol) and NaH (60%) (32.0 mg, 0.798 mmol) in anhydrous DMF (500 µL) analogous to the procedure described for the preparation of P402. After drying, 98.1 mg of P409 was isolated as a tan solid (73%). $^1$H NMR (400 MHz, DMSO-d6) LC/MS (98%).

Example 348

Preparation of P395

Compound I-36 (250 mg, 0.576 mmol) was reacted with 2-chloromethyl-imidazo[1,2-a]pyridine (115 mg, 0.692 mmol) and NaH (60%) (138 mg, 3.46 mmol) in anhydrous DMF (2.8 mL) analogous to the procedure described for the preparation of P402. After drying, 233 mg of P395 was isolated as a tan solid (72%). $^1$H NMR (400 MHz, DMSO-d6) 2.22 (s, 3H), 5.49 (s, 2H), 6.24 (d, J=15.6 Hz, 1H), 6.85-6.89 (m, 1H), 7.04 (dd, J=2.8, 10.8 Hz, 1H), 7.19-7.26 (m, 2H), 7.36 (bs, 1H), 7.47 (s, 1H), 7.48 (d, J=8.4 Hz, 1H), 8.22 (d, J=15.2 Hz, 1H), 8.27 (s, 1H), 8.43 (d, J=6.8 Hz, 1H). HPLC purity (89%), MS (ESI−) Calcd.: 562.5 m/z, Found: 563.1 m/z General Procedure (A-21) for Hydrogenation To a solution of compound I-131D in ethanol was added 10% Pd/C (0.1 g/g compound 1). The resultant mixture was degassed, and the atmosphere replaced with hydrogen 3 times. The mixture was stirred under hydrogen at ambient pressure for 5 days. The reaction mixture was filtered through celite, the cake washed with ethanol, and the filtrate concentrated. The crude reaction mixture was purified via silica gel chromatography, using dichloromethane as eluent, followed by silica gel chromatography using an EtOAc/hexanes gradient as eluent to provide compounds I-211 and I-212. I-211: 3-[1-(3,4-Difluoro-benzyl)-3a-methyl-2-oxo-octahydro-indol-7-yl]-propionic acid methyl ester, MS ESI+ Calcd. 365.4 m/z Found: 366.0 m/z $^1$H NMR(CDCl$_3$). I-212: 3-[1-(3,4-Difluoro-benzyl)-3a-methyl-2-oxo-2,3,3a,4,5,6-hexahydro-1H-indol-7-yl]-propionic acid methyl ester. MS ESI+ Calcd. 363.4 m/z Found: 364 m/z $^1$H NMR(CDCl$_3$)

General Procedure (A-22) for Hydrolysis of Methyl Esters

To a solution of the appropriate methyl ester in THF/MeOH (2:1), was added aqueous NaOH (3 eq), and the reaction stirred for 24-72 hours at room temperature. The mixture was concentrated to remove organics, diluted with water, and washed with 2 portions of dichloromethane. The pH was adjusted to 2-3 (litmus) with 1 N HCl, and extracted with EtOAc. The organics were washed with water and brine, dried over magnesium sulfate, and concentrated to obtain the desired compound.

General Procedure (A-23) for Acylsulfonamide Formation

To a solution of the appropriate starting acid, the appropriate sulfonamide (1.05 eq) and DMAP (2.4 eq) in CH2Cl2, was added EDCI (2.5 eq). The reaction mixture was stirred at room temperature for 1-5 days. The reaction was washed with 1N HCl$_{(aq)}$, water, and brine, dried over magnesium sulfate, and concentrated in vacuo. The residue was purified either via chromatography on silica gel, using a gradient of methanol in dichloromethane (0-5%) as eluent, or via trituration with dichloromethane/hexanes to obtain the title compound.

Example 349

Preparation of P410

Synthesis of 3-[1-(3,4-Difluoro-benzyl)-3a-methyl-2-oxo-octahydro-indol-7-yl]-propionic acid I-213.

Following general procedure (A-22), compound I-211 was converted to I-213 in quantitative yield. LC/MS (100%) APCI− Calcd. 351.4 m/z Found: 350.2 m/z $^1$H NMR(CDCl$_3$)

Synthesis of P410. Following general procedure A-23, compound I-213 was coupled with 2,4,5-trifluorobenzenesulfonamide to provide P410 in 46% yield. LC/MS (84%) ESI− Calcd. 544.5 m/z Found: 543.5 m/z. $^1$H NMR(CDCl$_3$)

Example 350

Preparation of P411

Synthesis of 3-[1-(3,4-Difluoro-benzyl)-3a-methyl-2-oxo-2,3,3a,4,5,6-hexahydro-1H-indol-7-yl]-propionic acid, I-214

Following general procedure (A-22), compound I-212 was converted to I-214 in 61% yield. LC/MS (98%) ESI+ Calcd. 349.4 m/z Found: 350.9 m/z $^1$H NMR(CDCl$_3$)

Synthesis of P411. Following general procedure A-23, compound I-214 was coupled with 2,4,5-trifluorobenzenesulfonamide to provide P411 in 81% yield. LC/MS (81%) ESI− Calcd. 542.5 m/z Found: 542.3 m/z $^1$H NMR(CDCl$_3$)

Example 351

Preparation of P415

Following general procedure A-23, compound I-213 was coupled with 4,5-dichlorothiophene-2-sulfonamide to provide P415 in 70% yield. LC/MS (93%) ESI− Calcd. 563.5 m/z Found: 563.4 m/z $^1$H NMR(CDCl$_3$)

Example 352

Preparation of P414

Following general procedure A-21, P306 was subjected to hydrogenation conditions to afford P414 in 40% yield. LC/MS (98.9%) ESI− Calcd. 537.5 m/z Found: 537.5 m/z $^1$H NMR(CDCl$_3$)

Example 353

Preparation of P412

Synthesis of 3-[1-Methyl-4-(naphthalen-2-yloxy)-1H-indol-3-yl]-propionic acid, I-215. Following general procedure A-21, I-137A was subjected to hydrogenation conditions to afford I-215 in 40% yield. $^1$H NMR(CDCl$_3$)

Synthesis of P412. Following general procedure A-23, compound I-215 was coupled with 2,4,5-trifluorobenzenesulfonamide to provide P412 in 46% yield. LC/MS (90%) ESI− Calcd. 538.4 m/z Found: 537.8 m/z $^1$H NMR(CDCl$_3$)

Example 354

Preparation of P362

Following general procedure A-23, compound I-215 was coupled with 3,4,-difluorobenzenesulfonamide to provide P362 in 54% yield. $^1$H-NMR (400 MHz, DMSO-$d_6$), MS (ESI$^-$): 519.6 (M−1), RP-HPLC: 94%

Example 355

Preparation of P257

Synthesis of 4-Iodo-1-methyl-1H-indazol-3-ylamine, I-216. To a 330 mL pressure vessel equipped with a magnetic stir bar was added 2-fluoro-6-iodobenzonitrile (4.5 g, 18.2 mmol), N,N-dimethylacetamide (45 mL), and methylhydrazine (1.2 mL 23.7 mmol). The vessel was flushed with N2 gas, sealed and heated at 87° C. overnight and at 120° C. for 5 h. The reaction mixture was cooled, diluted with EtOAc (300 mL, and washed with water. The aqueous layer was extracted and the combined EtOAc extracts were washed with water (3×150 mL), brine, dried (Na2SO4), filtered and concentrated to a brown solid. The solid was triturated with EtOAc/hexanes (1:1, 10 mL), filtered, washed with EtOAc/hexanes (1:1) and dried to give 4.04 g (81%) of I-216 as a beige solid. 1H NMR (400 MHz, DMSO-d6)

Synthesis of Naphthalene-2-carboxylic acid (4-iodo-1-methyl-1H-indazol-3-yl)-amide, I-217. To I-216 (470 mg, 1.71 mmol) dissolved in anhydrous THF (7 mL) was added triethylamine (477 uL, 346 mg, 3.42 mmol) and the stirring reaction mixture was cooled to 0° C. under a nitrogen atmosphere. To this stirring solution was added 2-naphthoyl chloride (326 mg, 1.71 mmol) in one portion and the reaction mixture was allowed to warm to rt and stir overnight. The reaction mixture was filtered, and the resulting solid was washed with THF and CH2Cl2. The solid was stirred with ethanol (15 mL), filtered, the resulting solid was washed with ethanol and dried to give 476 mg (65%) of I-217 as a white solid. 1H NMR (400 MHz, DMSO-d6)

Synthesis of (E)-3-{1-Methyl-3-[(naphthalene-2-carbonyl)-amino]-1H-indazol-4-yl}-acrylic acid methyl ester, I-218. To a pressure tube equipped with a magnetic-stir bar was added I-217 (200 mg, 0.468 mmol), triethylamine (10 mL), palladium (II) acetate (10.5 mg, 0.047 mmol) and tri-o-tolylphosphine (43 mg, 0.14 mmol). The solution was degassed by bubbling N2 gas through the solution for 30 min. Methyl acrylate (956 mg, 1 mL, 36 mmol) was added, the solution was degassed for an additional 5 min and then the tube was sealed, heated at 75° C. for 30 min and then at 100° C. for 6 h. The reaction mixture was cooled to rt, anhydrous DMF (20 mL) and additional palladium (II) acetate (11 mg, 0.049 mmol) was added. The solution was again degassed, sealed and heated in an oil bath at 105° C. for 6 h and then allowed to cool to rt. The reaction mixture was diluted with EtOAc and washed with water. The aqueous layer was extracted with EtOAc and the combined organic extracts were washed with water (3×), brine and dried (Na2SO4). The solution was filtered and concentrated to 210 mg of I-218, deemed of sufficient purity to be carried on to the next step. 1H NMR (400 MHz, DMSO-d6)

Synthesis of (E)-3-{1-Methyl-3-[(naphthalene-2-carbonyl)-amino]-1H-indazol-4-yl}-acrylic acid, I-219. To a 25 mL round-bottomed, one-necked flask equipped with a magnetic stir was added I-218 (210 mg, 0.468 mmol), methanol and THf (5 mL each). To this stirring solution was added 2M aqueous NaOH (0.85 mL, 1.70 mmol). After 2 h and additional portion of 2M aqueous NaOH (0.54 mL, 1.08 mmol) was added and the reaction mixture was heated at 40° C. overnight. The cooled reaction mixture was acidified with 1M aqueous HCl and extracted with EtOAc (3×). The combined organic extracts were washed with brine and dried (Na2SO4). The residue from evaporation of the solvent was purified by column chromatography using 2:2:1 CH2Cl2/THF/hexane and then 6:6:1 CH2Cl2/THF/methanol to give 95 mg of I-219. 1H NMR (400 MHz, DMSO-d6)

Synthesis of P257. Following the general Procedure A-8, the acrylic acid I-219, was reacted with 4,5-Dichlorothiophene-2-sulfonic acid amide to provide compound P257. 1H NMR (DMSO-d6) 4.06 (s, 3H), 6.61 (d, J=20.0), 7.47 (m, 2H), 7.56 (s, 1H), 7.66 (m, 2H), 7.72 (m, 1H), 8.01 (m, 3H), 8.16 (m, 1H), 8.67 (s, 1H), 10.74 (s, 1H) LC/MS (96%) ESI+ Calcd: 585.49 Found: 585.4 m/z Example 356

Preparation of P246

Synthesis of 1,3-Bis-trimethylsilanyloxy-2-(1-trimethylsilanyloxy-vinyl)-benzene, I-220.

1M LiHMDS (52 mL, 51.8 mmol, 3.15 equiv.) solution in THF was added gradually to a solution of 2,6-dihydroacetophenone (2.5 g, 16.4 mmol, 1 equiv.) in THF (100 mL) and the reaction mixture was stirred for 15 min at rt. Chlorotrimethylsilane (7.3 mL, 57.4 mmol, 3.5 equiv.) was added in one portion (exothermic) and the reaction mixture was stirred for 5 min. The reaction mixture was concentrated to about 11 g. Anhydrous CH2Cl2 (50 mL) was added, precipitate was filtered off, washed with CH2Cl2 and mother liquor was concentrated to afford I-220 (6.04 g, 100%) as brown liquid. $^1$H-NMR (500 MHz, CDCl$_3$) confirmed the structure.

Synthesis of 4-Hydroxy-benzofuran-3-one, I-221. A solution of N-bromosuccinimide (3.2 g, 18.02 mmol, 1.1 equiv.) in acetonitrile (22 mL) was gradually added to a solution of I-220 (6.04 g, 16.4 mmol, 1 equiv.) in acetonitrile (72 mL) and the reaction mixture was stirred for 20 min. The crude mixture was concentrated, diluted with CH2Cl2 (50 mL). The CH2Cl2 solution was washed successively with saturated aqueous NaHCO$_3$ (30 mL) solution, 1 N aqueous NaOH (20 ml×2), water (50 mL), brine (50 mL), and concentrated. MeOH (34 mL) and water (12 mL) was added. Conc. HCl (2 mL) was added slowly, the solution was stirred for 15 min, then water (50 mL) was added and the mixture was concentrated in vacuo. Water (50 mL) was added and the mixture was extracted with EtOAc (3×15 mL). The combined organic extracts were washed with water, brine, dried over MgSO$_4$ to afford yellow solid (3.21 g). Acetone (80 mL) was added, followed by K$_2$CO$_3$ (4.8 g) at rt. The suspension was stirred at rt for 1 h, then filtered and concentrated. CH2CL2 added followed by 10% HCl. Organic layer was washed with water, brine, dried over MgSO$_4$ to afford crude I-221 (2.0 g, 84% crude yield) as orange solid. MTBE (6 mL) added, suspension was cooled to 0° C. and filtered off to afford pure I-221 (1.24 g, 50%) as orange solid. MS (AP$^+$): 151 (M+1). $^1$H-NMR (500 MHz, CDCl$_3$) confirmed the structure.

Synthesis of 3-(Naphthalen-2-ylsulfanyl)-benzofuran-4-ol, I-222. HCl (2.0 M, in ether, 3.75 mL, 5 equiv.) solution was added to a preheated at 40° C. solution of I-221 (225 mg, 1.5 mmol, 1 equiv.) and 2-naphthalenethiol (240 mg, 1.5 mmol, 1 equiv.) in EtOH (3.75 mL) and stirred at rt for 23 h. The reaction mixture was concentrated in vacuo. The residue was dissolved in EtOAc, and the solution was washed with water, brine, dried over MgSO$_4$ to afford 470 mg as yellow solid. Solid was triturated with hexane (4 mL) at rt, then with hexane (2 mL) at reflux and filtered to afford I-222 (291 mg, 66%) as yellow solid.

Synthesis of [3-(Naphthalen-2-ylsulfanyl)-benzofuran-4-yloxy]-acetic acid methyl ester, I-123. To a solution of methyl bromoacetate (156 mg, 1.02 mmol, 1.2 equiv.) in acetone (1 mL) was added to a suspension of I-222 (249 mg, 0.85 mmpol, 1 equiv.) and K₂CO₃ (176 mg, 1.275 mmol, 1.5 equiv.) in acetone (2 mL). The reaction mixture was sealed in a 20 mL vial and heated at 70°-80° C. for 3 h. Water (8 mL) was added followed by EtOAc (4 mL), and the mixture was acidified with 10% HCl to pH=5. The organic layer was separated, washed with water, brine, dried over MgSO₄ to afford I-223 (310 mg, 100%) as red oil which crystallized upon standing. MS (ESI⁺): 366 (M+1). ¹H-NMR (500 MHz, CDCl₃) confirmed the structure.

Synthesis of [3-(Naphthalen-2-ylsulfanyl)-benzofuran-4-yloxy]-acetic acid, I-224. A solution of 2N aqueous NaOH (1.05 mL, 2.09 mmol, 2.5 equiv.) was added dropwise to a solution of I-223 (305 mg, 0.834 mmol, 1 equiv.) in THF-MeOH (1:1, 5 mL). The reaction mixture was stirred at rt for 15 min. Reaction was concentrated in vacuo, water was added followed by EtOAc. The mixture was acidified with 10% HCl. The organic layer was washed with water, brine, dried over MgSO₄ to afford I-224 (293 mg, 100%) as oil. MS (ESI⁻): 349 (M−1). ¹H-NMR (500 MHz, CDCl₃) confirmed the structure.

Synthesis of P246. To the I-224 (22 mg, 0.063 mmol, 1 equiv.) in 0.5 mL dichloromethane was added DMAP (15 mg, 0.126 mmol, 2 equiv.), 4,5-dichloro-2-thiophenesulfonamide (31 mg, 0.132 mmol, 2.1 equiv.), and EDCI (24 mg, 0.126 mmol, 2 equiv.). The mixture was stirred at room temperature for 3 h and then quenched with 10% HCl followed by water. Aqueous layer was extracted with EtOAc. The combined organic extracts were washed with water, brine, and then dried over MgSO₄. The solution was concentrated and the residue was chromatographed on silica gel with EtOAc/Hex, 3:7 then 1:1 to afford P246 (13 mg, 37%) as yellowish oil. LC-MS (ESI⁻): 563 (M−1) (92%). ¹H NMR (CDCl₃) 4.53 (s, 2H), 6.55 (m, 1H), 7.33 (bs, 2H), 7.35 (dd, J=11.0, 2.0 Hz, 1H), 7.40-7.47 (m, 3H), 7.60 (d, J=2.0 Hz, 1H), 7.64 (bd, J=8.5 Hz, 1H), 7.73-7.78 (m, 2H), 7.85 (bs, 1H), 10.10 (s, 1H). LC-MS (99%): ESI⁻ Calcd. 563 m/z Found: 563

Example 357

Preparation of P256

A solution of oxone (131 mg, 0.21 mmol, 3 equiv) in water (0.7 mL) was gradually added to a stirring solution of P246 (40 mg, 0.071 mmol, 1 equiv.) in dioxane/MeOH (1:1, 2 mL) at rt. The reaction mixture was stirred overnight at rt. Water (5 mL) was added, the precipitate was filtered, washed with water (2×1.5 mL) and ethanol (2 mL), and dried to afford P256 (32 mg, 78%) as a white solid. LC-MS (98%): ESI⁻ Calcd. 579 m/z Found: 579. ¹H-NMR (CDCl₃) 4.48 (d, J=14.8 Hz, 1H), 4.52 (d, J=14.8 Hz, 1H), 6.60 (dd, J=8.0, 0.8 Hz, 1H), 7.25 (dd, J=8.4, 0.4 Hz, 1H), 7.32 (d, J=8.4 Hz, 1H), 7.50 (dd, J=8.8, 2.0 Hz, 1H), 7.59-7.63 (m, 2H), 7.73 (d, J=4.8 Hz, 1H), 7.88-7.93 (m, 4H), 8.32 (d, J=2.0 Hz, 1H), 12.70 (br s, 1H)

Example 358

Preparation of P254

Synthesis of P254. Peracetic acid (0.45 mL, 32%, 2.13 mmol) was gradually added to a stirring solution of P246 (40 mg, 0.071 mmol, 1 equiv.) in CH2Cl2 (2 mL) at rt. The reaction was allowed to stir at rt for 3 days. The reaction was quenched with addition of water/CH₂Cl2 (4 mL each). Organic layer was separated and washed with water, brine, dried over MgSO₄ to afford P254 (32 mg, 76%) as an oil, which crystallized to a white solid. LC-MS (92%): ESI⁻ Calcd. 595 m/z Found: 595. ¹H-NMR (CDCl₃) 4.67 (s, 2H), 6.94 (dd, J=8.0, 0.4 Hz, 1H), 7.28 (dd, J=8.4, 0.8 Hz, 1H), 7.51 (dd, J=8.4, 0.8 Hz, 1H), 7.62-7.71 (m, 2H), 7.72 (s, 1H), 7.88-7.94 (m, 3H), 7.97 (d, J=9.2 Hz, 1H), 8.08 (s, 1H), 8.62 (d, J=0.8 Hz, 1H), 12.70 (br s, 1H).

Example 359

Preparation of P317

Compound I-205 (78 mg, 0.15 mmol) was reacted with 3,4-difluorobenzyl bromide (37 mg, 0.18 mmol) and NaH (60%) (13 mg, 0.33 mmol) in anhydrous DMF (2 mL) analogous to the procedure described for the preparation of P402. After drying, 57 mg of P317 was isolated as a yellow solid (73%). ¹H NMR (CDCl₃) 2.29 (d, J=1.2 Hz, 3H), 5.34 (s, 2H), 6.11 (d, J=15.2 Hz, 1H), 6.69 (m, 1H), 6.81 (m, 1H), 6.95 (s, 1H), 6.97 (dd, J=9.6, 2.4 Hz, 1H), 7.03 (m, 1H), 7.12 (m, 1H), 7.29 (dd, J=8.4, 2.4 Hz, 1H), 7.64-7.70 (m, 2H), 8.09 (dd, J=15.6, 1.2 Hz, 1H), 8.23 (bs, 1H). LC-MS (95%): ESI⁻ Calcd. 520.5 m/z Found: 520.5.

Example 360

Preparation of P321

Compound I-36 (70 mg, 0.16 mmol) was alkylated using NaH (60%) (8.5 mg, 0.36 mmol) and 3,4-difluorobenzyl bromide (50 mg, 0.24 mmol) in anhydrous DMF (2.8 mL) in a manner analogous to the preparation of P068. After filtration and column chromatography, 50 mg of P321 was isolated as a yellow solid (55%). ¹HNMR (DMSO-d₆) 5.51 (s, 2H), 6.26 (d, J=16 Hz, 1H), 6.66 (m, 1H), 6.99 (m, 1H), 7.04 (dd, J=10, 2.4 Hz, 1H), 7.41 (s, 1H), 7.23 (m, 1H), 7.43 (dd, J=12, 2.4 Hz, 1H), 7.87 (s, 1H), 7.98 (d, J=11.6 Hz, 1H), LC/MS (92%) (ESI−) Calcd. 558 m/z Found 557 m/z Example 361

Preparation of P258

Synthesis of 4-Methoxy-1-methyl-1H-indole-2,3-dione, I-225. 4-Methoxyisatin (prepared following the procedure of Hewawasam, P. and Meanwell, N. A. Tet. Lett. 1994, 35, 7303-7306, 1.5 g, 8.47 mmol) was dissolved in acetone (30 mL) and potassium carbonate (2.9 g, 21.2 mmol) and iodomethane (1.3 mL, 3.0 g, 21.2 mmol) were added. The resulting solution was stirred at rt overnight. The reaction mixture was filtered and the solids rinsed with acetone to give 1.5 g of a residue. This residue was heated in ethanol (13 mL) and 33% aqueous KOH (5 mL) at 70° C. for 1.5 h. The mixture was concentrated and then acidified with dilute aqueous HCl. The resulting red solid was filtered and dried to give 0.8 g of I-225. 1H NMR (500 MHz, DMSO-d6)

Synthesis of 4-Hydroxy-1-methyl-1H-indole-2,3-dione, I-226. Compound I-225 (0.446 g, 0.0023 mol) was dissolved in anhydrous CH2Cl2 (20 mL), and cooled to 0° C. under nitrogen. A solution of 1M BBr3 in CH2Cl2 (9.2 mL, 0.0092 mol) was added dropwise. The resulting mixture was stirred 1 h at rt, after which it was concentrated, taken into THF/EtOAc (2:1), washed with brine, dried over anhydrous sodium sulfate, filtered and concentrated to afford I-226 (0.300 g). MS (ESI⁻)=176.3 (M−1). LC/MS(ESI⁻) 91.3%. 1H NMR (400 MHz, DMSO-d6).

Synthesis of (1-Methyl-2,3-dioxo-2,3-dihydro-1H-indol-4-yloxy)-acetic acid methyl ester, I-227. I-226 (0.300 g, 0.0017 mol) was dissolved in EtCOMe (10 mL). Potassium carbonate (0.2573 g, 0.00186 mol) and methyl bromoacetate (0.21 mL, 0.0022 mol) were added. The mixture was stirred at rt for 3 days and then concentrated. The residue was diluted with EtOAc, washed with brine, and the organic layer was dried over anhydrous sodium sulfate, filtered, and concentrated to afford I-227 (0.300 g). MS (ESI+)=250.2 (M+1). LC/MS(ESI+) 92.8%.

Synthesis of (1-Methyl-2,3-dioxo-2,3-dihydro-1H-indol-4-yloxy)-acetic acid, I-228.

I-227 (0.300 g, 0.0012 mol) was dissolved in THF (10 mL). Aqueous 1M LiOH solution (2.4 mL, 0.0024 mol) was added and the mixture was stirred 1 h at rt. After concentration, the residue was triturated with 2M aqueous HCl, then with water, and dried to afford I-228 (0.280 g). MS (ESI+)=236.2 (M+1). LC/MS(ESI+) 86.4%. $^1$H NMR (400 MHz, DMSO-d6).

Synthesis of 4,5-Dichloro-thiophene-2-sulfonic acid [2-(1-methyl-2,3-dioxo-2,3-dihy
dro-1H-indol-4-yloxy)-acetyl]-amide, I-229. I-228 (0.280 g, 0.0012 mol) was dissolved in THF (2 mL). After addition of CH2Cl2 (1 mL), EDCI (0.4601 g, 0.0024 mol), DMAP (0.2928 g, 0.0024 mol), and 2,3-dichlorothiophene-5-sulfonamide (0.3062 g, 0.00132 mol), the mixture was stirred for two days at rt, concentrated, dissolved in THF/EtOAc (2:1), and partitioned with 2M aqueous HCl. The organic layer was washed with brine, dried over anhydrous sodium sulfate, filtered, concentrated, and triturated with ether/EtOAc (2:1) to afford I-229 (0.140 g). MS (ESI−)=447.2 (M−1). 1H NMR (400 MHz, DMSO-d6).

Synthesis of P258. I-229 (0.100 g, 0.223 mmol) was dissolved in methanol (2 mL). 3,4-Dichloroaniline (0.043 g, 0.267 mmol) was added, followed by p-toluenesulfonic acid hydrate (0.002 g, 0.010 mmol). The resulting mixture was stirred in closed vial, at 80° C. overnight, after which it was cooled to room temperature, concentrated, re-dissolved in acetic acid (1 mL), and sodium cyanoborohydride (0.100 g, 1.591 mmol) was added. The mixture was stirred at room temperature for 4 h, after which it was concentrated, washed with water, and chromatographed on silica gel (MeOH/CH2CL2 0.5%-20% gradient) to give P258 (9 mg). 1H NMR (500 MHz, DMSO-d6) 3.07 (s, 3H), 3.50-3.70 (m, 1H), 4.05-4.40 (m, 2H), 4.98 (d, J=7.0 Hz, 1H), 5.75 (s, 1H), 6.46 (d, J=8.5 Hz, 1H), 6.62 (d, J=7.5 Hz, 1H), 6.70 (s, 1H), 6.73 (m, 1H), 7.18 (dd, J=8.5, 8.0 Hz, 1H), 7.23 (s, 1H), 7.34 (s, 1H). LC/MS (90.2%) ESI+ Calcd. M=595.3 Found: 596.1 m/z Example 362

Preparation of P249

Using Method A-15 and substituting 2-naphthylsulfonamide for the aniline, I-186 was converted to P249 in 70%; $^1$HNMR (DMSO-d6) 3.15 (s, 3H), 6.81 (d, J=16 Hz, 1H), 7.15 (d, J=8 Hz, 1H), 7.39 (d, J=8 Hz, 1H), 7.44 (s, 1H), 7.68 (m, 3H), 7.81 (s, 1H), 7.88 (dd, J=8.8, 2.0 Hz, 1H), 8.04 (m, 2H), 8.13 (t, J=9.2 Hz, 2H), 8.22 (d, J=16.0 Hz, 1H), 8.43 (m, 1H)

Example 363

Preparation of P251

Using Method A-16, and substituting 2-naphthylsulfonamide for the aniline, I-186 was converted to P242 in 80% yield. $^1$HNMR (DMSO-$d_6$) 3.09 (s, 3H), 6.66 (d, J=16 Hz, 1H), 7.03 (d, J=7.6 Hz, 1H), 7.28 (d, J=8 Hz, 1H), 7.38 (t, J=7.6 Hz, 1H), 7.44 (s, 1H), 7.64-7.71 (m, 2H), 7.81 (s, 1H), 7.87-7.93 (m, 2H), 8.02 (d, J=7.6 Hz, 1H), 8.11 (t, J=9.2 Hz, 2H), 8.43 (d, J=1.6 Hz, 1H).

Example 364

Preparation of P323

Synthesis of (E)-3-[1-(2,4-Dichloro-benzyl)-5-fluoro-3-methyl-1H-indol-7-yl]-acrylic acid methyl ester, I-230. To I-191 (320 mg, 0.826 mmol) in anhydrous DMF (2 mL) was added palladium (II) acetate (4.6 mg, 0.0206 mmol), tri-o-tolylphosphine (25.2 mg, 0.0824 mmol), and triethylamine (0.574 mL, 4.12 mmol). The mixture was degassed by bubbling N2 gas through the solution for 20 min. Methyl acrylate (370 uL, 4.12 mmol) was added, the solution was degassed for an additional 5 min, the vial was capped and placed in an oil bath at 100° C. After 40 h, the reaction mixture was cooled to rt, diluted with EtOAc and water (4 ml each) and extracted. The aqueous layer was extracted (2×4 mL), and the combined organic extracts were washed with water (3×10 mL) and dried (Na2SO4). The solution was filtered and concentrated to give 337 mg of I-230 of sufficient purity to be carried on to the next step. 1H NMR (400 MHz, CDCl3)

Synthesis of (E)-3-[1-(2,4-Dichloro-benzyl)-5-fluoro-3-methyl-1H-indol-7-yl]-acrylic acid, I-231. In an 18 mL vial equipped with a stir bar was placed ester I-XXX (337 mg, 0.859 mmol), THF (4 mL), MeOH (2 mL) and 15% aq NaOH (1.28 mL, 4.81 mmol) at room temperature. The mixture was allowed to stir at room temperature for 24 hours. The reaction mixture was concentrated, washed with Et$_2$O (3×20 mL), acidified to pH 1 with 1M HCl and extracted with CH2Cl2 (2×35 mL). The organic portions were combined, dried (MgSO$_4$) and concentrated to produce 259 mg of acid I-XXX as a lime green solid (80%). $^1$H NMR (400 MHz, CDCl$_3$)

Synthesis of P323. In an 8 mL vial equipped with a stir bar was placed I-231 (41 mg, 0.108 mmol), 2,4,5-trifluorobenzenesulfonamide (23.2 mg, 0.110 mmol), DMAP (31.6 mg, 0.259 mmol), anhydrous CH2CL2 (2 mL), and EDCI (51.8 mg, 0.270 mmol) at room temperature. The vial was sealed with a cap and allowed to react for 22 hours at room temperature. The contents of the vial were washed with 1M HCl (5 mL), water (3×5 mL) and then brine (5 mL). The organic portion was dried (MgSO$_4$) and concentrated to produce P323 as a lime green solid. This crude material was dissolved in boiling Et$_2$O (1 mL) followed by the addition of hexanes (1 mL). The resulting solid was collected by suction filtration to produce 23.9 mg of P323 as a lime green solid (39%). $^1$H NMR (400 MHz, CDCl$_3$) 2.29 (s, 3H), 5.37 (s, 2H), 6.18 (d, J=15.2 Hz, 1H), 6.31 (d, J=8.4 Hz, 1H), 6.87 (s, 1H), 6.82 (dd, J=2.8, 10.0 Hz, 1H), 7.04 (dd, J=2.0, 8.4 Hz, 1H), 7.07-7.13 (m, 1H), 7.31 (dd, J=2.8, 8.8 Hz, 1H), 7.41 (d, J=2.4 Hz, 1H), 7.82 (d, J=14.8 Hz, 1H), 7.98-8.04 (m, 1H). LC/MS (96%) MS (ESI−) Calcd.: 570.4 m/z, Found: 569.4 m/z Example 365

Preparation of P371

Synthesis of 4-(3-Methoxyphenoxy)-1-methyl-1H-indole, I-134L: Following the general Procedure A-12, I-133, was reacted with 3-methoxy-phenol to provide compound I-134L. Consistent with 1H-NMR.

Synthesis of 4-(3-Methoxyphenoxy)-1-methyl-1H-indole-3-carbaldehyde, I-135L: Following the general Procedure A-13, I-134L, was converted to formaldehyde I-135L. Consistent with 1H-NMR.

Synthesis of (E)-3-[4-(3-Methoxyphenoxy)-1-methyl-1H-indol-3-yl]-acrylic acid ethyl ester, I-136L. Following the general Procedure A-14, I-135L, was converted to acrylic acid ethyl ester I-136L. Consistent with 1H-NMR.

Synthesis of (E)-3-[4-(3-Methoxyphenoxy)-1-methyl-1H-indol-3-yl]-acrylic acid, I-137L. Following the general Procedure A-7, I-136L, was hydrolyzed to acrylic acid I-137L. Consistent with 1H-NMR.

Synthesis of P371. Following the general Procedure A-8, the acrylic acid I-137L, was reacted with 2,4,5-Trifluoro-benzenesulfonamide to provide compound P371. Consistent with 1H-NMR.

Example 366

Preparation of P372

Synthesis of P372. Following the general Procedure A-8, the acrylic acid I-137L, was reacted with 2,3,4,5,6-Pentafluoro-benzenesulfonamide to provide compound P372. Consistent with 1H-NMR.

Example 367

Preparation of P376

Synthesis of 6-(1-Methyl-1H-indol-4-yloxy)-quinoline, I-134M: Following the general Procedure A-12, I-133, was reacted with 6-Hydroxyquinoline to provide compound I-134M. Consistent with 1H-NMR.

Synthesis of 1-Methyl-4-(quinolin-6-yloxy)-1H-indole-3-carbaldehyde, I-135M: Following the general Procedure A-13, I-134M, was converted to formaldehyde I-135M. Consistent with 1H-NMR.

Synthesis of (E)-3-[1-Methyl-4-(quinolin-6-yloxy)-1H-indol-3-yl]-acrylic acid ethyl ester, I-136M. Following the general Procedure A-14, I-135M, was converted to acrylic acid ethyl ester I-136M. Consistent with 1H-NMR.

Synthesis of (E)-3-[1-Methyl-4-(quinolin-6-yloxy)-1H-indol-3-yl]-acrylic acid, I-137M. Following the general Procedure A-7, I-136M, was hydrolyzed to acrylic acid I-137M. Consistent with 1H-NMR.

Synthesis of P376. Following the general Procedure A-8, the acrylic acid I-137M, was reacted with 3,4-Difluoro-benzenesulfonamide to provide compound P376. Consistent with 1H-NMR.

Example 367

Preparation of P377

Synthesis of P377. Following the general Procedure A-8, the acrylic acid I-137M, was reacted with 2,4,5-Trifluoro-benzenesulfonamide to provide compound P377. Consistent with 1H-NMR.

Example 368

Preparation of P393

Synthesis of 2-(1-Methyl-1H-indol-4-yloxy)-quinoxaline, I-134N: Following the general Procedure A-12, I-133, was reacted with 6-Hydroxyquinoline to provide compound I-134N. Consistent with 1H-NMR.

Synthesis of 1-Methyl-4-(quinoxalin-2-yloxy)-1H-indole-3-carbaldehyde, I-135N: Following the general Procedure A-13, I-134N, was converted to formaldehyde I-135N. Consistent with 1H-NMR.

Synthesis of (E)-3-[1-Methyl-4-(quinoxalin-2-yloxy)-1H-indol-3-yl]-acrylic acid ethyl ester, I-136N. Following the general Procedure A-14, I-135N, was converted to acrylic acid ethyl ester I-136N. Consistent with 1H-NMR.

Synthesis of (E)-3-[1-Methyl-4-(quinoxalin-2-yloxy)-1H-indol-3-yl]-acrylic acid, I-137N. Following the general Procedure A-7, I-136N, was hydrolyzed to acrylic acid I-137N. Consistent with 1H-NMR.

Synthesis of P393. Following the general Procedure A-8, the acrylic acid I-137N, was reacted with 3,4-Difluoro-benzenesulfonamide to provide compound P393. Consistent with 1H-NMR.

Example 369

Preparation of P394

Synthesis of P372. Following the general Procedure A-8, the acrylic acid I-137N, was reacted with 2,4,5-Trifluoro-benzenesulfonamide to provide compound P394. Consistent with 1H-NMR.

Example 371

Preparation of P349

Synthesis of a,a-Di-[$^2$H]-2,4-dichlorobenzyl alcohol, I-238. To a solution of methyl 2,4-dichlorobenzoate (2.0 g, 9.75 mmol) in ether (20 mL) was added LiAlD$_4$ (0.41 g, 9.75 mmol) at 0 DC under N$_2$. After stirring at 0° C. for 1 h, the reaction was quenched with water-NaOH (15% aq.)-water (1:1:3). The resulting solids were filtered off, and the filtrate was concentrated in vacuo. The crude product was purified by a column chromatography on silica gel to yield I-238. (1.2 g, 69%). $^1$H NMR (CDCl$_3$)

Synthesis of a,a-Di-[$^2$H]-2,4-dichlorobenzyl bromide, I-239 To a solution of I-238 (0.6 g, 3.35 mmol) and triphenylphosphine (0.97 g, 3.69 mmol) in CH$_2$Cl$_2$ (10 mL) was added N-bromosuccinimide (0.66 g, 3.69 mmol) at 0° C. under N$_2$. The reaction mixture was stirred at 0° C. for 10 min and at rt for 30 min. After the solvent was removed, the residue was triturated with 10% ether in hexane, and filtered through a pad of silica gel to yield I-239 (0.62 g, 77%). $^1$H NMR (CDCl$_3$)

Synthesis of I-240. To a solution chloral hydride (11.3 g, 68.4 mmol) in water (143 mL) were added Na$_2$SO$_4$ (15.7 g, 0.486 mol), 2-bromo-4-fluoroaniline (10.0 g, 52.6 mmol) in a mixture of 37% HCl (1.2 mL, 57.9 mmol) and water (54 mL) with vigorous stirring. After the addition was completed, the resulting reaction mixture was heated to reflux for 10 min, and allowed to cool to room temperature. The precipitate formed was collected by filtration, washed with water (3×100 mL) and dried in vacuo to yield the crude isonitrosoacetanilide. This product was added portion-wise to rapidly stirred concentrated H$_2$SO$_4$ (178 mL) at a rate to keep the reaction temperature between 50 and 70° C. The reaction mixture was heated to 80° C. for 20 min and allowed to cool to room temperature. The cooled mixture was poured into crushed ice (ca. 3200 g). The mixture was allowed to stand for 1 h. The resulting solid was filtered off, and the aqueous layer was extracted with CH$_2$Cl$_2$, washed with brine and dried over Na$_2$SO$_4$. After concentrated in vacuo, the residue was triturated with 20% ether in hexane to yield I-240 (2 g, 17%). $^1$H NMR (DMSO-d$_6$); MS (APCI$^-$): 243 (M−1).

Synthesis of I-241. To a mixture of Mg (0.44 g-atom) in anhydrous ether (4 mL) was added CD$_3$I in anhydrous ether (100 mL) at rt over a period of 3 h. The reaction mixture was then stirred for an additional 30 min.

To a solution of I-240 (1.65 g, 6.76 mmol) in anhydrous THF (85 mL) was added CD$_3$MgI prepared above at −78° C. over a period of 30 min and stirred for 1 h. After warming to −10° C., the reaction was quenched with water, extracted with EtOAc, washed with brine, dried over Na$_2$SO$_4$, and concentrated in vacuo. The residue was purified by a column chromatography on silica gel to yield I-241 (1.5 g, 84%). ¹H-NMR (DMSO-d₆); MS (APCI⁻): 262 (M−1).

Synthesis of I-242. To a solution of I-241 (1.2 g, 4.61 mmol) in THF (60 mL) was added BH₃ (1M in THF, 11 mL, 11 mmol.) at 0° C. and stirred at rt for 5 h. The reaction was quenched by addition of 1N aqueos HCl, extracted with EtOAc, washed with brine, dried over Na₂SO₄, and concentrated in vacuo. The residue was purified by column chromatography on silica gel to yield I-242 (1 g, 95%). ¹H NMR (DMSO-d₆)

Synthesis of I-243. A mixture of I-242 (1.0 g, 4.33 mmol) and methyl acrylate (0.75 g, 8.66 mmol) in triethylamine (6 mL), palladium(I) acetate (97 mg, 0.43 mmol) and tri-o-tolylphosphine (0.26 g, 0.866 mmol) in DMF (20 mL) was stirred at 100° C. for 4 h and then cooled to room temperature The reaction mixture was diluted with CH2Cl2 (70 mL), washed with water (3×40 mL), brine, and dried over sodium sulfate. After removal of solvent, the residue was purified by column chromatography on silica gel to yield I-243 (0.9 g, 90%). ¹H-NMR (CDCl₃); MS (APCI⁻): 235 (M−1).

Synthesis of I-244. To a solution of I-243 (1.0 g, 4.23 mmol) in THF (5 mL) and methanol (5 mL) was added 1N aqueous NaOH (0.51 g, 12.7 mmol) at room temperature. The reaction mixture was stirred at room temperature overnight and then the pH was adjusted to acidic by adding 2N aqueous HCl. The reaction mixture was extracted with EtOAc (2×40 mL). The combined organic phase was washed with water, brine and dried over sodium sulfate. After removal of solvent, I-244 (0.9 g, 96%) was obtained. ¹H-NMR (500 MHz, DMSO-d₆)

Synthesis of I-245. A mixture of I-244 (0.9 g, 4.1 mmol), 3,4-dichloro-2-thiophenesulfonamide (1.0 g, 4.45 mmol), 4-dimethylaminopyridine (0.99 g, 8.1 mmol) and EDCI (1.55 g, 8.1 mmol) in dichloromethane (20 mL) was stirred at room temperature overnight. The solution was diluted with dichloromethane, washed with dilute aqueous HCl and water. The crude product was purified by a column chromatography on silica gel to yield I-245 (1.6 g, 88%).

Synthesis of P349. To a solution of I-245 (0.8 g, 1.83 mmol) in DMF (30 mL), NaH (60% in mineral oil, 97 mg, 4.03 mmol) was added at 0° C. After stirring at rt for 1 h, I-239 (0.43 g, 2.2 mmol) was added. The reaction mixture was stirred at room temperature overnight and diluted with CH2Cl2 (12 ml). The reaction mixture was washed with dilute aqueous HCl, water, brine and dried over sodium sulfate. After removal of solvent, the residue was purified by a column chromatography on silica gel to yield P349 (0.34 g, 34%). ¹H & ¹³C-NMR (DMSO-d₆); HPLC: 99% pure. Anal. Calcd for C23H15Cl4FN2O3S2: C, 46.64; H, 2.55; N, 4.73; Cl, 23.94; S, 10.83. Found: C, 46.31; H, 2.63; N, 4.70; Cl, 23.78; S, 10.72

The invention claimed is:
1. A compound of formula

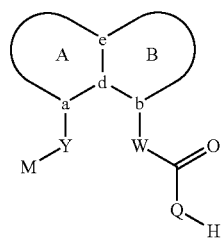

wherein
A and B represent a six-membered carbocycle fused to a five-membered nitrogen heterocycle, said A/B ring system chosen from indole, reduced indole, 2-oxoindole, and reduced 2-oxoindole, and said fused A/B ring system substituted with from zero to four substituents chosen independently from halogen, —OH, loweralkyl, —O-loweralkyl, fluoroloweralkyl, —O-lowerfluoroalkyl, methylenedioxy, ethylenedioxy, alkoxy-loweralkyl, hydroxylloweralkyl, oxo, oxide, —CN, nitro, —S-loweralkyl, amino, loweralkylamino, diloweralkylamino, diloweralkylaminoalkyl, carboxy, carboalkoxy, orthoester, acyl, acylalkyl, carboxamido, loweralkylsulfoxide, loweralkylsulfone, acylamino, phenyl, benzyl, spirothiazolidinyl, phenoxy and benzyloxy;

a and b represent points of attachment of residues Y and W respectively and a and b are in a peri relationship to one another on said fused A/B ring system;

d and e represent points of fusion between ring A and ring B in said fused A/B ring system;

Each of the nodes a, b, d and e may be either carbon or nitrogen;

W is chosen from —CH₂O—, —OCF₂—, —OC(CH₃)—, —CH=CH—, and —NHCH₂—;

Y is chosen from —CH₂—, —O—, —OCH₂—, —S—, —SO—, and —SO₂—;

M is chosen from aryl, substituted aryl, heterocyclyl, and substituted heterocyclyl wherein substituents on substituted aryl and heterocyclyl are chosen from halogen, loweralkyl, haloalkyl, hydroxy, loweralkoxy. carboxy, carboalkoxy, carboxamido, cyano, carbonyl, nitro, amino, alkylamino, dialkylamino, mercapto, alkylthio, sulfoxide, sulfone, acylamino, amidino, phenyl, benzyl, heteroaryl, phenoxy, benzyloxy, and heteroaryloxy;

Q is chosen from —N(SO₂R¹)—, —N(COR¹)—, —N(CO₂R¹)—, —N[PO(O-alkyl)₂]—, and —NHNR¹⁰(SO₂R¹)—;

R¹ is chosen from phenyl, isoxazole, thienyl, substituted isoxazole, substituted thienyl, C₃-C₂₀ alkyl and fluoroalkyl; and R¹⁰ is chosen from alkyl, aryl and heteroaryl.

2. A compound according to claim 1 wherein said A/B ring system is indole of formula:

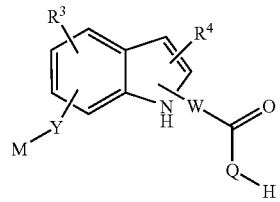

wherein
R³ and R⁴ are optional substituents in either or both rings, chosen independently from halogen, —OH, loweralkyl, —O-loweralkyl, fluoroloweralkyl, —O-lowerfluoroalkyl, methylenedioxy, ethylenedioxy, alkoxy-loweralkyl, hydroxyloweralkyl, oxo, oxide, —CN, nitro, —S-loweralkyl, amino, loweralkylamino, diloweralkylamino, diloweralkylaminoalkyl, carboxy, carboalkoxy, orthoester, acyl, acylalkyl, carboxamido, loweralkylsulfoxide, loweralkylsulfone, acylamino, phenyl, benzyl, spirothiazolidinyl, phenoxy and benzyloxy.

3. A compound according to claim 1 wherein said A/B ring system is 2-oxoindole of formula:

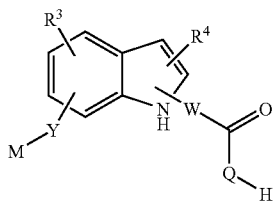

wherein

R³ and R⁴ are optional substituents in either or both rings, chosen independently from halogen, —OH, loweralkyl, —O-loweralkyl, fluoroloweralkyl, —O-lowerfluoroalkyl, methylenedioxy, ethylenedioxy, alkoxy-loweralkyl, hydroxyloweralkyl, oxo, oxide, —CN, nitro, —S-loweralkyl, amino, loweralkylamino, diloweralkylamino, diloweralkylaminoalkyl, carboxy, carboalkoxy, orthoester, acyl, acylalkyl, carboxamido, loweralkylsulfoxide, loweralkylsulfone, acylamino, phenyl, benzyl, spirothiazolidinyl, phenoxy and benzyloxy.

4. A compound according to claim 1 wherein said A/B ring system is a reduced 2-oxoindole of formula:

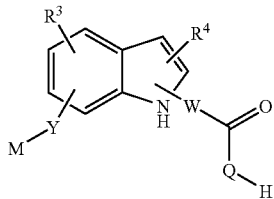

wherein

R³ and R⁴ are substituents in either or both rings, chosen independently from halogen, —OH, loweralkyl, —O-loweralkyl, fluoroloweralkyl, —O-lowerfluoroalkyl, methylenedioxy, ethylenedioxy, alkoxy-loweralkyl, hydroxyloweralkyl, oxo, oxide, —CN, nitro, —S-loweralkyl, amino, loweralkylamino, diloweralkylamino, diloweralkylaminoalkyl, carboxy, carboalkoxy, orthoester, acyl, acylalkyl, carboxamido, loweralkylsulfoxide, loweralkylsulfone, acylamino, phenyl, benzyl, spirothiazolidinyl, phenoxy and benzyloxy.

5. A compound according to any one of claims 1-4 wherein Q is —N(SO₂R¹)— and R¹ is chosen from phenyl, substituted phenyl, isoxazole, substituted isoxazole, thienyl, substituted thienyl, fluorophenyl and CF₃.

6. A compound according to claim 5 wherein M is chosen from substituted phenyl, naphthyl and bicyclic nitrogen heteroaryl.

7. A compound according to claim 6 wherein at least one of R¹ and M is fluorophenyl.

8. A compound according to claim 6 wherein Y is —CH₂— and W is —CH=CH—.

9. A compound according to claim 2 which is

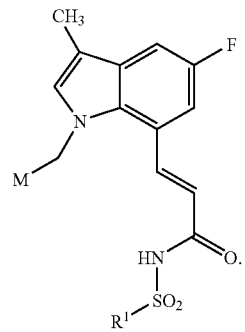

10. A compound according to claim 9 wherein M is 2,4—dichlorophenyl and R¹ is 4,5—dichlorothien—2—yl.

* * * * *

UNITED STATES PATENT AND TRADEMARK OFFICE
CERTIFICATE OF CORRECTION

| | |
|---|---|
| PATENT NO. | : 7,598,397 B2 |
| APPLICATION NO. | : 11/169161 |
| DATED | : October 6, 2009 |
| INVENTOR(S) | : Singh et al. |

Page 1 of 1

It is certified that error appears in the above-identified patent and that said Letters Patent is hereby corrected as shown below:

Claim 1, at Column 206, Line 18: Delete "Each" and insert -- each --

Claim 1, at Column 206, Line 20: after "W is chosen from -$CH_2O$-, -$OCF_2$-," and before "-CH=CH-, and -$NHCH_2$;" delete "OC($CH_3$)-," and insert -- -OC($CH_3$)$_2$-, -OCH($CH_3$)-, --

Claim 1, at Column 206, Line 35: after "$R^1$ is chosen from phenyl, isoxazole, thienyl," and before "substituted isoxazole, substituted thienyl, $C_3$-$C_{20}$ alkyl and fluoroalkyl; and" insert -- substituted phenyl, --

Signed and Sealed this

Nineteenth Day of January, 2010

David J. Kappos
*Director of the United States Patent and Trademark Office*